(12) United States Patent
Fernandez Rodriguez

(10) Patent No.: US 11,661,443 B2
(45) Date of Patent: May 30, 2023

(54) CHIMERIC RECEPTOR BINDING PROTEINS FOR USE IN BACTERIAL DELIVERY VEHICLES

(71) Applicant: Eligo Bioscience, Paris (FR)

(72) Inventor: Jesus Fernandez Rodriguez, Paris (FR)

(73) Assignee: ELIGO BIOSCIENCE, Paris (FR)

(*) Notice: Subject to any disclaimer, the term of this patent is extended or adjusted under 35 U.S.C. 154(b) by 783 days.

(21) Appl. No.: 16/696,769

(22) Filed: Nov. 26, 2019

(65) Prior Publication Data
US 2020/0190147 A1 Jun. 18, 2020

Related U.S. Application Data

(60) Provisional application No. 62/802,777, filed on Feb. 8, 2019, provisional application No. 62/771,761, filed on Nov. 27, 2018.

(51) Int. Cl.
| | | |
|---|---|---|
| *C07K 14/005* | (2006.01) | |
| *A61K 38/46* | (2006.01) | |
| *C12N 15/71* | (2006.01) | |
| *C12N 9/22* | (2006.01) | |
| *A61K 48/00* | (2006.01) | |

(52) U.S. Cl.
CPC .......... *C07K 14/005* (2013.01); *A61K 38/465* (2013.01); *C12N 9/22* (2013.01); *C12N 15/71* (2013.01); *A61K 48/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 8,673,553 B2 | 3/2014 | Scholl et al. | |
| 11,208,437 B2 | 12/2021 | Fernandez Rodriguez | |
| 11,236,133 B2 | 2/2022 | Fernandez Rodriguez | |

OTHER PUBLICATIONS

Salmond et al. "A century of the phage: past, present and future," Nat. Rev. Microbiol., (Dec. 2015), vol. 13, No. 12; pages ///-786.
Hyman et al., "Bacteriophage host range and bacterial resistance," Adv. Appl. Microbiol., (2010), vol. 70; pp. 217-248.
Chatterjee et al., "Interaction of Bacteriophage I with Its E. coli Receptor, LamB," Viruses, (Nov. 2012), vol. 4, No. 11; pp. 3162-3178.
Nobrega et al., "Targeting mechanisms of tailed bacteriophages," Natural Reviews, Microbiology, (Dec. 2018), vol. 16; pp. 760-773.
Flayhan, et al., "New insights into pb5, the receptor binding protein of bacteriophage T5, and its interaction with its Escherichia coli receptor Fhu A," Biochimie, (2012), vol. 94, No. 9; pp. 1982-1989.
Rossmann, et al., "The bacteriophage T4 Dna injection machine," Curr. Opin. Struct. Biol, (Apr. 2004), vol. 14, No. 2 pp. 171-180.
Zivanovic et al., "Insights into Bacteriophage T5 Structure from Analysis of Its Morphogenesis Genes and Protein Components," J Virol., (Jan. 2014), vol. 88, No. 2; pp. 1162-1174.
Hendrix et al., "Bacteriophage lambda PaPa: not the mother of all lambda phages," Science, (Nov. 1992), vol. 258, No. 5085; pp. 1145-1148.
Speed et al., "Conformation of P22 tailspike folding and aggregation intermediates probed by monoclonal antibodies," Protein Sci. Publ. Protein Soc., (Jan. 1997), vol. 6, No. 1; pp. 99-108.
Labrie et al., "Bacteriophage resistance mechanisms," Nat. Rev. Microbiol., (Mar. 2010), vol. 8, No. 5; pp. 317-327.
Whitfield, "Biosynthesis and assembly of capsular polysaccharides in Escherichia coli," Annu. Rev. Biochem., (2006), vol. 75; pp. 39-68.
Meyer et al., "Repeatability and contingency in the evolution of a key innovation in phage lambda," Science, (Jan. 2012), vol. 335, No. 6067; pp. 428-432.
Gupta et al., "Coliphage K5, specific for E. coli exhibiting the capsular K5 antigen," FEMS Microbiol. Lett., (May 1982), vol. 14, No. 1; pp. 75-78.
Gross, et al., "Isolation of bacteriophages specific for the K1 polysaccharide antigen of Escherichia coli," J. Clin. Microbiol., (Dec. 1977), vol. 6, No. 6; pp. 548-550.
Schwarzer et al., "A Multivalent Adsorption Apparatus Explains the Broad Host Range of Phage phi92: a Comprehensive Genomic and Structural Analysis," J Virol, (Oct. 2012), vol. 86, No. 19; p. 10384-10398.
Fetart et al., "Bacteriophage T4 host range is expanded by duplications of a small domain of the tail fiber adhesin," J. Mol. Biol., (May 1996), vol. 258, No. 5; pp. 726-731.
Haggard-Ljungquist, et al., "DNA sequences of the tail fiber genes of bacteriophage P2: evidence for horizontal transfer of tail fiber genes among unrelated bacteriophages.," J. Bacteriol., (Mar. 1992), vol. 174, No. 5; pp. 1462-1477.
Nu, et al., "Characterization of Extended-Host-Range Pseudo-T-Even Bacteriophage Kpp95 Isolated on Klebsiella oneumoniae," Appl. Environ. Microbiol., (Apr. 2007), vol. 73, No. 8; pp. 2532-2540.
Montag et al., "A component of the side tail fiber of Escherichia coli bacteriophage lambda can functionally replace the Yeceptor-recognizing part of a long tail fiber protein of the unrelated bacteriophage T4," J. Bacteriol., (Aug. 1989), vol. 171, No. 8; pp. 4378-4384.
Vimr, et al., "Use of prokaryotic-derived probes to identify poly(sialic acid) in neonatal neuronal membranes," Proc. Natl. Acad. Sci, (Apr. 1984), vol. 81, No. 7; pp. 1971-1975.
Stummeyer, et al., "Crystal structure of the polysialic acid-degrading endosialidase of bacteriophage K1F," Nat. Struct. Mol Biol., (Jan. 2005), vol. 12, No. 1; pp. 90-96.

(Continued)

*Primary Examiner* — Robert M Kelly
(74) *Attorney, Agent, or Firm* — Carter, DeLuca & Farrell LLP; Carmella Stephens

(57) ABSTRACT

The present disclosure relates generally to bacterial delivery vehicles for use in efficient transfer of a desired payload into a target bacterial cell. More specifically, the present disclosure relates to bacterial delivery vehicles with desired host ranges based on the presence of a chimeric receptor binding protein (RBP) composed of a fusion between the N-terminal region of a RBP derived from a lambda-like bacteriophage and the C-terminal region of a different RBP.

11 Claims, 15 Drawing Sheets

Specification includes a Sequence Listing.

(56) References Cited

OTHER PUBLICATIONS

Scholl et al., "Escherichia coli K1's Capsule Is a Barrier to Bacteriophage I f," Appl. Environ. Microbiol., (Aug. 2005), vol. 71, No. 8; pp. 4872-4874.
Jiang et al. "Multigene Editing in the *Escherichia coli* Genome via the CRISPR-Cas9 System," Appl. Environ. Microbiol., (Apr. 2015), vol. 81, No. 7; pp. 2506-2514.
Cronan, "Improved Plasmid-Based System for Fully Regulated Off-To-On Gene Expression in *Escherichia coli* Application to Production of Toxic Proteins," Plasmid, (Jan. 2013), vol. 69, No. 1; pp. 81-89.
Thompson et al.,"The K5 Lyase KflA Combines a Viral Tail Spike Structure with a Bacterial Polysaccharide Lyase Mechanism," J. Biol. Chem., (Jul. 2010), vol. 285, No. 31; pp. 23963-23969.
Potter et al., "HMMER web server: 2018 update," Nucleic Acids Res., (Jul. 2018), vol. 46, No. W1; pp. W200-W204.
Xu et al., "Chaperone-protein interactions that mediate assembly of the bacteriophage lambda tail to the correct length," J. Mol. Biol., (Mar. 2014), vol. 426, No. 5; pp. 1004-1018.
Schwarzer et al., "Proteolytic Release of the Intramolecular Chaperone Domain Confers Processivity to Endosialidase F," J. Biol. Chem., (Apr. 2009), vol. 284, No. 14; pp. 9465-9474.
Gilbert et al., "Current understanding of the human microbiome," Nat. Med., (Apr. 2018), vol. 24, No. 4; pp. 392-400.
Nkamga et al., "Archaea: Essential inhabitants of the human digestive microbiota," Hum. Microbiome J., (Mar. 2017), vol. 3; pp. 1-8.
Scholl et al., "The Genome of Bacteriophage K1F, a T7-Like Phage That Has Acquired the Ability To Replicate on K1 Strains of *Escherichia coli*," J. Bacteriol (Dec. 2005), vol. 187, No. 24; pp. 8499-8503.
Keen, "Tradeoffs in bacteriophage life histories," Bacteriophage, (Apr. 2014), vol. 4, No. 2; p. e28365.
Mirzaei et al., "Isolation of Phages for Phage Therapy: A Comparison of Spot Tests and Efficiency of Plating Analyses for Determination of Host Range and Efficacy," PLOS One, (Mar. 2015), vol. 10, No. 3, p. e0118557.
Goodridge et al., "Morphological, Host Range, and Genetic Characterization of Two Coliphages," Appl. Environ. Microbiol. (Sep. 2003), vol. 69, No. 9; pp. 5364-5371.
Ochman et al., "Standard reference strains of *Escherichia coli* from natural populations," J. Bacteriol, (Feb. 1984), vol. 157, No. 2; pp. 690-693.
McBurney et al., "Establishing What Constitutes a Healthy Human Gut Microbiome: State of the Science, Regulatory Considerations, and Future Directions," J. Nutr. (Nov. 2019), vol. 149, No. 11; pp. 1882-1895.
Nagpal et al., "Gut microbiome and aging: Physiological and mechanistic insights," Nutr. Healthy Aging (2018), vol. 4, No. 4; pp. 267-285.
Singh et al., "Influence of diet on the gut microbiome and implications for human health," J. Transl. Med. (Apr. 2017), vol. 15; pp. 1-17.
Tenaillon et al.,"The population genetics of commensal *Escherichia coli*," Nat. Rev. Microbiol., (Mar. 2010), vol. 8, No. 3; pp. 207-217.
Nowrouzian et al., "*Escherichia coli* strains belonging to phylogenetic group B2 have superior capacity to persist in the intestinal microflora of infants," J. Infect. Dis., (Apr. 2005), vol. 191, No. 7; pp. 1078-1083.
Smati et al., "Quantitative analysis of commensal *Escherichia coli* populations reveals host-specific enterotypes at the intra-species level," MicrobiologyOpen (Aug. 2015), vol. 4, No. 4; pp. 604-615.
Hyman, "Phages for Phage Therapy: Isolation, Characterization, and Host Range Breadth," Pharmaceuticals, (Mar. 2019), vol. 12, No. 1; pp. 1-23.
Pantucek et al., "The polyvalent *Staphylococcal* phage phi 812: its host-range mutants and related phages," Virology (Jul. 1998), vol. 246, No. 2; pp. 241-252.
Ross et al., "More Is Better: Selecting for Broad Host Range Bacteriophages," Front. Microbiol. (Sep. 2016), vol. 7; Article 1352; pp. 1-6.
Marusich et al.,"Chaperones in bacteriophage T4 assembly," Biochem. Biokhimiia, (Apr. 1998), vol. 63, No. 4; pp. 399-406 (Abstract Only).
Golomidova et al., "Branched Lateral Tail Fiber Organization in T5-Like Bacteriophages DT57C and DT571/2 is Revealed by Genetic and Functional Analysis," Viruses, (Jan. 2016), vol. 8, No. 26; pp. 1-21.
Chen et al., "Crystal structure of ORF210 from *E. coli* O157:H1 phage CBA120 (TSP1), a putative tailspike protein," PloS One, (2014), vol. 9, No. 3; pp. e93156, 2014.
Kutter et al., "Characterization of a Vil-like phage specific to *Escherichia coli* O157:H7," Virology Journal (2011), vol. 8, No. 430; pp. 1-14 (PubMed—NCBI. [Online]. Available: https://www.ncbi.nlm.nih.gov/pubmed/21899740).
Arumugam et al., Enterotypes of the human gut microbiom, Nature (May 2011), vol. 473, No. 7346; pp. 174-180.
Kapitan et al., "Fungi as Part of the Microbiota and Interactions with Intestinal Bacteria," Current Topics in Microbiology and Immunology, (2019), vol. 422; pp. 265-301.
Siponen, Marina, et al., "Crystal structure of a chimeric receptor binding protein constructed from two lactococcal phages," Journal of bacteriology, May 2009, pp. 3220-3225, 191.10.
Anonymous, "Short-chain Dehydrogenase," DATABASE: UniProt, Nov. 2018, A0A167SZV7 A0A167SZV7_ECOLX, 7 pages.
European Office Action for related application No. 19 812 752.4, dated Sep. 1, 2022, 7 pages.
Https://en.wikipedia.org/wiki/Lambdavirus, author unknown, published by Wikipedia, San Francisco, CA, downloaded as PDF on Mar. 1, 2021, 3 pages as printed. (Year: 2021).
Author(s) known, https://en.wikipedia.org/wiki/Bacteriophage, Wikimedia Foundation, Inc., San Francisco, CA, downloaded Nov. 5, 2020, 16 pages as printed.
Mobley, et al. (2009) Binding of Small-Molecule Ligands to Proteins: 'What You See' Is Not Always 'What You Get', Structure, 17:489-98.

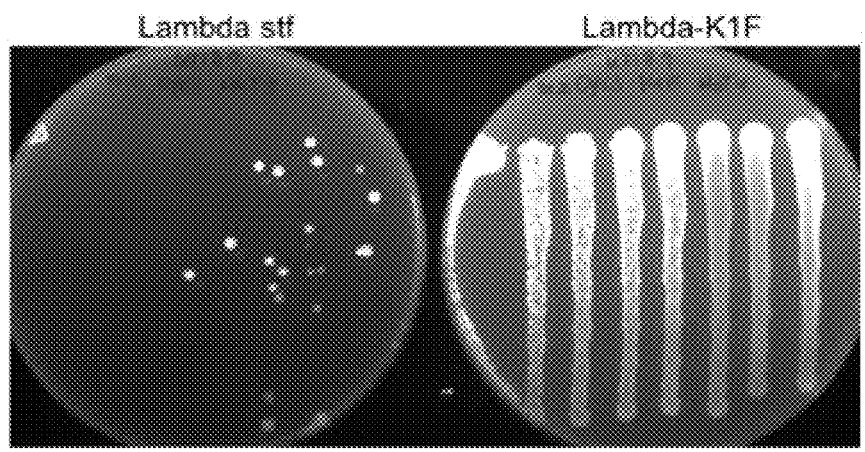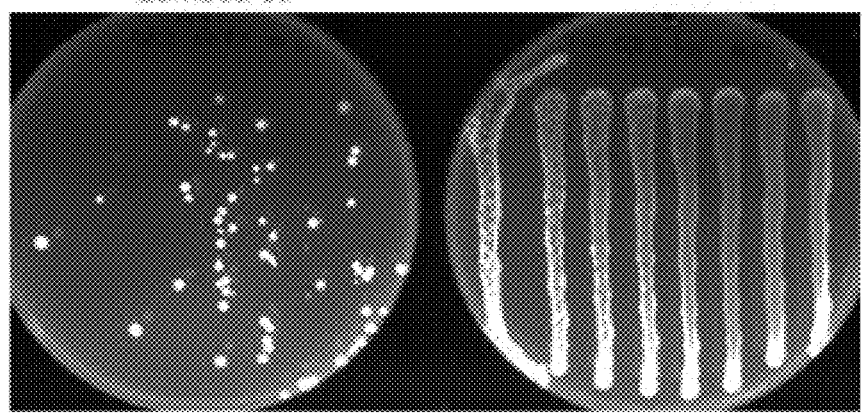
FIG. 2

CHIMERIC RECEPTOR BINDING PROTEINS FOR USE IN BACTERIAL DELIVERY VEHICLES

CROSS-REFERENCE TO RELATED APPLICATION

This application claims benefit and priority to U.S. Provisional Application No. 62/771,761 filed Nov. 27, 2018; and U.S. Provisional Application No. 62/802,777, filed Feb. 8, 2019, which are both incorporated herein by reference in their entireties.

REFERENCE TO SEQUENCE LISTING SUBMITTED VIA EFS-WEB

This application includes an electronically submitted sequence listing in .txt format. The .txt file contains a sequence listing entitled "2643-3 US TRK-1_ST25.txt" created on Mar. 9, 2020 and is 940,581 bytes in size. The sequence listing contained in this .txt file is part of the specification and is hereby incorporated by reference herein in its entirety.

TECHNICAL FIELD

The present disclosure relates generally to bacterial delivery vehicles for use in efficient transfer of a desired payload into a target bacterial cell. More specifically, the present disclosure relates to bacterial delivery vehicles with desired host ranges based on the presence of a chimeric receptor binding protein (RBP) composed of a fusion between the N-terminal region of a RBP derived from a lambda-like, or lambda bacteriophage and the C-terminal region of a different RBP.

BACKGROUND

Bacteriophages are parasites that infect and multiply in bacteria. In general, the infection process can be divided in several stages: (i) adsorption corresponding to recognition and binding to the bacterial cell; (ii) injection of the DNA genome into the bacterial cell cytoplasm; (iii) production of a set of viral proteins that can lead to insertion in the host target genome (lysogenic phages) or to the production of infective particles (lytic phages) and (iv) release of mature virions from the infected cell, usually by controlled lysis [1].

Being the first step necessary for a successful infection, recognition and binding to the target cell is an essential process in the bacteriophage life cycle. Bacteriophages can in some cases recognize several strains of the same species, having a "broad host range", but very commonly are able to recognize a specific antigen present only on some strains of the same species [2]. It is thus not surprising that this step of the infection process is central in the competition between bacteriophage and bacteria for successful infection.

As a general mechanism, a bacteriophage encodes two main sets of proteins that are involved in the recognition process. The first set is able to attach to the bacteriophage's primary receptor on the cell surface, an event that triggers DNA ejection into the cytoplasm and is usually viewed as an "irreversible" binding process [3]. Different bacteriophage genera differ in the organization of this set of proteins, and hence the naming can be different. In some *Siphovirus*, for example, they are called the "central tail fiber" or "tail tip", which binds irreversibly to the LamB receptor in *Escherichia coli*. In the siphoviridae lambda, the "central tail fiber" or "tail tip" is composed of the protein gpJ [4]. In some other *Siphovirus*, like T5, a protein located at the very tip of the tail mediates this process. In the case of T5, a protein called pb5 recognizes the FhuA receptor [5]. This type of protein can be found in many other bacteriophages. In *Myoviruses*, like T4, the irreversible binding to the primary receptor or to the cell surface in general is mediated by the "short tail fibers", which are also located at the end of the tail tube [5].

The second set of proteins in the bacteriophage (herein referred to as "receptor binding proteins") encodes recognition and binding activities to the so-called "secondary receptor" on the bacterium. This secondary receptor allows for transient binding of the phage particle on the cell surface in order to scan the surface and position the first set of proteins in contact with the primary receptor. Since this binding is reversible, it allows the phage to "walk" on the cell surface until a primary receptor is found and the infection process starts. These protein complexes are sometimes referred to as "L-shape fibers", such as in T5, "side tail fibers" such as in lambda, "long tail fibers" as in T4, or tailspikes such as in phage P22 [5]-[8]. For some phages, the presence of this second set of proteins is necessary for the infection process to occur, such as T4 [5]. In some other phages, like lambda, this second set of proteins is not strictly necessary for the infection process to happen, but it may allow for a more efficient binding to the target cell [7].

Since the adsorption process is strictly necessary for a successful infection to happen, bacteria can develop multiple ways to avoid being recognized by a bacteriophage. For example, they can mutate the primary or secondary receptor to which the bacteriophage binds; they can mask this receptor by attaching proteins to it (receptor masking); or they can grow physical barriers around them in the form of bacterial capsules, thus blocking any access to the cell surface [9]. Bacteria can produce many different types of extracellular polymeric capsules [10]. In turn, bacteriophages have evolved different strategies to bypass these defense mechanisms. For instance, mutating the tail tip proteins allows them to use a different receptor [11]. However, the presence of a polymeric capsule around the bacterium requires a different approach, as it blocks all contact to any receptors on the cell surface. In these cases, bacteriophages have evolved specific proteins that can enzymatically degrade this capsule to gain access to the cells. These depolymerase activities are encoded in protein complexes that are distinct to the primary receptor recognition machinery, in the form of side tail fibers, long tail fibers or tailspikes [12], [13], [14].

The concept of a bacteriophage's host range needs to be redefined when only the adsorption and injection processes are taken into account. Since all incompatibilities or defense mechanisms related to the phage replication cycle are left out of the picture, the "adsorption host range" of a given phage is usually larger than the "classical host range" in which the infectious cycle leads to newly produced mature virions. The concept of host range becomes even more different to the classical definition when packaged phagemids based on a given bacteriophage capsid is used. Packaged phagemids do not contain the information necessary to replicate the viral particles, because they do not package their cognate viral genome. Thus, the host range of a packaged phagemid tends to be larger than that of the parental bacteriophage it derives from. Therefore, for development of novel bacterial delivery vehicles, designed for the efficient delivery of exogenous DNA payload into target strains, it is of utmost importance to be able to engineer delivery vehicles with desired host ranges as well as the ability to bypass bacterial mechanisms that can lead to unsuccessful binding of the packaged phagemid to the bacterial cell surface.

SUMMARY

As a general mechanism, a bacteriophage encodes sets of proteins that are involved in the bacterial cell recognition process. Described herein are novel approaches to engineering synthetic bacterial delivery vehicles with desired target host ranges. In some aspects, synthetic bacterial delivery vehicles are provided that are characterized by a chimeric receptor binding protein (RBP), wherein the chimeric RBP comprises a fusion between an N-terminal domain of a RBP from a lambda-like bacteriophage, or lambda bacteriophage, and a C-terminal domain of a different bacteriophage RBP. Such bacteriophage RBPs, from which the chimeric RBP are derived, include, for example, and depending on phages families, "L-shape fibers", "side tail fibers (stfs)", "long tail fibers" or "tailspikes." As disclosed herein, it has been demonstrated that a significant portion of a lambda-like bacteriophage receptor binding protein (RBP), such as a stf protein, can be exchanged with a portion of a different RBP. Moreover, specific fusion positions in the RBPs have been identified which allow one to obtain functional chimeric RBPs.

The chimeric receptor binding protein (RBP) is one wherein the chimeric RBP comprises a fusion between an N-terminal domain of a RBP derived from a lambda-like bacteriophage, or lambda bacteriophage, and a C-terminal domain of a different RBP wherein said N-terminal domain of the RBP is fused to said C-terminal domain of a different RBP within one of the amino acids regions selected from positions 1-150, 320-460, or 495-560 of the N-terminal RBP with reference to the lambda stf sequence (SEQ ID NO: 1) or a similar region of a RBP having homology with one or more of three amino acid regions ranging from positions 1-150, 320-460, and 495-560 of the RBP with reference to the lambda stf sequence. In one specific aspect of the invention, the different RBP domain of the chimeric receptor binding protein (RBP) is derived from any bacteriophage or from any bacteriocin.

In one specific aspect, the RBP from the lambda-like bacteriophage, or the lambda bacteriophage, or the different RBP contains homology in one or more of three amino acid regions ranging from positions 1-150, 320-460, and 495-560 of the RBP with reference to the lambda bacteriophage stf sequence (SEQ ID NO: 1). In certain aspects, the homology between the lambda-like bacteriophage, the lambda bacteriophage, or the different RBP and the one or more of three amino acids regions is around 35% identity for 45 amino acids or more, around 50% identify for 30 amino acids or more, and around 90% identity for 18 amino acids or more with reference to the lambda bacteriophage stf sequence (SEQ ID NO:1). Determination of homology can be performed using alignment tools such as the Smith-Waterman algorithm (Smith et al., 1981, J. Mol. Biol 147:195-197) or EMBOSS Matcher (Rice, Longden, Bleasby 2000 EMBOSS Trends in Genetics 16: 276-277).

In one aspect of the invention, the chimeric RBP comprises the N-terminal domain of a RBP fused to the C-terminal domain of a different RBP within one of the amino acid regions selected from positions 80-150, 320-460, or 495-560 of the N-terminal RBP with reference to the lambda bacteriophage stf sequence (SEQ ID NO:1). In another embodiment of the invention, the chimeric RBP comprises an N-terminal domain and a C-terminal domain fused within one of the amino acids regions selected from positions 1-150, 320-460 or 495-560 at an insertion site having at least 80% identity with an insertion site selected from the group consisting of amino acids SAGDAS (SEQ ID NO: 248), ADAKKS (SEQ ID NO: 249), MDETNR (SEQ ID NO: 250), SASAAA (SEQ ID NO: 251) and, GAGENS (SEQ ID NO: 252).

In another aspect, the chimeric RBP comprises the N-terminal domain of a RBP fused to the C-terminal domain of different RBP wherein the different RBP is a protein or group a different proteins that confers an altered host range. In one embodiment, the different RBP is a T4-like or T4 long tail fiber composed of a proximal tail fiber and a distal tail fiber (DTF), and the C-terminal domain of a T4-like or T4 RBP is the distal tail fiber (DTF). In another embodiment, the N-terminal domain of a RBP is fused to the T4-like or T4 distal tail fiber at an insertion site within the T4-like or T4 DTF having at least 80% identity with an insertion site selected from the group consisting of amino acids ATLKQI (SEQ ID NO: 253), IIQLED (SEQ ID NO: 254), GNIIDL (SEQ ID NO: 255), IATRV (SEQ ID NO: 256), TPGEL (SEQ ID NO: 257), GAIIN (SEQ ID NO: 258), NQIID (SEQ ID NO: 259), GQIVN (SEQ ID NO: 260) and, VDRAV (SEQ ID NO: 261). In a specific embodiment, the N-terminal domain of a RBP is fused to the T4-like or T4 distal tail fiber within a region from amino acid 1 to 90, with a preferred region from amino acid 40 to 50 of the DTF.

In specific embodiments, the disclosure provides specific chimeric RBPs. SEQ ID NOS 2-61, 123-153, 216-244 and 246-247 disclose the amino acid sequences of such chimeric RBPs as well as, in some instances, their corresponding natural chaperone proteins (designated "AP"). Such AP proteins assist in the folding of the chimeric RBPs. In a specific embodiment, the RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 123-129, 130, 131, 132, 135, 138, 139, 142, 145, 148, 151, 216, 219, 221, 223, 227, 230, 232, 234, 236, 238, 240, 243, 245 or 246.

In another aspect, the present disclosure provides nucleotide sequences encoding for the chimeric RBPs disclosed herein. In a specific embodiment, nucleic acids encoding such chimeric RBPs, as well as their corresponding AP proteins, are depicted in SEQ ID NOS 62-120, 122, 154-177, 182-210 and 212-213. In a specific embodiment, the nucleic acids encoding such chimeric RBPs comprise the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172 175, 182, 187, 189, 193, 196, 198, 200, 202, 204, 206, 209 or 212.

In one specific non-limiting aspect of the invention, it has been demonstrated that engineering the chimeric RBP to encode depolymerase activity can dramatically increases the delivery efficiency of the provided bacterial delivery vehicles comprising the chimeric RBP disclosed herein. In an embodiment of the invention, the different RBP domain of the chimeric RPB comprises depolymerase activity against an encapsulated bacterial strain. In a specific embodiment, the depolymerase is an endosialidase such as, for example, a K1F or K5 endosialidase.

In an embodiment of the invention, nucleic acid molecules encoding the chimeric RBPs disclosed herein are provided. Such nucleic acids may be included in vectors such as bacteriophages, plasmids, phagemids, viruses, and other vehicles which enable transfer and expression of the chimeric RBP encoding nucleic acids.

Bacterial delivery vehicles are provided which enable transfer of a nucleic acid payload, encoding a protein or nucleic acid of interest, into a desired target bacterial host cell. Such bacterial delivery vehicles are characterized by having a chimeric RBP comprising a fusion between the N-terminal domain of a RBP from a lambda-like bacteriophage, or lambda bacteriophage, and the C-terminal domain of a different RBP. In an embodiment of the invention, the bacterial delivery vehicles contain a chimeric RBP comprising a fusion between an N-terminal domain of a RBP derived from a lambda-like bacteriophage, or lambda bacteriophage, and a C-terminal domain of a different RBP wherein said N-terminal domain of the chimeric RBP is fused to said C-terminal domain of a different RBP within one of the amino acids regions selected from positions 1-150, 320-460, or 495-560 of the N-terminal domain with reference to the lambda stf sequence (SEQ ID NO: 1). In one aspect, the RBP from the lambda-like bacteriophage, the lambda bacteriophage, and the different RBP contain homology in one or more of three amino acids regions ranging from positions 1-150, 320-460, and 495-560 of the RBP with reference to the lambda bacteriophage stf sequence (SEQ ID NO: 1). In certain aspects, the homology is around 35% identity for 45 amino acids or more, around 50% identify for 30 amino acids or more, or around 90% identity for 18 amino acids or more within the one or more of three amino acids regions ranging from positions 1-150, 320-460, and 495-560 of the RBP with reference to the lambda bacteriophage stf sequence. In one specific aspect of the invention, the different RBP domain of the chimeric receptor binding protein (RBP) is derived from a bacteriophage or a bacteriocin. In one aspect of the invention, the chimeric RBP comprises an N-terminal domain of a RBP fused to a C-terminal domain of a RBP within one of the amino acids regions selected from positions 80-150, 320-460, or 495-560 of the N-terminal RBP domain with reference to the lambda stf sequence. In another embodiment of the invention, the chimeric RBP comprises an N-terminal domain of a RBP and a C-terminal domain of a RBP fused within a site of the N-terminal RBP domain having at least 80% identity with a site selected from the group consisting of amino acids SAGDAS (SEQ ID NO: 248), ADAKKS (SEQ ID NO: 249), MDETNR (SEQ ID NO: 250), SASAAA (SEQ ID NO: 251), and GAGENS (SEQ ID NO: 252).

In specific embodiments, the disclosure provides a bacterial delivery vehicle comprising a chimeric RBP. SEQ ID NOS 2-61, 123-153, 216-244 and 246-247 disclose the amino acid sequences of such chimeric RBPs and in addition, in some instances, their corresponding natural chaperone proteins (designated "AP"). Such AP proteins assist in the folding of the chimeric RBPs. In a specific embodiment, the RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 130, 131, 132, 135, 138, 139, 142, 145, 148,151, 216, 219, 221, 223, 227, 230, 232, 234,236, 238, 240, 243, 245 or 246.

In one aspect, the present disclosure also provides nucleotide sequences encoding for the chimeric RBPs disclosed herein. In a specific embodiment, nucleic acids encoding such chimeric RBPs, as well as corresponding AP proteins, are depicted in SEQ ID NOS 62-120, 122, 154-177, 182-210 and 212-213. In a specific embodiment, the nucleic acids encoding such chimeric RBPs comprise the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172, 175, 182, 185, 187, 189, 193, 196, 198, 200, 202, 204, 206, 209 or 212.

In other specific embodiments and to increase the delivery efficiency of the bacterial delivery vehicles disclosed herein the different RBP domain of the chimeric RBP comprises a domain having depolymerase activity against an encapsulated bacterial strain. In a specific embodiment, the depolymerase is an endosialidase, such as for example, a K1F or K5 endosialidase.

The bacterial delivery vehicles provided herein enable transfer of a nucleic acid payload, encoding one or more protein or nucleic acid of interest, into a desired target bacterial host cell. In certain embodiments of the invention, the nucleic acid of interest is selected from the group consisting of a Cas nuclease gene, a Cas9 nuclease gene, a guide RNA, a CRISPR locus, a toxin gene, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor, and a gene expressing a virulence protein or a virulence factor, or any of their combination. In an embodiment of the invention, the nucleic acid payload encodes a therapeutic protein. In another embodiment, the nucleic acid payload encodes an anti-sense nucleic acid molecule. In some embodiment, the nucleic acid payload encodes 2 nucleic acid of interest, one being a nuclease gene, for instance a Cas nuclease gene, and one being any other nucleic acid of interest. In one aspect, the bacterial delivery vehicle enables the transfer of a nucleic acid payload that encodes a nuclease that targets cleavage of a host bacterial cell genome or a host bacterial cell plasmid. In some aspects, the cleavage occurs in an antibiotic resistant gene. In another embodiment of the invention, the nuclease mediated cleavage of the host bacterial cell genome is designed to stimulate a homologous recombination event for insertion of a nucleic acid of interest into the genome of the bacterial cell.

The present invention also provides pharmaceutical or veterinary compositions comprising one or more of the bacterial delivery vehicles disclosed herein and a pharmaceutically-acceptable carrier. Also provided is a method for treating a bacterial infection comprising administering to a subject having a bacterial infection in need of treatment the provided pharmaceutical or veterinary composition. A method for reducing the amount of virulent and/or antibiotic resistant bacteria in a bacterial population is provided comprising contacting the bacterial population with the bacterial delivery vehicles disclosed herein.

BRIEF DESCRIPTION OF FIGURES

In order to better understand the subject matter that is disclosed herein and to exemplify how it may be carried out in practice, embodiments will now be described, by way of non-limiting example, with reference to the accompanying drawings. With specific reference to the drawings, it is stressed that the particulars shown are by way of example and for purposes of illustrative discussion of embodiments of the invention FIG. 1 demonstrates delivery in wild-type *E. coli* strains with lambda and OMPF-lambda packaged phagemids. Lambda packaged phagemids were diluted 1:5 in LB plus 5 mM $CaCl_2$) and 10 uL added in each well. 90 uL of cells grown to an OD600 of around 0.5 were then added to each phagemid-containing well, incubated for 30 min at 37° C. and 10 uL spotted on LB-agar supplemented with chloramphenicol. Left panel, wild type lambda packaged phagemids; right panel, OMPF-lambda variant. Arrows show strains with modified delivery as compared to lambda wild-type.

DETAILED DESCRIPTION

Figure 1:
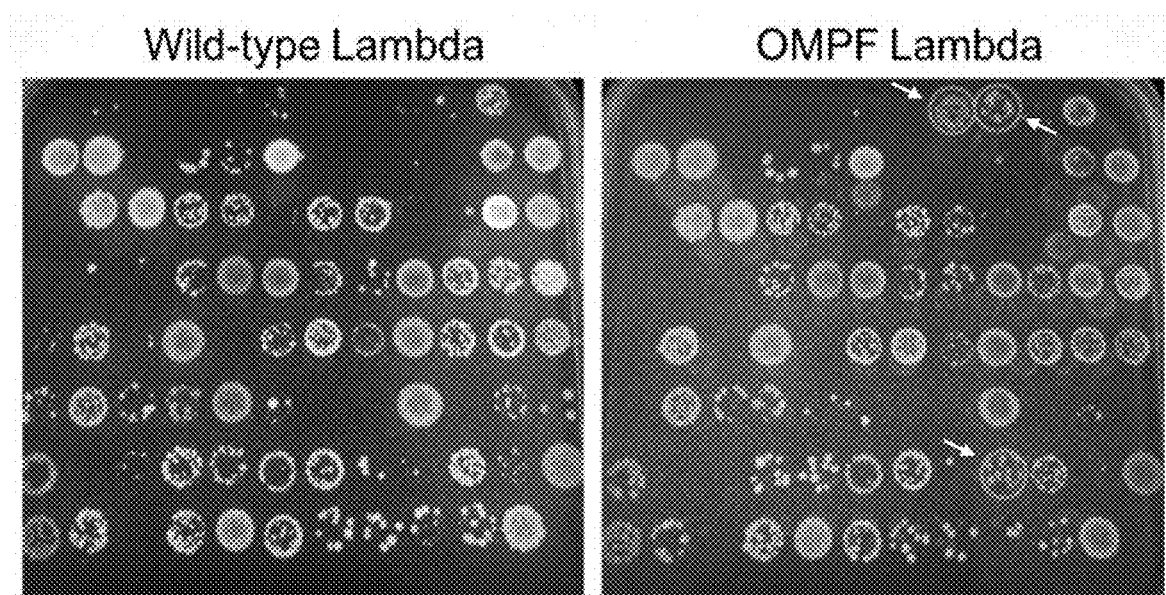

Disclosed herein are novel approaches to engineering synthetic bacterial delivery vehicles with desired target host ranges. The synthetic bacterial delivery vehicles are characterized by a chimeric receptor binding protein (RBP), wherein the chimeric RBP comprises a fusion between the N-terminal domain of a RBP from a lambda-like bacteriophage, or lambda bacteriophage, and the C-terminal domain of a different RBP. It has been demonstrated herein that a significant portion of a lambda-like RBP, such as a stf protein, can be exchanged with a portion of a different RBP. Moreover, specific fusion positions of the receptor binding protein have been identified which allow one to obtain a functional chimeric RBP.

As used herein, a receptor binding protein or RBP is a polypeptide that recognizes, and optionally binds and/or modifies or degrades a substrate located on the bacterial outer envelope, such as, without limitation, bacterial outer membrane, LPS, capsule, protein receptor, channel, structure such as the flagellum, pili, secretion system. The substrate can be, without limitation, any carbohydrate or modified carbohydrate, any lipid or modified lipid, any protein or modified protein, any amino acid sequence, and any combination thereof. As used herein, a lambda-like bacteriophage refers to any bacteriophage encoding a RBP having amino acids sequence homology of around 35% identity for 45 amino acids or more, around 50% identify for 30 amino acids or more, or around 90% identity for 18 amino acids or more in one or more of three amino acids regions ranging from positions 1-150, 320-460, and 495-560 with reference to the lambda bacteriophage stf sequence of SEQ ID NO: 1, independently of other amino acids sequences encoded by said bacteriophage.

The present disclosure provides a chimeric receptor binding protein (RBP), wherein the chimeric RBP comprises a fusion between an N-terminal domain of a RBP from a lambda-like bacteriophage, or lambda bacteriophage, and a C-terminal domain of a different bacteriophage RBP. Such bacteriophage RBPs, from which the chimeric RBP are derived, include, for example, "L-shape fibers", "side tail fibers (stfs)", "long tail fibers" or "tailspikes." As disclosed herein, it has been demonstrated that a significant portion of a lambda-like bacteriophage receptor binding protein (RBP), such as a stf protein, can be exchanged with a portion of a different RBP. Moreover, specific fusion positions in the RBPs have been identified which allow one to obtain a functional chimeric RBP. Such chimeric RBPs include those having an altered host range and/or biological activity such as, for example, depolymerase activity.

The chimeric receptor binding protein (RBP) is one wherein the chimeric RBP comprises a fusion between an N-terminal domain of a RBP derived from a lambda-like bacteriophage, or lambda bacteriophage, and a C-terminal domain of a different RBP wherein said N-terminal domain of the RBP is fused to said C-terminal domain of a different RBP within one of the amino acids regions selected from positions 1-150, 320-460, or 495-560 of the N-terminal RBP with reference to the lambda stf sequence (SEQ ID NO: 1) or a similar region of a RBP having homology with one or more of three amino acids regions ranging from positions 1-150, 320-460, and 495-560 of the RBP with reference to the lambda stf sequence. In one specific aspect of the invention, the different RBP of the chimeric receptor binding protein (RBP) is derived from any bacteriophage or from any bacteriocin.

In one specific aspect, the RBP from the lambda-like bacteriophage, the lambda bacteriophage, or the different RBP contain homology with one or more of three amino acids regions ranging from positions 1-150, 320-460, and 495-560 of the RBP with reference to the lambda bacteriophage stf sequence (SEQ ID NO:1). In certain aspects, the homology between the lambda-like bacteriophage, the lambda bacteriophage, or the different RBP and the one or more amino acids regions is around 35% identity for 45 amino acids or more, around 50% identify for 30 amino acids or more, and around 90% identity for 18 amino acids or more. Determination of homology can be performed using alignment tools such as the Smith-Waterman algorithm (Smith et al., 1981, J. Mol. Biol 147:195-197) or EMBOSS Matcher (Rice, Longden, Bleasby 2000 EMBOSS Trends in Genetics 16: 276-277). In one aspect of the invention, the chimeric RBP comprises the N-terminal domain of the chimeric RBP fused to the C-terminal domain of the chimeric RBP within one of the amino acids regions selected from positions 80-150, 320-460, or 495-560 with reference to the lambda bacteriophage stf sequence (SEQ ID NO: 1). In another embodiment of the invention, the chimeric RBP comprises an N-terminal domain and a C-terminal domain fused within one the three amino acids regions at an insertion site having at least 80% identity with an insertion site selected from the group consisting of amino acids SAGDAS (SEQ ID NO: 248), ADAKKS (SEQ ID NO: 249), MDETNR (SEQ ID NO: 250), SASAAA (SEQ ID NO: 251), and GAGENS (SEQ ID NO: 252).

In specific embodiments, the invention provides chimeric RBPs. SEQ ID NOS 2-61, 123-153, 216-244 and 246-247 disclose the amino acid sequences of such chimeric RBPs and in addition, in some instances, their corresponding natural chaperone proteins (designated "AP"). Such AP proteins assist in the folding of the chimeric RBPs. In a specific embodiment, the RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 130, 131, 132, 135, 138, 139, 142, 145, 148, 151, 216, 219, 221, 223, 227, 230, 232, 234,236, 238, 240, 243, 245 or 246

In one aspect, the present disclosure also provides nucleotide sequences encoding for the chimeric RPBs disclosed herein. In a specific embodiment, nucleic acids encoding such chimeric RBPs, as well as corresponding AP proteins, are depicted in SEQ ID NOS 62-120, 122, 154-177, 182-210, 212-213. In a specific embodiment, the nucleic acids encoding the chimeric RBP comprise the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172, 175 182, 185, 187, 189, 193, 196, 198, 200, 202, 204, 206, 209 or 212.

In one specific non-limiting aspect of the invention, it has been demonstrated that engineering the chimeric RBP to encode depolymerase activity can dramatically increases the delivery efficiency of the provided bacterial delivery vehicles comprising the chimeric RBP disclosed herein. In an embodiment of the invention, the different RBP domain of the chimeric RPB comprises depolymerase activity against an encapsulated bacterial strain. In a specific embodiment, the depolymerase is an endosialidase such as, for example, a K1F or K5 endosialidase.

Nucleic acid molecules encoding the chimeric RBPs disclosed herein are provided. Such nucleic acids may be included in vectors such as bacteriophages, plasmids, phagemids, viruses, and other vehicles which enable transfer and expression of the chimeric RBP encoding nucleic acids.

Bacterial delivery vehicles are provided which enable transfer of a nucleic acid payload, encoding a protein or nucleic acid of interest, into a desired target bacterial host cell. Such bacterial delivery vehicles are characterized by having a chimeric RBP comprising a fusion between the N-terminal domain of a RBP from a lambda-like bacteriophage, or lambda bacteriophage, and the C-terminal domain of a different RBP. In an embodiment of the invention, the bacterial delivery vehicles contain a chimeric RBP comprising a fusion between an N-terminal domain of a RBP derived from a lambda-like bacteriophage, or lambda bacteriophage, and a C-terminal domain of a different RBP wherein said N-terminal domain of the chimeric RBP is fused to said C-terminal domain of a different RBP within one of the amino acids regions selected from positions 1-150, 320-460, or 495-560 of the N-terminal domain RBP with reference to the lambda stf sequence (SEQ ID NO: 1). In one aspect, the RBP from the lambda-like bacteriophage, the lambda bacteriophage, and the different RBP contain homology in one or more of three amino acids regions ranging from positions 1-150, 320-460, and 495-560 of the N-terminal RBP with reference to the lambda bacteriophage stf sequence (SEQ ID NO: 1). In certain aspects, the homology is around 35% identity for 45 amino acids or more, around 50% identify for 30 amino acids or more, or around 90% identity for 18 amino acids or more within the one or more of three amino acids regions ranging from positions 1-150, 320-460, and 495-560 of the N-terminal RBP with reference to the lambda bacteriophage stf sequence (SEQ ID NO: 1). In one specific aspect of the invention, the different RBP domain of the chimeric receptor binding protein (RBP) is derived from a bacteriophage or a bacteriocin. In one aspect of the invention, the chimeric RBP comprises an N-terminal domain of a RBP fused to a C-terminal domain of a RBP within one of the amino acids regions selected from 80-150, 320-460, or 495-560 of the RBPs with reference to the lambda stf sequence (SEQ ID NO: 1). In another embodiment of the invention, the chimeric RBP comprises an N-terminal domain of a RBP and a C-terminal domain of a RBP fused within a site of the N-terminal RBPs having at least 80% identity with a site selected from the group consisting of amino acids SAGDAS (SEQ ID NO. 248), ADAKKS (SEQ ID NO. 249), MDE-TNR (SEQ ID NO. 250), SASAAA (SEQ ID NO. 251), and GAGENS (SEQ ID NO. 252).

In specific embodiments, the disclosure provides a bacterial delivery vehicle comprising a chimeric RBP. SEQ ID NOS 2-61, 123-153, 216-244 and 246-247 disclose the amino acid sequences of such chimeric RBPs and in addition, in some instances, their corresponding natural chaperone proteins (designated "AP"). Such AP proteins assist in the folding of the chimeric RBPs. In a specific embodiment, the RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 130, 131, 132, 135, 138, 139, 142, 145, 148 151, 216, 219, 221, 223, 227, 230, 232, 234, 236, 238, 240, 243, 245 or 246

In one aspect, the present disclosure also provides nucleotide sequences encoding for the chimeric RPBs disclosed herein. In a specific embodiment, nucleic acids encoding such chimeric RBPs, as well as corresponding AP proteins, are depicted in SEQ ID NOS 62-120, 122, 154-177, 182-210, 212-213. In a specific embodiment, the nucleic acids encoding the chimeric RBPs comprise the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172,175, 182, 185, 187, 189, 193, 196, 198, 200, 202, 204, 206, 209 or 212.

In other specific embodiments and to increase the delivery efficiency of the bacterial delivery vehicles disclosed herein the different RBP domain of the chimeric comprises a domain having depolymerase activity against an encapsulated bacterial strain. In a specific embodiment, the depolymerase is an endosialidase, such as for example, a K1F or K5 endosialidase.

The bacterial delivery vehicles provided herein enable transfer of a nucleic acid payload, encoding a protein or nucleic acid of interest, into a desired target bacterial host cell. As used herein, the term "delivery vehicle" refers to any means that allows the transfer of a payload into a bacterium. There are several types of delivery vehicles encompassed by the present invention including, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention. The delivery vehicle can refer to a bacteriophage derived scaffold and can be obtained from a natural, evolved or engineered capsid. In some embodiments, the delivery vehicle is the payload as bacteria are naturally competent to take up a payload from the environment on their own.

As used herein, the term "payload" refers to any one or more nucleic acid sequence and/or amino acid sequence, or a combination of both (such as, without limitation, peptide nucleic acid or peptide-oligonucleotide conjugate) transferred into a bacterium with a delivery vehicle. The term "payload" may also refer to a plasmid, a vector or a cargo. The payload can be a phagemid or phasmid obtained from natural, evolved or engineered bacteriophage genome. The payload can also be composed only in part of phagemid or plasmid obtained from natural, evolved or engineered bacteriophage genome.

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xathanine, hypoxathanine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present invention.

Origins of replication known in the art have been identified from species-specific plasmid DNAs (e.g. ColE1, R1, pT181, pSC101, pMB1, R6K, RK2, p15a and the like), from bacterial virus (e.g. φX174, M13, F1 and P4) and from bacterial chromosomal origins of replication (e.g. oriC). In one embodiment, the phagemid according to the disclosure comprises a bacterial origin of replication that is functional in the targeted bacteria.

Alternatively, the plasmid according to the disclosure does not comprise any functional bacterial origin of replication or contain an origin of replication that is inactive in the targeted bacteria. Thus, the plasmid of the disclosure cannot replicate by itself once it has been introduced into a bacterium by the bacterial virus particle.

In one embodiment, the origin of replication on the plasmid to be packaged is inactive in the targeted bacteria, meaning that this origin of replication is not functional in the bacteria targeted by the bacterial virus particles, thus preventing unwanted plasmid replication.

In one embodiment, the plasmid comprises a bacterial origin of replication that is functional in the bacteria used for the production of the bacterial virus particles.

Plasmid replication depends on host enzymes and on plasmid-controlled cis and trans determinants. For example, some plasmids have determinants that are recognized in almost all gram-negative bacteria and act correctly in each host during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microhio and Molec Biol.

Rev 62:434-464) that start at the origin of replication. These replication origins contain sites that are required for interactions of plasmid and/or host encoded proteins.

Origins of replication used on the plasmid of the disclosure may be of moderate copy number, such as colE1 ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pJD101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

More preferably, the bacterial origin of replication is a *E. coli* origin of replication selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5 and pPS10.

More preferably, the bacterial origin of replication is selected in the group consisting of pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

Even more preferably, the bacterial origin of replication is ColE1.

The delivered nucleic acid sequence according to the disclosure may comprise a phage replication origin which can initiate, with complementation of a complete phage genome, the replication of the delivered nucleic acid sequence for later encapsulation into the different capsids.

A phage origin of replication comprised in the delivered nucleic acid sequence of the disclosure can be any origin of replication found in a phage.

Preferably, the phage origin of replication can be the wild-type or non-wildtype sequence of the M13, f1, φX174, P4, lambda, P2, lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 P1-like, P2-like, P22, P22-like, N15 and N15-like bacteriophages.

More preferably, the phage origin of replication is selected in the group consisting of phage origins of replication of M13, f1, φX174, P4, and lambda.

In a particular embodiment, the phage origin of replication is the lambda or P4 origin of replication.

The delivered nucleic acid of interest comprises a nucleic acid sequence under the control of a promoter. In certain embodiments of the invention, the nucleic acid of interest is selected from the group consisting of a Cas nuclease gene, a Cas9 nuclease gene, a guide RNA, a CRISPR locus, a toxin gene, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor, and a gene expressing a virulence protein or a virulence factor, or any of their combination. In an embodiment of the invention, the nucleic acid payload encodes a therapeutic protein. In another embodiment, the nucleic acid payload encodes an anti-sense nucleic acid molecule. In some embodiment, the nucleic acid payload encodes 2 nucleic acids of interest, one being a nuclease gene, for instance a Cas nuclease gene, and one being any other nucleic acid of interest.

In one embodiment, the sequence of interest is a programmable nuclease circuit to be delivered to the targeted bacteria. This programmable nuclease circuit is able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed nuclease circuits provided herein may be used to selectively cleave DNA encoding a gene of interest such as, for example, a toxin gene, a virulence factor gene, an antibiotic resistance gene, a remodeling gene or a modulatory gene (cf. WO2014124226).

Other sequences of interest, preferably programmable, can be added to the delivered nucleic acid sequence so as to be delivered to targeted bacteria. Preferably, the sequence of interest added to the delivered nucleic acid sequence leads to cell death of the targeted bacteria. For example, the nucleic acid sequence of interest added to the plasmid may encode holins or toxins.

Alternatively, the sequence of interest circuit added to the delivered nucleic acid sequence does not lead to bacteria death. For example, the sequence of interest may encode reporter genes leading to a luminescence or fluorescence signal. Alternatively, the sequence of interest may comprise proteins and enzymes achieving a useful function such as modifying the metabolism of the bacteria or the composition of its environment.

In a particular embodiment, the nucleic sequence of interest is selected in the group consisting of Cas9, a single guide RNA (sgRNA), a CRISPR locus, a gene expressing an enzyme such as a nuclease or a kinase, a TALEN, a ZFN, a meganuclease, a recombinase, a bacterial receptor, a membrane protein, a structural protein, a secreted protein, resistance to an antibiotic or to a drug in general, a gene expressing a toxic protein or a toxic factor and a gene expressing a virulence protein or a virulence factor.

In a particular embodiment, the delivered nucleic acid sequence according to the disclosure comprises a nucleic acid sequence of interest that encodes a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocin had been described from gram negative bacteria (e.g. microcins, colicin-like bacteriocins and tailocins) and from gram positive bacteria (e.g. Class I, Class II, Class III or Class IV bacteriocins).

In one embodiment, the delivered nucleic acid sequence according to the disclosure further comprises a sequence of interest encoding a toxin selected in the group consisting of microcins, colicin-like bacteriocins, tailocins, Class I, Class II, Class III and Class IV bacteriocins.

In a particular embodiment, the corresponding immunity polypeptide (i.e. anti-toxin) may be used to protect bacterial cells (Cotter et al., Nature Reviews Microbiology 11: 95, 2013, which is hereby incorporated by reference in its entirety) for delivered nucleic acid sequence production and encapsidation purpose but is absent in the pharmaceutical composition and in the targeted bacteria in which the delivered nucleic acid sequence of the disclosure is delivered.

In one aspect of the disclosure, the CRISPR system is included in the delivered nucleic acid sequence. The CRISPR system contains two distinct elements, i.e. i) an endonuclease, in this case the CRISPR associated nuclease (Cas or "CRISPR associated protein") and ii) a guide RNA. The guide RNA is in the form of a chimeric RNA which consists of the combination of a CRISPR (RNAcr) bacterial RNA and a RNAtracr (trans-activating RNA CRISPR) (Jinek et al., Science 2012). The guide RNA combines the targeting specificity of the RNAcr corresponding to the "spacing sequences" that serve as guides to the Cas proteins, and the conformational properties of the RNAtracr in a single transcript. When the guide RNA and the Cas protein are expressed simultaneously in the cell, the target genomic sequence can be permanently modified or interrupted. The modification is advantageously guided by a repair matrix. In general, the CRISPR system includes two main classes depending on the nuclease mechanism of action. Class 1 is made of multi-subunit effector complexes and includes type I, III and IV. Class 2 is made of single-unit effector modules, like Cas9 nuclease, and includes type II (II-A, II-B, II-C, II-C variant), V (V-A, V-B, V-C, V-D, V-E, V-U1, V-U2, V-U3, V-U4, V-U5) and VI (VI-A, VI-B1, VI-B2, VI-C, VI-D)

The sequence of interest according to the present disclosure comprises a nucleic acid sequence encoding Cas protein. A variety of CRISPR enzymes are available for use as a sequence of interest on the plasmid. In some embodiments, the CRISPR enzyme is a Type II CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a sgRNA. In certain embodiments, the sgRNA targets a gene selected in the group consisting of an antibiotic resistance gene, virulence protein or factor gene, toxin protein or factor gene, a bacterial receptor gene, a membrane protein gene, a structural protein gene, a secreted protein gene and a gene expressing resistance to a drug in general.

Non-limiting examples of Cas proteins as part of a multi-subunit effector or as a single-unit effector include Cas1, Cas1B, Cas2, Cas3, Cas4, Cas5, Cash, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the disclosure can be obtained from any known Cas9 protein (Fonfara et al., Nucleic Acids Res 42 (4), 2014; Koonin et al., Nat Rev Microbiol 15(3), 2017). Examples of Cas9 proteins useful in the present disclosure include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the disclosure can be obtained from any known Cpf1 (Cas12a) protein (Koonin et al., 2017). Examples of Cpf1 (Cas12a) proteins useful in the present disclosure include, but are not limited to, Cpf1 (Cas12a) proteins of *Acidaminococcus* sp, *Lachnospiraceae bacteriu* and *Francisella novicida*.

The sequence encoding Cas13a (the entire protein or a fragment thereof) can be obtained from any known Cas13a (C2c2) protein (Abudayyeh et al., 2017). Examples of Cas13a (C2c2) proteins useful in the present disclosure include, but are not limited to, Cas13a (C2c2) proteins of *Leptotrichia wadei* (LwaCas13 a).

The sequence encoding Cas13d (the entire protein or a fragment thereof) can be obtained from any known Cas13d protein (Yan et al., 2018). Examples of Cas13d proteins useful in the present disclosure include, but are not limited to, Cas13d proteins of *Eubacterium siraeum* and *Ruminococcus* sp.

In a particular embodiment, the nucleic sequence of interest is a CRISPR/Cas9 system for the reduction of gene expression or inactivation a gene selected in the group consisting of an antibiotic resistance gene, virulence factor or protein gene, toxin factor or protein gene, a gene expressing a bacterial receptor, a membrane protein, a structural protein, a secreted protein, and a gene expressing resistance to a drug in general.

In one embodiment, the CRISPR system is used to target and inactivate a virulence factor. A virulence factor can be any substance produced by a pathogen that alter host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), fimA, fimF, fimH, neuC, kpsE, sfa, foc, iroN, aer, iha, papC, papGI, papGII, papGIII, hlyC, cnfl, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCD1) T3SS external needle subunit). For example, such targeted virulence factor gene can be *Francisella tularensis* virulence factor gene such as, without limitation, fs1A. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdl, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft.

In another embodiment, the CRISPR/Cas9 system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecl, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-To1C, MsbA, MsrA, VgaB, EmrD, EmrAB-To1C, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.cal).

In another embodiment, the CRISPR/Cas9 system is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, *Staphylococus* toxins, Diphteria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

The bacteria targeted by bacterial delivery vehicles disclosed herein can be any bacteria present in a mammal organism. In a certain aspect, the bacteria are targeted through interaction of the chimeric RBPs expressed by the delivery vehicles with the bacterial cell. It can be any commensal, symbiotic or pathogenic bacteria of the microbiota or microbiome.

A microbiome may comprise of a variety of endogenous bacterial species, any of which may be targeted in accordance with the present disclosure. In some embodiments, the genus and/or species of targeted endogenous bacterial cells may depend on the type of bacteriophages being used for preparing the bacterial delivery vehicles. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucelia* spp., *Campylobacter* spp., *Chlamydophilia* spp., *Cutibacterium* spp., *Propionibacterium* spp., *Gardnerella* spp., *Ehrlichia* spp., *Haemophilus* spp., *Leptospira* spp., *Listeria* spp., *Mycoplasma* spp.,

*Nocardia* spp., *Rickettsia* spp., *Ureaplasma* spp., and *Lactobacillus* spp, and a mixture thereof.

Thus, bacterial delivery vehicles may target (e.g., specifically target) a bacterial cell from any one or more of the foregoing genus of bacteria to specifically deliver the payload of interest according to the disclosure.

Preferably, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. and *Gardnerella* spp.

In some embodiments, bacterial cells of the present disclosure are anaerobic bacterial cells (e.g., cells that do not require oxygen for growth). Anaerobic bacterial cells include facultative anaerobic cells such as but not limited to *Escherichia coli, Shewanella oneidensis, Gardnerella vaginalis* and *Listeria*. Anaerobic bacterial cells also include obligate anaerobic cells such as, for example, *Bacteroides, Clostridium, Cutibacterium, Propionibacterium, Fusobacterium* and *Porphyromona* species. In humans, anaerobic bacteria are most commonly found in the gastrointestinal tract. In some particular embodiment, the targeted bacteria are thus bacteria most commonly found in the gastrointestinal tract. Bacteriophages used for preparing the bacterial virus particles, and then the bacterial virus particles, may target (e.g., to specifically target) anaerobic bacterial cells according to their specific spectra known by the person skilled in the art to specifically deliver the plasmid.

In some embodiments, the targeted bacterial cells are, without limitation, *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans,* cyanobacteria, *Escherichia coli, Helicobacter pylori, Selnomonas ruminatium, Shigella sonnei, Zymomonas mobilis, Mycoplasma mycoides, Treponema denticola, Bacillus thuringiensis, Staphilococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aerigunosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium acnes*), *Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexnerii, Shigella dysenteriae, Staphylococcus saprophyticus, Streptococcus pneumoniae, Streptococcus pyogenes, Gardnerella vaginalis, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aerigunosa,* and a mixture thereof, preferably the bacteria of interest are selected from the group consisting of *Escherichia coli, Enterococcus faecium, Staphylococcus aureus, Klebsiella pneumoniae, Acinetobacter baumanii, Pseudomonas aeruginosa, Enterobacter cloacae,* and *Enterobacter aerogenes,* and a mixture thereof.

In one embodiment, the targeted bacteria are *Escherichia coli*.

Thus, bacteriophages used for preparing the bacterial delivery vehicles, and then the bacterial delivery vehicles, may target (e.g., specifically target) a bacterial cell from any one or more of the foregoing genus and/or species of bacteria to specifically deliver the plasmid.

In one embodiment, the targeted bacteria are pathogenic bacteria. The targeted bacteria can be virulent bacteria.

The targeted bacteria can be antibacterial resistance bacteria, preferably selected from the group consisting of extended-spectrum beta-lactamase-producing (ESBL) *Escherichia coli*, ESBL *Klebsiella pneumoniae,* vancomycin-resistant *Enterococcus* (VRE), methicillin-resistant *Staphylococcus aureus* (MRSA), multidrug-resistant (MDR) *Acinetobacter baumannii,* MDR *Enterobacter* spp., and a combination thereof. Preferably, the targeted bacteria can be selected from the group consisting of extended-spectrum beta-lactamase-producing (ESBL) *Escherichia coli* strains.

Alternatively, the targeted bacterium can be a bacterium of the microbiome of a given species, preferably a bacterium of the human microbiota.

The present disclosure is directed to bacterial delivery vehicle containing the payload as described herein. The bacterial delivery vehicles are prepared from bacterial virus. The bacterial delivery vehicles are chosen in order to be able to introduce the payload into the targeted bacteria.

Bacterial viruses, from which the bacterial delivery vehicles having chimeric receptor binding proteins may be derived, are preferably bacteriophages. Optionally, the bacteriophage is selected from the Order Caudovirales consisting of, based on the taxonomy of Krupovic et al, Arch Virol, 2015:

Bacteriophages may be selected from the family Myoviridae (such as, without limitation, genus Cp220virus, Cp8virus, Ea214virus, Felixolvirus, Mooglevirus, Suspvirus, Hp1virus, P2virus, Kayvirus, P100virus, Silviavirus, Spo1virus, Tsarbombavirus, Twortvirus, Cc31virus, Jd18virus, Js98virus, Kpl5virus, Moonvirus, Rb49virus, Rb69virus, S16virus, Schizot4virus, Sp18virus, T4virus, Cr3virus, Selvirus, V5virus, Abouovirus, Agatevirus, Agrican357virus, Ap22virus, Arvlvirus, B4virus, Bastillevirus, Bc431virus, Bcep78virus, Bcepmuvirus, Biquartavirus, Bxz1virus, Cd119virus, Cp51virus, Cvm10virus, Eah2virus, Elvirus, Hapunavirus, Jimmervirus, Kpp10virus, M12virus, Machinavirus, Marthavirus, Msw3virus, Muvirus, Myohalovirus, Nitivirus, P1virus, Pakpunavirus, Pbunavirus, Phikzvirus, Rheph4virus, Rs12virus, Rslunavirus, Secunda5virus, Seplvirus, Spn3virus, Svunavirus, Tglvirus, Vhmlvirus and Wphvirus)

Bacteriophages may be selected from the family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, T12011virus, Bcep22virus, Bpp1virus, Cba41virus, Dfl12virus, Ea92virus, Epsilon15virus, F116virus, G7cvirus, Jwa1phavirus, Kf1virus, Kpp25virus, Litivirus, Luz24virus, Luz7virus, N4virus, Nonanavirus, P22virus, Pagevirus, Phieco32virus, Prtbvirus, Sp58virus, Una961virus and Vp5virus)

Bacteriophages may be selected from the family Siphoviridae (such as, without limitation, genus Camvirus, Likavirus, R4virus, Acadianvirus, Coopervirus, Pglvirus, Pipefishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Roguelvirus, Rtpvirus, T1virus, T1svirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjwlvirus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1virus, Phic31virus, Phicbkvirus, Phietavirus, Phifelvirus, Phijl1virus, Pis4avirus, Psavirus, Psimunavirus, Rdj1virus, Rer2virus, Sap6virus, Send513virus, Septima3virus, Seuratvirus, Sextaecvirus, Sfi11virus, Sfi21dtivirus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus)

Bacteriophages may be selected from the family Ackermannviridae (such as, without limitation, genus Ag3virus, Limestonevirus, Cba120virus and Vilvirus)

Optionally, the bacteriophage is not part of the order Caudovirales but from families with unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus Cystovirus), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

Optionally, the bacteriophage is targeting Archea not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

A non-exhaustive listing of bacterial genera and their known host-specific bacteria viruses is presented in the following paragraphs. The chimeric RBPs and the bacterial delivery vehicles disclosed herein may be engineered, as non-limiting examples, from the following phages. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-I, Av-2, Av-3, BF307, CT1, CT2, CT3, CT4, CT6, CT7, CT8 and 1281.

Bacteria of the genus *Aeromonas* can be infected by the following phages: AA-I, Aeh2, N, PM1, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, A1-K-I, B, BCJA1, BC1, BC2, BLL1, BL1, BP142, BSL1, BSL2, BS1, BS3, BS8, BS15, BS18, BS22, BS26, BS28, BS31, BS104, BS105, BS106, BTB, B1715V1, C, CK-I, Col1, Cor1, CP-53, CS-I, CSi, D, D, D, D5, entl, FPB, FP9, FSi, FS2, FS3, FS5, FS8, FS9, G, GH8, GT8, GV-I, GV-2, GT-4, g3, g12, g13, g14, g16, g17, g21, g23, g24, g29, H2, kenl, KK-88, Kuml, Kyul, J7W-1, LP52, (syn=LP-52), L7, Mexl, MJ-I, mor2, MP-7, MP1O, MP12, MP14, MP15, Neol, N° 2, N5, N6P, PBC1, PBLA, PBP1, P2, S-a, SF2, SF6, Sha1, Sil1, SP02, (syn=TSPP1), SPf3, STI, STi, SU-Il TbI, Tb2, Tb5, TbIO, Tb26, Tb51, Tb53, Tb55, Tb77, Tb97, Tb99, Tb560, Tb595, Td8, Td6, Td15, TgI, Tg4, Tg6, Tg7, Tg9, TgIO, TgI1, Tgl3, Tg15, Tg21, Tin1, Tin7, Tin8, Tin13, Tm3, Tocl, Togl, toll, TP-I, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yun1, α, γ, p11, φmed-2, φT, φu-4, φ3T, φ75, φ1O5, (syn=φ1O5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), ale1, AR1, AR2, AR3, AR7, AR9, Bace-11, (syn=11), Bastille, BL1, BL2, BL3, BL4, BLS, BL6, BL8, BL9, BP124, BS28, BS80, Ch, CP-51, CP-54, D-5, darl, denl, DP-7, entl, FoSi, FoS2, FS4, FS6, FS7, G, gall, gamma, GEl, GF-2, GSi, GT-I, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. 1, N17, N19, PBS1, PK1, PMB1, PMB12, PMJ1, S, SP01, SP3, SP5, SP6, SP7, SP8, SP9, SP10, SP-15, SP50, (syn=SP-50), SP82, SST, sub1, SW, Tg8, Tgl2, Tgl3, Tgl4, thu1, thuA, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megateriwn*), 4 (*B. sphaericus*), AR13, BPP-IO, BS32, BS107, B1, B2, GA-I, GP-IO, GV-3, GV-5, g8, MP20, MP27, MP49, Nf, PP5, PP6, SF5, Tg18, TP-I, Versailles, φ15, φ29, 1-97, 837/IV, mï-*Bacillus* (1), Bat1O, BSL1O, BSLI1, BS6, BSI1, BS16, BS23, BS1O1, BS102, g18, morl, PBL1, SN45, thu2, thu3, TmI, Tm2, TP-20, TP21, TP52, type F, type G, type IV, HN-BacMus (3), BLE, (syn=θc), BS2, BS4, BS5, BS7, BlO, B12, BS20, BS21, F, MJ-4, PBA12, AP50, AP50-04, AP50-11, AP50-23, AP50-26, AP50-27 and Bam35. The following

*Bacillus*-specific phages are defective: DLP10716, DLP-11946, DPBS, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: ad 12, Baf-44, Baf-48B, Baf-64, Bf-I, Bf-52, B40-8, F1, β1, φA1, φBrO1, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages: 134 and NN-*Bordetella* (3).

Bacteria of the genus *Borrellia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=FO1), (syn=FQ1), D, FP2, (syn=FP2), (syn=FD2), Fz, (syn=Fz75/13), (syn=Firenze 75/13), (syn=Fi), Fi, (syn=F1), Fim, (syn=FIm), (syn=Fim), FiU, (syn=F1U), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn-F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=FlO), 371/XXIX, (syn=371), (syn=Fn), (syn=Fl 1) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chp1.

Bacteria of the genus *Clostridium* can be infected by the following phages: CAK1, CA5, Ca7, CEβ, (syn=1C), CEγ, Cld1, c-n71, c-203 Tox-, DEβ, (syn=ID), (syn=1Dt0X+), HM3, KMl, KT, Ms, NA1, (syn=Naltox+), PA135Oe, Pfó, PL73, PL78, PL81, P1, P50, P5771, P19402, 1CtOX+, 2CtOX\ 2D3 (syn=2Dt0X+), 3C, (syn=3Ctox+), 4C, (syn=4CtOX+), 56, III-1, NN-*Clostridium* (61), NB1t0X+, α1, CA1, HMT, HM2, PF15 P-23, P-46, Q-05, Q-oe, Q-16, Q-21, Q-26, Q-40, Q-46, S111, SA02, WA01, WA03, Wm, W523, 80, C, CA2, CA3, CPT1, CPT4, c1, c4, c5, HM7, H11/A1, H18/Ax, FWS23, Hi58ZA1, K2ZA1, K21ZS23, ML, NA2t0X; Pf2, Pf3, Pf4, S9ZS3, S41ZA1, S44ZS23, a2, 41, 112ZS23, 214/S23, 233/Ai, 234/S23, 235/S23, II-1, 11-2, 11-3, NN-*Clostridium* (12), CA1, F1, K, S2, 1, 5 and NN-*Clostridium* (8).

Bacteria of the genus *Corynebacterium* can be infected by the following phages: CGK1 (defective), A, A2, A3, A101, A128, A133, A137, A139, A155, A182, B, BF, B17, B18, B51, B271, B275, B276, B277, B279, B282, C, capi, CC1, CG1, CG2, CG33, CL31, Cog, (syn=CGS), D, E, F, H, H-I, hqi, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γ19, δ, (syn=δ'ox+), p, (syn=ptoχ-), Φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, F1, F2, 1, 2, 4, 14, 41, 867, Dl, SB24, 2BV, 182, 225, C2, C2F, E3, E62, DS96, H24, M35, P3, P9, SB1O1, S2, 2B1I, 5, 182a, 705, 873, 881, 940, 1051, 1057, 21096C, NN-*Enterococcus* (1), PE1, F1, F3, F4, VD13, 1, 200, 235 and 341.

Bacteria of the genus *Erysipelothrix* can be infected by the following phage: NN-*Eiysipelothrix* (1).

Bacteria of the genus *Escherichia* can be infected by the following phages: BW73, B278, D6, D108, E, E1, E24, E41, FI-2, FI-4, FI-5, HI8A, Ff18B, i, MM, Mu, (syn=mu), (syn=MuI), (syn=Mu-I), (syn=MU-I), (syn=MuI), (syn=μ), 025, PhI-5, Pk, PSP3, Pl, P1D, P2, P4 (defective), S1, Wφ, φK13, φR73 (defective), φ1, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FI1, FI3, H, H1, H3, H8, K3, M, N, ND-2, ND-3, ND4, ND-5, ND6, ND-7, Ox-I (syn=OX1), (syn=HF), Ox-2 (syn=0x2), (syn=0X2), Ox-3, Ox-4, Ox-5, (syn=0X5), Ox-6, (syn=66F), (syn=φ66t), (syn=φ66t)5 0111, PhI-I, RB42, RB43, RB49, RB69, S, SaI-I, Sal-2, Sal-3, Sal-4, Sal-5, Sal-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, al, 1, IA, 3, (syn=Ac3), 3A, 3T+, (syn=3), (syn=Ml), 5φ, (syn=φ5), 9266Q, CFO103, HK620, J, K, K1F, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φ1, φ1.2, φ20, φ95, φ263, φlO92, φl, φ11, (syn=cpW), S28, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, (syn=Φ1-1K97), HK139, HK253, HK256, K7, ND-I, no. D, PA-2, q, S2, T1, (syn=α), (syn=P28), (syn=T-I), (syn=Tx), T3C, T5, (syn=T-5), (syn=T5), UC-I, w, β4, γ2, λ (syn=lambda), (syn=Φλ), ΦD326, φγ, Φ06, Φ7, Φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, KlO, ZG/3A, 5, 5A, 21EL, H19-J and 933H.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HP1, S2 and N3.

Bacteria of the genus *Helicobacter* are infected by the following phage: HP1 and ^^-*Helicobacter* (1).

Bacteria of the genus *Klebsiella* are infected by the following phage: AIO-2, KI4B, Kl6B, Kl9, (syn=Kl9), Kl14, Kl15, Kl21, Kl28, Kl29, Kl32, Kl33, Kl35, Kl106B, Kl171B, Kl181B, Kl832B, AIO-I, AO-I, AO-2, AO-3, FC3-10, K, K11, (syn=KI1), K12, (syn=K12), K13, (syn=K13), (syn=Kl 70/11), K14, (syn=K14), K15, (syn=K15), K16, (syn=K16), K17, (syn=K17), Kl8, (syn=K18), Kl19, (syn=K19), Kl27, (syn=K127), Kl31, (syn=K131), Kl35, Kl171B, II, VI, IX, CI-I, Kl4B, Kl8, Kl11, Kl12, Kl13, Kl16, Kl17, Kl18, Kl20, Kl22, Kl23, Kl24, Kl26, Kl30, Kl34, Kl106B, Kli65B, K1328B, KLXI, K328, P5046, 11, 380, III, IV, VII, VIII, FC3-11, Kl2B, (syn=K12B), Kl25, (syn=K125), Kl42B, (syn=K142), (syn=K142B), Kl181B, (syn=Kll 81), (syn=Kl181B), Kl765/!, (syn=Kl765/1), Kl842B, (syn=K1832B), Kl937B, (syn=K1937B), L1, φ28, 7, 231, 483, 490, 632 and 864/100.

Bacteria of the genus *Lepitospira* are infected by the following phage: LE1, LE3, LE4 and ~NN-*Leptospira* (1).

Bacteria of the genus *Listeria* are infected by the following phage: A511, 01761, 4211, 4286, (syn=BO54), A005, A006, A020, A500, A502, A511, A1 18, A620, A640, B012, B021, B024, B025, B035, B051, B053, B054, B055, B056, B1Ol, BI1O, B545, B604, B653, C707, D441, HS047, HlOG, H8/73, H19, H21, H43, H46, H107, H108, HI10, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-Lisferia (15).

Bacteria of the genus *Morganella* are infected by the following phage: 47.

Bacteria of the genus *Mycobacterium* are infected by the following phage: 13, AG1, ALi, ATCC 11759, A2, B.C3, BG2, BK1, BK5, butyricum, B-I, B5, B7, B30, B35, Clark, C1, C2, DNAIII, DSP1, D4, D29, GS4E, (syn=GS4E), GS7, (syn=GS-7), (syn=GS7), IPa, lacticola, Legendre, Leo, L5, (syn=ΦL-5), MC-I, MC-3, MC-4, minetti, MTPHI 1, Mx4, MyF3P/59a, phlei, (syn=phlei 1), phlei 4, Polonus II, rabinovitschi, *smegmatis*, TM4, TM9, TMlO, TM20, Y7, YlO, φ630, IB, IF, IH, 1/1, 67, 106, 1430, Bl, (syn=Bol), B24, D, D29, F-K, F-S, HP, Polonus I, Roy, Rl, (syn=Rl-Myb), (syn=Ri), 11, 31, 40, 50, 103a, 103b, 128, 3111-D, 3215-D and NN-*Mycobacterium* (1).

Bacteria of the genus *Neisseria* are infected by the following phage: Group I, group II and NP1.

Bacteria of the genus *Nocardia* are infected by the following phage: MNP8, NJ-L, NS-8, N5 and TtiN-*Nocardia*.

Bacteria of the genus *Proteus* are infected by the following phage: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI 1, Pv2, πl, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phage: PfI, (syn=Pf-I), Pf2, Pf3, PP7, PRR1, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PB1), pfl6, PMN17, PP1, PP8, Psa1, PsP1, PsP2, PsP3, PsP4, PsP5, PS3, PS17, PTB80, PX4, PX7, PYO1, PYO2, PYOS, PYO6, PYO9, PYO1O, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, P1K, SLP1, SL2, S2, UNL-I, wy, Yai, Ya4, Yan, φBE, φCTX, φC17, φKZ, (syn=φKZ), φ-LT, φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, Fl 16, HF, H90, K5, K6, Kl 04, K109, K166, K267, N4, N5, 06N-25P, PE69, Pf, PPN25, PPN35, PPN89, PPN91, PP2, PP3, PP4, PP6, PP7, PP8, PP56, PP87, PP1 14, PP206, PP207, PP306, PP651, Psp231a, Pssy401, Pssy9220, psi, PTB2, PTB20, PTB42, PX1, PX3, PX1O, PX12, PX14, PYO70, PYO71, R, SH6, SH133, tf, YaS, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, F10, g, gd, ge, gξ Hw12, Jb 19, KFl, L°, OXN-32P, 06N-52P, PCH-I, PC13-1, PC35-1, PH2, PH51, PH93, PH132, PMW, PM13, PM57, PM61, PM62, PM63, PM69, PM105, PMl 13, PM681, PM682, PO4, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SD1, SL1, SL3, SL5, SM, φC5, φC11, φC11-1, φC13, φC15, φMO, φX, φO4, φl 1, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), G101, M6, M6a, L1, PB2, Pssy15, Pssy4210, Pssy4220, PY012, PY034, PY049, PY050, PY051, PY052, PY053, PY057, PY059, PY0200, PX2, PX5, SL4, φO3, φO6 and 1214.

Bacteria of the genus *Rickettsia* are infected by the following phage: NN-*Rickettsia*.

Bacteria of the genus *Salmonella* are infected by the following phage: b, Beccles, CT, d, Dundee, f, FeIs 2, GI, GUI, GVI, GVIII, k, K, i, j, L, 01, (syn=0-1), (syn=O1), (syn=O-I), (syn=7), 02, 03, P3, P9a, P10, Sab3, Sab5, SanlS, Sanl7, SI, Taunton, ViI, (syn=ViI), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22a1, P22-4, P22-7, P22-11, SNT-I, SNT-2, SP6, Villi, ViIV, ViV, ViVI, ViVII, Worksop, Sj5, c34, 1,37, 1(40), (syn=φl[40]), 1,422, 2, 2.5, 3b, 4, 5, 6,14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, G173, h, IRA, Jersey, MB78, P22-1, P22-3, P22-12, Sab1, Sab2, Sab2, Sab4, San1, San2, San3, San4, San6, San7, San8, San9, San13, San14, San16, San18, San19, San20, San21, San22, San23, San24, San25, San26, SasL1, SasL2, SasL3, SasL4, SasL5, S1BL, SII, ViII, φ1, 1, 2, 3a, 3a1, 1010, Ym-*Salmonella* (1), N-4, SasL6 and 27.

Bacteria of the genus *Serratia* are infected by the following phage: A2P, PS20, SMB3, SMP, SMPS, SM2, V40, V56, ic, ΦCP-3, ΦCP-6, 3M, 10/1a, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCW1, ΦCP6-1, ΦCP6-2, ΦCP6-5, 3T, 5, 8, 9F, 10/1, 2OE, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/10a, L.359 and SMB1.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PES, P90, SfII, Sh, SHm, SHrv, (syn=HIV), SHvi, (syn=HVI), SHVvm, (syn=HVIII), SKγ66, (syn=gamma 66), (syn=yββ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVHIA, (syn=SvmA), (syn=VIIIA), STvi, STK, STx1, STxn, S66, W2, (syn=D2c), (syn=D20), φ1, φIVb 3-SO-R, 8368-SO-R, F7, (syn=FS7), (syn=K29), F10, (syn=FS10), (syn=K31), I1, (syn=alfa), (syn=FSa), (syn=Kl 8), (syn=α), I2, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO—S-R), W1, (syn=D8), (syn=FSD8), W2a, (syn=D2A), (syn=FS2a), DD-2, Sf6, FSi, (syn=F1), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, BII, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI 1, P2-SO-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx 1, SHxπ, (syn=HXn), SKI, KI, (syn=S1), (syn=SsI), SKVII, (syn=KVII), (syn=Slur), (syn=SsVII), SKIX, (syn=KIX), (syn=S1x), (syn=SsIX), SKXII, (syn=KXII), (syn=Sxn), (syn=SsXII), STi, STfll, STrv, STVi, STvπ, S70, S206, U2-SO-S, 3210-SO-S, 3859-SO-S, 4020-SO-S, φ3, φ5, φ7, φ8, φ9, φIO, φl 1, φ13, φ14, φ18, SHm, (syn=Hπi), SHχi, (syn=HXt) and SKxI, (syn=KXI), (syn=Sri), (syn=SsXI), (syn=XI).

Bacteria of the genus *Staphylococcus* are infected by the following phage: A, EW, K, Ph5, Ph9, PhIO, Phl3, P1, P2, P3, P4, P8, P9, P10, RG, SB-i, (syn=Sb-I), S3K, Twort, ΦSK311, φ812, 06, 40, 58, 119, 130, 131, 200, 1623, STC1, (syn=stc1), STC2, (syn=stc2), 44AHJD, 68, AC1, AC2, A6"C", A9"C", b581, CA-I, CA-2, CA-3, CA-4, CA-5, DI1, L39x35, L54a, M42, N1, N2, N3, N4, N5, N7, N8, N10, Ni 1, N12, N13, N14, N16, Ph6, Ph12, Ph14, UC-18, U4, U15, 51, S2, S3, S4, S5, X2, Z1, φB5-2, φD, ω, 11, (syn=φ11), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, A10, A13, b594n, D, HK2, N9, N15, P52, P87, 51, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phage: EJ-I, NN-Streptococais (1), a, C1, FL0Ths, H39, Cp-I, Cp-5, Cp-7, Cp-9, Cp-IO, AT298, A5, alO/Jl, alO/J2, alO/J5, alO/J9, A25, BTI1, b6, CAI, c20-1, c20-2, DP-I, Dp-4, DT1, ET42, elO, FA101, FETHs, FK, FKKIOI, FKLIO, FKP74, FKH, FLOTHs, FyIOl, fl, F10, F20140/76, g, GT-234, HB3, (syn=HB-3), HB-623, HB-746, M102, O1205, φO1205, PST, PO, P1, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, SfIl 1, (syn=SFiI1), (syn=(syn=ΦSfil 1), (syn=φSfil 1), sfi19, (syn=SFil9), (syn=φSFil9), (syn=φSfil9), Sfi21, (syn=SFi21), (syn=φSFi21), (syn=φSfi21), ST0, STX, st2, ST2, ST4, S3, (syn=φS3), s265, Φ17, φ42, Φ57, φ80, φ81, φ82, φ83, φ84, φ85, φ86, φ87, φ88, φ89, φ90, φ91, φ92, φ93, φ94, φ95, φ96, φ97, φ98, φ99, φlOO, φlOl, φlO2, φ227, Φ17201, ω1, ω2, ω3, ω4, ω5, ω6, ω8, ω10, 1, 6, 9, lOF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/5T16, 80/15, 80/47, 80/48, 101, 103/39, 103/40, 121/41, 121/42, 123/43, 123/44, 124/44, 337/ST17 and mStreptococcus (34).

Bacteria of the genus *Treponema* are infected by the following phage: NN-*Treponema* (1).

Bacteria of the genus *Vibrio* are infected by the following phage: CTXΦ, fs, (syn=si), fs2, Ivpf5, Vfl2, Vf33, VPIΦ, VSK, v6, 493, CP-T1, ET25, kappa, K139, Labol, )XN-69P, OXN-86, 06N-21P, PB-I, P147, rp-1, SE3, VA-I, (syn=VcA-I), VcA-2, VP1, VP2, VP4, VP7, VP8, VP9, VP10, VP17, VP18, VP19, X29, (syn=29 d'Herelle), t, THAWI-1, THAWI-2, THAWI-3, ΦHAWI-4, ΦHAWI-5, ΦHAWI-6, ΦHAWI-7, XHAWI-8, ΦHAWI-9, ΦHAWI-10, ΦHC1-1, ΦHC1-2, ΦHC1-3, ΦHC1-4, ΦHC2-1, >HC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, φ16, φ138, 1-II, 5, 13, 14, 16, 24, 32, 493, 6214, 7050, 7227, II, (syn=group II), (syn=φ2), V, VIII, ~m-*Vibrio* (13), KVP20, KVP40, nt-1, O6N-22P, P68, e1, e2, e3, e4, e5, FK, G, I, K, nt-6, N1, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pA1, 7, 7-8, 70A-2, 71A-6, 72A-5, 72A-8, 108A-10, 109A-6, 109A-8,110A-1, 110A-5, 110A-7, hv-1, OXN-52P, P13, P38, P53, P65, P108, Pi11, TP13 VP3, VP6, VP12, VP13, 70A-3, 70A-4, 70A-10, 72A-1, 108A-3, 109-B1, 110A-2, 149, (syn=φ149), IV, (syn=group IV), NN-*Vibrio* (22), VP5, VPI1, VP15, VP16, α1, α2, α3a, α3b, 353B and HN-*Vibrio* (7).

Bacteria of the genus *Yersinia* are infected by the following phage: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, yYer03-12, 3, 4/C1324-76, 7/F783-76, 903, 1/M6176 and Yer2AT.

More preferably, the bacteriophage is selected in the group consisting of *Salmonella* virus SKML39, *Shigella* virus AG3, Dickeya virus Limestone, Dickeya virus RC2014, *Escherichia* virus CBA120, *Escherichia* virus Phaxl, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus ViI, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaE1, *Escherichia* virus wV8, *Salmonella* virus FelixO1, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus S253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus J598, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phi1, *Escherichia* virus RB49, *Escherichia* virus HX01, *Escherichia* virus JS09, *Escherichia* virus RB69, *Shigella* virus UTAM, *Salmonella* virus S16, *Salmonella* virus STML198, *Vibrio* virus KVP40, *Vibrio* virus ntl, *Vibrio* virus ValKK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HY01, *Escherichia* virus Ime09, *Escherichia* virus RB3, *Escherichia* virus RB14, *Escherichia* virus T4, *Shigella* virus PssI, *Shigella* virus Shf12, *Yersinia* virus D1, *Yersinia* virus PST, *Acinetobacter* virus 133, *Aeromonas* virus 65, *Aeromonas* virus Aehl, *Escherichia* virus RB16, *Escherichia* virus RB32, *Escherichia* virus RB43, *Pseudomonas* virus 42, *Cronobacter* virus CR3, *Cronobacter* virus CR8, *Cronobacter* virus CR9, *Cronobacter* virus PBES02, *Pectobacterium* virus phiTE, *Cronobacter* virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus V5, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthrobacter* virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcep1, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus 13, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, *Edwardsiella* virus MSW3, *Edwardsiella* virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepFl, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLAC1C, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, *Microcystis* virus Ma-LMM01, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abp1, *Acinetobacter* virus Fril, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kpl, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, *Xylella* virus Prado, *Erwinia* virus Era103, *Escherichia* virus K5, *Escherichia* virus K1-5, *Escherichia* virus K1E, *Salmonella* virus SP6, *Escherichia* virus T7, *Kluyvera* virus Kvp1, *Pseudomonas* virus gh1, *Prochlorococcus* virus PSSP7, *Synechococcus* virus P60, *Synechococcus* virus Syn5, *Streptococcus* virus Cp1, *Streptococcus* virus Cp1, *Staphylococcus* virus 44AHJD, *Streptococcus* virus C1, *Bacillus* virus B103, *Bacillus* virus GA1, *Bacillus* virus phi29, *Kurthia* virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepi102, *Burkholderia* virus Bcepmigl, *Burkholderia* virus DC1, *Bordetella* virus BPP1, *Burkholderia* virus BcepC6B, *Cellulophaga* virus Cba41, *Cellulophaga* virus Cba172, *Dinoroseobacter* virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APECS, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, *Edwardsiella* virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septimal 1, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961P, *Helicobacter* virus KHP30, *Helicobacter* virus KHP40, *Hamiltonella* virus APSE1, *Lactococcus* virus KSY1, *Phormidium* virus WMP3, *Phormidium* virus WMP4, *Pseudomonas* virus 119X, *Roseobacter* virus SIO1, *Vibrio* virus VpV262, *Vibrio* virus VC8, *Vibrio* virus VP2, *Vibrio* virus VP5, *Streptomyces* virus Amela, *Streptomyces* virus phiCAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* virus Baee, *Mycobacterium* virus Reprobate, *Mycobacterium* virus Adawi, *Mycobacterium* virus Banel, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pgl, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wks13, *Escherichia* virus K1G, *Escherichia* virus K1H, *Escherichia* virus K1ind1, *Escherichia* virus K1ind2, *Salmonella* virus SP31, *Leuconostoc* virus Lmd1, *Leuconostoc* virus LN03, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Roguel, *Escherichia* virus ACGM12, *Escherichia* virus Rtp, *Escherichia* virus ADB2, *Escherichia* virus JMPW1, *Escherichia* virus JMPW2, *Escherichia* virus Ti, *Shigella* virus PSf2, *Shigella* virus Shfll, *Citrobacter* virus Stevie, *Escherichia* virus TLS, *Salmonella* virus SP126, *Cronobacter* virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faithl, *Mycobacterium* virus Joedirt, *Mycobacterium* virus Rumpelstiltskin, *Lactococcus* virus bIL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, *Cellulophaga* virus Cba121, *Cellulophaga* virus Cba171, *Cellulophaga* virus Cba181, *Cellulophaga* virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus Llij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shaunal, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSLSP030, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phil026b, *Burkholderia* virus phiE125, Edwardsiella virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, Sodalis virus SOL *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb 1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littlee, *Mycobacterium* virus Omega, *Mycobacterium* virus Optimus, *Mycobacterium* virus Thibault, *Polaribacter* virus P12002L, *Polaribacter* virus P12002S, Nonlabens virus P12024L, Nonlabens virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P i OOD, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHLOO9M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071N05, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrassl, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PBI1, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cIP1, *Aeromonas* virus pIS4A, *Listeria* virus LP302, *Listeria* virus PSA, *Methanobacterium* virus psiM1, *Roseobacter* virus RDJL1, *Roseobacter* virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus 01205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb 10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus bIL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus skl, *Lactococcus* virus S14, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus s1ur09, *Escherichia* virus T5, *Salmonella* virus 118970sa12, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphylococcus* virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phi17, *Xanthomonas* virus Xop411, *Xanthomonas* virus Xp10, *Streptomyces* virus TP1604, *Streptomyces* virus YDN12, Alphaproteobacteria virus phiJ1001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi2, *Pseudomonas* virus phi3, *Pseudomonas* virus phi2954, *Pseudomonas* virus phiNN, *Pseudomonas* virus phiYY, *Vibrio* virus fsl, *Vibrio* virus VGJ, *Ralstonia* virus RS603, *Ralstonia* virus RSM1, *Ralstonia* virus RSM3, *Escherichia* virus M13, *Escherichia* virus 122, *Salmonella* virus IKe, Acholeplasma virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, *Spiroplasma* virus SVTS2, *Stenotrophomonas* virus PSH1, *Stenotrophomonas* virus SMA6, *Stenotrophomonas* virus SMA7, *Stenotrophomonas* virus SMAS, *Vibrio* virus CTXphi, *Vibrio* virus KSF1, *Vibrio* virus VCY, *Vibrio* virus Vf33, *Vibrio* virus VfO3K6, *Xanthomonas* virus Cflc, Spiroplasma virus C74, Spiroplasma virus R8A2B, Spiroplasma virus SkV1CR23x, *Escherichia* virus FI, *Escherichia* virus Qbeta, *Escherichia* virus BZ13, *Escherichia* virus MS2, *Escherichia* virus alpha3, *Escherichia* virus ID21, *Escherichia* virus ID32, *Escherichia* virus ID62, *Escherichia* virus NC28, *Escherichia* virus NC29, *Escherichia* virus NC35, *Escherichia* virus phiK, *Escherichia* virus Stl, *Escherichia* virus WA45, *Escherichia* virus G4, *Escherichia* virus ID52, *Escherichia* virus Talmos, *Escherichia* virus phiX174, Bdellovibrio virus MAC1, Bdellovibrio virus MH2K, *Chlamydia* virus Chpl, *Chlamydia* virus Chp2, *Chlamydia* virus CPAR39, *Chlamydia* virus CPG1, Spiroplasma virus SpV4, Acholeplasma virus L2, *Pseudomonas* virus PR4, *Pseudomonas* virus PRD1, *Bacillus* virus AP50, *Bacillus* virus Bam35, *Bacillus* virus GIL16, *Bacillus* virus Wipl, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-I, *Escherichia* virus Stxlphi, *Escherichia* virus Stx2phi-II, *Escherichia* virus CP-1639, based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus ECO26 P06, *Escherichia* virus ECO103 P15, *Escherichia* virus ECO103 P12, *Escherichia* virus ECO111 P16, *Escherichia* virus ECO111 P11, *Escherichia* virus VT2phi 272, *Escherichia* virus TL-2011c, *Escherichia* virus P13374, *Escherichia* virus Sp5.

In one embodiment, the bacterial virus particles target *E. coli* and includes the capsid of a bacteriophage selected in the group consisting of BW73, B278, D6, D108, E, E1, E24, E41, FI-2, FI-4, FI-5, HI8A, Ffl8B, i, MM, Mu, 025, PhI-5, Pk, PSP3, P1, P1D, P2, P4, S1, Wφ, φK13, φ1 φ2, φ7, φ92, 7 A, 8φ, 9φ, 18, 28-1, 186, 299, HH-*Escherichia* (2), AB48, CM, C4, C16, DD-VI, E4, E7, E28, FE, FI3, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, Sal-2, Sal-3, Sal-4, Sal-5, Sal-6, TC23, TC45, TuII*-6, TuIP-24, TuII*46, TuIP-60, T2, T4, T6, T35, α1, 1, IA, 3, 3A, 3T+, 5φ, 9266Q, CFO103, HK620, J, K, K1F, m59, no. A, no. E, no. 3, no. 9, N4, sd, T3, T7, WPK, W31, ΔH, φC3888, φK3, φK7, φK12, φV-1, Φ04-CF, Φ05, Φ06, Φ07, φ1, φ1.2, φ20, φ95, φ263, φ1O92, φ1, φ11, Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, HK139, HK253, HK256, K7, ND-I, PA-2, q, S2, T1, ), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, K10, ZG/3A, 5, 5A, 21EL, H19-J and 933H.

Prebiotics include, but are not limited to, amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

Probiotics include, but are not limited to lactobacilli, bifidobacteria, streptococci, enterococci, propionibacteria, saccaromycetes, lactobacilli, bifidobacteria, or proteobacteria.

The antibiotic can be selected from the group consisting in penicillins such as penicillin G, penicillin K, penicillin N, penicillin 0, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; lluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomycin, nalidixice acide, rifampin, derivatives and combination thereof.

The present invention provides pharmaceutical or veterinary compositions comprising one or more of the bacterial delivery vehicles disclosed herein and a pharmaceutically-acceptable carrier. Generally, for pharmaceutical use, the bacterial delivery vehicles may be formulated as a pharmaceutical preparation or compositions comprising at least one bacterial delivery vehicles and at least one pharmaceutically acceptable carrier, diluent or excipient, and optionally one or more further pharmaceutically active compounds. Such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such administration forms may be solid, semi-solid or liquid, depending on the manner and route of administration. For example, formulations for oral administration may be provided with an enteric coating that will allow the synthetic bacterial delivery vehicles in the formulation to resist the gastric environment and pass into the intestines. More generally, synthetic bacterial delivery vehicle formulations for oral administration may be suitably formulated for delivery into any desired part of the gastrointestinal tract. In addition, suitable suppositories may be used for delivery into the gastrointestinal tract. Various pharmaceutically acceptable carriers, diluents and excipients useful in bacterial delivery vehicle compositions are known to the skilled person.

Also provided are methods for treating a bacterial infection using the synthetic bacterial delivery vehicles disclosed herein. The methods include administering the synthetic bacterial delivery vehicles or compositions disclosed herein to a subject having a bacterial infection in need of treatment. In some embodiments, the subject is a mammal. In some embodiments, the subject is a human.

The pharmaceutical or veterinary composition according to the disclosure may further comprise a pharmaceutically acceptable vehicle. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidine, low melting waxes and ion exchange resins.

The pharmaceutical or veterinary composition may be prepared as a sterile solid composition that may be suspended at the time of administration using sterile water, saline, or other appropriate sterile injectable medium. The pharmaceutical or veterinary compositions of the disclosure may be administered orally in the form of a sterile solution or suspension containing other solutes or suspending agents (for example, enough saline or glucose to make the solution isotonic), bile salts, acacia, gelatin, sorbitan monoleate, polysorbate 8o (oleate esters of sorbitol and its anhydrides copolymerized with ethylene oxide) and the like. The particles according to the disclosure can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The bacterial delivery vehicles according to the disclosure may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

The diseases or disorders caused by bacteria may be selected from the group consisting of abdominal cramps, acne vulgaris, acute epiglottitis, arthritis, bacteraemia, bloody diarrhea, botulism, Brucellosis, brain abscess, chancroid venereal disease, *Chlamydia*, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Widermere syndrome, Legionaire's disease, meningitis, mucopurulent conjunctivitis, multi-drug resistant bacterial infections, multi-drug resistant bacterial carriage, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection, whooping cough.

The infection caused by bacteria may be selected from the group consisting of skin infections such as acne, intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, post-partum infection, hospital acquired gastro-enteritis, hospital acquired urinary tract infections, or a combination thereof. Preferably, the infection according to the disclosure is caused by a bacterium presenting an antibiotic resistance. In a particular embodiment, the infection is caused by a bacterium as listed above in the targeted bacteria.

The disclosure concerns a pharmaceutical or veterinary composition for use in the treatment of metabolic disorder including, for example, obesity and diabetes.

In a particular embodiment, the disclosure concerns a pharmaceutical or veterinary composition for use in the treatment of pathologies involving bacteria of the human microbiome, such as inflammatory and auto-immune diseases, cancers, infections or brain disorders. Indeed, some bacteria of the microbiome, without triggering any infection, can secrete molecules that will induce and/or enhance inflammatory or auto-immune diseases or cancer development. More specifically, the present disclosure relates also to modulating microbiome composition to improve the efficacy of immunotherapies based, for example, on CAR-T (Chimeric Antigen Receptor T) cells, TIL (Tumor Infiltrating Lymphocytes) and Tregs (Regulatory T cells) also known as suppressor T cells. Modulation of the microbiome composition to improve the efficacy of immunotherapies may also include the use of immune checkpoint inhibitors well known in the art such as, without limitation, PD-1 (programmed cell death protein 1) inhibitor, PD-L1 (programmed death ligand 1) inhibitor and CTLA-4 (cytotoxic T lymphocyte associated protein 4).

Some bacteria of the microbiome can also secrete molecules that will affect the brain.

Therefore, a further object of the disclosure is a method for controlling the microbiome of a subject, comprising administering an effective amount of the pharmaceutical composition as disclosed herein in said subject.

In a particular embodiment, the disclosure also relates to a method for personalized treatment for an individual in need of treatment for a bacterial infection comprising: i) obtaining a biological sample from the individual and determining a group of bacterial DNA sequences from the sample; ii) based on the determining of the sequences, identifying one or more pathogenic bacterial strains or species that were in the sample; and iii) administering to the individual a pharmaceutical composition according to the disclosure capable of recognizing each pathogenic bacterial strain or species identified in the sample and to deliver the packaged plasmid.

Preferably, the biological sample comprises pathological and non-pathological bacterial species, and subsequent to administering the pharmaceutical or veterinary composition according to the disclosure to the individual, the amount of pathogenic bacteria on or in the individual are reduced, but the amount of non-pathogenic bacteria is not reduced.

In another particular embodiment, the disclosure concerns a pharmaceutical or veterinary composition according to the disclosure for use in order to improve the effectiveness of drugs. Indeed, some bacteria of the microbiome, without being pathogenic by themselves, are known to be able to metabolize drugs and to modify them in ineffective or harmful molecules.

In another particular embodiment, the disclosure concerns the in-situ bacterial production of any compound of interest, including therapeutic compound such as prophylactic and therapeutic vaccine for mammals. The compound of interest can be produced inside the targeted bacteria, secreted from the targeted bacteria or expressed on the surface of the targeted bacteria. In a more particular embodiment, an antigen is expressed on the surface of the targeted bacteria for prophylactic and/or therapeutic vaccination.

The present disclosure also relates to a non-therapeutic use of the bacterial delivery particles. For instance, the non-therapeutic use can be a cosmetic use or a use for improving the well-being of a subject, in particular a subject who does not suffer from a disease. Accordingly, the present disclosure also relates to a cosmetic composition or a non-therapeutic composition comprising the bacterial delivery particles if the disclosure.

Example 1

The example below demonstrates that a significative portion of a lambda receptor binding protein (RBP), e.g. the stf protein, can be exchanged with a portion of a different RBP. More particularly, specific fusion positions in the lambda RBP have been identified which allow one to obtain a functional chimeric RBP. Specifically, the data demonstrate, in a non-limiting embodiment, that in the case of phagemids derived from bacteriophage lambda, modifying the side tail fiber protein results in an expanded host range. The addition of chimeric stf proteins to lambdoid phagemids, is demonstrated to be a very powerful approach to modify and increase their host range, and in some cases is more efficient than the modification of the gpJ gene. In addition, modification of the side tail fiber protein to encode depolymerase activities can dramatically increase the delivery efficiency. In some cases, the addition of this enzymatic activity allows for 100% delivery efficiency while the wild-type lambda phagemid showed no entry at all. These two approaches can be combined to generate phagemid variants with different specificities and delivery efficiencies to many strains of bacterial species.

Tests were conducted to determine whether the modification of the tail tip gene (gpJ) would have an impact in the host range of lambda phagemids. The lambda tail tip was modified to include the mutations described in [11] to generate OMPF-lambda. This phagemid should now use OmpF instead of LamB as a primary receptor in the cell surface. Next, the delivery efficiency was tested in a collection of *E. coli* strains that spans a variety of O and K serotypes, as shown in FIG. 1.

As can be seen in FIG. 1, using phagemids that recognize a different cell surface receptor has a minimal impact on efficiency delivery and host range. Only 3 strains show a marginal improvement in the number of colonies after treatment with the modified phagemid. This result may be due to the presence of a capsule around the majority of the cells that forms a physical barrier to the phagemids, thus rendering this approach unsuccessful. In view of these results, the lambda stf gene was modified to include enzymatic activities against bacterial capsules.

The sequence of lambda stf (SEQ ID NO:1) is:

MAVKISGVLKDGTGKPVQNCTIQLKARRNSTTVVVNTVGSENPDEAGRYSM

DVEYGQYSVILQVDGFPPSHAGTITVYEDSQPGTLNDFLCAMTEDDARPEV

LRRLELMVEEVARNASVVAQSTADAKKSAGDASASAAQVAALVTDATDSAR

AASTSAGQAASSAQEASSGAEAASAKATEAEKSAAAAESSKNAAATSAGAA

KTSETNAAASQQSAATSASTAATKASEAATSARDAVASKEAAKSSETNASS

SAGRAASSATAAENSARAAKTSETNARSSETAAERSASAAADAKTAAAGSA

STASTKATEAAGSAVSASQSKSAAEAAAIRAKNSAKRAEDIASAVALEDAD

TTRKGIVQLSSATNSTSETLAATPKAVKVVMDETNRKAPLDSPALTGTPTA

PTALRGTNNTQIANTAFVLAAIADVIDASPDALNTLNELAAALGNDPDFAT

TMTNALAGKQPKNATLTALAGLSTAKNKLPYFAENDAASLTELTQVGRDIL

AKNSVADVLEYLGAGENSAFPAGAPIPWPSDIVPSGYVLMQGQAFDKSAYP

KLAVAYPSGVLPDMRGWTIKGKPASGRAVLSQEQDGIKSHTHSASASGTDL

GTKTTSSFDYGTKTTGSFDYGTKSTNNTGAHAHSLSGSTGAAGAHAHTSGL

RMNSSGWSQYGTATITGSLSTVKGTSTQGIAYLSKTDSQGSHSHSLSGTAV

SAGAHAHTVGIGAHQHPVVIGAHAHSFSIGSHGHTITVNAAGNAENTVKNI

AFNYIVRLA

The bold and underlined sequence represents the part of the protein that was introduced in the T4 phage [47]. Experiments were conducted to investigate if it was possible to exchange the C-terminus of the lambda stf with a tail fiber from a different phage to yield chimeric side tail fibers with an enzymatic activity against encapsulated *E. coli*. The tail fiber from the K1F phage which has been studied in depth and its structure solved [19], [20] was chosen. K1F encodes an enzyme with endosialidase activity, which is active against polymer of sialic acid secreted by K1-encapsulated *E. coli*. In fact, K1+ strains are immune to T7 infection because the capsule forms a physical barrier that prevents attachment of the phage, but if purified K1F enzyme is added to the cells before infection, T7 is able to lyse them [21], confirming that the presence of bacterial capsules is a powerful mechanism to avoid recognition by bacteriophages. Thus, by testing delivery of modified lambda-stf-K1 phagemids in K1+ strains it was possible to verify whether the lambda-stf chimeric proteins retain its enzymatic activity.

The sequence of K1F tail fiber (SEQ ID NO: 121) is:

MSTITQFPSGNTQYRIEFDYLARTFVVVTLVNSSNPTLNRVLEVGRDYRFL

NPTMIEMLVDQSGFDIVRIHRQTGTDLVVDFRNGSVLTASDLTTAELQAIH

IAEEGRDQTVDLAKEYADAAGSSAGNAKDSEDEARRIAESIRAAGLIGYMT

RRSFEKGYNVTTWSEVLLWEEDGDYYRWDGTLPKNVPAGSTPETSGGIGLG

AWVSVGDAALRSQISNPEGAILYPELHRARWLDEKDARGWGAKGDGVTDDT

AALTSALNDTPVGQKINGNGKTYKVTSLPDISRFINTRFVVERIPGQPLYY

ASEEFVQGELFKITDTPYYNAWPQDKAFVYENVIYAPYMGSDRHGVSRLHV

SWVKSGDDGQTWSTPEWLTDLHPDYPTVNYHCMSMGVCRNRLFAMIETRTL

AKNALTNCALWDRPMSRSLHLTGGITKAANQRYATIHVPDHGLFVGDFVNF

-continued

SNSAVTGVSGDMTVATVIDKDNFTVLTPNQQTSDLNNAGKNWHMGTSFHKS

PWRKTDLGLIPSVTEVHSFATIDNNGFAMGYHQGDVAPREVGLFYFPDAFN

SPSNYVRRQIPSEYEPDASEPCIKYYDGVLYLITRGTRGDRLGSSLHRSRD

IGQTWESLRFPHNVHHTTLPFAKVGDDLIMFGSERAENEWEAGAPDDRYKA

SYPRTFYARLNVNNWNADDIEWVNITDQIYQGGIVNSGVGVGSVVVKDNYI

YYMFGGEDHFNPWTYGDNSAKDPFKSDGHPSDLYCYKMKIGPDNRVSRDFR

YGAVPNRAVPVFFDTNGVRTVPAPMEFTGDLGLGHVTIRASTSSNIRSEVL

MEGEYGFIGKSIPTDNPAGQRIIFCGGEGTSSTTGAQITLYGANNTDSRRI

VYNGDEHLFQSADVKPYNDNVTALGGPSNRFTTAYLGSNPIVTSNGERKTE

PVVFDDAFLDAWGDVHYIMYQWLDAVQLKGNDARIHFGVIAQQIRDVFIAH

GLMDENSTNCRYAVLCYDKYPRMTDTVFSHNEIVEHTDEEGNVTTTEEPVY

TEVVIHEEGEEWGVRPDGIFFAEAAYQRRKLERIEARLSALEQK

The bold and underlined sequence represents the part of the protein that has been crystalized and has been shown to retain its endosialidase activity. Since there is no identity between the lambda stf protein and the K1F tail fiber, the insertion point was made based on conclusions extracted from different sources of information, including literature and crystal structures.

Figures 1, 12:
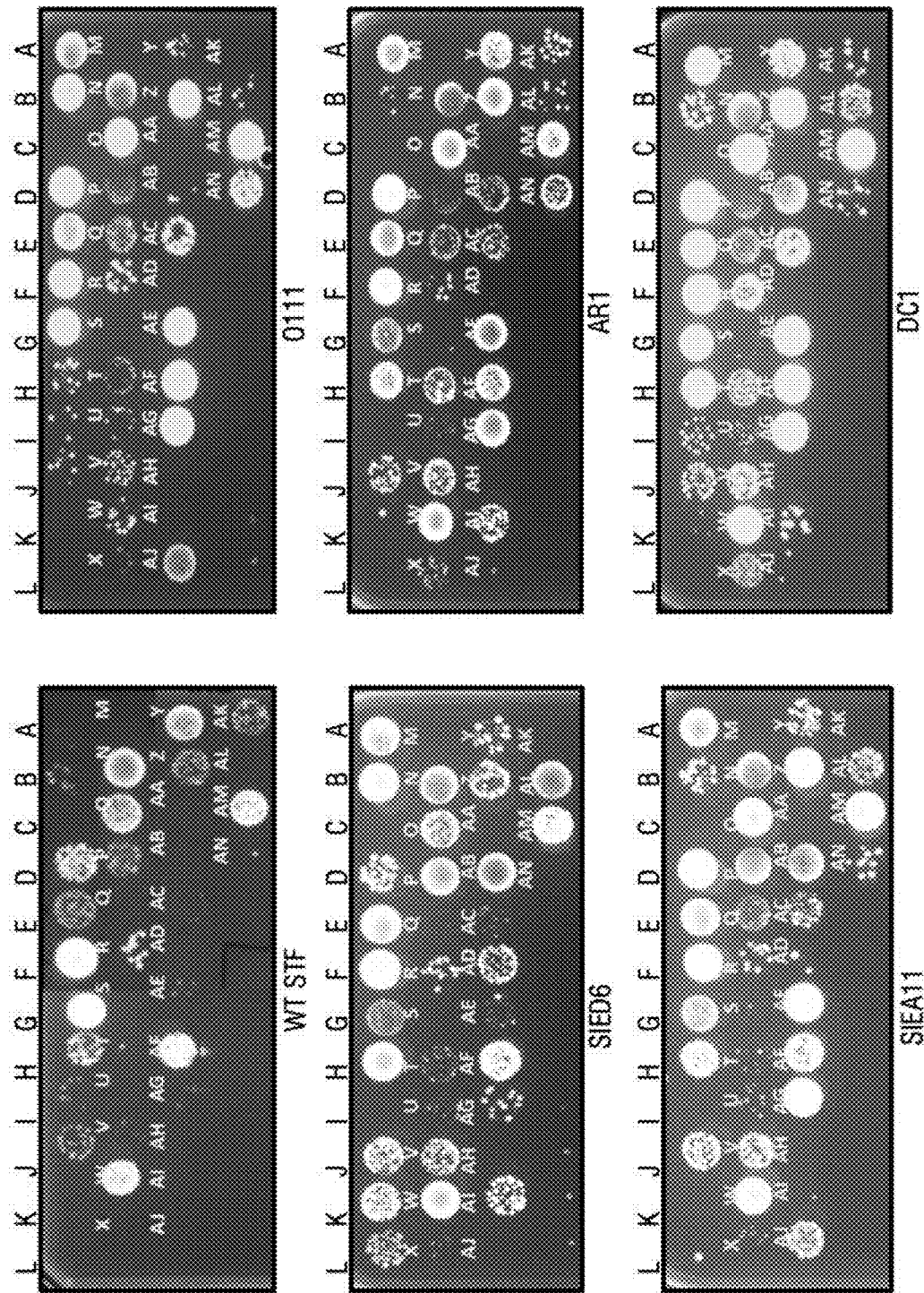
FIG. 12 depicts raw dot titrations of delivery particles with chimeric stf in 40 human strains of the ECOR collection. Below each panel, the name of the chimeric stf. Above each dot, the 1-2 letter code used to identify strains in FIG. 13.
Figures 2, 12:
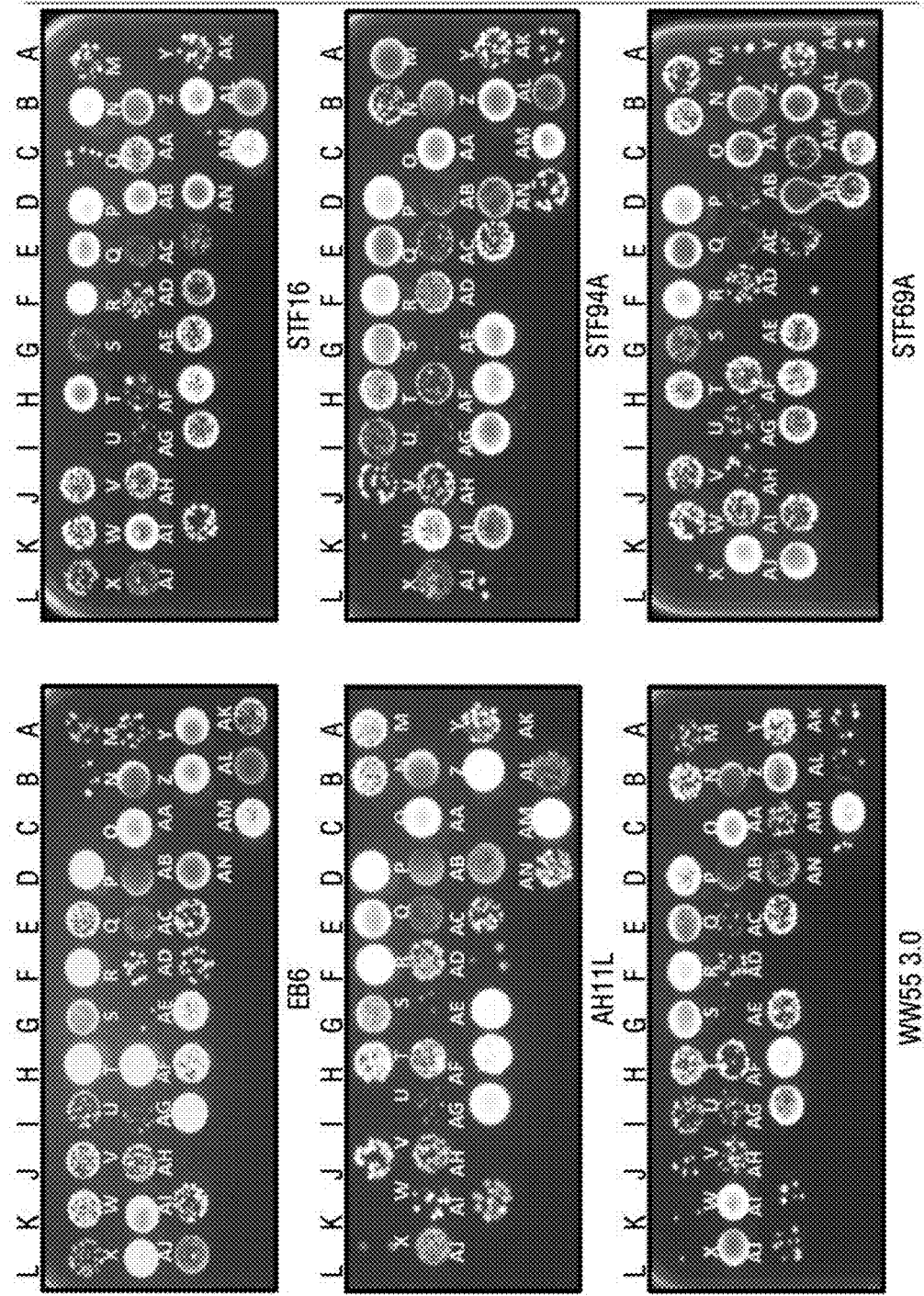
FIG. 2 depicts wild-type lambda and lambda-stf-K1F chimeric delivery vehicles on K1+ strains. Lambda packaged phagemids were sequentially diluted 10× in LB plus 5 mM CaCl2 and 10 uL added in each well. Cells grown to an OD600 of around 0.5 were then added to each phagemid dilution, incubated for 30 min at 37° C. and 10 uL plated on LB supplemented with chloramphenicol. Top panel, strain UTI89; bottom panel, strain S88. Left plates, wild type lambda packaged phagemids; right plates, stf-K1F lambda packaged phagemids.
Figures 3, 12:
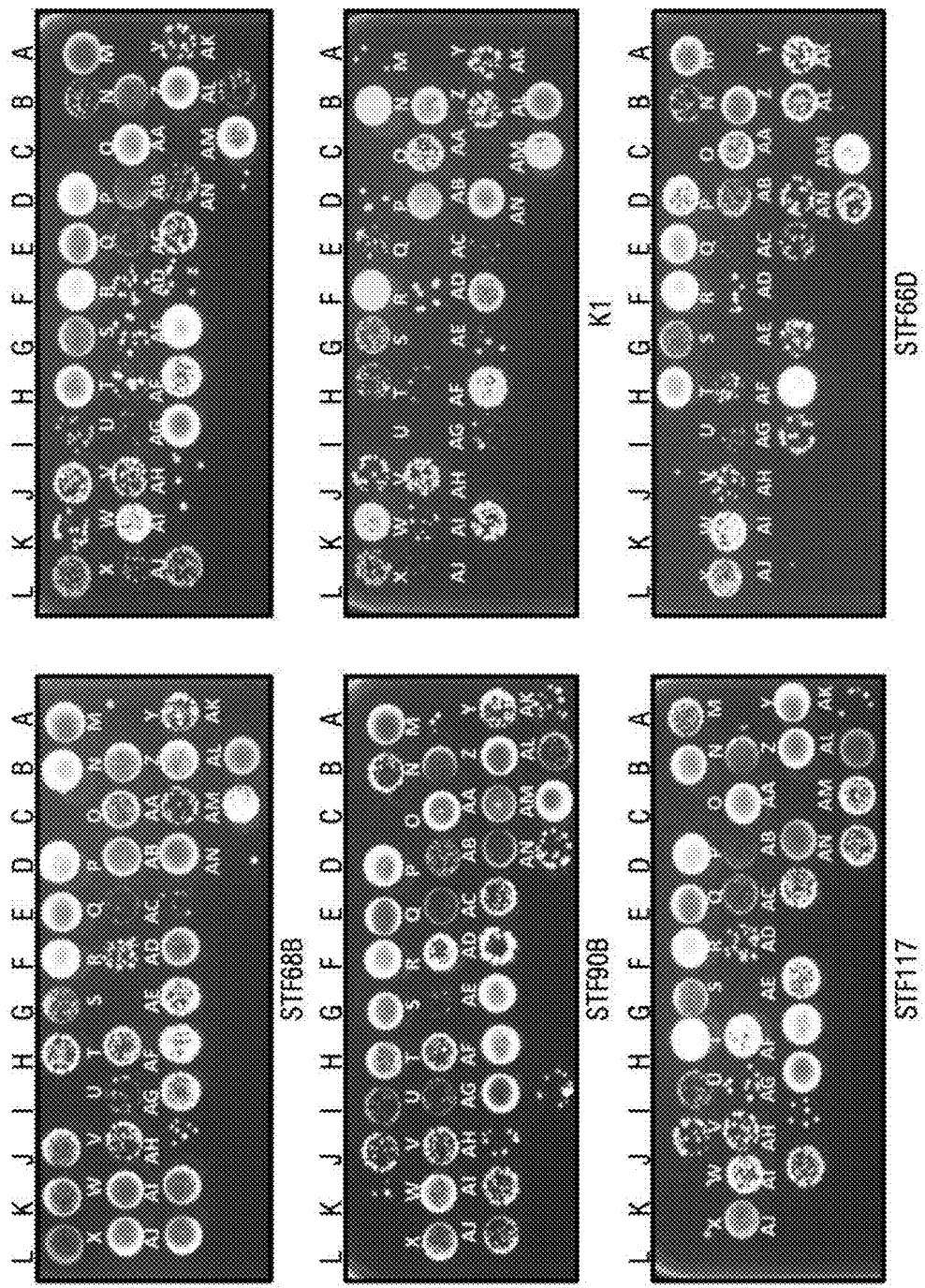

The stf gene was modified to include the K1F endosialidase at its C-terminus using a Cas9-mediated gene exchange protocol [22]. lambda-K1F phagemids were produced as in [23] and titrated against some K1+ strains, specifically *E. coli* UTI89 and S88. The results were striking; in these strains, there is no delivery if lambda wild-type stf is used, but the addition of the K1F variant gives 100% delivery (FIG. 2).

Figure 3:
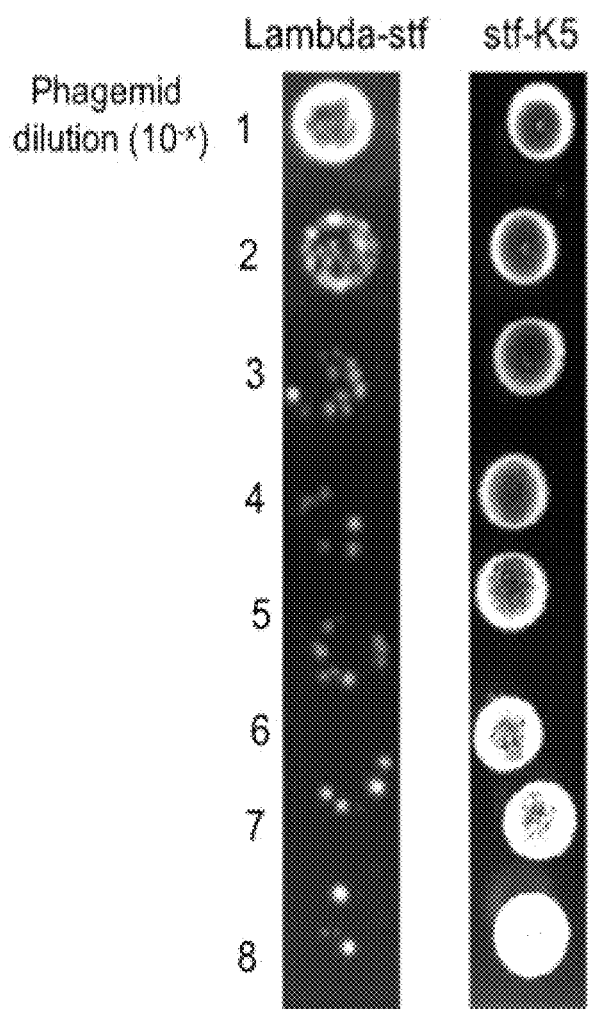
FIG. 3 depicts wild-type lambda and lambda-stf-K5 chimeric delivery vehicles on a K5+ strain. Lambda packaged phagemids were sequentially diluted 10× in LB plus 5 mM CaCl2 and 10 uL added in each well. ECOR55 grown to an OD600 of around 0.5 were then added to each phagemid dilution, incubated for 30 min at 37° C. and 10 uL plated on LB supplemented with chloramphenicol. Left panel, wild type lambda packaged phagemids; right panel, stf-K15 lambda packaged phagemids.

The same principle was followed to create a different variant of lambda-stf, this time with K5-capsule degrading activity (K5 lyase tail fiber from phage K5A). As in the case of K1F, there is no homology between lambda-stf and K5 lyase, but its crystal structure has been published [24]. Hence, the same approach as for K1F was used to generate stf-K5 chimeric side tail fibers and tested the produced phagemids against a K5-encapsulated strain of *E. coli* (ECOR 55). In this case, however, a delta-stf lambda production strain was produced with the stf fusion gene expressed in trans under the control of an inducible promoter. As depicted in FIG. 3, there was some residual delivery using the wild-type lambda-stf, probably due to the presence of some cells with a thinner K5 capsule. However, the addition of lambda-stf-K5 chimeras allows for an improvement in delivery of more than $10^6$ fold.

In some other cases, side tail fibers can be found that have some degree of homology to lambda stf, although no crystal structure is available. In these cases, the insertion point was designed as the last stretch of amino acids with identity to lambda stf. For example, in two in-house sequenced phages, the predicted side tail fiber proteins are as follows:

Phage AG22 stf (SEQ ID NO: 262)
MAIYRQGQASMDAQGYVTGYGTKWREQLTLIRPGATIFFLAQPLQAAVITE

VISDTSIRAITTGGAVVQKTNYLILLHDSLTVDGLAQDVAETLRYYQGKES

EFAGFIEIIKDFDWDKLQKIQEDVKTNADAAAASQQAAKTSENNAKTSATN

AANSKKGADTAKAAAESARDAANTAKTGAEAAKSGAESARDAANTAKAGAE

SARDQAEEYAKQAAEPYKDLLQPLPDVWIPFNDSLDMITGFSPSYKKIVIG

DDEITMPGDKIVKFKRASTATYINKSGVLTNAAIDEPRFEKDGLLIEGQRT

NLLINSTNPSKWNKSSNMILDRSGVDDFGFQYAKFTLKPEMVGQTSSINIV

TVSGSRGFDVTGNEKYVTISCRAQSGTPNLRCRLRFENYDGSAYASLGDAY

VNLTDLSIEKTGGAANRITARAVKDEASKWIFFEATIKALDTENMIGAMVQ

YAPAKDGGGTGADDYIYIATPQVEGGVCASSFIITEATPVTRASDMVTIPI

KNNLYNLPFTVLCEVHKNWYITPNAAPRVFDTGGHQSGAAIILAFGSADGD

NDGFPYCDIGKSNRRVNENAKLKKMIIGMRVKSDYNTCCVSNARISSETKT

EWRYIVSTATIRIGGQTSTGERHLFGHVRNFRIWHKALTDHQLGEIV

Its alignment to lambda stf is as follows:

```
Lambda 156  STSAGQAASSAQEASSGAEAASAKATEAEKSAAAAESSKNAAATSAGAAKTSETNAAASQ
AG22    92  ETLRYYQGKESEFAGFIEIIKDFDWDKLQKIQEDVKTNADAAAASQQAAKTSENNAKTSA
             *         *           *        *** *  ****** **  *
```

The sequence of the stf of a second in-house phage is as follows:

Phage SIEA11 stf (SEQ ID NO: 263)
MSTKFKTVITTAGAAKLAAATVPGGKKVTLSAMAVGDGNGKLPVPDAGQTK

LVHEVWRHALNKVSVDNKNKNYIVAELVVPPEVGGFWMRELGLYDDAGTLI

AVSNMAESYKPELAEGSGRAQTCRMVIIVSNVASVELSIDASTVMATQDYV

DDKIAEHEQSRRHPDATLTEKGFTQLSSATNSTSESLAATPKAVKAANDNA

NSRLAKNQNGADIQDKSAFLDNVGVTSLTFMKNNGEMPVDADLNTFGSVKA

YSGIWSKATSTNATLEKNFPEDNAVGVLEVFTGGNFAGTQRYTTRDGNLYI

RKLIGTWNGNDGPWGAWRHVQAVTRALSTTIDLNSLGGAEHLGLWRNSSSA

IASFERHYPEQGGDAQGILEIFEGGLYGRTQRYTTRNGTMYIRGLTAKWDA

ENPQWEDWNQIGYQTSSTFYEDDLDDLMSPGIYSVTGKATHTPIQGQSGFL

EVIRRKDGVYVLQRYTTTGTSAATKDRLYERVFLGGSFNAWGEWRQIYNSN

SLPLELGIGGAVAKLTSLDWQTYDFVPGSLITVRLDNMTNIPDGMDWGVID

GNLINISVGPSDDSGSGRSMHVWRSTVSKANYRFFMVRISGNPGSRTITTR

RVPIIDEAQTWGAKQTFSAGLSGELSGNAATATKLKTARKINNVSFDGTSD

INLTPKNIGAFASGKTGDTVANDKAVGWNWSSGAYNATIGGASTLILHFNI

GEGSCPAAQFRVNYKNGGIFYRSARDGYGFEADWSEFYTTTRKPTAGDVGA

LPLSGGQLNGALGIGTSSALGGNSIVLGDNDTGFKQNGDGNLDVYANSVHV

MRFVSGSVQSNKTINITGRVNPSDYGNFDSRYVRDVRLGTRVVQTMQKGVM

YEKAGHVITGLGIVGEVDGDDPAVFRPIQKYINGTWYNVAQV

Its alignment to lambda stf is as follows:

```
Lambda 367 SSATNSTSETLAATPKAVKVVMDETNRKAPLDSPALTGTPTAPTALRGTNNTQIANTAFV

SIEA11 180 SSATNSTSESLAATPKAVKAANDNANSRL---AKNQNGADIQDKSAF-LDNVGVTSLTFM
           ********* *********  *  *           *          *      *
```

In these two specific cases, it was unknown which antigen these side tail fibers were able to recognize, so lambda packaged phagemids with the chimeric side tail fibers were produced and their delivery efficiency was tested in a E. coli collection that contains a very diverse group of O and K serotypes.

Figure 4:
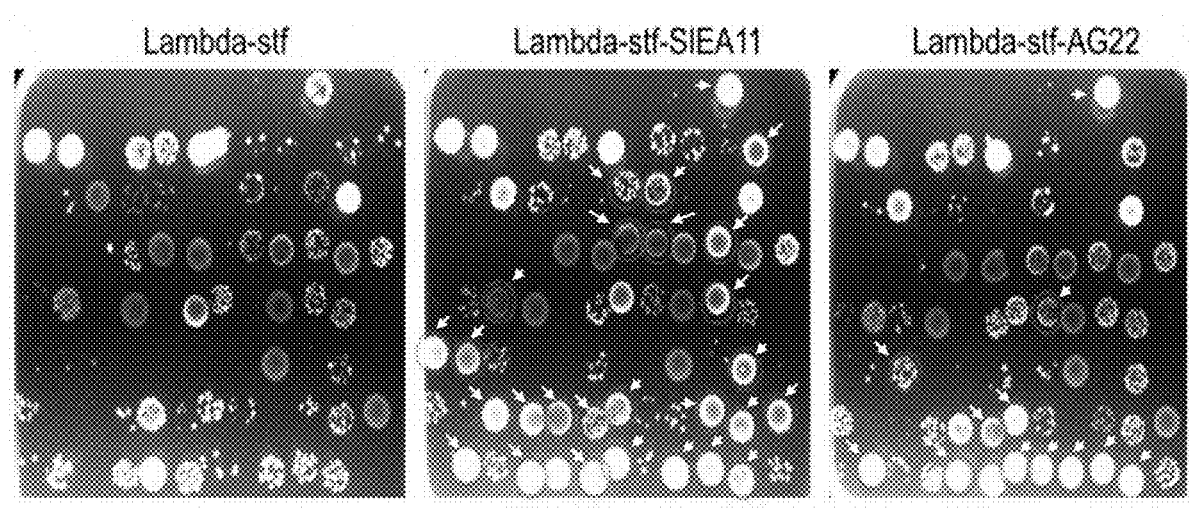
FIG. 4 depicts wild-type lambda, lambda-stf-AG22 and lambda-stf-SIEA11 chimeric delivery vehicles on a variety of encapsulated strains (O and K capsules). Lambda phagemids were diluted 1:5 in LB plus 5 mM CaCl$_2$) and 10 uL added in each well. 90 uL of cells grown to an OD600 of around 0.5 were then added to each phagemid-containing well, incubated for 30 min at 37° C. and 10 uL spotted on LB-agar supplemented with chloramphenicol. Left panel, wild type lambda phagemids; middle panel, lambda stf-SIEA11 variant; right panel, lambda-stf-AG22 variant. Arrows show strains with modified delivery as compared to lambda wild-type.

As shown in FIG. 4, the addition of a chimeric stf allows the lambda-based phagemid to show increased delivery efficiency in 25 out of 96 strains tested (more than 25% of the collection). In some cases, the increase is modest; in others, it allows for very good delivery efficiency in strains that had no or very low entry with wild-type lambda phagemids. It is also worth noting that AG22 belongs to the Siphovirus family, like lambda, but SIEA11 is a P2-like phage. This highlights the significant observation that stf modules can be exchanged across bacteriophage genera.

Other side tail fiber genes have been analyzed as shown in FIG. 4 and several insertion points into the lambda stf gene have been identified that give chimeric variants with differential entry in the E. coli collection as shown previously. These insertion points are based on the results for the non-homologous tail fiber variants (such as in the cases for K1F and K5 above) or on varying degrees of homology between lambda stf and the variant to be tested. This homology can be short, about 5-10 aminoacids, or substantially similar. The insertion points tested are shown in bold and underlined below:

```
Lambda stf
                                              (SEQ ID NO: 1)
MAVKISGVLKDGTGKPVQNCTIQLKARRNSTTVVVNTVGSENPDEAGRYSM

DVEYGQYSVILQVDGFPPSHAGTITVYEDSQPGTLNDFLCAMTEDDARPEV

LRRLELMVEEVARNASVVAQSTADAKKSAGDASASAAQVAALVTDATDSAR

AASTSAGQAASSAQEASSGAEAASAKATEAEKSAAAAESSKNAAATSAGAA

KTSETNAAASQQSAATSASTAATKASEAATSARDAVASKEAAKSSETNASS

SAGRAASSATAAENSARAAKTSETNARSSETAAERSASAAADAKTAAAGSA

STASTKATEAAGSAVSASQSKSAAEAAAIRAKNSAKRAEDIASAVALEDAD

TTRKGIVQLSSATNSTSETLAATPKAVKVVMDETNRKAPLDSPALTGTPTA

PTALRGTNNTQIANTAFVLAAIADVIDASPDALNTLNELAAALGNDPDFAT

TMTNALAGKQPKNATLTALAGLSTAKNKLPYFAENDAASLTELTQVGRDIL

AKNSVADVLEYLGAGENSAFPAGAPIPWPSDIVPSGYVLMQGQAFDKSAYP

KLAVAYPSGVLPDMRGWTIKGKPASGRAVLSQEQDGIKSHTHSASASGTDL

GTKTTSSFDYGTKTTGSFDYGTKSTNNTGAHAHSLSGSTGAAGAHAHTSGL

RMNSSGWSQYGTATITGSLSTVKGTSTQGIAYLSKTDSQGSHSHSLSGTAV

SAGAHAHTVGIGAHQHPVVIGAHAHSFSIGSHGHTITVNAAGNAENTVKNI

AFNYIVRLA
```

Figure 5:
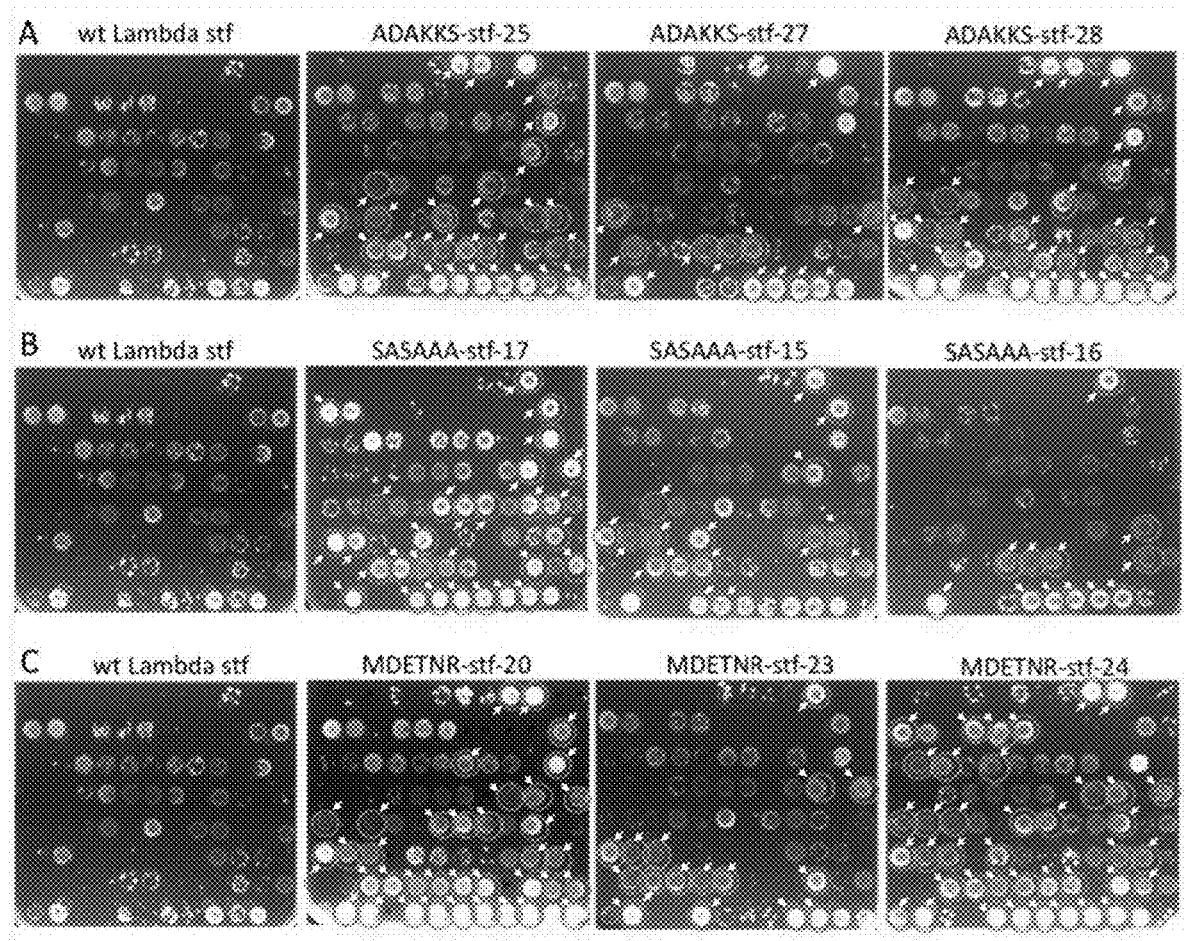
FIG. 5 demonstrates delivery of wild-type lambda and stf chimeras with different insertion sites on a variety of encapsulated strains (0 and K capsules). Lambda packaged phagemids were diluted 1:5 in LB plus 5 mM CaCl$_2$) and 10 uL added in each well. 90 uL of cells grown to an OD600 of around 0.5 were then added to each phagemid-containing well, incubated for 30 min at 37° C. and 10 uL spotted on LB-agar supplemented with chloramphenicol. A) Left panel, wild type lambda packaged phagemids; rest of panels, three different ADAKKS-stf variants. B) Left panel, wild type lambda packaged phagemids; rest of panels, three different SASAAA-stf variants. C) Left panel, wild type lambda packaged phagemids; rest of panels, three different MDE-TNR-stf variants. For all panels, arrows show strains with improved delivery efficiency as compared to lambda wild-type.

The lambda stf protein consists of 774 aminoacids. The insertion points can be found closer to the N-terminus (amino acid 131, insertion point ADAKKS (SEQ ID NO: 249)) or closer to the C-terminus (amino acid 529, insertion point GAGENS (SEQ ID NO: 252)). FIG. 5 depicts some selected examples for the insertion points ADAKKS (SEQ ID NO: 249), SASAAA (SEQ ID NO: 251) and MDETNR (SEQ ID NO: 250).

Figure 6:
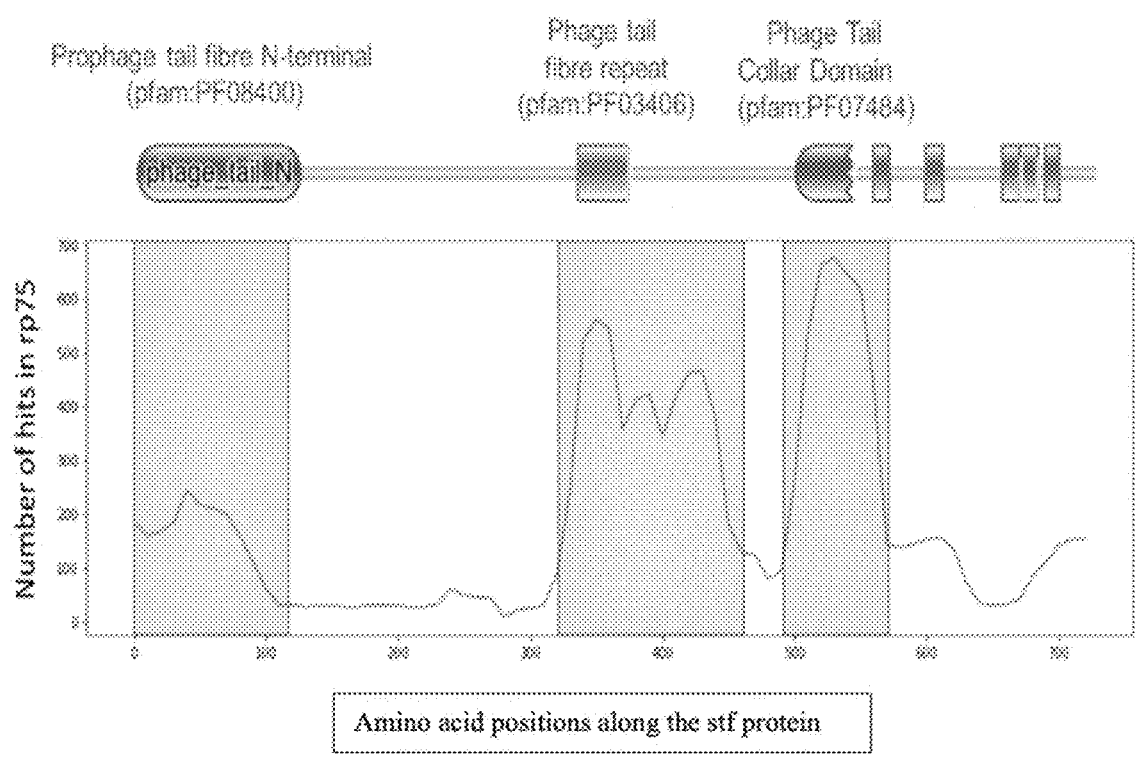
FIG. 6 depicts a phmmer search that was performed with a 50aa sliding window (step 10) on the representative proteome database (rp75). The number of significant hits (E-value<0.01) is reported.

The results described herein show that it is possible to build chimeric tail fibers that combine the part of one tail fiber that attaches to the capsid of one phage (usually the N-terminus of the protein) with the part of another fiber that interacts with the bacterium (usually the C-terminus of the protein). Stretches of homology between the sequence of different tail fibers can be considered as preferable recombination points. In order to identify such points for the stf protein of phage lambda a scan of the stf sequence was performed with a 50aa window and a phmmer search [25] was performed on each window to identify homologous sequences in the representative proteome 75 database (FIG. 6).

Example 2

T4-like phages are a very diverse family of bacteriophages that share a common long tail fiber architecture: a proximal tail fiber that attaches to the phage particle and a distal tail fiber (DTF) that encodes host specificity linked by proteins acting as "hinge connectors" (Desplats and Krisch, 2003, Res. Microbiol. 154:259-267; Bartual et al. 2010, Proc. Natl. Acad. Sci. 107: 20287-20292). It is thought that the main host range determinants of the tail fiber reside in the distal part. Hence, it is very important to understand if it is possible to translate the host range of a given T4-like phage, which are known to be very broad, to any other phage or phagemid of interest. The distal tail fiber (C-terminal domain of the T4-like long tail fiber) of several T4-like phages were screened for possible functional insertion sites, several fusions with the Lambda stf gene were generated and their host range screened.

Figure 7:
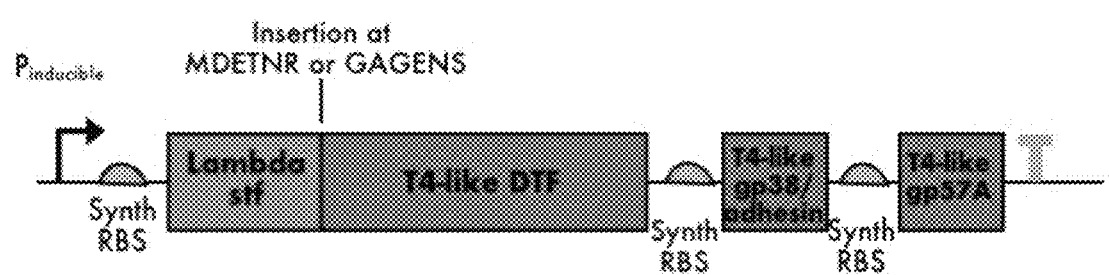
FIG. 7. depicts architecture of the engineered lambda stf-T4-like DTF chimera. The semicircles denote RBS sites; the T sign, a transcriptional terminator; the arrow, a promoter.

Possible insertion sites in the DTF that, when fused to a heterologous tail fiber (the lambda phage stf), will give a functional chimera were searched. The DTF of the phage (WW13) was used as a testbed. This phage possesses a classical T4-like architecture, with a proximal and a distal tail fiber separated by hinge connectors, a gp38 chaperone/adhesin (to assist folding of the tail fiber and recognition of the host (Troj et al., 2011, Genome Biol. Evol. 3:674-686) and a gp57A chaperone known to be needed for proper folding of the tail fiber (Matsui et al., 1997, J. Bacteriol. 179:1846-1851). Since the endogenous genomic regulation of T4-like phages is complex and may include unknown layers of regulation (Miller et al., 2003, Microbio. Mol. Biol. Rev. 67:86-156), a synthetic linker encoding a RBS was designed to replace the natural DNA linker between the DTF gene and the adhesin; immediately downstream, another synthetic RBS preceding the chaperone gp57A was added, hence creating a polycistronic mRNA encoding for all the functions needed for the proper folding of the DTF (FIG. 7). This construct was built in a plasmid under the control of an inducible promoter and complemented in trans in a strain producing lambda-based phagemids.

Figure 11:
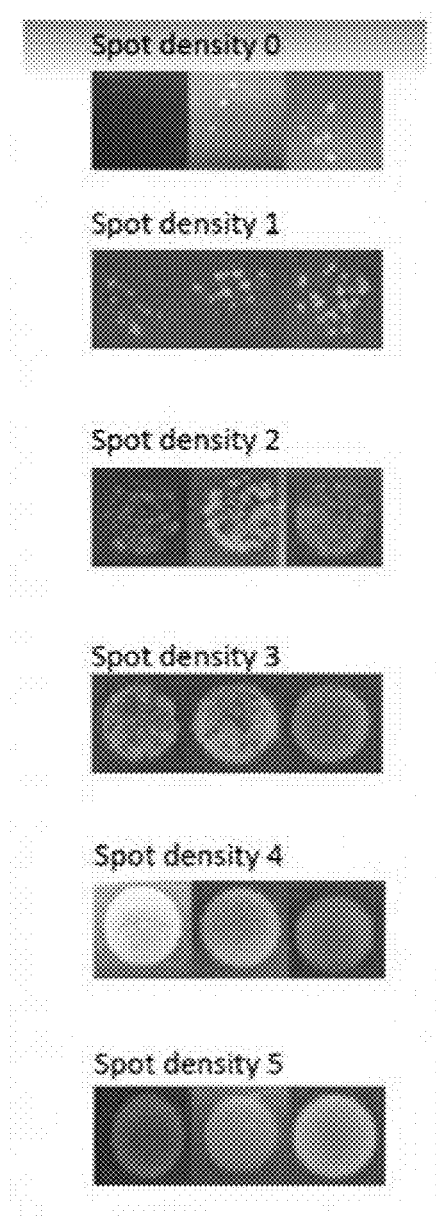
FIG. 11. depicts dot scoring system to quantify delivery efficiency. Density 0, 5 or fewer colonies; density 1, more than 5 colonies but not enough to define a clear circular drop; density 2, several colonies, but the background is clearly visible and some colonies are still separated; density 3, many colonies, the background is still visible but the colonies are hardly discernible as separate; density 4, spot almost completely dense, the background can only be seen faintly in some parts of the drop; density 5, spot looks completely dense, background cannot be seen.

FIG. 7. depicts the architecture of an engineered lambda stf-T4-like DTF chimera. The semicircles denote RBS sites; the T sign, a transcriptional terminator; the arrow, a promoter. Several parts of the C-terminus of the DTF were screened and fused to the lambda stf gene at the GAGENS (SEQ ID NO: 252) insertion site. Several variants of the chimera lambda stf-WW13 were functional, as assessed by production of phagemid particles and transduction of a chloramphenicol marker in a collection of *E. coli* strains. The functional chimeras shown in FIG. 8 were obtained with fusion at the IIQLED (SEQ ID NO: 254) insertion site in WW13. Additional functional chimeras were obtained by fusion at the lambda stf MDETNR (SEQ ID NO: 250) insertion site and at the WW13 DTF GNIIDL (SEQ ID NO: 255), VDRAV (SEQ ID NO: 261) and IIQLED (SEQ ID NO: 254) insertion sites (FIG. 11).

Figure 8:
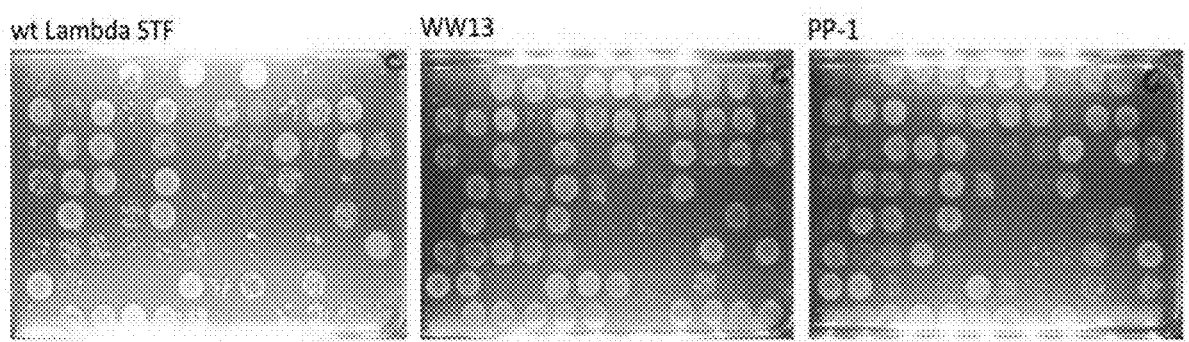
FIG. 8. shows screening of phagemid particles with chimeric lambda stf-T4-like DTFs. A collection of 96 different wild type E. coli strains, encompassing different serotypes, was transduced with lambda-based phagemids and plated on Cm LB agar. Left panel, wild-type lambda stf; middle panel, chimeric lambda-stf-WW13; right panel, chimeric lambda-stf-PP-1.

Other T4-like phages, like PP-1, sharing sequence homology with WW13 were also tested and verified to produce functional chimeras (FIG. 8). These functional chimeras show a IATRV insertion site at the beginning of PP-1 DTF part.

FIG. 8 depicts screening of phagemid particles with chimeric lambda stf-T4-like DTFs. A collection of 96 different wild type *E. coli* strains, encompassing different serotypes, was transduced with lambda-based phagemids and plated on Cm LB agar. Left panel represents wild-type lambda stf; the middle panel represents chimeric lambda-stf-WW13; and the right panel, represents chimeric lambda-stf-PP-1.

The insertion sites found for WW13 do not always exist in a given T4-like DTF, thereby complicating the analysis. Another functional insertion site without homology to WW13 was discovered for a second phage (WW55, FIG. 9). The same TPGEL insertion site could be found in a subset of T4-like phages and proven to yield functional chimeras with at least one of them, WW34 (FIG. 9), and at MDETNR (SEQ ID NO: 250) insertion site in lambda stf.

Figure 9:
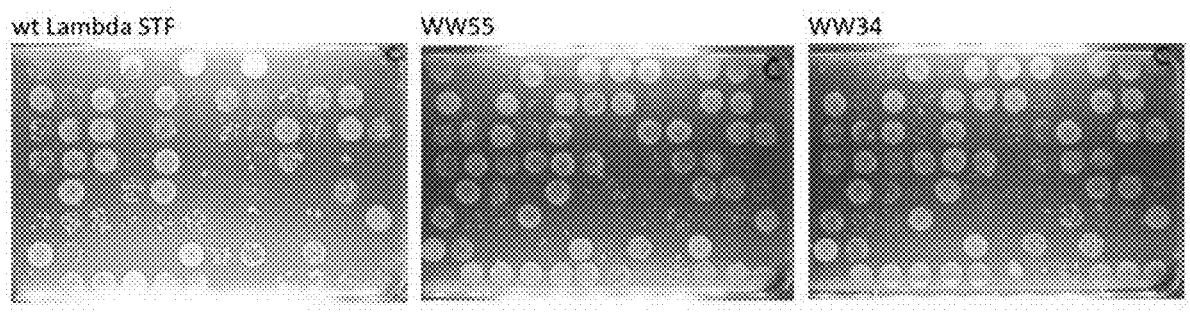
FIG. 9. demonstrates screening of phagemid particles with chimeric lambda stf-T4-like DTFs. A collection of 96 different wild type E. coli strains, encompassing different serotypes, was transduced with lambda-based phagemids and plated on Cm LB agar. Left panel, wild-type lambda stf; middle panel, chimeric lambda-stf-WW55; right panel, chimeric lambda-stf-WW34.

FIG. 9. shows screening of phagemid particles with chimeric lambda stf-T4-like DTFs. A collection of 96 different wild type *E. coli* strains, encompassing different serotypes, was transduced with lambda-based phagemids and plated on Cm LB agar. The left panel represents wild-type lambda stf; the middle panel represents chimeric lambda-stf-WW55; and the right panel represents chimeric lambda-stf-WW34.

Since T4-like DTF proteins may or may not share common sites for insertion, attempts were made to identify a universal insertion site that exists in all T4-like DTFs. When several T4-like DTFs are aligned, no homology along the whole DTF gene present in all the sequences exists, except for the N-terminus which is well conserved. The N-terminus of the DTF is thought to interact with the hinge connectors for attachment to the main phage particle.

Figure 10:
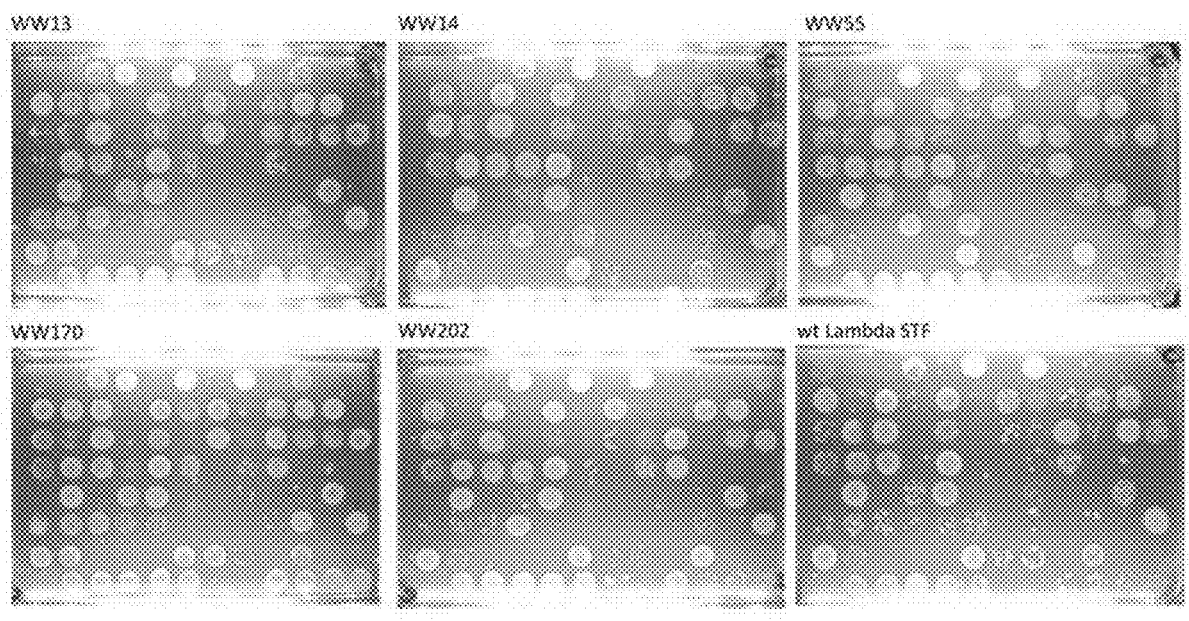
FIG. 10. depicts screening of phagemid particles with chimeric lambda stf-T4-like DTFs. All points shown refer to the universal insertion site of the DTF, located within aminoacid range from position 1 to 90 with reference to WW13 aminoacid sequence. A collection of 96 different wild type E. coli strains, encompassing different serotypes, was transduced with lambda-based phagemids and plated on Cm LB agar (names on top).

Although the classic view is that the host range determinants reside in the C-terminal part of the DTF, recent studies have proven that the N-terminus may also be involved in this process (Chen et al., 2017, Appl. Environ. Microbiol. V1. 83 No. 23). The N-terminus of the DTF was then scanned to look for an insertion site that exists in all T4-like phages and that is able to yield functional chimeras. Phage WW13 DTF and insertion site MDETNR (SEQ ID NO: 250) in lambda stf were used. While the direct fusion of the complete DTF gene (starting at amino acid 2) gives particles with some activity, a region from amino acid 1 to 90, with a preferred region from amino acid 40 to 50 of the DTF, that recapitulates the behavior of the DTF fusion was identified and is shown in FIG. 10. Importantly, this region exists in all T4-like phages screened and could be very rapidly used to generate chimeras with a diverse set of DTFs, including WW55 (FIG. 10).

Accordingly, the present disclosure is useful for the generation of phage and phagemid particles with altered host ranges, since it provides a practical framework for the construction of chimeras using the DTFs from any T4-like phage, highlighting its modularity and translatability.

Example 3

The human microbiome comprises different zones of the body, including gut, skin, vagina and mouth [29]. The microbiota in these areas is composed of different communities of microorganisms, such as bacteria, archaea and fungi [29]-[31]. While numerous studies have been made that try to elucidate the specific composition of these communities, it is becoming clear that while there may exist a "core microbiome", there are many variations in the relative content of each microorganism depending on several factors, such as geographical location, diet or age [32]-[35].

Specifically, in the case of the human gut microbiota, it is not possible to know a priori what are the bacterial species that a given person possesses without running a diagnostic method. In the case of *Escherichia coli*, some studies have been made that point out to the prevalence of some serotypes and phylogenetic groups in the majority of humans; however, there are significant changes in the composition of the samples depending on the geographic distribution as well as the time of sampling: for example, samples isolated from Europe, Africa, Asia and South America in the 1980s show a prevalence for phylogroups A and B1 (55% and 21%, respectively); but samples obtained in the 2000s in Europe, North America, Asia and Australia belong mainly to the B2 group (43%), followed by the A (24%), D (21%), and B1 (12%) [36]. It is also thought that phylogenetic groups B2 and D are usually more commonly associated with pathogenic strains than with commensal strains [37], but there are studies showing a number of human- and non-human-specific strains belonging to phylogenetic group B2 that are commensals and belong to different serotypes [38].

The intrinsic variability of the human microbiome, and specifically that of *Escherichia coli* subtypes, makes it difficult to design targeted therapeutic approaches. In the case of phage therapy aimed at killing a target bacterial population, for instance, two possible approaches are possible: first, the use of narrow host range particles that are able to recognize and target a specific *E. coli* serotype or second the use of broad host range phages that are able to recognize many different strains, sometimes even from different genera [39]. This difficulty is exacerbated if one takes into account strategies that do not aim to kill the target bacterial population, but that seek to add a function to them (i.e. delivery of a factor that will have an effect in the host and that will be expressed by the targeted microbiota). In this specific case, the use of packaged phagemids is of great interest, since they do not kill the host (unless their payload carries genes aimed at killing the host), payload does not replicate and expand and does not contain any endogenous phage genes. However, as in the case of phages, a diagnostic study would be needed to identify the specific serotypes/variants of bacteria that exist in the patient before the treatment in order to find or design a packaged phagemid that allows for delivery of a payload adding a function to the target bacteria without killing them.

By combining these two approaches, it was proposed to use engineered delivery vehicles that are able to recognize a large number of strains belonging to different serotypes and phylogenetic groups (i.e., engineered particles having a "broad host range"), with a focus on *Escherichia coli*. As opposed to a killing-oriented approach, where the targeted bacterial population needs to be as close as possible to 100% to reduce their numbers, a therapeutic delivery approach does not need a priori to reach a large percentage of bacteria; the delivery needs to be high enough for the therapeutic payload to be expressed at the correct levels, which may be highly variable depending on the application. Additionally, the payload can be expressed by different serotypes or phylogenetic groups. This approach increases the chance that the particle will deliver a payload expressed in vivo in the majority of patients.

To achieve the delivery in bacterial communities composed of unknown serotypes/variants of target strains, delivery vehicles were engineered to contain chimeric side tail fibers (stf) that have been selected due to their ability to recognize a large variety of target strains. There are many phages that have been described as having a broad host range in *E. coli* and many of these belong to the T4 family, although in general, phages against *E. coli* and related bacteria have a restricted host range.

However, according to [41], there is no consensus as to how many strains need to be targeted by a phage to be considered as a "broad host range".

In the case of *Escherichia coli*, the ECOR collection is a set of strains isolated from different sources that is thought to represent the variability of this bacterium in Nature [42]. Some phage have been shown to have a broad host range against this collection (for instance, about 53% of the ECOR strains can be lysed with phage AR1 [43] and about 60% with phage SU16 [44]). As opposed to this, a single phage is able to infect 95% of *Staphylococcus aureus* strains [40].

It was decided to use human strains of this collection to test engineered delivery vehicles with chimeric stf and assess their host range in an attempt to identify variants that are able to recognize as many hosts as possible, as has been described in the literature [45]. The difference is that the present assays measure delivery efficiency as opposed to lysis.

Strains from an overnight culture were diluted 1:100 in 600 uL of LB supplemented with 5 mM CaCl2 in deep 96 well plates and grown for 2 hours at 37° C. at 900 rpm. 10 uL of packaged phagemids produced at an average of $10^6$/uL were then added to 90 uL of the bacterial cultures, incubated 30 minutes at 37° C. and 10 uL of the mixtures plated on LB agar supplemented with 24 ug/mL chloramphenicol and incubated overnight at 37° C. The next day, the density of the dots was scored from 0 to 5, with 0 being no transductants and 5 being a spot with very high density [FIG. 11]. The density of the spots is directly related to the delivery efficiency of the packaged phagemids, since it corresponds to the number of bacteria that have received a payload containing a chloramphenicol acetyltransferase gene.

Figure 13:
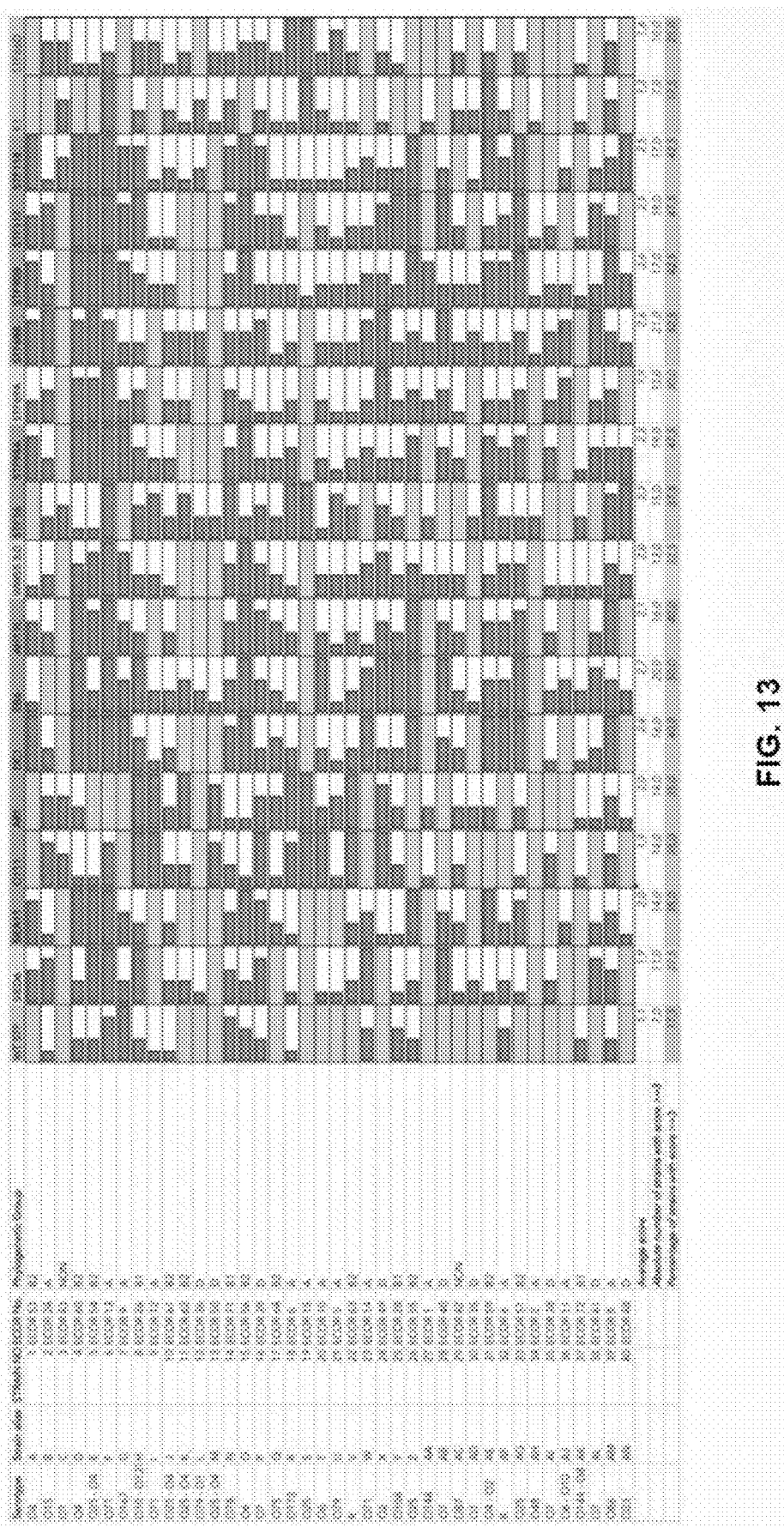
FIG. 13 represents bar-formatted delivery data of FIG. 12. From 0 (no entry, grey background) to 5 (maximum delivery). The bar length is proportional to the entry score from 1 (smallest bars) to 5 (longest bars).

Several stf chimeras were tested and screened in 40 human strains of the ECOR collection. As a control, the delivery efficiency of the wild-type stf was tested. The packaged phagemid variant used for the delivery experiments was modified so that its tail tip gpJ now recognizes a receptor other than LamB (1A2 variant)(SEQ ID NO: 214). In FIG. 12, the raw dot titrations for 18 stf are shown and in FIG. 13 a bar-formatted table is shown with the delivery efficiencies scored by dot density as well as the delivery statistics.

Taking only into account dots with density scores of 3 and higher (considered as medium to high delivery efficiency), some stf s can be considered as broad host range because the delivery efficiency in the selected ECOR strains is significantly higher than when using the wild type stf. For example, for stf EB6 or stf 68B, about 50% of the strains show medium to high delivery efficiencies, as compared to 17.5% of the strains with the wild type stf. These stf are good candidates for in vivo delivery, since they are able to deliver in different phylogenetic groups as well as serotypes. At the bottom of the Table in FIG. 13, a bar-formatted representation for density scores higher than 3 is shown, where the threshold for a broad host range stf is set at an increase of at least 2×compared to the basal line of the wild type stf; this is, stf that are able to deliver with scores of 3 and higher in at least 35% of the strains. Other stf also show an increased delivery as compared to the wild type stf, so a less stringent threshold was set for stf able to deliver with scores 3 or higher with at least a 50% increase compared to the number of strains delivered with the wild-type stf (this is, delivery with scores of 3 and higher in at least 26.25% of the strains). As a comparison, data for stf K1 and stf 66D is shown: these stf seem to be delivering efficiently in a small number of strains (for instance, strains B and AB for stf K1; and strains E and AF for stf 66D), which means that they probably have a narrow host range; this is to be expected, since in the case of the K1 stf the cognate receptor is the K1 capsule [46]. Additionally, data are shown for a chimera with a stf originating in a T4-like phage; as the literature suggests, this chimera shows a broad host range although it does not seem to be the best candidate.

Taken together, these results suggest that the stf of a delivery vehicle can be engineered to recognize a wide number of target *E. coli* strains, hence rendering it "broad host range". This type of particles can be very useful to deliver payloads adding a function to the target bacteria without having to engineer a specific variant that recognizes a given bacterial strain.

LIST OF REFERENCES CITED

Each of the reference cited within the specification and those listed below are hereby incorporated by reference in their entirety.

[1] G. P. C. Salmond and P. C. Fineran, "A century of the phage: past, present and future," Nat. Rev. Microbiol., vol. 13, no. 12, pp. 777-786, December 2015.

[2] P. Hyman and S. T. Abedon, "Bacteriophage host range and bacterial resistance," Adv. Appl. Microbiol., vol. 70, pp. 217-248, 2010.

[3] S. Chatterjee and E. Rothenberg, "Interaction of Bacteriophage λ with Its *E. coli* Receptor, LamB," Viruses, vol. 4, no. 11, pp. 3162-3178, November 2012.

[4] Nobrega et al, Nat Rev, 2018 "Targeting mechanisms of tailed bacteriophages"

[5] A. Flayhan, F. Wien, M. Paternostre, P. Boulanger, and C. Breyton, "New insights into pb5, the receptor binding protein of bacteriophage T5, and its interaction with its *Escherichia coli* receptor FhuA," Biochimie, vol. 94, no. 9, pp. 1982-1989, September 2012.

[5] M. G. Rossmann, V. V. Mesyanzhinov, F. Arisaka, and P. G. Leiman, "The bacteriophage T4 DNA injection machine," Curr. Opin. Struct. Biol., vol. 14, no. 2, pp. 171-180, April 2004.

[6] Y. Zivanovic et al., "Insights into Bacteriophage T5 Structure from Analysis of Its Morphogenesis Genes and Protein Components," J. Virol., vol. 88, no. 2, pp. 1162-1174, January 2014.

[7] R. W. Hendrix and R. L. Duda, "Bacteriophage lambda PaPa: not the mother of all lambda phages," Science, vol. 258, no. 5085, pp. 1145-1148, November 1992.

[8] M. A. Speed, T. Morshead, D. I. Wang, and J. King, "Conformation of P22 tailspike folding and aggregation intermediates probed by monoclonal antibodies," Protein Sci. Publ. Protein Soc., vol. 6, no. 1, pp. 99-108, January 1997.

[9] S. J. Labrie, J. E. Samson, and S. Moineau, "Bacteriophage resistance mechanisms," Nat. Rev. Microbiol., vol. 8, no. 5, pp. 317-327, March 2010.

[10] C. Whitfield, "Biosynthesis and assembly of capsular polysaccharides in *Escherichia coli*," Annu. Rev. Biochem., vol. 75, pp. 39-68, 2006.

[11] J. R. Meyer, D. T. Dobias, J. S. Weitz, J. E. Barrick, R. T. Quick, and R. E. Lenski, "Repeatability and contingency in the evolution of a key innovation in phage lambda," Science, vol. 335, no. 6067, pp. 428-432, January 2012.

[12] D. S. Gupta et al., "Coliphage K5, specific for *E. coli* exhibiting the capsular K5 antigen," FEMS Microbiol. Lett., vol. 14, no. 1, pp. 75-78, May 1982.

[13] R. J. Gross, T. Cheasty, and B. Rowe, "Isolation of bacteriophages specific for the K1 polysaccharide antigen of *Escherichia coli*," J. Clin. Microbiol., vol. 6, no. 6, pp. 548-550, December 1977.

[14] D. Schwarzer et al., "A Multivalent Adsorption Apparatus Explains the Broad Host Range of Phage phi92: a Comprehensive Genomic and Structural Analysis," J. Virol., vol. 86, no. 19, pp. 10384-10398, October 2012.

[15] F. Tétart, F. Repoila, C. Monod, and H. M. Krisch, "Bacteriophage T4 host range is expanded by duplications of a small domain of the tail fiber adhesin," J. Mol. Biol., vol. 258, no. 5, pp. 726-731, May 1996.

[16] E. Haggard-Ljungquist, C. Halling, and R. Calendar, "DNA sequences of the tail fiber genes of bacteriophage P2: evidence for horizontal transfer of tail fiber genes among unrelated bacteriophages.," J. Bacteriol., vol. 174, no. 5, pp. 1462-1477, March 1992.

[17] L.-T. Wu, S.-Y. Chang, M.-R. Yen, T.-C. Yang, and Y.-H. Tseng, "Characterization of Extended-Host-Range Pseudo-T-Even Bacteriophage Kpp95 Isolated on *Klebsiella pneumoniae*," Appl. Environ. Microbiol., vol. 73, no. 8, pp. 2532-2540, April 2007.

[18] D. Montag, H. Schwarz, and U. Henning, "A component of the side tail fiber of *Escherichia coli* bacteriophage lambda can functionally replace the receptor-recognizing part of a long tail fiber protein of the unrelated bacteriophage T4," J. Bacteriol., vol. 171, no. 8, pp. 4378-4384, August 1989.

[19] E. R. Vimr, R. D. McCoy, H. F. Vollger, N. C. Wilkison, and F. A. Troy, "Use of prokaryotic-derived probes to identify poly(sialic acid) in neonatal neuronal membranes," Proc. Natl. Acad. Sci., vol. 81, no. 7, pp. 1971-1975, April 1984.

[20] K. Stummeyer, A. Dickmanns, M. Mühlenhoff, R. Gerardy-Schahn, and R. Ficner, "Crystal structure of the polysialic acid-degrading endosialidase of bacteriophage K1F," Nat. Struct. Mol. Biol., vol. 12, no. 1, pp. 90-96, January 2005.

[21] D. Scholl, S. Adhya, and C. Merril, "*Escherichia coli* K1's Capsule Is a Barrier to Bacteriophage T7," Appl. Environ. Microbiol., vol. 71, no. 8, pp. 4872-4874, August 2005.

[22] Y. Jiang, B. Chen, C. Duan, B. Sun, J. Yang, and S. Yang, "Multigene Editing in the *Escherichia coli* Genome via the CRISPR-Cas9 System," Appl. Environ. Microbiol., vol. 81, no. 7, pp. 2506-2514, April 2015.

[23] J. E. Cronan, "Improved Plasmid-Based System for Fully Regulated Off-To-On Gene Expression in *Escherichia coli*: Application to Production of Toxic Proteins," Plasmid, vol. 69, no. 1, pp. 81-89, January 2013.

[24] J. E. Thompson et al., "The K5 Lyase Kf1A Combines a Viral Tail Spike Structure with a Bacterial Polysaccharide Lyase Mechanism," J. Biol. Chem., vol. 285, no. 31, pp. 23963-23969, July 2010.

[25] S. C. Potter, A. Luciani, S. R. Eddy, Y. Park, R. Lopez, and R. D. Finn, "HMMER web server: 2018 update," Nucleic Acids Res., vol. 46, no. W1, pp. W200-W204, July 2018.

[26] E. I. Marusich, L. P. Kurochkina, and V. V. Mesyanzhinov, "Chaperones in bacteriophage T4 assembly," Biochem. Biokhimiia, vol. 63, no. 4, pp. 399-406, April 1998.

[27] J. Xu, R. W. Hendrix, and R. L. Duda, "Chaperone-protein interactions that mediate assembly of the bacteriophage lambda tail to the correct length," J. Mol. Biol., vol. 426, no. 5, pp. 1004-1018, March 2014.

[28] D. Schwarzer et al., "Proteolytic Release of the Intramolecular Chaperone Domain Confers Processivity to Endosialidase F," J. Biol. Chem., vol. 284, no. 14, pp. 9465-9474, April 2009.

[29] J. A. Gilbert, M. J. Blaser, J. G. Caporaso, J. K. Jansson, S. V. Lynch, and R. Knight, "Current understanding of the human microbiome," Nat. Med., vol. 24, no. 4, pp. 392-400, April 2018.

[30] M. Kapitan, M. J. Niemiec, A. Steimle, J. S. Frick, and I. D. Jacobsen, "Fungi as Part of the Microbiota and Interactions with Intestinal Bacteria," Curr. Top. Microbiol. Immunol., vol. 422, pp. 265-301, 2019.

[31] V. D. Nkamga, B. Henrissat, and M. Drancourt, "Archaea: Essential inhabitants of the human digestive microbiota," Hum. Microbiome J., vol. 3, pp. 1-8, March 2017.

[32] M. Arumugam et al., "Enterotypes of the human gut microbiome," Nature, vol. 473, no. 7346, pp. 174-180, May 2011.

[33] M. I. McBurney et al., "Establishing What Constitutes a Healthy Human Gut Microbiome: State of the Science, Regulatory Considerations, and Future Directions," J. Nutr., vol. 149, no. 11, pp. 1882-1895, November 2019.

[34] R. Nagpal et al., "Gut microbiome and aging: Physiological and mechanistic insights," Nutr. Healthy Aging, vol. 4, no. 4, pp. 267-285.

[35] R. K. Singh et al., "Influence of diet on the gut microbiome and implications for human health," J. Transl. Med., vol. 15, April 2017.

[36] O. Tenaillon, D. Skurnik, B. Picard, and E. Denamur, "The population genetics of commensal *Escherichia coli*," Nat. Rev. Microbiol., vol. 8, no. 3, pp. 207-217, March 2010.

[37] F. L. Nowrouzian, A. E. Wold, and I. Adlerberth, "*Escherichia coli* strains belonging to phylogenetic group B2 have superior capacity to persist in the intestinal microflora of infants," J. Infect. Dis., vol. 191, no. 7, pp. 1078-1083, April 2005.

[38] M. Smati et al., "Quantitative analysis of commensal *Escherichia coli* populations reveals host-specific enterotypes at the intra-species level," MicrobiologyOpen, vol. 4, no. 4, pp. 604-615, August 2015.

[39] P. Hyman, "Phages for Phage Therapy: Isolation, Characterization, and Host Range Breadth," Pharmaceuticals, vol. 12, no. 1, March 2019.

[40] R. Pantůcek et al., "The polyvalent staphylococcal phage phi 812: its host-range mutants and related phages," Virology, vol. 246, no. 2, pp. 241-252, July 1998.
[41] A. Ross, S. Ward, and P. Hyman, "More Is Better: Selecting for Broad Host Range Bacteriophages," Front. Microbiol., vol. 7, September 2016.
[42] H. Ochman and R. K. Selander, "Standard reference strains of *Escherichia coli* from natural populations," J. Bacteriol., vol. 157, no. 2, pp. 690-693, February 1984.
[43] L. Goodridge, A. Gallaccio, and M. W. Griffiths, "Morphological, Host Range, and Genetic Characterization of Two Coliphages," Appl. Environ. Microbiol., vol. 69, no. 9, pp. 5364-5371, September 2003.
[44] M. K. Mirzaei and A. S. Nilsson, "Isolation of Phages for Phage Therapy: A Comparison of Spot Tests and Efficiency of Plating Analyses for Determination of Host Range and Efficacy," PLOS ONE, vol. 10, no. 3, p. e0118557, March 2015.
[45] E. C. Keen, "Tradeoffs in bacteriophage life histories," Bacteriophage, vol. 4, no. 2, p. e28365, April 2014.
[46] D. Scholl and C. Merril, "The Genome of Bacteriophage K1F, a T7-Like Phage That Has Acquired the Ability To Replicate on K1 Strains of *Escherichia coli*," J. Bacteriol., vol. 187, no. 24, pp. 8499-8503, December 2005.
[47] D Montag et al, «A component of the side tail fiber of *Escherichia coli* bacteriophage lambda can functionally replace the receptor-recognizing part of a long tail fiber protein of the unrelated bacteriophage T4» J. Bacteriol., 171(8), pp. 4378-4384, August 1989

Sequences
1) Insertion Point ADAKKS

STF-25
(SEQ ID NO: 2)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSETAAASSRNAAKTS
ETNAGNSAKAAASSKTAAQNAATAAERSETNARASEEASADSEEASRR
NAESAAENAGVATTKAREAAADATKAGQKKDEALSAATRAEKAADRAE
AAAEVTAEPCANIVPPLPDVWIPFNDSLDMIAGFSPGYKKIAIGDDVV
QVASDKQVNFSRASTATYINKSGELKTAEINEPRFECDGLLIEGQRTN
YMLNSESPASWGKSSNMDVPETGTDSFGFTYGKFVCNDSLVGQTSAIN
MASIAATKSVDVSGDNKYVTTSCRFKTERQVRLRIRFDKYDGSATTFL
GDAYIDTQTLEISMTGGAAGRITARVRKDKTTGWIFAEATIQAIDGEL
KIGSQIQYSPGQGGATVSGDYIYLATPQVENGPCVSSFIISGGSATTR
ASDLVSIPTRNNLYKLPFTFLLEIHKNWDIAPNAAPRVWDIAAANTGQ
SAIAAINRGSGKLYMSLSNPSGSYVNSAATDVFAEKTTFGCIAKADGH
FHVVTNGKAVNEVYCEYNGVTADKNIRFGGQTNTGERHLFGHIRNFRI
WHKELNDRQLKEVV

STF25-AP1
(SEQ ID NO: 3)
MKDLTLKFHDKLQFKAFLSSLGWAEDEDLQNKLLVDEIGFTYTETGVT
EEGEPVCIRNDGYFVNIRILDDLFDVSVFSDYVVELETPLREWS

STF-27
(SEQ ID NO: 4)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSETAAASSKNAAKTS
ETNAANSAQAAAASQTASANSATAAKKSETSAKNSETATKASEKNAKS
SQTAAKTSETNAKDSEANAKVSETAAANSAKASAASQTAAKASEDAAR
EYANQTAEPYRYVLQPLPDVWIPFNDSLDMITGYSPGYKKVKIGDNVV
QVASDKQVNFSRASTATYINKSGELKTAEINEPRFECDGLLIEGQRTN
FFQNSTDPSKWNKSTSLDVTETGTDSFGFNYGRFVVQDSIVGTSKAHT
IIGLYSSTGGVDTSGDEKHVTISCRVKSEVDNIAVRILFEHYDGEVRT
SIGAANLNLTTRIISKTGQTSRVTARSVKDDATGWIFFEATLKADTTE
NTVGGFVQYSPDTGQMVTSGDYLDVTTPQIEAGTGASSFIVTGTAPAT
RASDMVTVPIKNNLYNLPFTVLCEVHKNWYKTPNVAPRVFDTGGHQTG
AGIVMGFGSSGGYDGFPYCDIGGSDRRINENAGLEKMLIGMRVKSERS
TCVVSNGKLSSETKTKWEYIRSTATIRIGGQTTAGLRHLFGHVRNFRL
WHKELTDAQLGEVVE

STF27-AP1
(SEQ ID NO: 5)
VRDFTLRFSDKADFRAFLRKLNWEEDEELQNAVLVDEIGFTFRETDVS
DDGEPEYTRNEGYFVNIRLLDDGFEDSVFREWVVTPERPLREWF

STF27-AP2
(SEQ ID NO: 6)
MLPQHSDIEIAWYASIQQEPNGWKTVTTQFYIQEFSEYIAPLQDAVDL
EIATEEERSLLEAWNKYRVLLNRVDTSTAPDIEWPTSPAE

>STF-28
(SEQ ID NO: 7)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSETAAASSRNAAKTS
ETNAGNSAKAAASSKTAAQNAATAAERSETNARASEEASADSEEASRR
NAESAAENAGVATTKAREAAADATKAGQKKDEALSAATRAEKAADRAE
SAAEVTAEPCANIVPPLPDVWIPFNDSLDMITGFSPSYKKIVIGDDEI
TMPGDKIVKFKRASTATYINKSGQLKLAEVDEPRFERDGLLIEGQRTN
YLRNSNKPDSWTVHSALNKTFGTDKQGFNYATVTPTESIVGTTGGYTV
HGVVAADRFPLASGECFTFSCRVKGAKARCRLRVSVIIGGTDTFSADS
YLDLDTRIATVSGNTSLITAKAEQQGEWTYYEATYTANTDIDTVNCAF
YMTNKISNEPFYDDSTLTMTTPQIELGNTASSFIVTTMPTTRASDVVT
IPSANNLSTRPFTVLCEVRRNWSTPPNVAPRIFDVGGHSIDDNYLSLG
FVSTGKISANVGMVQPQISSDGERFIVGVRAKSDLSVNAICNGNYTTN
LNGKIFGVTATSYRFGGQTAAGTRHLFGHIRNFRVWFKELNDRQIKEA
V

STF28-AP1
(SEQ ID NO: 8)
MKDLTLKFPGNREFKSFLSSLDWEEDEDLQNKLLVDEIGFTYTETGVT
EEGEPVCIRNNGYFVNIRILDDLFDVSVFSDYVVELETPLREWS

2) Insertion Point SASAAA

STF-15 (SEQ ID NO: 9)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAAASATASANSQKAAKTSETNAKVSETAAANSAKASAASQTA
AKASEDAAREYASQAAEPYKYVLQPLPDVWIPFNDSLDMITGFSPSYK
KIVIGDDEITMPGDKVVKFKRASTATYINKSGVFSVAKIDEPRFEKEG
LLIEGQRTNYFVKSNTPAEWTSTSNIDKTNNGVDEFGFSYAKMRTKDN
MTGQSSALSLHRCSASRGIDVSGDNKYCTVSCRVKAPDGLRCRLRFEK
YDGSVYTFLGDAYLTFGTLIIEKTGGAANRIAATATKDPVTGWIFYEA
TIEAVEGETLIGAMIQYAPKKGGITEAGDYIYLATPQFENGGCASSFV
ITTTAPATRSSDMVTIPTKNNIYNRPLTCLVEVNRIWGDIPPNVAPRI
FDFSGVPPIESITYAFNTTEKYYGQLYMQTYKASTSTYVSSVFAGRAD
VRKFIGGFNIYSDGTKRVVSNGEATKTMKTEWTGVKTRTFIRIGGQAT
SGTRHLFGHLRNLRLWHKELTDAQMGESIK

STF15-AP1 (SEQ ID NO: 10)
MKDLTLKFADRADFSAFMESIGYYDDESMQDDILIDVIGNVYKETGEL
TEDGEPACVKEDGYFVNVRIINDSQISSLFDEHAVAVEHQLRSWM

STF15-AP2 (SEQ ID NO: 11)
MATSTVIPDDIKTLKGDVSKAKEDISSINVKVSTLQTDMDSAKQDIST
RYTKTEVDNKLKNKVEVNDLESGRYGGDFYPLTGREAFYLWGLGTTTA
AANLYLNPDPAISSVLRSTSSIRYKHSVETIDSEHADLIFRMRPVWYR
SQCENDRRDWGFYGLIAEEVGEIAPQFVHWRPANEDDAPETISSNGLV
AEGVMYERLVVPLIHHIQKLTERVDELESELKLLSTSQSDIG

STF-16 (SEQ ID NO: 12)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAAASATASANSQKAAKTSETNAKTSETAAANSAKASAASQTA
AKASEDAAREYASQAADPYKYVLQPLPDVWIPFNDSLDMITGFSPSYK
KIVIGDDEITMPGDKIVKFKRASKATYINKSGVLTEAAIDEPRFERDG
LLIEGQRTNLLLNSTNPSKWNKSGNLELTEISTDSFNFTYGRFTVKDT
LIGQTSAINIVTISGSKGFDVTGDEKYVTISCRVRSDVENIRCRLRFE

HHDGYTYTFLGDAYLNLSTLVIDKTGTAADRIIAKAVKDEVTGWIFYQ
ATINALDTESMIGAMVQYAPVKGSGTASGDYLDIATPQVEGGSSASSF
IVTDITASTRASDMVTVPIKNNLYNLPFTVLCEVHKNWYKTPNAAPRV
FDTGGHQTGAAIILGFGRSTDYDGFPYCDIGLANRRVNENASLEKMVM
GMRVKSDQSTCSVSNGRISSEKKATWSYIQNSAIIRIGGQTTAGLRHL
FGHVRNFRIWHKALTDAQMGESI

STF16-AP1 (SEQ ID NO: 13)
MKDLTLKFADRADFSAFMDSIGYYDDESMQDDILIDVIGNVYKETGEL
TEDGEPVCVKEDGYYVNVRIINDAKKSSIFDEYAVVVEHQLRGWM

STF16-AP2 (SEQ ID NO: 14)
MATSTVIPGDITTLKGDVSKAKEDISSSINGKVSTLQADMTSAKQDIST
RYTKTEVDNKLKNKLEVNALESGRYGGDFYPLTGREAFYLWGLGTTTA
AANLYLNPDPAISSVLRSTSSIRYKHSVETIDSEHADLIFRMRPVWYR
SQCENDRRDWGFYGLIAEEVGEIAPQFVHWRPANEDDAPEAISSNGLV
AEGVMYERLVVPLIHHIQKLTERVDELESELKLLSVSRSDIG

STF-17 (SEQ ID NO: 15)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAAGSKTAAALSASAASTSAGQASASATAAGKSAESAASSAST
ATTKAGKATEQATAAARSASAAKTSETNAKTSADNAASSKAAAASSAS
SAASSASSASASASKDEATRQASAAKGSATTASTKATEAAGSATAAAQSK
STAESAATRAETAAKRAEDIASAVALEDASTTKKGIVQLSSATNSTSE
SLAATPKAVKAVMGETNKKAPLNSPALTGTPTTPTARQGTNNTQIAST
AYVMAAIAALVDSSPDALNTLNELAAALGNDPNFATTMTSALAGKQPK
DATLTALAGLATAADRFPYFTGNDVASLATLTKVGRDILAKSTVAAVI
EYLGLRELGTSGEKIPLLSTANTWTNRQTFSGGLSGELSGNASTAAKL
KTARKISNVAFDGSSDITLKASHVGAFALGKTGSTVANDKAVGWNWSS
GAYNATISGASTLIIHFYMGEGSCPAAQFRINYKNGGIFYRSARDGYG
FEADWSEFYTTTRKPSAGDVGALPLSGGQLNGALGIGTSSALGGNSIV
LGDNDTGFKQNGDGNLDVYANNVHVMRFVSGSIQSNKTINITGRVNPS
DYGNFDSRYVKDVRLGSQQYYGVNNWQTWNFQCPSGHVLSGINVQDTG
SNSADNIAGVYYRPVQKYINGTWYNVASV

STF17-AP1 (SEQ ID NO: 16)
MMHLKNIKAGNAKTLEQYELTKKHGVIWLYSEDGKNWYEEVKNFQPDT
IKIVYDENNIIVAITKDASTLNPEGYSVVEIPDITANRRADDSGKWMF
KDGAVIKRVYTEEELRLQTENQKKILLQQAREKTQFWQTQLTLGIITD
SDRQQLMNWMRYVQQVETTDTSVLPVTFPEPPE

-continued

STF-13
(SEQ ID NO: 17)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAASSATASANSQKAAKTSETNAKASETAAANSAKASAASQTA
AKASEDAAREYASQAAEPYKQVLQPLPDVWIPFNDSLDMLAGFSPGYK
QITVGDDVIKMPSDKVVSFKRASGATYINKSGVLTVAEVDEPRFEREG
LLIEGQRTNYHLNSLTPSKWGATTSVTITESGVDEFGFTYGRFQIKDE
KIGTNTTMNIAAVSGGRGVDVTGTEKYVTTSCRVKSDSANIQCRIRFE
RYDGSAYFYLADAYLNITDMSIRKTGGGAARITARAEKESNGWIYFEV
TYQSEAIDNMVGSQIQIAPPVSPGTYLGGEYLDVTTPQFEGGSCASSF
IISDTVASTRASDIVTLPCKNNMASKPLTCMVEVNKNWSIAPNSAPRI
YDITGFKTKDDAFVFAFRNTAGSVGTPYVQFGNPISFPPGNYPRKIIA
VYRIKSDGKFQAGCNGVLSTPASTTWKSVSGATGIRTGGQTTAGLRHL
FGYIRNFRIWHKELTDAQMGEII

STF13-AP1
(SEQ ID NO: 18)
MRDLIIKFTDKADFSAFMKSAGYYDDESMQDDILIDVIGNVYKETGEL
TEDGEPVCVKEDGYFVNVRIINDAKKSSIFDKYAVVVEHQLRGWM

STF13-AP2
(SEQ ID NO: 19)
MATSTVIPGDITKLKGDVSKAKEDISSISRKVSTLQTEMTSAKQDISS
RYTKTEVDNKLKNKVEVNDLESGRYGGDFYPLTGREAFYLWNLATTTA
AANLYLNPDPAISSVLRSTSSIRYKHSVETIDSEHADLIFRMRPVWYR
SQCENDRRDWGFYGLIAEEVGEIAPQFVHWRPANEDDAPEAISSNGLV
AEGVMYERLVVPLIHHIQKLTERVDELESELKLLLTSRSDIR

STF-12
(SEQ ID NO: 20)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAAASATASANSQKAAKTSETNAKTSETAAANSAQASAASQTA
AKASEDAAREYASQAAEPYKYVLQPLPDVWIPFNDSLDMLAGFSPGYK
QITVGDDVIKMPSDKVVSFKRASGATYINKSGVLTVAEVDEPRFEREG
LLIEGQRTNYFRNSNTPEAWNNTGSVSVESFDSDKGFNYGRITVINEN
PTAQGYQAIAVNTNDAYTCPAGSYTTISCLTKSDNSRCRARFGKMSDN
GAFVFHSDAVLDPVTGNVVHGNNVTVTAERVGEWWLFTATLFADAEMI

ISSRFEILAMPGISIIPNGSTLDTAMPQAEIGSYRTSFIITEGAPGTR
SSDMVTIPVRNNIHRLPFSALVEVNKNWDIPPSKSPLIFNVKDYQENG
LFTHGFRGNNFSDAGSPFISMGGCNKYVATTQRKIISGFRCGADGDVQ
AVCNGELSVAAKTTWTSIVPRAVLRIGGQGTNGEYHLFGHIRNLRIWH
KELTDAQMGESIK

STF12-AP1
(SEQ ID NO: 21)
MKDLTLKFADRADFSAFMESIGYYDDESMQDDILIDVIGNVYKETGEL
TEDGEPVCVKEDGYFVNVRIINDVKKSSIFDKYAVVVEHQLRGWM

STF12-AP2
(SEQ ID NO: 22)
MATSTVIPGDITTLKGDVSKTKEDISSSINGKVSTLQTDMTSAKQDIST
RYTKTEVDNKLKNKLEVNDLESGRYGGDFYPLTGREAFYMWGLGTTTA
AANLYLNPDPAISSVLRSTSSIRYKHSVETIDSEHADLIFRMRPVWYR
SQCENDRRDWGFYGLIAEEVGEIAPQFVHWRPANEDDAPEAISSNGLV
AEGVMYERLVVPLIHHIQKLTERVDELESELKLLSVSRSDIG

STF-63
(SEQ ID NO: 23)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAANSATAAKKSETNAKNSESAAKVSETNAKASENKAKEYLDK
VGGLVSPMTQYDWPVVTGNESFYIKIAKLSDPGSNNCHVTLMVTNGGD
YGSPYGNIDFIEISARGLPSSLTADNVSRYLSIRRLGPTGLINSMQMR
YGLVKDDGFIEVWAFQRAFINGAKVAVLAQTARTELYIPDGFVKQTAA
PSGYVESPVVRIYDQLNKPTKADLGLSNAMLTGAFGLGGSGISTNGKM
SDVEILKALRDKGGHFWRGDKPTGSTATIYSHGSGIFSRCGDTWSAIN
IDYSTAKIKIYAGNDARLNNGTFSINELYGSANKPSKSDVGLGNVTND
AQVKKTGDTMTGDLTIKKGTPSVFLRADSGVTALRFYTGDNTERGIIY
AGPNTDSLGEVRIRAKTAGGTSGGDLVVRH

STF-62
(SEQ ID NO: 24)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAANSATAAKKSETNAKNSEAAAKVSETNAKASENKAKEYLDK
VGGLVSPMTQYDWPVVTASESLYIKIAKLSDPGTSRSHVTLMVTNAGN
YGSPYGNIDFIEISARGLPSSLSADNVSRHLSIRRLGSTGLTDNNQMR
YGLVKGDGFIEVWAFQGAFINDAKVAVLAQTTLNTELYIPDGFVKQTA

APSGYIEGNVVRIYDQVNKPTKADLGLSNAMLTGAFGLGGSGISTNGK
MSDVEILKALRDKGGHFWRGDKPTGSTATIYSHGSGIFSRCGDTWSAI
NIDYSTAKIKIYAGNDARLNNGTFSVNELYGSANKPSKSDVGLGNVTN
DAQVKKSGDVMSGDLDILKETPSIRLKSAKGTAHLWFMNNDGSERGVV
WSPENNESLGEIHIRAKNTKGESSGDFIVRHDGRVEARNLKITYKISA
ATAEFANTSTSSDNTTVSIKGSQHTPLVLTSNNTIKNLSIGFKVDDVD
QKYLGIAGDGDLYFGSYSDHTKNSKVITQAKLDSGVTVGGKTTFSDLA
TFNAGMAGSIEPETIDNKTIDLNDLIIANTVAGSVKYYQCKTVAGGAY
ITNKPDGVSGNFLLRVESTRKTTGSDYAIMQTLIGSDTKRIYVRFVVN
GSWTEWSQVVVSGWNQDVTVRSLTSTTPSKLGGGRVDVLGSTSDYSSM
NCAVRGVDSTGTNSAWSVGTSKNTGKMLCLKNHRSSAQVLLNGDDGAV
QLLSGTVNGATAQALTINKDEVNSTADLVIRKQTGTGNRFALLNSGNS
ELPVGIRVWGSSTRQNVFEVGTSTAYLFYAQKTSAGQLFDVNGAINCT
TLNQSSDRDLKDDILVISDATKAIRKMNGYTYTLRENGMPYAGVIAQE
VMEAIPEAVGSFTHYGEELQGPTVDGNELREETRYLNVDYAAVTGLLV
QFARETDDRVTALEEENTTLRQNLATADTRISTLENQVSELVALVRQL
TGSEH

STF-71
(SEQ ID NO: 25)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAASSATASANSQKAAKTSETNAKASETAAANSAKASAASQTA
AKASEDAAREYASQAAEPYKQVLQPLPDVWIPFNDSLDMITGFSPSYK
KIVIGDDEITMSGDKVVKFKRASKATYINKSGVLTEAAIDEPRFERDG
LLIEGQRTNYMLNSESPASWGRSSNMDVPETGTDNFGFTYGKFVCNDS
LIGQTSAINMASIAATKSVDVSGDNKHVTTSCRFKTELQVRLRIRFDK
YDGSATTFLGDAYIDTQTLEINMTGGAASRITARVRKDEATGWIFAEA
TIQAIDGELKIGSQIQYSPKQGGATVSGDYIYLATPQVENGPCVSSFI
ISGTTAATRASDIVTVPIKNNLYNLPFTVLCEVHKNWYKTPNAAPRVF
DTGGHQTGAAIILGFGSSADYDGFPYCDIGGANRRVNENALLEKMVMG
MRVKSDQSTCSVSNGRISSETKTTWSYIQNTAIIRIGGQTTAGLRHLF
GHVRNFRIWHKALTDAQVGESI

STF71-AP1
(SEQ ID NO: 26)
MKDLTLKLADRADFSAFMESTGYYDDESMQDDILIDVIGNVYKETGEL
NEDGEPVCVKEDGYFVNVRIINDVKTPSIFDEYVVAVEHQLRGWM

3) Insertion Point MDETNR

STF-20
(SEQ ID NO: 27)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRRLAKNQNGADIQDKSAFLDNIGVTSLTFMKNNGEMPVDA
DLNTFGPVKAYVGVWYKSTSSNATLEKNFPEDGAVGVLEVFNGGNFSG
MQRYTTRTGNVYMRNLSGTWNGSDGPWIYWRQIQSATRPLSTTIDLNT
LGGAEHLGLWRNSSGSIASFDRNYPEEGSYGQGFLEVLEGGGYSRTQR
YTTRRNVYVRCLSAIWNAQNPQWEPWSRVGHQSECRYYEGDLNDLTSP
GIYSVTGKASNGPMQDTAGATLLGILEVIRRFDGVSVWQRYTTTGKSE
TTQGRTFERVYAGSKWTEWREVYNSFSLPLNLGIGGAVAKLSSLDWQT
YDFVPGSLITVRLDNMTNIPDGMDWGVIDGNLINISVGPSDDSGSGRS
MHVWRSTVSKANYRFFMVRISGNPGSRTITTRRVPIIDEAQTWGAKQT
FSAGLSGELSGNAATATKLKTARKINNVSFDGTSDINLTPKNIGAFAS
GKTGDTVANDKAVGWNWSSGAYNATIGGASTLILHFNIGEGSCPAAQF
RVNYKNGGIFYRSARDGYGFEADWSEFYTTTRKPTAGDVGALPLSGGQ
LNGALGIGTSSALGGNSIVLGDNDTGFKQNGDGNLDVYANSVHVMRFV
SGSVQSNKTINITGRVNPSDYGNFDSRYVRDVRLGTRVVQTMQKGVMY
EKAGHVITGLGIVGEVDGDDPAVFRPIQKYINGTWYNVAQV

STF20-AP1
(SEQ ID NO: 28)
MQHLKNITAGNPKTVAQYQLTKNFDVIWLWSEEGKNWYEEVSNFQEDT
IKIVYDENNIIVGITRDASTLNPEGFSVVEVPDITANRRADDSGKWMF
KDGAVIKRIYTADEQLQLAELQKSALLSEAETIIQPLERSVRLNMATD
DERSRLEAWERYSVLVSRVDPANPEWPEMPQ

STF-23
(SEQ ID NO: 29)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRKAPLNSPALTGTPTTPTARQGTNNTQIASTAFVMAAIAA

LVDSSPDALNTLNELAAALGNDPNFATTMTNALAGKQPKDATLTALAG
LATAADRFPYFTGNDVASLATLTKVGRDILAKSTVAAVIEYLGLRELG
TSGEKIPLLSTANTWTNRQTFSGGLSGGLSGNAATATKLKTARKIAGV
GFDGSSDISISAKNVNAFALRQTGNTVNGDTSVGWNWDSGAYNALIGG
ASALILHFNINAGSCPAVQFRVNYKNGGISYRSARDGYGFELGWSDFY
TTTRKPSAGDVGAYTRAECNSRFITGIRLGGLSSVQTWNGPGWSDRSG
YVVTGSVNGNRDELIDTTQARPIQYCINGTWYNAGSI

STF23-AP1
(SEQ ID NO: 30)
MMHLKNITAGNPKTKEQYQLTKQFNIKWLYSDDGKNWYEEQKNFQPDT
LKMVYDHNGVIICIEKDVSAINPEGASVVELPDITANRRADISGKWLF
KDGVVIKRTYTEEEQRQQAENEKQSLLQLVRDKTQLWDSQLRLGIISD
ENKQKLTEWMLYAQKVESTDTSSLPVTFPEQPE

STF-24
(SEQ ID NO: 31)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRRLQKDQNGADIPDKRLFLRNIGATNSTTMSFSGGTGWFR
LATVTMPQASSVVYISLIGGAGYNVNSPMQAGISELVLRAGNGNPKGL
TGALWRRTSVGFTNFAWVNTSGDTYDVYVEIGNYATGVNIQWDYTSNA
SVTIHTSPTYTANKPTGLTDGTVYVIYSSYIKPTAADVGALSLSGGQL
NGALGIGTSSALGGNSIVLGDNDTGFKQNGDGNLDVYANSVHVMRFVS
GSVQSNKTINITGRVNPSDYGNFDSRYVRDVRLGTRVVQTMQKGVMYE
KAGHVITGLGIVGEVDGDDPAVFRPIQKYINGTWYNVAQV

STF24-AP1
(SEQ ID NO: 32)
MQHLKNITAGNPKTVAQYQLTKNFDVIWLWSEEGKNWYEEVSNFQEDT
IKIVYDENNIIVGITRDASTLNPEGFSVVEVPDITANRRADDSGKWMF
KDGAVIKRIYTADEQLQLAELQKSALLSEAETIIQPLERSVRLNMATD
EERSRLEAWERYSVLVSRVDPANPEWPEMPQ

O111-2.0
(SEQ ID NO: 33)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRKAPLNSPALTGTPTTPTAPQGTNSTQIASTAFVMAAIAA
LVDSSPDALNTLSELAAALGNDPNFATTMTNALAGKQPKDATLTALAG
LVTAADRFPYFTGNDVASLATLTEVGRDILAKSTVAAVIEYLGLQETV
NQASGALQKNQNGADIPGKDTFTKNIGACRAYSAWLNIGGDSQVWTTA
QFISWLESQGAFNHPYWMCKGSWAYANNKVITDTGCGNICLAGAVVEV
IGTRGAMTIRVTTPSTSSGGGITNAQFTYINHGDAYAPGWRRDYNTKN
QQPAFALGQTGSRVANDKAVGWNWNSGVYNADISGASTLILHFNMNAG
SCPAVQFRVNYRNGGIFYRSARDGYGFEANWSEFYTTTRKPSAGDVGA
YTQAECNSRFITGIRLGGLSSVQTWNGPGWSDRSGYVVTGSVNGNRDE
LIDTTQARPIQYCINGTWYNAGSI

O111 2.0-AP1
(SEQ ID NO: 34)
MMHLKNITAGNPKTKEQYQLTKQFNIKWLYSEDGKNWYEEQKNFQPDT
LKMVYDHNGVIICIEKDVSAINPEGASVVELPDITANRRADISGKWMF
KDGVVVKRTYTEEEQRQQAENEKQSLLQLVRDKTQLWDSQLRLGIISD
ENKQKLTEWMLFAQKVESTDTSSLPVTFPEQPE

STF-74
(SEQ ID NO: 35)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRKYTAQDASTAQKGLVKLSSATDSTSETLAATPKAVKAVN
DNANGRVPSERKVNGHSLAGDISVTSQDIFDGQCVEIGPGQDLDNYQT
PGLYFQPANANTSAALHYPENNAGSLMVLRSAGITQVYRVYSGSRSYL
RSKYSTQPWTTWTPDDAFPVGAPIPWPSDTAPPAYALMQGQSFDKSAY
PLLAVAYPSGVIPDMRGQTIKGKPDGRAVLSYEQDGIKSHAHTASISD
TDLGTKYTNSFDYGSKPTTSFDYGNKSSTEGGWHVHNFRYCATSAYRD
TPGSGLGMHSSNISWSAGDRIEGSGNHAHVTWIGPHDHWVGIGEHNHY
VVMGYHGHTATVHATGNTENTVKNIAFNYIVRLA

STF74-AP1
(SEQ ID NO: 36)
MAFEMTGENRTIILYNLRSDTNEFIGKSDGFIPANTGLPAYSTDIAPP
KVTAGFVAVFDAQTNKWSRVEDYRGTTVYDISTGKPAVIEKLGALPDN
VVSVAPDGEYVKWDGAKWIHDAEAEKTFRQGQAAQEKSNLLMIATSAI
APLQDAVDLDMATEDEATALNEWKKYRVMLNRVKPEDAPDITWPELPA

STF-86

(SEQ ID NO: 37)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRRVPASRKVNGHALNGDINVTSRDIFDGQVIAIGANKNLD
DYQVPGLYFQEANNNTSAAMNYPENSAGSLMVLRGAGVTQVYRVYNSS
RSYSRSKYSTLAWTPWMPEDSYPVGAPIPWPSDVTPTGYALMQGQPFD
KAVYPLLAIAYPAGIIPDMRGQTIKGKPNGRAVLSYEQDGVISHTHGA
SISDTDLGTKYTSSFDYGSKPTTSFDYGNKSSTEGGWHAHNFRYCATS
AYRDTPGQGLGMHSSNVSWAAGDRIEGSGNHAHVTWIGPHDHWVGIGA
HNHYVVMGYHGHTATVHAAGNAENTVKNIAFNYIVRLA

STF86-AP1

(SEQ ID NO: 38)
MTFEMTGENRTITIYNLRADTNEFIGKSDGFIPANTGLPANSTNIAPP
PMKAGFVAVFNSASEKWSLVEDHRGKIVYDILTGKSITIDELGQLPDD
VVSVAPEGHFVKWNGKKWVHDADAEKTAQIITQATQQKDSLLALAASKI
APLQDAVDLDIATEEETALLLAWKKYRVLINRIKPEDAPDIDWPEVPG
DVA

STF-84

(SEQ ID NO: 39)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRKYTAQDATTAQKGIVQLSNATNSTSEMLAATPKSVKAAY
DLANGKYTAQDATTAQKGIVQLSSATNSASETLAATPKAANDNANGRV
PSARKVNGKALSADITLTPKDIGTLNSTTMSFSGGAGWFKLATVTMPQ
ASSVVSITLIGGAGFNVGSPQQAGISELVLRAGNGNPKGITGALWQRT
STGFTNFAWVNTSGDTYDIYVAIGNYATGVNIQWDYTSNASVTIHTSP
AYSANKPEGLTDGTVYSLYTPSGQFYPPGAPIPWPSDTVPSGYALMQG
QTFDKSAYPKLAAAYPSGVIPDMRGWTIKGKPASGRAVLSQEQDGIKS
HTHSASASSTDLGTKTTSSFDYGTKSTNNTGAHTHSVSGTAASAGNHT
HSVTGASAVSQWSQNGSVHKVVSAASVNTSAAGAHTHSVSGTAASAGA
HAHTVGIGAHTHSVAIGSHGHTITVNAAGNAENTVKNIAFNYIVRLA

STF84-AP1

(SEQ ID NO: 40)
MAFRMSEQPRTIKIYNLLAGTNEFIGEGDAYIPPHTGLPANSTYIAPP
DIPAGFVAVFNSDEGSWHLVEDHRGKTVYDVASGDALFISELGPLPEN
VTWLSPEGEFQKWNGTAWVKDAEAEKLFRIREAEETKNSLMQVASEHI
APLQDAVDLEIATEEETSLLEAWKKYRVLLNRVDTSTAPDIEWPTNPV
RE

STF-93

(SEQ ID NO: 41)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRRVPSNRKVNGKALTADITLTPKDIGTLNSVTMSFSGGAG
WFKLATVTMPQASSIVYIALIGGAGYNVGSPHQAGISELVLRAGNGNP
KGITGALWKRTAVGLTNFAWINTSGDTYDIYVEIGNYATSVNIHWDCT
ANATVSIYTSPTYSASKPSSVTDGVVYTMYSTHQKPTPLDIGALPTTG
GTVSGPLSVTGGITGTLNGNASTATKLQTARSIGGVGFDGSANINLPG
VNTTGNQNTTGNAATATKLQTARTIGGVSFDGTANINLPGVNTTGNQN
TTGNAATATKLQTARTINGVSFDGSANISLSPANIGCPASPTGWLTTG
SNGGAITTAQLVTLLQNNGAFNTKSWIARCAWAYANSATIPNSETGCG
VIPLAGAVIEVFNNGSSSNNYTIRITTATTTSVSGALTNAEFIYVFNG
TDYSPGWRRVYNTKNKPTASDVGALPLTGGTLSGGLTSSGEIISKYAN
GFRIAYGSFGFFIRNDGSNTYFMLTASGDTLGSWNGLRPITINNTSGA
VSIGNGLNVTGGVNGSLNGNASTATKLQTARNINGVKFDGSGDININT
LVSRGRVTALSGSTQGTAGIQMYEAYNNSYPTTYGNVLHMKGASAAGE
GELLIGWSGTSGAHAPVFIRSRRDTTDAAWSAWAQLYTAKDSIPGVNT
TGNQNTTGNAATATKLQTARKIAGVAFDGSADITLTAANLNAYTKTEV
TNLLSSYASRSSLTGYSGNLDIIAETLVVKSGGSGGFAIWDIGTTTSG
ANMYIDPNPGINTVWRSTSSRRYKKDIETLQDRYADELLSLRPVWYRS
ICRGDRKDWGYYGLIAEEVGEIAPQYVHWREPTNNDSPEDISSNGMVA
EGVMYERLVVPLIHHIQQLTKRVEELETKLNSPKE

>STF-95

(SEQ ID NO: 42)
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL

```
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRRVPSARKVNGKALSADITLTPKDIGTLNSTTMSFSGGAG
WFKLATVTMPQASSVVSITLIGGAGFNVGSPQQAGISELVLRAGNGNP
KGITGALWQRTSTGFTNFAWVNTSGDTYDIYVAIGNYATGVNIQWDYT
SNASVTIHTSPAYSANKPEGLTDGTVYSLYTPSEQFYPPGAPIPWPSD
TVPSGYALMQGQTFDKSAYPKLAAAYPSGVIPDMRGWTIKGKPASGRA
VLSQEQDGIKSHTHSASASSTDLGTKNTSSFDYGTKSTNNTGAHTHSL
SGSTGSAGDHTHGNGIRWPGGGGSALAFYDGGGFTYVQDSQYQVSPGT
SSRRSYYQRIQTQSAGAHTHSLSGTAASSGAHAHTVGIGAHTHSVAIG
SHGHTITVNAAGNAENTVKNIAFNYIVRLA
```

STF95-AP1
(SEQ ID NO: 43)
```
MAFRMSEQARTIKIYNLLAGTNEFIGEGDAYIPPHTGLPANSTDIAPP
DIPAGFVAVFNSDEASWHLVEDHRGKTVYDVASGDELFISELGPLPEN
VTWLSPEGEFQKWNGTAWVKDTEAEKMFRIREAEETKNNLMQVASEHI
APLQDAADLEIATEEETSLLEAWKKYRVLLNRVDTSTAPDIEWPTNPV
RE
```

STF-132
(SEQ ID NO: 44)
```
MAVKISGVLKDGTGKPVQNCTIQLKARRNSTTVVVNTVGSENPDEAGR
YSMDVEYGQYSVILQVDGFPPSHAGTITVYEDSQPGTLNDFLCAMTED
DARPEVLRRLELMVEEVARNASVVAQSTADAKKSAGDASASAAQVAAL
VTDATDSARAASTSAGQAASSAQEASSGAEAASAKATEAEKSAAAAES
SKNAAATSAGAAKTSETNAAASQQSAATSASTAATKASEAATSARDAV
ASKEAAKSSETNASSSAGRAASSATAAENSARAAKTSETNARSSETAA
ERSASAAADAKTAAAGSASTASTKATEAAGSAVSASQSKSAAEAAAIR
AKNSAKRAEDIASAVALEDADTTRKGIVQLSSATNSTSETLAATPKAV
KVVMDETNRAVQRDGDTMTGELKIRGVNALRIFNDAFGLIFRRSEECL
HLIPTSEGQGENGDIGPLRPFTINLRTGEISMSHKVSVGGGSQVNGAL
GIGVQNALGGNSIAFGDNDTGIKQNGDGILDVYANGQHVFRFQNGALQ
SHRAVNVSGRVTPTDYGNFDERYQTKTGGVQNFQYTSEVFHKPAGNEV
SWVFRAPSGCTLSGINVQETGSNSADNIGGVYYKQAQIYINGAWRSVS
G
```

STF132-AP1
(SEQ ID NO: 45)
```
MALSIRLIKAKIMELRNVTRYYPENMPYGEGVQYFRSEDGQDFYESLD
KFAKKYKLCTHPETGVIYSMAEDVSRLYPAGFTIVEVDELPDGFCIEA
RWYYKDGEVLPVPVDYRLLAESERARLTAIAEREISDKKTDLLLGIIN
NGEKEMLKLWRMYIRNLKNIDFNHIHDKSSFDSIKWPCDPENSH
```

4) Insertion Point GAGENS

K1F
(SEQ ID NO: 46)
```
MAVKISGVLKDGTGKPVQNCTIQLKARRNSTTVVVNTVGSENPDEAGRYSMDVEYGQYSVILQVDGFPPSHAGTITVYEDSQPGTLN
DFLCAMTEDDARPEVLRRLELMVEEVARNASVVAQSTADAKKSAGDASASAAQVAALVTDATDSARAASTSAGQAASSAQEASSGAE
AASAKATEAEKSAAAAESSKNAAATSAGAAKTSETNAAASQQSAATSASTAATKASEAATSARDAVASKEAAKSSETNASSSAGRAA
SSATAAENSARAAKTSETNARSSETAAERSASAAADAKTAAAGSASTASTKATEAAGSAVSASQSKSAAEAAAIRAKNSAKRAEDIA
SAVALEDADTTRKGIVQLSSATNSTSETLAATPKAVKVVMDETNRKAPLDSPALTGTPTAPTALRGTNNTQIANTAFVLAAIADVID
ASPDALNTLNELAAALGNDPDFATTMTNALAGKQPKNATLTALAGLSTAKNKLPYFAENDAASLTELTQVGRDILAKNSVADVLEYL
GAGENSGAKGDGVTDDTAALTSALNDTPVGQKINGNGKTYKVTSLPDISRFINTRFVYERIPGQPLYYASEEFVQGELFKITDTPYY
NAWPQDKAFVYENVIYAPYMGSDRHGVSRLHVSWVKSGDDGQTWSTPEWLTDLHPDYPTVNYHCMSMGVCRNRLFAMIETRTLAKNA
LTNCALWDRPMSRSLHLTGGITKAANQRYATIHVPDHGLFVGDFVNFSNSAVTGVSGDMTVATVIDKDNFTVLTPNQQTSDLNNAGK
NWHMGTSFHKSPWRKTDLGLIPSVTEVHSFATIDNNGFAMGYHQGDVAPREVGLFYFPDAFNSPSNYVRRQIPSEYEPDASEPCIKY
YDGVLYLITRGTRGDRLGSSLHRSRDIGQTWESLRFPHNVHHTTLPFAKVGDDLIMFGSERAENEWEAGAPDDRYKASYPRTFYARL
NVNNWNADDIEWVNITDQIYQGGIVNSGVGVGSVVVKDNYIYYMFGGEDHFNPWTYGDNSAKDPFKSDGHPSDLYCYKMKIGPDNRV
SRDFRYGAVPNRAVPVFFDTNGVRTVPAPMEFTGDLGLGHVTIRASTSSNIRSEVLMEGEYGFIGKSIPTDNPAGQRIIFCGGEGTS
STTGAQITLYGANNTDSRRIVYNGDEHLFQSADVKPYNDNVTALGGPSNRFTTAYLGSNPIVTSNGERKTEPVVFDDAFLDAWGDVH
YIMYQWLDAVQLKGNDARIHFGVIAQQIRDVFIAHGLMDENSTNCRYAVLCYDKYPRMTDTVFSHNEIVEHTDEEGNVTTTEEPVYT
EVVIHEEGEEWGVRPDGIFFAEAAYQRRKLERIEARLSALEQK
```

K5

(SEQ ID NO: 47)
MAVKISGVLKDGTGKPVQNCTIQLKARRNSTTVVVNTVGSENPDEAGRYSMDVEYGQYSVILQVDGFPPSHAGTITVYEDSQPGTLN

DFLCAMTEDDARPEVLRRLELMVEEVARNASVVAQSTADAKKSAGDASASAAQVAALVTDATDSARAASTSAGQAASSAQEASSGAE

AASAKATEAEKSAAAAESSKNAAATSAGAAKTSETNAAASQQSAATSASTAATKASEAATSARDAVASKEAAKSSETNASSSAGRAA

SSATAAENSARAAKTSETNARSSETAAERSASAAADAKTAAAGSASTASTKATEAAGSAVSASQSKSAAEAAAIRAKNSAKRAEDIA

SAVALEDADTTRKGIVQLSSATNSTSETLAATPKAVKVVMDETNRKAPLDSPALTGTPTAPTALRGTNNTQIANTAFVLAAIADVID

ASPDALNTLNELAAALGNDPDFATTMTNALAGKQPKNATLTALAGLSTAKNKLPYFAENDAASLTELTQVGRDILAKNSVADVLEYL

GAGENSPKTEGILHKGQSLYEYLDARVLTSKPFGAAGDATTDDTEVIAASLNSQKAVTISDGVFSSSGINSNYCNLDGRGSGVLSHR

SSTGNYLVFNNPRTGRLSNITVESNKATDTTQGQQVSLAGGSDVTVSDVNFSNVKGTGFSLIAYPNDAPPDGLMIKGIRGSYSGYAT

NKAAGCVLADSSVNSLIDNVIAKNYPQFGAVELKGTASYNIVSNVIGADCQHVTYNGTEGPIAPSNNLIKGVMANNPKYAAVVAGKG

STNLISDVLVDYSTSDARQAHGVTVEGSDNVINNVLMSGCDGTNSLGQRQTATIARFIGTANNNYASVFPSYSATGVITFESGSTRN

FVEVKHPGRRNDLLSSASTIDGAATIDGTSNSNVVHAPALGQYIGSMSGRFEWRIKSMSLPSGVLTSADKYRMLGDGAVSLAVGGGT

SSQVRLFTSDGTSRTVSLTNGNVRLSTSSTGYLQLGADAMTPDSTGTYALGSASRAWSGGFTQAAFTVTSDARCKTEPLTISDALLD

AWSEVDFVQFQYLDRVEEKGADSARWHFGIIAQRAKEAFERHGIDAHRYGFLCFDSWDDVYEEDANGSRKLITPAGSRYGIRYEEVL

ILEAALMRRTIKRMQEALAALPK

STF-37

(SEQ ID NO: 48)
MAVKISGVLKDGTGKPVQNCTIQLKARRNSTTVVVNTVGSENPDEAGRYSMDVEYGQYSVILQVDGFPPSHAGTITVYEDSQPGTLN

DFLCAMTEDDARPEVLRRLELMVEEVARNASVVAQSTADAKKSAGDASASAAQVAALVTDATDSARAASTSAGQAASSAQEASSGAE

AASAKATEAEKSAAAAESSKNAAATSAGAAKTSETNAAASQQSAATSASTAATKASEAATSARDAVASKEAAKSSETNASSSAGRAA

SSATAAENSARAAKTSETNARSSETAAERSASAAADAKTAAAGSASTASTKATEAAGSAVSASQSKSAAEAAAIRAKNSAKRAEDIA

SAVALEDADTTRKGIVQLSSATNSTSETLAATPKAVKVVMDETNRKAPLDSPALTGTPTAPTALRGTNNTQIANTAFVLAAIADVID

ASPDALNTLNELAAALGNDPDFATTMTNALAGKQPKNATLTALAGLSTAKNKLPYFAENDAASLTELTQVGRDILAKNSVADVLEYL

GAGENSELSGEHGSFLIGGVIDCYSTVSDLISSSPSVGRVCRTIGYYSPGDGGGADYIISIGTPMQDFSDSGSIVIDECKFAKLIQQ

SQYDLKQFGVKPSDPSYAEKNDIFISQAITRSRVGRCKIIISDVIYHKKPLIFDYYNHMEGSCIGSDPEFTPRFIKIDNTTSGLPDM

GYPGVADVVSYDVDAGIIIKRQNSGTSFARGFIIKGFLLQSEKKSAWAIYAPHMADFDIDIDSRGFNGGIRWFVNFLGRMAGRHIGL

GANSSDPTLSIGAWCSKFSTIPDCGNSVVFRLSFNGFNRGMQMEYFGNGVLDRVTLENISKPTPTSPTTHGIYATDTWLTGQVSCES

SSTCIIRAGNNANFDITLSAVFHVTQDDPSEGIVHVLNGGRLTLRSSTILADLADTKIINENGGYLDIAANTRTGNIVYSNSDNYRF

KDRTIGFGQTAATTKTSFSSGEEITFSLLNGTPKANLSGGTIQFNSPCLIKITVQGRGITSGALTFGINGESSESVSQGQQVSMVVG

VVSGDILNLKATSSLTLGSAGGVRVLLEPVN

1JL (SEQ ID NO: 49)
MAVKISGVLKDGTGKPVQNCTIQLKARRNSTTVVVNTVGSENPDEAGRYSMDVEYGQYSVILQVDGFPPSHAGTITVYEDSQPGTLN

DFLCAMTEDDARPEVLRRLELMVEEVARNASVVAQSTADAKKSAGDASASAAQVAALVTDATDSARAASTSAGQAASSAQEASSGAE

AASAKATEAEKSAAAAESSKNAAATSAGAAKTSETNAAASQQSAATSASTAATKASEAATSARDAVASKEAAKSSETNASSSAGRAA

SSATAAENSARAAKTSETNARSSETAAERSASAAADAKTAAAGSASTASTKATEAAGSAVSASQSKSAAEAAAIRAKNSAKRAEDIA

SAVALEDADTTRKGIVQLSSATNSTSETLAATPKAVKVVMDETNRKAPLDSPALTGTPTAPTALRGTNNTQIANTAFVLAAIADVID

ASPDALNTLNELAAALGNDPDFATTMTNALAGKQPKNATLTALAGLSTAKNKLPYFAENDAASLTELTQVGRDILAKNSVADVLEYL

GAGENSGYKVQSLAILSDTQAVHDATNTIKTQTDKIKADTQAIKTQTNQIKTETGVIRDKANTAKTDAQAASAAAQGFRDQAKEWAQ

SVNADNLLTKTGNLAGLTDKSAARSNLGLGSVATENTVPIKKGGTAATTVAAARSNLGLGSVATENTVPIEKGGTAATTAAKARSNL

GLGSVATENTVPIEKGGTAATTAAKARSNFGLGDNNKVKLGTLRLNGGESLVFNDVERNGLIISNASFGIDSWVGQTMHKWYTDWTR

-continued

AGLVRAGDAHLSDYRVHVWKDGFTEALFRFLPDGRLISGNSGNPSVNEFQKAPLSDRDLKKEIKYTDGEESYNRVRQWLPAMFKYKE

SDVQRYGLIAQDLARIDPEYVHLLPGYAIYEDVKGVDEEGNEVVVDRKEIGYTDDVLSLDSNVLLMDLCAAFVHLLHKVEKLEGK

STF-48

(SEQ ID NO: 50)

MAVKISGVLKDGTGKPVQNCTIQLKARRNSTTVVVNTVGSENPDEAGRYSMDVEYGQYSVILQVDGFPPSHAGTITVYEDSQPGTLN

DFLCAMTEDDARPEVLRRLELMVEEVARNASVVAQSTADAKKSAGDASASAAQVAALVTDATDSARAASTSAGQAASSAQEASSGAE

AASAKATEAEKSAAAAESSKNAAATSAGAAKTSETNAAASQQSAATSASTAATKASEAATSARDAVASKEAAKSSETNASSSAGRAA

SSATAAENSARAAKTSETNARSSETAAERSASAAADAKTAAAGSASTASTKATEAAGSAVSASQSKSAAEAAAIRAKNSAKRAEDIA

SAVALEDADTTRKGIVQLSSATNSTSETLAATPKAVKVVMDETNRKAPLDSPALTGTPTAPTALRGTNNTQIANTAFVLAAIADVID

ASPDALNTLNELAAALGNDPDFATTMTNALAGKQPKNATLTALAGLSTAKNKLPYFAENDAASLTELTQVGRDILAKNSVADVLEYL

GAGENSQLESDADGMGDALVAVKQPYIGSIALTQHDKNTNFISAKDFGATADGTLHPLSEKFSTLSAAQAVYPFVTSLTQSLDYAGI

QAAINTGRNVLLTSGTYFVNATIEMNSNCTINGETNSNINRPETFIAVIGNIACFHYHAAFNTINIENVYIFYDGGRPTSPTGNDGK

IGILIDGGTTSPGVMHIKNVEVDGAWWAIYDDSGNYLTKYTQVWARRVAHGFYKANGTTIQWDTCYVLDAAQAWYVVNCLSPQLINC

AGDQITVDGSQYTFDSSGLYFSGCKCLTITGYDGESNIIKNTNGITASYIKLNDTIAHISGLAGHGNSMQTTGSGTAAFIFATGTSI

VNIKSSTDSFLDSESITYTGSGYPNTLLTDSTAKIIAEGCRFKAPTGGTPVISTYSTGNGVFTDCSLTGTQTSGSYVESRSSAGNQL

PAVYTAKGTQAVAANVATTLFELPNSQGMYLISVWAESSGTNFSSLQLAMWDGTTLTLTPLKSGGLISFTVTGRIVTITSQGTTTFN

WTYTKAG

STF-49

(SEQ ID NO: 51)

MAVKISGVLKDGTGKPVQNCTIQLKARRNSTTVVVNTVGSENPDEAGRYSMDVEYGQYSVILQVDGFPPSHAGTITVYEDSQPGTLN

DFLCAMTEDDARPEVLRRLELMVEEVARNASVVAQSTADAKKSAGDASASAAQVAALVTDATDSARAASTSAGQAASSAQEASSGAE

AASAKATEAEKSAAAAESSKNAAATSAGAAKTSETNAAASQQSAATSASTAATKASEAATSARDAVASKEAAKSSETNASSSAGRAA

SSATAAENSARAAKTSETNARSSETAAERSASAAADAKTAAAGSASTASTKATEAAGSAVSASQSKSAAEAAAIRAKNSAKRAEDIA

SAVALEDADTTRKGIVQLSSATNSTSETLAATPKAVKVVMDETNRKAPLDSPALTGTPTAPTALRGTNNTQIANTAFVLAAIADVID

ASPDALNTLNELAAALGNDPDFATTMTNALAGKQPKNATLTALAGLSTAKNKLPYFAENDAASLTELTQVGRDILAKNSVADVLEYL

GAGENSGAIGDGVHDDTSALSELLSVATGGEKIDGRGLTFKVSTLPDVSRFKNARFLFERIPGQPLFYASEDFIQGELFKITDTPWY

NAWTQDKTFVYDNVIYAPFMAGDRHGVNNLHVAWVRSGDDGRTWTTPEWLTDLHENYPTVNYHCMSMGVVRNRLFAVIETRTVSGNK

LQVAELWDRPMSRSLRAYGGITKAANQQVAYIRITDHGLFAGDFVNFSNSGVTGVTGNMTVTTVIDKNTFTVTTQNTQDVDQNNEGR

YWSFGTSFHSSPWRKTSLGTIPSFVDGSTPVTEIHSFATISDNSFAVGYHNGDIGPRELGILYFSDAFGSPGSFVRRRIPAEYEANA

SEPCVKYYDGILYLTTRGTLSTQPGSSLHRSSDLGTSWNSLRFPNNVHESNLPFAKVGDELIIFGSERAFGEWEGGEPDNRYAGNYP

RTFMTRVNVNEWSLDNVEWVNVTDQIYQGGIVNSAVGVGSVCIKDNWLYYIFGGEDFLNPWSIGDNNRKYPYVHDGHPADLYCFRVK

IKQEEFVSRDFVYGATPNRTLPTFMSTSGVRTVPVPVDFTDDVAVQSLTVHAGTSGQVRAEVKLEGNYAIIAKKVPSDDVTAQRLIV

SGGETTSSADGAMITLHGSGSSTPRRAVYNALEHLFENGDVKPYLDNVNALGGPGNRFSTVYLGSNPVVTSDGTLKTEPVSPDEALL

DAWGDVRYIAYKWLNAVAIKGEEGARIHHGVIAQQLRDVLISHGLMEEESTTCRYAFLCYDDYPAVYDDVITGQREMPLTDNDGSII

VDEDDNPVMVMEDIIERVEITPAGSRWGVRPDLLFYIEAAWQRREIERIKARLDLIEGKH

STF-52

(SEQ ID NO: 52)

MAVKISGVLKDGTGKPVQNCTIQLKARRNSTTVVVNTVGSENPDEAGRYSMDVEYGQYSVILQVDGFPPSHAGTITVYEDSQPGTLN

DFLCAMTEDDARPEVLRRLELMVEEVARNASVVAQSTADAKKSAGDASASAAQVAALVTDATDSARAASTSAGQAASSAQEASSGAE

AASAKATEAEKSAAAAESSKNAAATSAGAAKTSETNAAASQQSAATSASTAATKASEAATSARDAVASKEAAKSSETNASSSAGRAA

SSATAAENSARAAKTSETNARSSETAAERSASAAADAKTAAAGSASTASTKATEAAGSAVSASQSKSAAEAAAIRAKNSAKRAEDIA

SAVALEDADTTRKGIVQLSSATNSTSETLAATPKAVKVVMDETNRKAPLDSPALTGTPTAPTALRGTNNTQIANTAFVLAAIADVID

ASPDALNTLNELAAALGNDPDFATTMTNALAGKQPKNATLTALAGLSTAKNKLPYFAENDAASLTELTQVGRDILAKNSVADVLEYL

-continued

GAGENSQLASSEDGMGDALVAVKQPYIGSIALTQHDKNTNFISAKDFGATADGTLHPLSEKFSTLSAAQAVYPFVTSLTQSLDYAGI
QAAINTGRNVLLTSGTYFVNATIEMNSNCTINGETNSNINRPETFIAVIGNIACFHYHAAFNTINIENVYIFYDGGRPTSPTGNDGK
IGILIDGGTTSPGVMHIKNVEVDGAWWAIYDDSGNYLTKYTQVWARRVAHGFYKANGTTIQWDTCYVLDAAQAWYVVNCLSPQLINC
AGDQITVDGSQYTFDSSGLYFSGCKCLTITGYDGESNIIKNTNGITASYIKLNDTIAHISGLAGHGNSMQTTGSGTAAFIFATGTSI
VNIKSSTDSFLDSESITYTGSGYPNTLLTDSTAKIIAEGCRFKAPTGGTPVISTYSTGNGVFTDCSLTGTQTSGSYVESRSSAGNQL
PAVYTAKGTQAVAANVATTLFELPNSQGMYLISVWAESSGTNFSSLQLAMWDGTTLTLTPLKSGGLISFTVTGRIVTITSQGTTTFN
WTYTKAG

1AR (SEQ ID NO: 53)

MAVKISGVLKDGTGKPVQNCTIQLKARRNSTTVVVNTVGSENPDEAGRYSMDVEYGQYSVILQVDGFPPSHAGTITVYEDSQPGTLN
DFLCAMTEDDARPEVLRRLELMVEEVARNASVVAQSTADAKKSAGDASASAAQVAALVTDATDSARAASTSAGQAASSAQEASSGAE
AASAKATEAEKSAAAAESSKNAAATSAGAAKTSETNAAASQQSAATSASTAATKASEAATSARDAVASKEAAKSSETNASSSAGRAA
SSATAAENSARAAKTSETNARSSETAAERSASAAADAKTAAAGSASTASTKATEAAGSAVSASQSKSAAEAAAIRAKNSAKRAEDIA
SAVALEDADTTRKGIVQLSSATNSTSETLAATPKAVKVVMDETNRKAPLDSPALTGTPTAPTALRGTNNTQIANTAFVLAAIADVID
ASPDALNTLNELAAALGNDPDFATTMTNALAGKQPKNATLTALAGLSTAKNKLPYFAENDAASLTELTQVGRDILAKNSVADVLEYL
GAGENSIATRVSKEGDTMTGKLTLSAGNDALVLTAGEGASSHIRSDVGGTNNWYIGKGSGDNGLGFYSYITQGGVYITNNGEIALSP
QGQGTFNFNRDRLHINGTQWTAHQGGGWENQWNQEAPIFIDFGNVGNDSYYPIIKGKSGITNEGYISGVDFGMRRITNTWAQGIIRV
GNQENGSDPQAIYEFHHNGVLYVPNMVKTGARLSAGGGDPVWQGACVVIGDNDTGLVHGGDRINMVANGMHIASWSSAYHLHEGLW
DTTGALWTEQGRAIISFGHLVQQSDAYSTFVRDVYVRSDIRVKKDLVKFENASEKLSKINGYTYMQKRGLDEEGNQKWEPNAGLIAQ
EVQAILPELVEGDPDEALLRLNYNGVIGLNTAAINEHTAEIAELKSEIEELKKIVKSLLK

1AR-AP1

(SEQ ID NO: 54)

MAVTGPWVGSSAVVNTGQNWMVGAAQRLRMGAPFWMSNMIGRSVEVIHTLGADHNFNGQWFRDRCFEAGSAPIVFNITGDLVSYSRD
VPLFFMYGDTPNEYVQLNIHGVTMYGRGGNGWAAGAIGASDGGVCIQNDIGGRLRINNGGAIAGGGGGGGGYSQANNWAGKYVCGGG
GGRPFGLGGNNGARWPGGNASLTSPGAGGNTGTRYYAGGGGEVGQPGQYANPGAGYSTPPTSPGAAVAGSAPTWQNVGAIYGPRV

1AR-AP2

(SEQ ID NO: 55)

MSEQTIEQKLSAEIVTLKSRILDTQDQAARLMEESKILQGTLAEIARAVGITGDTIKVEEIVEAVKNLTAESTDEAKDEE 13-13.0

(SEQ ID NO: 56)

MAVKISGVLKDGTGKPVQNCTIQLKARRNSTTVVVNTVGSENPDEAGRYSMDVEYGQYSVILQVDGFPPSHAGTITVYEDSQPGTLN
DFLCAMTEDDARPEVLRRLELMVEEVARNASVVAQSTADAKKSAGDASASAAQVAALVTDATDSARAASTSAGQAASSAQEASSGAE
AASAKATEAEKSAAAAESSKNAAATSAGAAKTSETNAAASQQSAATSASTAATKASEAATSARDAVASKEAAKSSETNASSSAGRAA
SSATAAENSARAAKTSETNARSSETAAERSASAAADAKTAAAGSASTASTKATEAAGSAVSASQSKSAAEAAAIRAKNSAKRAEDIA
SAVALEDADTTRKGIVQLSSATNSTSETLAATPKAVKVVMDETNRKAPLDSPALTGTPTAPTALRGTNNTQIANTAFVLAAIADVID
ASPDALNTLNELAAALGNDPDFATTMTNALAGKQPKNATLTALAGLSTAKNKLPYFAENDAASLTELTQVGRDILAKNSVADVLEYL
GAGENSIIQLEDSQGAHFSTERTLATGAIKTRFFGETFTDGTLYLNQMNNSSERFSINNWGNSEVGRPAVLEVGDSKGYHFYTERGT
DNSLNFDVAGNFTVHGPSGITIKTSTGARHIWFRDDSDAEKAVIWATDEGILHIRNNYGGSFSHHFQGAMILAGERVPYNSEYALIR
GNISGGAWVDWRGRPAGLLVDCQDSRNQAYNIWKATHWGDQHLAAMGVHAGGGNPQVVLHVGGNDYAFASNGDFTAGAAVYCNDVYI
RSDRRLKINVKDYEENAVDKVNKLKVKTYDKVKSLSDREVIGHEIGIIAQDLQEVLPEAVSTSSVGSQDNPEEILTISNSAVNALLI
KAIQEMSEEIKELKTPLFTKIARKISKYFKF 13-13.0-AP1

(SEQ ID NO: 57)

MAVVGVPGWIGSSAVNETGQRWMSQAAGQLRLGVPCWMSQFAGRSREIIHTLGADHNFNGQWFRDRCFEAGSTPIVFNITGDLVSYS
KDVPLFFMYGDTPNEYVQLNIHGVTMYGRGGNGGSNSPGSAGGHCIQNDIGGRLRINNGGAIAGGGGGGGGGRYGRLSFGGGGGRPF
GAGGSSSHMSSGATAGTISAPGAGSVGEGSLWVYTGGSGGNVGAAGGRCNIQGNGTEYDGGAAGYAVIGSAPTWINVGAIYGPRV 13-13.0-AP2

(SEQ ID NO: 58)
MSEQTIEQKLSAEIVTLKSRILDTQDQAARLMEESKILQGTLAEIARAVGITGDTIKVEEIVEAVKNLTAESADEAKDEE

5. Insertion Point SAGDAS 13-14.3

(SEQ ID NO: 59)
MAVKISGVLKDGTGKPVQNCTIQLKARRNSTTVVVNTVGSENPDEAGRYS
MDVEYGQYSVILQVDGFPPSHAGTITVYEDSQPGTLNDFLCAMTEDDARP
EVLRRLELMVEEVARNASVVAQSTADAKKSAGDASISDDIGWMHYIQRNK
DNTVEAVLNGQQTINENIIAKKDIWVDRAVHTLGEITTNAVNGLRIWNND
YGVIFRRSEGSLHIIPTAFGEGETGDIGPLRPLSIALDTGKVTIPDLQSS
YNTFAANGYIKFVGHGAGAGGYDIQYAQAAPIFQEIDDDAVSKYYPIVKQ
KFLNGKSVWSLGTEIESGTFVIEIFILKEDGSQGHASRFNQDGTVNFPDN
VLVGGDINMKGMMTFDAGRLGSRDYFKFNHWGDSNNGRDNIIQLEDSQGA
HFSTERTLATGAIKTRFFGETFTDGTLYLNQMNNSSERFSINNWGNSEVG
RPAVLEVGDSKGYHFYTERGTDNSLNFDVAGNFTVHGPSGITIKTSTGAR
HIWFRDDSDAEKAVIWATDEGILHIRNNYGGSFSHHFQGAMILAGERVPY
NSEYALIRGNISGGAWVDWRGRPAGLLVDCQDSRNQAYNIWKATHWGDQH
LAAMGVHAGGGNPQVVLHVGGNDYAFASNGDFTAGAAVYCNDVYIRSDRR
LKINVKDYEENAVDKVNKLKVKTYDKVKSLSDREVIGHEIGIIAQDLQEV
LPEAVSTSSVGSQDNPEEILTISNSAVNALLIKAIQEMSEEIKELKTPLF
TKIARKISKYFKF 13-14.3-AP1

(SEQ ID NO: 60)
MAVVGVPGWIGSSAVNETGQRWMSQAAGQLRLGVPCWMSQFAGRSREIIH
TLGADHNFNGQWFRDRCFEAGSTPIVFNITGDLVSYSKDVPLFFMYGDTP
NEYVQLNIHGVTMYGRGGNGGSNSPGSAGGHCIQNDIGGRLRINNGGAIA
GGGGGGGGGRYGRLSFGGGGGRPFGAGGSSSHMSSGATAGTISAPGAGSV
GEGSLWVYTGGSGGNVGAAGGRCNIQGNGTEYDGGAAGYAVIGSAPTWIN
VGAIYGPRV 13-14.3-AP2

(SEQ ID NO: 61)
MSEQTIEQKLSAEIVTLKSRILDTQDQAARLMEESKILQGTLAEIARAVG
ITGDTIKVEEIVEAVKNLTAESADEAKDEE

Nucleotide Sequences

```
>STF-25
                                                                    (SEQ ID NO: 62)
ATGGCAGTAAAGATTTCAGGAGTCCTGAAAGACGGCACAGGAAAACCGGTACAGAACTGCACCATTCAGCTGAAAGCCAGACGTAACA
GCACCACGGTGGTGGTGAACACGGTGGGCTCAGAGAATCCGGATGAAGCCGGGCGTTACAGCATGGATGTGGAGTACGGTCAGTACAG
TGTCATCCTGCAGGTTGACGGTTTTCCACCATCGCACGCCGGGACCATCACCGTGTATGAAGATTCACAACCGGGGACGCTGAATGAT
TTTCTCTGTGCCATGACGGAGGATGATGCCCGGCCGGAGGTGCTGCGTCGTCTTGAACTGATGGTGGAAGAGGTGGCGCGTAACGCGT
CCGTGGTGGCACAGAGTACGGCAGACGCGAAGAAATCAgaaacagcagcggcatcgtccaggaacgcggcgaaaacatcagagacgaa
tgcaggtaacagcgcgaaagcggcagcttcttcaaaaacagccgcacaaaacgcagcaacagcggcagaacgttcagagacaaatgcc
cgtgcgtcagaagaagcctccgcagacagtgaagaggcttccgccgtaatgcagagtcagccgctgaaaatgccggagtcgccacca
caaaagcgcgggaggccgcagcagacgcaacaaaggccgggcagaaaaaggatgaggctctgtcggcagcgacacgagctgaaaaggc
ggcagaccgcgcagaagccgcagcggaagtgactgcagagccctgtgcgaatatagtgccgccgctgcctgatgtgtggataccgttt
aacgattcactggatatgattgcgggttttctccgggctataaaaaaatagctattggtgacgatgtggttcaggtcgccagtgata
aacaggttaatttcagtcgcgcatcaacggcaacatatatcaacaaatctggcgaactgaaaacgcgcgaaattaatgagccgcgatt
tgagtgtgatggcctgcttattgagggacaaagaacgaactacatgctcaattcggaaagtccagccagctgggggaagtcatcaaac
atggatgtgcccgaaaccgggacggatagttttggttttacttatggaaagtttgtctgcaacgattctctggttgggcaaacttcgg
ctattaatatggcatcaattgctgcaacaaagtcagttgatgtctcaggcgataacaagtacgtgacaacctcatgccgttttaaaac
agaacgacaggtaaggttacgtatacggtttgataagtatgatggtagtgcaacaacttttcttggcgatgcgtacattgatacgcaa
acgcttgaaattagtatgacaggtggtgctgccggcagaattacggcacgagtcaggaaggataagaccacgggctggattttgcag
aggcaacgattcaggcaattgatggtgagttaaaaataggctctcagatacagtattctcctgggcagggtggggcaacagtatctgg
tgactatatttatcttgccacccccacaagtagagaatgggccgtgtgtatcatcatttattatttcaggaggcagcgcaacgacaaga
gccagtgatttggttagtatccccaccagaaaataatctttataagttaccatttacttttttacttgagattcataaaaactgggata
ttgcaccaaacgccgcaccccgcgtgtgggatatagcagcagccaataccgggcaatcagcaattgcagcaatcaacagaggtagtgg
```

-continued taagttatatatgagtctgtcaaaccccttcaggctcgtatgttaatagcgcagcgacagatgtatttgcagagaaaaccacatttgga
tgtattgcaaaagctgatggtcactttcatgtggtgacaaatggtaaagcggttaatgaagtttattgtgaatataatggcgtgaccg
ctgataaaaatatccgatttggagggcagacgaatactggagaacgacatctgtttggccatattcgcaatttccgcatatggcataa
agaattaaatgacaggcaattaaaagaggtcgta

STF-25-AP1

(SEQ ID NO: 63)

atgaaagatttaactttgaagtttcatgacaaactgcagtttaaggccttcctgtcatctcttggctgggcggaagatgaagacctcc
agaataaactgttagttgatgaaattggtttcacctacacagaaacaggggtaacagaagagggagaacctgtctgtatccggaatga
tggttattttgtcaacattcgcattcttgatgacttgtttgatgtttctgtattctctgattatgtcgtggagctggaaacaccgctt
cgggaatggagc

STF-27

(SEQ ID NO: 64)

ATGGCAGTAAAGATTTCAGGAGTCCTGAAAGACGGCACAGGAAAACCGGTACAGAACTGCACCATTCAGCTGAAAGCCAGACGTAACA
GCACCACGGTGGTGGTGAACACGGTGGGCTCAGAGAATCCGGATGAAGCCGGGCGTTACAGCATGGATGTGGAGTACGGTCAGTACAG
TGTCATCCTGCAGGTTGACGGTTTTCCACCATCGCACGCCGGGACCATCACCGTGTATGAAGATTCACAACCGGGGACGCTGAATGAT
TTTCTCTGTGCCATGACGGAGGATGATGCCCGGCCGGAGGTGCTGCGTCGTCTTGAACTGATGGTGGAAGAGGTGGCGCGTAACGCGT
CCGTGGTGGCACAGAGTACGGCAGACGCGAAGAAATCAgaaacggcagcagcctcatcgaagaatgcggcgaaaacctcagaaacgaa
tgcagctaacagcgcacaggcggcagcggcctcgcgactgcatcggcaaactccgcgacagcagccaaaaatcagaaaccagcgcga
aaatagcgagacagccacaaaggccagcgaaaaaaacgcaaaatccagccagacggcagcgaaaaccagtgagacgaatgccaaaga
cagtgaagccaacgcaaaggtgagcgaaacagcggcggcgaactcggcgaaagcatcggcagcaagccagacggcagcaaaagcaagt
gaagatgctgccagagaatacgcaaaccagacagcagagccgtacagatatgttttacagccgctgccggatgtgtggatacccttta
atgattcgctggatatgattacgggctattctccgggttataaaaaagtgaagattggtgataatgtggttcaggttgccagtgataa
acaggttaatttcagtcgcgcatcaacggcaacatatatcaacaaatctggcgaactgaaaacggcggaaattaatgagccgcgattt
gagtgtgatggcctgcttattgagggacaaagaacgaacttcttccagaacagtacagaccttcgaagtggaataagtcaacttcac
tggacgttacagaaacaggcacagatagtttcgggtttaattatggtcggtttgtcgtacaggattcgattgttggtacaagtaaagc
gcataccattatcggactgtattcgagtaccggaggggttgatacttcaggggacgaaaagcatgtaactatatcctgtcgggtaaaa
agtgaagttgataatatcgccgttcgtattttatttgaacattatgatggggaggtaaggacatcaataggagcagcaaacctgaacc
ttaccacccgcataattagcaagacaggtcagacaagccgtgttacagcaaggtctgttaaggatgatgcaactggctggatattttt
tgaggctacattaaaagcagatacaacagaaaatacggttggtggttttgtccagtattctccggatacagggcagatggttacatca
ggggattatctcgatgtaaccactccacagattgaggctggtacaggcgcatcatctttttattgttacggggacggcaccggcaacgc
gggcaagcgatatggtgacagtcccaatcaagaataaccctttataatcttccttttacggttctttgtgaggtacataagaactggta
taaaacgccaaatgtagcgccgcgtgttttgataccggcggtcatcaaaccggagcggggatcgtaatggggtttggttcatcaggt
gggtacgacggttttccgtattgcgatataggtggttcagaccgacgaataaatgaaatgccgggctggaaaaaatgcttattggta
tgcgggtaaagtccgaacggtccacatgtgtagtcagtaacggtaagttaagcagcgaaactaaaaccaatgggaatatatccggag
tacagcaaccattcgcattggtggacaaactacagcaggattacgccatttatttgggcatgtgaggaattttcgtctctggcataaa
gagctaacagatgcgcagcttgggaggttgtggag

STF27-AP1

(SEQ ID NO: 65)

gtgagagatttcacgttgcgtttcagtgataaagcagatttcagggcatttctcaggaaacttaactgggaagaggacgaagagctgc
agaatgccgttctggttgatgagattggttttacgttcaggagacagatgtttctgatgacggagaaccagaatacacgcgaaacga
agggtacttgttaatatccgtcttcttgacgatggatttgaggattccgtgttccgtgagtgggtggttacaccagagcgcccgctc
agggagtggttt

STF27-AP2

(SEQ ID NO: 66)

atgctgccgcagcatagcgatattgaaatagcctggtatgcttcgatacagcaggagccgaatggctggaagaccgtcaccacacagt tctacatccaggaattcagtgagtatattgcgccactgcaggatgctgtagatctggaaatcgcaacggaggaagaaagatcgttgct ggaggcatggaataaatatcgggtattgttgaatcgtgttgatacatcaactgcacctgatattgagtggccgacttcacctgcagag

STF-28

(SEQ ID NO: 67)

ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAgaaacagcagcggcatcgtccaggaacgcggcgaaaacatcagagacgaa tgcaggtaacagcgcgaaagcggcagcttcttcaaaaacagccgcacaaaacgcagcaacagcggcagaacgttcagagacaaatgcc cgtgcgtcagaagaagcctccgcagacagtgaagaggcttcccgccgtaatgcagagtcagccgctgaaaatgccggagtcgccacca caaaagcgcgggaggccgcagcagacgcaacaaaggccgggcagaaaaaggatgaggctctgtcggcagcgacacgagctgaaaaggc ggcagaccgcgcagaatccgcagcggaagtgactgcagagccctgtgcgaatatagtgccgccgctgcctgatgtgtggataccgttt aacgattcgctggatatgattacgggttttttcgccatcttataaaaagattgttattggtgacgatgaaataacaatgccaggcgaca agattgttaagtttaaacgtgcttcaacagcaacgtatattaataagtccggccaactcaagcttgctgaagttgacgaaccgcgatt tgagcgcgatggcttattgattgaaggacagaggacaaattatctgaggaactcaaataaaccagactcatggactgttcattccgca ctgaataaaacatttggcactgataaacaggggttcaattatgccacggtgacacccacggaaagtatagtgggaacaacaggtggct atactgtgcatggtgtggttgcagcagacagattcccgctggcaagtggtgaatgtttcacttttttcgtgccgggttaaaggcgctaa agcacgatgcaggttaagagtttcagttattattggtggaacagatacattctctgctgactcttatcttgatctggatacccggatc gcaacagtaagcggtaatacatcccttataacagccaaagctgaacaacagggcgagtggacctactatgaggccacttatacagcta atacggacattgataccgttaactgtgcttttttatatgacaaataaaataagtaatgagccattctatgatgactcaacattaaccat gacgacgccgcaaattgaactgggcaatacggcatcgtcatttattgtaactacaatgccaacaacacgcgcaagtgatgtggttact atcccctcggcgaataacctgtcaacacggccttttacagtattgtgcgaagtaaggaggaactggagtacaccgcccaatgttgcgc caaggatatttgatgttggagggcacagtattgatgataattatttatcgctggggtttgtttcaacaggaaagataagcgccaacgt aggaatggttcagccacaaatttcctcagatggagaaaggttcattgtgggtgtgagagctaaatctgatttatcagtaaatgcaata tgcaatggtaattatacaacaaaccttaatggtaaaatatttggagttacagcaacatcgtaccggtttggtgggcagaccgcagcag gaacgcgtcatttgtttggacacatcagaaatttcagagtctggtttaaagaattaaatgacaggcaaatcaaggaggcagta

STF28-AP1

(SEQ ID NO: 68)

atgaaagatttaactttgaaatttcctggtaacagagagtttaaatccttcctgtcatctcttgactgggaggaagatgaagacctcc agaataaactgttagtcgatgaaattggtttcacctacacagaaacaggggtaactgaagagggagaacctgtctgtatccggaataa cggttattttgtcaacattcgcattcttgatgacttgtttgatgtttctgtattctctgattatgtcgtggagctggaaacaccgctt cgggaatggagc

55

2) Insertion Point SASAAA

STF-15

(SEQ ID NO: 69)

ATGGCAGTAAAGATTTCAGGAGTCCTGAAAGACGGCACAGGAAAACCGGTACAGAACTGCACCATTCAGCTGAAAGCCAGACGTAACAGC

ACCACGGTGGTGGTGAACACGGTGGGCTCAGAGAATCCGGATGAAGCCGGGCGTTACAGCATGGATGTGGAGTACGGTCAGTACAGTGTC

ATCCTGCAGGTTGACGGTTTTCCACCATCGCACGCCGGGACCATCACCGTGTATGAAGATTCACAACCGGGGACGCTGAATGATTTTCTC

TGTGCCATGACGGAGGATGATGCCCGGCCGGAGGTGCTGCGTCGTCTTGAACTGATGGTGGAAGAGGTGGCGCGTAACGCGTCCGTGGTG

-continued

```
GCACAGAGTACGGCAGACGCGAAGAAATCAGCCGGCGATGCCAGTGCATCAGCTGCTCAGGTCGCGGCCCTTGTGACTGATGCAACTGAC
TCAGCACGCGCCGCCAGCACGTCCGCCGGACAGGCTGCATCGTCAGCTCAGGAAGCGTCCTCCGGCGCAGAAGCGGCATCAGCAAAGGCC
ACTGAAGCGGAAAAAAGTGCCGCAGCCGCAGAGTCCTCAAAAAACGCGGCGGCCACCAGTGCCGGTGCGGCGAAAACGTCAGAAACGAAT
GCTGCAGCGTCACAACAATCAGCCGCCACGTCTGCCTCCACCGCGGCCACGAAAGCGTCAGAGGCCGCCACTTCAGCACGAGATGCGGTG
GCCTCAAAAGAGGCAGCAAAATCATCAGAAACGAACGCATCATCAAGTGCCGGTCGTGCAGCTTCCTCGGCAACGGCGGCAGAAAATTCT
GCCAGGGCGGCAAAAACGTCCGAGACGAATGCCAGGTCATCTGAAACAGCAGCGGAACGGAGCGCCTCTGCCGCGGCAgcttctgcaact
gcatcagctaacagtcaaaaagcagcaaaaaccagtgaaaccaacgcaaaggtgagcgaaacagcggctgcgaactcagcgaaagcatcg
gcagcaagccgacggcagctaaagcaagcgaagatgcagccagagagtatgcaagtcaggcagcagagccgtataaatatgtcttacag
ccactgcctgatgtgtggataccgtttaacgattcactggatatgattacgggcttttcgccgtcatataaaaaaattgttattggtgat
gatgaaataacgatgcctggcgacaaggttgttaagtttaaacgcgcatcaactgccacatatatcaataaatcaggcgtatttagtgtt
gctaaaattgatgagccacgatttgaaaaagaaggtttattgattgaaggacagcgcactaactattttgttaaatccaatactcccgct
gaatggacgagtaccagcaatatcgataaaactaataatggtgttgatgaatttggtttttcatatgccaaaatgcgaacaaaagataat
atgacaggacaatcatctgcacttagtctgcatagatgcagtgcatcccgggggattgatgttagtggcgataataagtattgcactgtt
tcatgcagggttaaagctcctgatggtcttcgttgtcgtttgcgttttgaaaaatacgatgggtcggtttatacattttaggagatgct
tatttaactttcggaactctgataatagaaaaactggcggggcagccaatagaatagcagctactgcaactaaagatccggttacaggg
tggattttctatgaggcaactatagaagctgttgaaggtgaaaccttaattggcgcaatgattcagtatgcgccgaaaaaaggtggtata
actgaagcgggagattatatttaccttgcaacaccacaatttgaaaacggcggatgtgcttcatcttttgttattacgacaactgcaccc
gcaacccgctccagtgatatggtgacgattccaactaaaaataatatctataatagaccgcttacgtgtcttgtcgaggttaatagaatt
tggggcgatattcctcctaatgtagcaccgcgtattttgattttctggtgtgccacctattgagtcaattacatacgcttttaacaca
actgagaaatattacggtcagctttatatgcaaacttataaagcgtcgacaagtacttacgtttctagtgtgtttgctggtcgagctgat
gttcgaaaattcattggtggttttaatatttattctgatggtactaaacgagtagtttctaacggtgaggctactaaaactatgaaaacg
gagtggacgggcgtaaaaacacggacctttattcgaattggaggtcaagccacatcgggaactcgtcatctattcggccatttgagaaat
cttcgtctctggcataaagaattaactgatgcgcaaatgggggagagtattaaa
```

STF15-AP1

(SEQ ID NO: 70)

```
atgaaagatttaacactcaaatttgcagacagggccgactttttcggcctttatggagagcattggctattatgatgacgagtcgatgcag
gatgatattcttattgacgtgataggtaatgtgtacaaagaaaccggagaacttactgaagatggcgagccggcatgtgttaaggaggac
ggatattttgtaaatgtgcgcatcattaatgattcgcaaatatcgtcattattcgatgaacacgcggttgctgttgagcatcaactccgt
agctggatg
```

STF15-AP2

(SEQ ID NO: 71)

```
atggctacatcgacagtaattcctgatgacatcaaaacgctaaaggagatgtcagtaaggcaaaggaagatatttcctcaattaacgta
aaagtatcaacgcttcagactgatatggacagtgcaaagcaggatatcagtaccagatacacaaaaacagaagtggataataagctgaaa
aacaaagtggaagtgaacgatctggaaagtggtcgttatggcggagattttttacccgctgactggccgtgaagcgttttatttatgggga
ttgggcacaactacagcggcggcaaatctttatcttaatcctgaccctgcaatttcgtctgtgctgcggtcaacatcgtctatccgctat
aaacattcagtagagacgatagattcagagcacgccgatctcattttcaggatgcgccctgtgtggtacaggtcgcaatgcgaaaatgac
aggcgtgactgggattctatggattgattgccgaggaagtaggagaaattgcccctcagtttgttcactggcgaccagccaacgaagat
gatgcaccggaaaccatttccagcaatggccttgttgccgaaggtgtaatgtacgaacgtctggttgttccactgattcaccatatccag
aaactgactgaaagagttgatgaacttgagtcagaattgaagttgttatcaacttcccaaagcgatatcgga
```

STF-16

(SEQ ID NO: 72)

```
ATGGCAGTAAAGATTTCAGGAGTCCTGAAAGACGGCACAGGAAAACCGGTACAGAACTGCACCATTCAGCTGAAAGCCAGACGTAACAGC
ACCACGTGGTGGTGAACACGTGGGCTCAGAGAATCCGGATGAAGCCGGGCGTTACAGCATGGATGTGGAGTACGGTCAGTACAGTGTC
ATCCTGCAGGTTGACGGTTTTCCACCATCGCACGCCGGGACCATCACCGTGTATGAAGATTCACAACCGGGGACGCTGAATGATTTTCTC
```

-continued

```
TGTGCCATGACGGAGGATGATGCCCGGCCGGAGGTGCTGCGTCGTCTTGAACTGATGGTGGAAGAGGTGGCGCGTAACGCGTCCGTGGTG

GCACAGAGTACGGCAGACGCGAAGAAATCAGCCGGCGATGCCAGTGCATCAGCTGCTCAGGTCGCGGCCCTTGTGACTGATGCAACTGAC

TCAGCACGCGCCGCCAGCACGTCCGCCGGACAGGCTGCATCGTCAGCTCAGGAAGCGTCCTCCGGCGCAGAAGCGGCATCAGCAAAGGCC

ACTGAAGCGGAAAAAAGTGCCGCAGCCGCAGAGTCCTCAAAAAACGCGGCGGCCACCAGTGCCGGTGCGGCGAAAACGTCAGAAACGAAT

GCTGCAGCGTCACAACAATCAGCCGCCACGTCTGCCTCCACCGCGGCCACGAAAGCGTCAGAGGCCGCCACTTCAGCACGAGATGCGGTG

GCCTCAAAAGAGGCAGCAAAATCATCAGAAACGAACGCATCATCAAGTGCCGGTCGTGCAGCTTCCTCGGCAACGGCGGCAGAAAATTCT

GCCAGGGCGGCAAAAACGTCCGAGACGAATGCCAGGTCATCTGAAACAGCAGCGGAACGGAGCGCCTCTGCCGCGGCAgcttctgccact gcatcagccaacagtcaaaaagcagcaaaaccagtgaaaccaatgcaaagacaagcgagactgcagcggcgaactcggcgaaagcatccg ctgcaagccagaccgctgcaaaagcaagtgaagacgcagccagagagtatgcaagccaggcagcagatccgtataaatatgtcttacagc cgctgcctgatgtgtggataccgtttaacgattcactggatatgattacgggcttttcgccatcatataaaaagattgttattggtgacg acgaaataacgatgcctggcgacaagattgttaagtttaaacgtgcatcgaaagcaacctatattaacaaatctggtgtgctgacagagg ctgccattgatgagccacgatttgaacgtgatggcctgcttattgagggcaaagaactaatcttctgcttaattcaacaaatccatcta aatggaataagtcaggcaatctggaactcacagaaatatccacggattcttttaattttacttatgggagatttactgtaaaagatactc ttattggtcagacaagtgctattaatatcgtaacgatttctggcagtaaagggtttgatgtcacaggtgatgaaaaatatgtgaccattt catgccgtgaagaagtgatgttgaaaatataaggtgtcgtttaagatttgaacaccatgatggttatacttacactttttttgggagatg cttacctcaatttatcaacacttgtaattgataaaactggtactgctgcagaccgtattattgcaaaggctgtaaaagatgaggttactg gttggattttctatcaggctacaattaatgcactagatacagagagcatgattggtgcgatggttcaatacgctcctgtaaaaggttcag gtacagcatctggagactatctggatatcgcaactccacaagtggaaggtggatcaagtgcttcgtcatttattgtaactgatataactg caagcactcgcgcaagcgatatggtgacagtcccaatcaagaataaccctttataatcttccttttacggttctttgtgaggtacataaga actggtataaaacgccaaatgcagcaccgcgtgttttgataccggcggtcatcaaaccggagcggctattattcttggcttcggtcgttc aacagattacgacggatttccttattgtgatataggtttggctaacagacgggtaaacgaaaacgcatcgcttgaaaaaatggttatggg gatgcgtgtaaagtcagatcagtctacgtgctcagtaagtaacgggcgtatatccagcgaaaagaaagccacatggtcctatattcagaa ctccgcaattatccgtattggaggccagactacagccgggttgcgtcatttatttggtcatgtcaggaatttcagaatatggcacaaggc attgactgatgctcagatgggggagtcaatc
```

STF16-AP1

(SEQ ID NO: 73)

```
atgaaagatttaacactcaaatttgcagacagggccgacttttcggcctttatggatagcattggctattatgatgacgagtcgatgcag gatgatattcttattgacgtgataggtaacgtgtacaaagaaaccggagaactgactgaagatggcgaaccggtatgtgttaaggaagat ggatattatgtaaacgtgcgcatcattaatgatgcaaaaaatcgtcaatattcgatgaatacgcggttgtagttgaacatcaacttcgt ggctggatg
```

STF16-AP2

(SEQ ID NO: 74)

```
atggctacatcgacagtaattccaggagacatcaccacgttaaagggagatgtcagtaaagccaaggaagatatttcctcaattaacgga aaagtatcaacgcttcaggctgatatgaccagtgcaaagcaggatatcagcaccagatacacaaaaactgaagttgataataagctgaaa aacaaactggaagtgaacgctctggaaagcggtcgttatggtggagatttttacccgttgactggccgtgaagcgttttatttgtgggga ttgggcacgactacgcggcggcaaacctttatcttaatcctgaccccgcaatttcgtctgtgctgcggtcaacatcgtctatccgctata aacattcagtagagacaatagattcagagcacgccgatctcattttcaggatgcgccctgtgtggtacaggtcacaatgcgaaaatgaca ggcgtgactggggattctacggattgattgccgaggaagtaggagaaattgcccctcaggtttgtacactggcgaccagctaacgaagat gatgcaccggaagctatttccagcaatggccttgttgccgaaggtgtaatgtacgaacgtctggttgttccactgattcaccatatccag aagctgactgaaagagttgatgaacttgagtcagaattaaagttgttatccgtttcccgaagcgatatcgga
```

STF-17

(SEQ ID NO: 75)

ATGGCAGTAAAGATTTCAGGAGTCCTGAAAGACGGCACAGGAAAACCGGTACAGAACTGCACCATTCAGCTGAAAGCCAGACGTAACAGC

ACCACGGTGGTGGTGAACACGGTGGGCTCAGAGAATCCGGATGAAGCCGGGCGTTACAGCATGGATGTGGAGTACGGTCAGTACAGTGTC

ATCCTGCAGGTTGACGGTTTTCCACCATCGCACGCCGGGACCATCACCGTGTATGAAGATTCACAACCGGGGACGCTGAATGATTTTCTC

TGTGCCATGACGGAGGATGATGCCCGGCCGGAGGTGCTGCGTCGTCTTGAACTGATGGTGGAAGAGGTGGCGCGTAACGCGTCCGTGGTG

GCACAGAGTACGGCAGACGCGAAGAAATCAGCCGGCGATGCCAGTGCATCAGCTGCTCAGGTCGCGGCCCTTGTGACTGATGCAACTGAC

TCAGCACGCGCCGCCAGCACGTCCGCCGGACAGGCTGCATCGTCAGCTCAGGAAGCGTCCTCCGGCGCAGAAGCGGCATCAGCAAAGGCC

ACTGAAGCGGAAAAAGTGCCGCAGCCGCAGAGTCCTCAAAAAACGCGGCGGCCACCAGTGCCGGTGCGGCGAAAACGTCAGAAACGAAT

GCTGCAGCGTCACAACAATCAGCCGCCACGTCTGCCTCCACCGCGGCCACGAAAGCGTCAGAGGCCGCCACTTCAGCACGAGATGCGGTG

GCCCTCAAAAGAGGCAGCAAAATCATCAGAAACGAACGCATCATCAAGTGCCGGTCGTGCAGCTTCCTCGGCAACGGCGGCAGAAAATTCT

GCCAGGGCGGCAAAAACGTCCGAGACGAATGCCAGGTCATCTGAAACAGCAGCGGAACGGAGCGCCTCTGCCGCGGCAgcttctgccact gcatcagccaacagtcaaaaagcagcaaaaaccagtgaaaccaatgcaaagacaagcgagactgcagcggcgaactcggcgaaagcatcc gctgcaagccagaccgctgcaaaagcaagtgaagacgcagccagagagtatgcaagccaggcagcagatccgtataaatatgtcttacag ccgctgcctgatgtgtggataccgtttaacgattcactggatatgattacgggcttttcgccatcatataaaaagattgttattggtgac gacgaaataacgatgcctggcgacaagattgttaagtttaaacgtgcatcgaaagcaacctatattaacaaatctggtgtgctgacagag gctgccattgatgagccacgatttgaacgtgatggcctgcttattgaggggcaaagaactaatcttctgcttaattcaacaaatccatct aaatggaataagtcaggcaatctggaactcacagaaatatccacggattcttttaattttacttatgggagatttactgtaaaagatact cttattggtcagacaagtgctattaatatcgtaacgatttctggcagtaaagggtttgatgtcacaggtgatgaaaaatatgtgaccatt tcatgccgtgtaagaagtgatgttgaaaatataaggtgtcgtttaagatttgaacaccatgatggttatacttacacttttttgggagat gcttacctcaatttatcaacacttgtaattgataaaactggtactgctgcagaccgtattattgcaaaggctgtaaaagatgaggttact ggttggattttctatcaggctacaattaatgcactagatacagagagcatgattggtgcgatggttcaatacgctcctgtaaaaggttca ggtacagcatctggagactatctggatatcgcaactccacaagtggaaggtggatcaagtgcttcgtcatttattgtaactgatataact gcaagcactcgcgcaagcgatatggtgacagtcccaatcaagaataaccctttataatcttccttttacggttctttgtgaggtacataag aactggtataaaacgccaaatgcagcaccgcgtgttttgataccggcggtcatcaaaccggagcggctattattcttggcttcggtcgt tcaacagattacgacggatttccttattgtgatataggtttggctaacagacgggtaaacgaaaacgcatcgcttgaaaaaatggttatg gggatgcgtgtaaagtcagatcagtctacgtgctcagtaagtaacgggcgtatatccagcgaaaagaaagccacatggtcctatattcag aactccgcaattatccgtattggaggccagactacagccgggttgcgtcatttatttggtcatgtcaggaatttcagaatatggcacaag gcattgactgatgctcagatgggggagtcaatc

>STF-17-AP1

(SEQ ID NO: 76)

atgaaagatttaacactcaaatttgcagacagggccgacttttcggcctttatggatagcattggctattatgatgacgagtcgatgcag gatgatattcttattgacgtgataggtaacgtgtacaaagaaaccggagaactgactgaagatggcgaaccggtatgtgttaaggaagat ggatattatgtaaacgtgcgcatcattaatgatgcaaaaaaatcgtcaatattcgatgaatacgcggttgtagttgaacatcaacttcgt ggctggatg

STF-13

(SEQ ID NO: 77)

ATGGCAGTAAAGATTTCAGGAGTCCTGAAAGACGGCACAGGAAAACCGGTACAGAACTGCACCATTCAGCTGAAAGCCAGACGTAACAGC

ACCACGGTGGTGGTGAACACGGTGGGCTCAGAGAATCCGGATGAAGCCGGGCGTTACAGCATGGATGTGGAGTACGGTCAGTACAGTGTC

ATCCTGCAGGTTGACGGTTTTCCACCATCGCACGCCGGGACCATCACCGTGTATGAAGATTCACAACCGGGGACGCTGAATGATTTTCTC

TGTGCCATGACGGAGGATGATGCCCGGCCGGAGGTGCTGCGTCGTCTTGAACTGATGGTGGAAGAGGTGGCGCGTAACGCGTCCGTGGTG

GCACAGAGTACGGCAGACGCGAAGAAATCAGCCGGCGATGCCAGTGCATCAGCTGCTCAGGTCGCGGCCCTTGTGACTGATGCAACTGAC

TCAGCACGCGCCGCCAGCACGTCCGCCGGACAGGCTGCATCGTCAGCTCAGGAAGCGTCCTCCGGCGCAGAAGCGGCATCAGCAAAGGCC

-continued

ACTGAAGCGGAAAAAAGTGCCGCAGCCGCAGAGTCCTCAAAAAACGCGGCGGCCACCAGTGCCGGTGCGGCGAAAACGTCAGAAACGAAT
GCTGCAGCGTCACAACAATCAGCCGCCACGTCTGCCTCCACCGCGGCCACGAAAGCGTCAGAGGCCGCCACTTCAGCACGAGATGCGGTG
GCCTCAAAAGAGGCAGCAAAATCATCAGAAACGAACGCATCATCAAGTGCCGGTCGTGCAGCTTCCTCGGCAACGGCGGCAGAAAATTCT
GCCAGGGCGGCAAAAACGTCCGAGACGAATGCCAGGTCATCTGAAACAGCAGCGGAACGGAGCGCCTCTGCCGCGGCAtcttctgccact
gcatcagccaacagtcaaaaagctgcaaaaaccagtgaaaccaacgcaaaggcgagcgagactgcggcggctaactcggcgaaagcatcc
gctgcaagccagacggctgcaaaagcaagtgaagacgcagccagagagtatgcaagccaggctgcggagccgtataaacaagttttgcag
ccgcttcccgatgtgtggataccgtttaacgattcactggatatgcttgctggcttttcgcctggttataagcaaataactgtaggtgat
gatgttattaaaatgccatccgataaggttgttagcttcaaacgcgcatcaggtgcaacatacattaataaatcaggagtattaaccgtt
gctgaagttgacgaaccgcgatttgaacgagaaggtttgctgattgaaggacaaagaaccaactatcatcttaattcacttacgccatct
aagtggggagctacaacaagtgtaactataacagaaagtggtgttgatgagtttggctttacttatgggcggtttcaaataaaggacgaa
aaaattgggacaaatacgacaatgaatatcgctgcggtttcaggaggaagaggtgtcgatgttactggaactgaaaagtatgttacaaca
tcatgtcgtgtaaaaagcgatagtgctaatatacaatgtcgtataagatttgaaagatatgacgggtccgcatatttttatctggcagat
gcatatcttaatataacagatatgtccattaggaaaacgggaggaggggctgcaagaataaccgcccgagcggagaaagaatctaatgga
tggatttatttcgaggttacatatcaatctgaagctattgataatatggtGtggctctcagatccaaattgctccacctgtttcacctgg
aacttatttgggcggggaatatttggatgttacgacaccacaatttgaaggcggctcatgcgcatcatcttttatcatttccgatacagt
tgcatcaacgcgagcaagcgatattgttacattgccttgtaaaaataacatggccagcaaaccttttaacctgcatggttgaagtgaataa
aaaattggtctatagcaccaaattccgcgcctagaatttatgatataacaggatttaaaacaaaagacgacgcttttgtttttgcattcag
aaatacagcaggtagtgtaggaactccatatgttcaatttggtaatccaatatcatttccacctggaaatttacccaagaaagattatcgc
tgtatatagaataaaaagcgatggcaagtttcaggctggctgcaatgggggttttatcaacaccagcatcaacaacgtggaagagtgttag
tggtgctacaggtataaggattggaggccagactacagccggcttacgtcatttatttggttatatcaggaatttttagaatatggcataa
agaattaaccgatgcgcaaatgggagagataata STF-13-AP1
(SEQ ID NO: 78)
atgcgagatttaattatcaaattcacagacaaggccgacttttcggcctttatgaagagtgctggctattatgatgacgagtcgatgcag
gatgatattcttattgacgtgataggtaacgtgtacaaagaaaccggagaacttactgaagatggcgagccggtatgtgttaaggaagac
ggatattttgtaaacgtgcgcatcattaatgatgcaaaaaaatcgtcaatattcgataaatacgcggttgttgttgagcatcaacttcgt
ggctggatg STF-13-AP2
(SEQ ID NO: 79)
atggctacatcgacagtaattccaggagatatcaccaagctaaaggggatgtcagtaaagctaaggaagatatttcatcaattagcaga
aaagtatcaacgcttcagactgagatgaccagtgcaaagcaggatatcagctccagatacacaaaaactgaagttgataataagctgaaa
aacaaagtggaagtgaacgatctggaaagtggtcgttatggcggagattttatccactgacaggtcgtgaagcgttttatttatggaat
ttggccacgactacagcggcggcaaacctttatcttaatcctgaccctgcaatttcgtctgtgctgcggtcaacatcgtctatccgctat
aaacattcagtagagacaatagattcagagcacgccgatctcattttcaggatgcgccctgtgtggtacaggtcgcaatgcgaaaatgac
aggcgtgactggggattctacggattgattgccgaggaagtaggagaaattgctcctcagtttgtacactggcgaccagctaacgaagat
gatgctcctgaagctatttccagcaatggccttgttgccgaaggtgtaatgtacgaacgtctggttgttccactgattcaccatatccag
aaactgactgaaagagttgatgaacttgagtcagaattaaagttgttattaacttcccgaagcgatattaga STF-12
(SEQ ID NO: 80)
ATGGCAGTAAAGATTTCAGGAGTCCTGAAAGACGGCACAGGAAAACCGGTACAGAACTGCACCATTCAGCTGAAAGCCAGACGTAACAGC
ACCACGGTGGTGGTGAACACGGTGGGCTCAGAGAATCCGGATGAAGCCGGGCGTTACAGCATGGATGTGGAGTACGGTCAGTACAGTGTC
ATCCTGCAGGTTGACGGTTTTCCACCATCGCACGCCGGGACCATCACCGTGTATGAAGATTCACAACCGGGGACGCTGAATGATTTTCTC
TGTGCCATGACGGAGGATGATGCCCGGCCGGAGGTGCTGCGTCGTCTTGAACTGATGGTGGAAGAGGTGGCGCGTAACGCGTCCGTGGTG
GCACAGAGTACGGCAGACGCGAAGAAATCAGCCGGCGATGCCAGTGCATCAGCTGCTCAGGTCGCGGCCCTTGTGACTGATGCAACTGAC -continued

```
TCAGCACGCGCCGCCAGCACGTCCGCCGGACAGGCTGCATCGTCAGCTCAGGAAGCGTCCTCCGGCGCAGAAGCGGCATCAGCAAAGGCC

ACTGAAGCGGAAAAAAGTGCCGCAGCCGCAGAGTCCTCAAAAAACGCGGCGGCCACCAGTGCCGGTGCGGCGAAAACGTCAGAAACGAAT

GCTGCAGCGTCACAACAATCAGCCGCCACGTCTGCCTCCACCGCGGCCACGAAAGCGTCAGAGGCCGCCACTTCAGCACGAGATGCGGTG

GCCTCAAAAGAGGCAGCAAAATCATCAGAAACGAACGCATCATCAAGTGCCGGTCGTGCAGCTTCCTCGGCAACGGCGGCAGAAAATTCT

GCCAGGGCGGCAAAAACGTCCGAGACGAATGCCAGGTCATCTGAAACAGCAGCGGAACGGAGCGCCTCTGCCGCGGCAgcttctgccact gcatcagcaaacagtcaaaaagctgcaaaaaccagtgaaaccaatgcaaagacaagcgagactgcagcggcgaactcggcgcaagcatcg gcagcaagccagacagcagctaaagcaagtgaggatgcagccagagagtatgcaagccaggcagcagagccgtataaatatgtcttacag ccactgcctgatgtgtggataccgtttaacgattcactggatatgcttgctggttttcgcctggttataagcaaataaccgtaggtgat gatgttattaaaatgccatccgataaggttgttagcttcaaacgcgcatcaggtgcaacatacattaataaatcaggtgtattaaccgtt gctgaagttgacgaaccgcgatttgaacgagaaggtttgctgattgaaggacagagaacaaactatttcagaaattcaaatacaccagaa gcatggaataacacgggtagtgtgtctgttgagtcgttcgacagtgataagggtttaactatggaaggataactgttattaatgaaaat ccgacagcacaaggatatcaggcaattgctgtaaacacgaatgatgcttacacctgcccggcaggttcttatacgacgatatcgtgtctg acgaaaagtgataattcccggtgtcgtgcaaggttcggaaaaatgtctgataatggtgcgtttgtttttcattcagatgcagttctggat cctgttacgggaaatgttgttcatggaaataatgtgacggtgacggcagaaagagtcggtgaatggtggttgtttaccgccactcttttt gcagatgcggaaatgataatcagctcaagatttgaaatcctggcgatgcctggaatcagtattatccccaatggctctacgttagatatt gcgatgcctcaggcggagattgggtcgtacaggacgtcatttatcattactgaagggctcctggcactcgctccagcgacatggtgaca atacctgtaagaaacaatattcaccgattaccattcagtgctcttgttgaagttaataaaaactgggatatccctcccagcaaatcacca ttaatctttaatgttaaagattatcaggaaatggtctgttcacgcatgattccgtggtaataatttctctgatgccggttctccttttt atttctatgggagggtgtaataaatatgtggcaacaacccagaggaaaatcatttcaggcttccgttgtggcgctgatggagatgttcag gccgtatgtaatggtgaattatctgttgcggcaaaaacaacatggacttcaattgttccacgggcagtattgcgaattggagggcagggc actaatggggagtatcatctttttggtcatatccgtaatctgcgtatctggcataaagaattaactgatgcgcaaatgggggagagtatt aaa
```

STF-12-AP1  
(SEQ ID NO: 81)
```
atgaaagatttaacactcaaatttgcagacagggccgacttttcggcctttatggagagtattggctattatgatgacgagtcgatgcag gatgatattcttattgacgtgataggtaacgtgtacaaagaaaccggagaactgactgaagatggcgaaccggtatgtgttaaggaagac ggatattttgtaaacgtgcgcatcattaatgatgtaaaaaaatcgtcaatattcgataaatacgcggttgttgttgagcatcaacttcgt ggctggatg
```

STF-12-AP2  
(SEQ ID NO: 82)
```
atggctacatcgacagtaattccaggagatatcaccacgctaaagggagatgtcagtaaaactaaggaagatatttcctcaattaacgga aaagtatcaacgcttcagactgatatgaccagtgcaaagcaggatatcagcaccagatacacaaaaactgaagttgataataagctgaaa aacaaactggaagtgaacgatctggaaagcggtcgttatggtggagattttttacccgttgactggccgtgaagcgttttatatgtgggga ttgggcacgactacagcggcggcaaaccttatcttaatcctgaccctgcaatttcgtctgtactgcggtcaacatcgtctattcgctat aaacattcagtagagacgatagattcagagcacgccgatctcatttcaggatgcgccctgtgtggtacaggtcgcaatgcgaaaatgac aggcgtgactggggattctacggattgattgccgaggaagtaggagaaattgcccctcagtttgtacactggcgaccagctaacgaagat gatgctcctgaagctatttccagcaatggccttgttgccgaaggtgtaatgtacgaacgtctggttgttccactgattcaccatatccag aagctgactgaaagagttgatgaacttgagtcagaattaaagttgttatccgtttcccgaagcgatatcgga
```

STF-63  
(SEQ ID NO: 83)
```
ATGGCAGTAAAGATTTCAGGAGTCCTGAAAGACGGCACAGGAAAACCGGTACAGAACTGCACCATTCAGCTGAAAGCCAGACGTAACAGC

ACCACGGTGGTGGTGAACACGGTGGGCTCAGAGAATCCGGATGAAGCCGGGCGTTACAGCATGGATGTGGAGTACGGTCAGTACAGTGTC

ATCCTGCAGGTTGACGGTTTTCCACCATCGCACGCCGGGACCATCACCGTGTATGAAGATTCACAACCGGGGACGCTGAATGATTTTCTC
```

```
TGTGCCATGACGGAGGATGATGCCCGGCCGGAGGTGCTGCGTCGTCTTGAACTGATGGTGGAAGAGGTGGCGCGTAACGCGTCCGTGGTG
GCACAGAGTACGGCAGACGCGAAGAAATCAGCCGGCGATGCCAGTGCATCAGCTGCTCAGGTCGCGGCCCTTGTGACTGATGCAACTGAC
TCAGCACGCGCCGCCAGCACGTCCGCCGGACAGGCTGCATCGTCAGCTCAGGAAGCGTCCTCCGGCGCAGAAGCGGCATCAGCAAAGGCC
ACTGAAGCGGAAAAAAGTGCCGCAGCCGCAGAGTCCTCAAAAAACGCGGCGGCCACCAGTGCCGGTGCGGCGAAAACGTCAGAAACGAAT
GCTGCAGCGTCACAACAATCAGCCGCCACGTCTGCCTCCACCGCGGCCACGAAAGCGTCAGAGGCCGCCACTTCAGCACGAGATGCGGTG
GCCTCAAAAGAGGCAGCAAAATCATCAGAAACGAACGCATCATCAAGTGCCGGTCGTGCAGCTTCCTCGGCAACGGCGGCAGAAAATTCT
GCCAGGGCGGCAAAAACGTCCGAGACGAATGCCAGGTCATCTGAAACAGCAGCGGAACGGAGCGCCTCTGCCGCGGCAAATTCCGCGACA
GCAGCCAAAAAATCAGAAACCAACGCGAAAAATAGTGAGTCAGCAGCAAAGGTCAGCGAAACCAACGCTAAAGCGTCAGAGAACAAGGCG
AAAGAATATCTCGACAAGGTCGGGGGACTCGTCAGCCCGATGACGCAATACGATTGGCCCGTTGTTACTGGTAATGAGTCTTTTTACATA
AAGATCGCGAAACTTTCCGATCCCGGAAGCAACAATTGCCATGTAACGCTAATGGTTACTAACGGCGGTGACTACGGCTCCCCTTACGGA
AACATTGACTTTATCGAGATCTCGGCGCGCGGTCTGCCTTCTTCGCTTACTGCTGATAATGTATCTCGTTACCTGAGTATACGCCGTTTA
GGGCCAACCGGGCTAATCAATAGCATGCAAATGCGTTACGGCCTGGTTAAAGATGATGGCTTTATTGAGGTTTGGGCCTTCCAGCGTGCA
TTTATCAACGGCGCAAAGGTTGCGGTACTGGCGCAGACGGCACGCACGGAATTATACATTCCAGACGGATTTGTTAAGCAAACCGCCGCG
CCTTCTGGATATGTTGAAAGCCCCGTTGTAAGGATTTACGACCAGTTAAACAAGCCGACTAAAGCAGATTTGGGTCTTTCTAATGCTATG
CTTACAGGCGCTTTCGGTCTTGGCGGTAGCGGGATATCAACAAACGGCAAGATGAGCGATGTAGAGATCTTAAAAGCTCTGCGTGACAAA
GGTGGTCATTTCTGGCGCGGTGATAAGCCGACCGGAAGCACGGCGACCATTTATAGCCACGGTTCTGGTATATTCTCGCGGTGCGGCGAT
ACGTGGTCAGCGATCAATATCGACTACTCAACCGCGAAGATTAAGATCTATGCCGGCAACGATGCCCGGCTTAACAACGGGACTTTTAGC
ATCAATGAGCTATACGGCTCGGCAAACAAGCCGTCGAAATCGGATGTTGGACTTGGCAACGTAACGAACGATGCGCAGGTAAAAAAAACC
GGCGATACAATGACCGGTGACTTGACAATCAAAAAAGGTACACCGTCAGTCTTCCTGCGGGCAGACAGTGGAGTCACCGCTTTGCGGTTT
TATACTGGCGATAACACAGAGCGCGGCATAATCTATGCTGGTCCTAACACTGATTCGCTTGGCGAAGTTCGCATCAGGGCAAAGACAGCA
GGGGGGACATCAGGAGGGGATCTTGTTGTTCGTCACGACGGGAGGGTTGAAGTCCGTGATCTCACAGTAGCGTATAAAATTAAAAGCAGA
ACGATTGAGATTGCAAATACCGATACTGACTCATCGGCAACTACGCTCAGCATCTATGGAGTACAGCACACGCCGTTGGTTTTAACGCGT
TCTGGTTCTTCTGAAAATGTGTCCATTGGGTTTAAGTTAGACAACATGAACCCAAAGTATCTTGGAATTGATACTAATGGGGATCTGGCT
TTTGGTGAGAGTCCTGATCAGAAACAAAACAGCAAATTGATCACGCAAGCGAAACTCGACAAGGGATTAACGATTGGTGGTCAACTGGCT
TTCAAAGGTACGACAGCGTTTTCAGCCGTTGCTACGTTCATTGCCGGGATAGCAGGAGCCATCGAGCCGAAAACATTGACGGCCAGACG
GTTAATCTTAACAACCTGACCATCATCAAGTCAGATGCCGGGGCAGTTAAATACTATATTTGTCCATCCTCTGCAGGTGGTGCAAATATT
ACCAATAAGCCTGACGGCATAGCCGGTAACTTTTTGCTCCGTGTAGAGTCGACTCGTAAGGTTAGGGATTCAGATTATGCGAACATGCAA
ACGCTGATTAACAGCGACACAAAACGTATATACGTTCGCTTTGTTGTTAATGGAAACTGGACAGCGTGGAGTCAGGTTGTTGTTTCCGGA
TGGAATCAGGATATAACTGTCAGGTCGTTAACCACATCTAGTCCGGTAAAATCTGGCGGAGGGCGAATTGATGTCCTTGGAAGCACGTCA
GACTATAGCAAAATGGATTGCTTTGTACGTGGGTTTGATAGCACCGGTAATTCTCTCGCGTGGGCGTTGGGTTCATCAGCCGGCGTAAGT
AAGATGCTGTCGCTAAAAAATTTCTTTAGCGGAGCTGAGATACTGTTAAATGGTAATGACGGCACGGTTCAACTCAAAACAGGTGCTGTT
AACGGGGCTACAGCGCAGGCGCTCACTATCAACAGGAATGAGGTTAACTCAACTGTTGATTTAACCCTTACAAAACAATCAGGGACTGGC
AATCGTTTTGTTTTACAGAACTCAGGTAATGCAGAACTACCGTTTTCTGTCAGGGTGTGGGGTTCCAGTACTCGACAAAACGTTTTTGAG
GTTGGCACGTCTGCTGCGTATCTGTTTTATGCGCAAAAAACGTCAGCAGGCCAGTTGTTTGATGTAAATGGCGCTATTAATTGCACAACG
CTGAATCAGTCATCAGACCGCGACCTTAAAGACGATATTCTCGTTATCAGCGACGCGACGAAAGCAATCCGTAAAATGAACGGATACACC
TACACGCTCAGGGAAAACGGGATGCCTTATGCTGGCGTTATTGCACAGGAAGTAATGGAGGCGATACCAGAAGCTGTGGGATCGTTTACT
CATTATGGTGAAGAGTTGCAAGGTCCGACCGTTGACGGCAACGAGCTACGCGAAGAAACGCGCTATCTTAATGTTGACTACGCCGCCGTG
ACGGGCTTACTTGTTCAGTTCGCCCGTGAAACAGATGATCGCGTTACCGCGCTGGAAGAGGAAAACACAACGCTACGTCAAAATCTGGCA
ACAGCAGACACCCGGATCAGCACTCTGGAAAATCAGGTAAGCGAACTGGTTGCACTTGTCCGGCAGTTAACAGGAAGCGAACATTGA
```

STF-62

(SEQ ID NO: 84)
ATGGCAGTAAAGATTTCAGGAGTCCTGAAAGACGGCACAGGAAAACCGGTACAGAACTGCACCATTCAGCTGAAAGCCAGACGTAACAGC

ACCACGGTGGTGGTGAACACGGTGGGCTCAGAGAATCCGGATGAAGCCGGGCGTTACAGCATGGATGTGGAGTACGGTCAGTACAGTGTC

ATCCTGCAGGTTGACGGTTTTCCACCATCGCACGCCGGGACCATCACCGTGTATGAAGATTCACAACCGGGGACGCTGAATGATTTTCTC

TGTGCCATGACGGAGGATGATGCCCGGCCGGAGGTGCTGCGTCGTCTTGAACTGATGGTGGAAGAGGTGGCGCGTAACGCGTCCGTGGTG

GCACAGAGTACGGCAGACGCGAAGAAATCAGCCGGCGATGCCAGTGCATCAGCTGCTCAGGTCGCGGCCCTTGTGACTGATGCAACTGAC

TCAGCACGCGCCGCCAGCACGTCCGCCGGACAGGCTGCATCGTCAGCTCAGGAAGCGTCCTCCGGCGCAGAAGCGGCATCAGCAAAGGCC

ACTGAAGCGGAAAAAGTGCCGCAGCCGCAGAGTCCTCAAAAAACGCGGCGGCCACCAGTGCCGGTGCGGCGAAAACGTCAGAAACGAAT

GCTGCAGCGTCACAACAATCAGCCGCCACGTCTGCCTCCACCGCGGCCACGAAAGCGTCAGAGGCCGCCACTTCAGCACGAGATGCGGTG

GCCTCAAAAGAGGCAGCAAAATCATCAGAAACGAACGCATCATCAAGTGCCGGTCGTGCAGCTTCCTCGGCAACGGCGGCAGAAAATTCT

GCCAGGGCGGCAAAAACGTCCGAGACGAATGCCAGGTCATCTGAAACAGCAGCGGAACGGAGCGCCTCTGCCGCGGCAAACTCCGCGACA

GCAGCCAAAAAATCAGAAACCAACGCGAAAAATAGTGAGGCAGCAGCAAAGGTCAGCGAAACCAACGCTAAAGCGTCAGAGAACAAGGCG

AAAGAATATCTCGACAAGGTCGGGGGACTCGTCAGCCCGATGACGCAATACGATTGGCCTGTTGTTACTGCTAGTGAGTCTCTTTACATC

AAGATCGCGAAACTTTCCGATCCTGGAACCAGCAGAAGTCATGTAACGCTAATGGTTACTAACGCTGGTAACTACGGCTCCCCTTACGGA

AACATTGACTTTATCGAGATCTCGGCGCGCGGTCTGCCTTCTTTGCTTAGTGCGGATAATGTTTCTCGTCATCTGAGTATACGCCGCTTA

GGGTCAACCGGGCTGACCGATAACAACCAGATGCGTTACGGCCTGGTTAAAGGTGACGGCTTTATTGAGGTTTGGGCATTCCAGGGTGCG

TTTATTAACGACGCAAAGGTTGCGGTGCTGGCGCAGACAACACTAAACACAGAATTATACATTCCAGACGGATTTGTTAAGCAAACCGCC

GCGCCTTCTGGATATATTGAAGGCAACGTTGTAAGGATTTACGACCAGGTAAACAAGCCGACTAAAGCAGATTTGGGTCTTTCTAATGCT

ATGCTTACAGGCGCTTTCGGTCTTGGCGGTAGCGGGATATCAACAAACGGCAAGATGAGCGATGTAGAGATCTTAAAAGCTCTGCGTGAC

AAAGGTGGTCATTTCTGGCGCGGTGATAAGCCGACCGGAAGCACGGCGACCATTTATAGCCACGGTTCTGGTATATTCTCGCGGTGCGGC

GATACGTGGTCAGCGATCAATATCGACTACTCAACCGCGAAGATTAAGATCTATGCCGGCAACGATGCCCGGCTTAACAACGGGACTTTT

AGCGTCAATGAGCTATACGGCTCGGCAAACAAGCCGTCGAAATCGGATGTTGGACTTGGCAACGTAACGAACGATGCGCAGGTGAAAAAA

TCCGGCGATGTTATGTCTGGTGATCTTGATATATTGAAAGAAACGCCATCTATCAGGCTAAAATCAGCAAAAGGAACCGCTCATCTGTGG

TTCATGAACAACGACGGAAGCGAGCGCGGCGTTGTTTGGTCGCCTGAAAACAACGAATCACTTGGCGAAATCCACATCAGGGCGAAAAAC

ACAAAAGGTGAATCAAGTGGTGATTTTATTGTTCGCCACGACGGGAGGGTTGAGGCCCGCAATCTAAAAATAACTTACAAAATCAGCGCA

GCCACCGCAGAATTTGCAAACACAAGCACCAGTTCCGATAACACTACGGTAAGCATCAAAGGATCTCAGCATACGCCTTTGGTTTTAACG

AGCAACAACACAATTAAAAACTTGTCCATTGGGTTTAAGGTTGATGATGTTGATCAAAAATACCTAGGTATAGCTGGTGACGGTGATTTG

TATTTTGGTAGTTATTCTGACCACACAAAAAACAGCAAAGTAATCACACAAGCAAAACTCGATAGCGGGGTGACGGTAGGCGGTAAAACA

ACCTTTTCTGACCTTGCCACATTTAACGCAGGTATGGCGGGATCTATCGAGCCGGAAACCATTGACAACAAGACTATTGATTTAAACGAC

TTGATCATTGCTAATACAGTGGCTGGATCTGTTAAATACTATCAATGCAAAACTGTCGCAGGTGGTGCATATATTACCAATAAGCCTGAC

GGCGTAAGCGGTAACTTTTTGCTACGTGTAGAATCTACTCGTAAAACTACGGGTTCAGATTATGCGATCATGCAAACGCTGATTGGCAGC

GACACAAAACGCATATACGTTCGCTTTGTTGTCAATGGAAGTTGGACGGAGTGGAGTCAGGTAGTTGTTTCAGGATGGAATCAGGATGTA

ACCGTCAGGTCGTTAACCTCGACGACTCCATCAAAATTAGGCGGCGGGCGTGTTGATGTGCTGGGGAGTACGTCAGATTACAGTAGTATG

AATTGTGCTGTGCGCGGTGTTGATAGCACTGGAACCAATTCGGCGTGGTCAGTAGGTACATCGAAAAACACGGGAAAAATGTTGTGCCTT

AAAAACCACAGAAGCAGCGCTCAAGTGCTGTTAAATGGCGATGATGGCGCGGTGCAACTACTAAGCGGTACTGTCAACGGTGCTACAGCA

CAGGCGCTAACCATCAACAAAGATGAGGTTAACTCAACTGCCGATTTAGTAATTAGAAAACAAACAGGGACTGGCAATCGTTTTGCTTTA

CTTAATTCAGGTAATTCAGAACTACCAGTTGGTATCAGGGTGTGGGGTTCCAGTACTCGTCAAAACGTTTTTGAGGTTGGAACGTCTACT

GCGTATCTGTTTTATGCGCAAAAAACGTCAGCAGGCCAGTTGTTTGATGTAAATGGCGCTATTAATTGCACAACGCTGAATCAGTCATCA

GACCGCGACCTTAAAGACGATATTCTCGTTATCAGCGACGCGACGAAAGCAATCCGTAAAATGAACGGATACACCTACACGCTCAGGGAA

AACGGGATGCCTTATGCTGGCGTTATTGCACAGGAAGTAATGGAGGCGATACCAGAAGCTGTGGGATCGTTTACTCATTATGGTGAAGAG

-continued

TTGCAAGGTCCGACCGTTGACGGCAACGAGCTACGCGAAGAAACGCGCTATCTTAATGTTGACTACGCCGCCGTGACGGGCTTACTTGTT

CAGTTCGCCCGTGAAACAGATGATCGCGTTACCGCGCTGGAAGAGGAAAACACAACGCTACGTCAAAATCTGGCAACAGCAGACACCCGG

ATCAGCACTCTGGAAAATCAGGTAAGCGAACTGGTTGCACTTGTCCGGCAGTTAACAGGAAGCGAACATTGA

STF-71

(SEQ ID NO: 85)

ATGGCAGTAAAGATTTCAGGAGTCCTGAAAGACGGCACAGGAAAACCGGTACAGAACTGCACCATTCAGCTGAAAGCCAGACGTAACAGC

ACCACGGTGGTGGTGAACACGGTGGGCTCAGAGAATCCGGATGAAGCCGGGCGTTACAGCATGGATGTGGAGTACGGTCAGTACAGTGTC

ATCCTGCAGGTTGACGGTTTTCCACCATCGCACGCCGGGACCATCACCGTGTATGAAGATTCACAACCGGGGACGCTGAATGATTTTCTC

TGTGCCATGACGGAGGATGATGCCCGGCCGGAGGTGCTGCGTCGTCTTGAACTGATGGTGGAAGAGGTGGCGCGTAACGCGTCCGTGGTG

GCACAGAGTACGGCAGACGCGAAGAAATCAGCCGGCGATGCCAGTGCATCAGCTGCTCAGGTCGCGGCCCTTGTGACTGATGCAACTGAC

TCAGCACGCGCCGCCAGCACGTCCGCCGGACAGGCTGCATCGTCAGCTCAGGAAGCGTCCTCCGGCGCAGAAGCGGCATCAGCAAAGGCC

ACTGAAGCGGAAAAAAGTGCCGCAGCCGCAGAGTCCTCAAAAAACGCGGCGGCCACCAGTGCCGGTGCGGCGAAAACGTCAGAAACGAAT

GCTGCAGCGTCACAACAATCAGCCGCCACGTCTGCCTCCACCGCGGCCACGAAAGCGTCAGAGGCCGCCACTTCAGCACGAGATGCGGTG

GCCTCAAAAGAGGCAGCAAATCATCAGAAACGAACGCATCATCAAGTGCCGGTCGTGCAGCTTCCTCGGCAACGGCGGCAGAAAATTCT

GCCAGGGCGGCAAAAACGTCCGAGACGAATGCCAGGTCATCTGAAACAGCAGCGGAACGGAGCGCCTCTGCCGCGGCATCTTCTGCCACT

GCATCAGCCAACAGTCAAAAAGCTGCAAAAACCAGTGAAACCAACGCAAAGGCGAGCGAGACTGCGGCGGCTAACTCGGCGAAAGCATCC

GCTGCAAGCCAGACGGCAGCTAAAGCAAGTGAAGATGCAGCCAGAGAGTACGCAAGCCAGGCTGCGGAGCCGTATAAACAAGTTTTGCAG

CCGCTTCCCGATGTGTGGATACCGTTTAACGATTCACTGGATATGATTACGGGCTTTTCGCCGTCATATAAAAAGATTGTTATTGGTGAT

GATGAAATAACGATGTCTGGCGATAAGGTTGTAAAGTTTAAACGCGCATCGAAAGCAACCTATATTAATAAATCTGGTGTGCTGACAGAG

GCTGCCATTGACGAGCCACGATTTGAACGTGATGGCCTGCTTATTGAGGGGCAAAGAACAAACTACATGCTCAATTCGGAAAGCCCTGCC

AGTTGGGGGCGATCGTCAAATATGGATGTGCCCGAAACAGGGACGGATAATTTTGGTTTTACCTATGGAAAGTTTGTCTGCAACGATTCT

CTGATTGGGCAAACCTCAGCCATTAATATGGCATCAATTGCTGCAACAAAGTCAGTTGATGTCTCAGGCGATAATAAACACGTGACAACC

TCATGTCGTTTTAAAACAGAACTGCAGGTAAGGTTGCGTATCCGGTTTGATAAATATGACGGTAGCGCAACAACTTTTCTTGGTGATGCG

TATATTGATACACAAACGCTTGAAATTAATATGACAGGCGGTGCTGCCTCAAGGATTACAGCGAGAGTCAGAAAGGACGAAGCTACCGGA

TGGATTTTTGCAGAGGCAACAATTCAGGCAATTGATGGGGAGTTAAAAATAGGTTCTCAGATACAGTATTCTCCTAAGCAGGGCGGGGCA

ACCGTATCTGGTGACTATATTTATCTGGCCACCCCACAAGTAGAAAATGGGCCTTGTGTATCATCTTTTATTATATCAGGAACGACGGCG

GCGACCCGCGCAAGCGATATAGTCACAGTTCCCATTAAGAATAATCTTTATAATCTTCCTTTTACGGTTCTTTGTGAGGTACATAAGAAC

TGGTATAAAACGCCAAATGCAGCGCCGCGTGTTTTTGACACCGGCGGTCATCAAACCGGAGCGGCAATTATTCTTGGATTCGGTTCTTCA

GCAGATTACGACGGATTTCCTTATTGCGATATTGGAGGAGCTAACAGACGGGTAAACGAAAACGCATTGCTTGAAAAAATGGTTATGGGG

ATGCGTGTAAAGTCAGATCAGTCTACGTGCTCAGTAAGTAACGGGCTATATCCAGCGAAACAAAAACCACATGGTCCTATATTCAGAAC

ACCGCAATTATCCGTATTGGAGGCCAAACTACAGCCGGGTTACGTCATTTATTTGGTCATGTCAGGAATTTCAGAATATGGCACAAGGCA

TTGACTGATGCTCAGGTGGGGGAGTCAATCTAA

STF-71-AP1

(SEQ ID NO: 86)

ATGAAAGATTTAACACTCAAATTAGCCGACAGGGCCGACTTTTCGGCCTTTATGGAGAGTACTGGCTATTATGATGACGAGTCGATGCAG

GATGATATTCTTATTGACGTGATAGGTAACGTGTACAAAGAAACCGGAGAACTGAATGAAGATGGCGAACCGGTATGTGTTAAGGAAGAC

GGATATTTTGTAAACGTGCGCATCATTAATGATGTGAAAACACCGTCAATATTCGATGAATACGTGGTTGCTGTTGAGCATCAACTTCGT

GGCTGGATGTGA

3) Insertion Point MDETNR

STF-20

(SEQ ID NO: 87)

ATGGCAGTAAAGATTTCAGGAGTCCTGAAAGACGGCACAGGAAAACCGGTACAGAACTGCACCATTCAGCTGAAAGCCAGACGTAACAG

CACCACGGTGGTGGTGAACACGGTGGGCTCAGAGAATCCGGATGAAGCCGGGCGTTACAGCATGGATGTGGAGTACGGTCAGTACAGTG

-continued

```
TCATCCTGCAGGTTGACGGTTTTCCACCATCGCACGCCGGGACCATCACCGTGTATGAAGATTCACAACCGGGGACGCTGAATGATTTT

CTCTGTGCCATGACGGAGGATGATGCCCGGCCGGAGGTGCTGCGTCGTCTTGAACTGATGGTGGAAGAGGTGGCGCGTAACGCGTCCGT

GGTGGCACAGAGTACGGCAGACGCGAAGAAATCAGCCGGCGATGCCAGTGCATCAGCTGCTCAGGTCGCGGCCCTTGTGACTGATGCAA

CTGACTCAGCACGCGCCGCCAGCACGTCCGCCGGACAGGCTGCATCGTCAGCTCAGGAAGCGTCCTCCGGCGCAGAAGCGGCATCAGCA

AAGGCCACTGAAGCGGAAAAAAGTGCCGCAGCCGCAGAGTCCTCAAAAAACGCGGCGGCCACCAGTGCCGGTGCGGCGAAAACGTCAGA

AACGAATGCTGCAGCGTCACAACAATCAGCCGCCACGTCTGCCTCCACCGCGGCCACGAAAGCGTCAGAGGCCGCCACTTCAGCACGAG

ATGCGGTGGCCTCAAAAGAGGCAGCAAAATCATCAGAAACGAACGCATCATCAAGTGCCGGTCGTGCAGCTTCCTCGGCAACGGCGGCA

GAAAATTCTGCCAGGGCGGCAAAAACGTCCGAGACGAATGCCAGGTCATCTGAAACAGCAGCGGAACGGAGCGCCTCTGCCGCGGCAGA

CGCAAAAACAGCGGCGGCGGGGAGTGCGTCAACGGCATCCACGAAGGCGACAGAGGCTGCGGGAAGTGCGGTATCAGCATCGCAGAGCA

AAAGTGCGGCAGAAGCGGCGGCAATACGTGCAAAAAATTCGGCAAAACGTGCAGAAGATATAGCTTCAGCTGTCGCGCTTGAGGATGCG

GACACAACGAGAAAGGGGATAGTGCAGCTCAGCAGTGCAACCAACAGCACGTCTGAAACGCTTGCTGCAACGCCAAAGGCGGTTAAGGT

GGTAATGGATGAGACTAATCGTcgtctggcgaaaaatcagaacggtgcagatatccaggataaatcagcttttctggacaatattggtg ttaccagcctgacgtttatgaaaaacaacggcgaaatgccggttgatgctgatctcaatacatttggtccagttaaggcttatgtgggt gtctggtataaatccacatcctccaacgcaacactggagaaaaatttccctgaagacggtgcagtcggtgttcttgaggtattcaatgg cggtaatttttccggaatgcagcgttataccaccagaactggcaatgtttatatgcgtaactctttctggcacctggaatggctcagac ggtccgtggatctactggcgtcagattcagtctgcaacacgcccctgagcacaactattgacctgaacacgctaggaggcgcagagca tcttggtttatggcgaaacagtagtggctctatcgcttcatttgaccgcaactatccggaagaaggaagttatggtcagggattccttg aagttcttgagggtggtgggtactcacgcacgcaacgctatacgacccgccgtgggaacgtatatgttcgctgcctttctgctatatgg aatgcacagaacccacagtgggagccgtggtcaagagtaggccatcagtcagaatgtcgttattacgaaggtgatttgaatgatctgac ttcgccaggcatttacagcgttacagggaaggcgtcaaacggtccaatgcaggataccgctggagcgacactgcttggaatactggaag taatcaggcgttttgatggtgtatctgtctggcagcgttacacaaccacagggaaatcagaaaccacacaggggcgcacttttgagcgc gtctatgccgggagcaaatggaccgaatggcgagaagtatataactccttttcgttgcctctgaatctgggcatcggtggcgcagtggc aaaactatccagtctggactggcagacctacgattttgtgccgggcagtctgataaccgttcggcttgataatatgaccaacattcccg acggtatggactggggcgtcattgatggcaacctgataaacatctcagtcggtccgagtgatgattctggttcggggggcgctcaatgca tgtatggcgcagcactgtaagtaaagccaactaccgcttttttatggtgcgcatttcaggaaatccgggaagccgcacgatcacaacaa gacgagtaccaatcattgacgaagcccagacatggggcgcgaaacagacattcagtgctggccttttctggtgaactgtccggcaatgcg gcgacagcaacaaagctgaaaacagcccgtaaaattaataacgtttcgtttgatggaacatcagatattaacctgacgccgaaaaatat tggtgcatttgcttcaggaaaaacaggagacaccgttgcgaatgataaagccgttggatggaactggagtagcggagcctataacgcaa ctattggtggggcatcaacgttaattcttcatttttaatatcggggaaggaagttgtcccgccgcccagtttcgcgttaattataagaac ggtggtatttttttatcgttctgctcgtgacggttacggattcgaggctgactggtctgagttttataccacaacgcgaaaacctacagc gggagatgtcggtcactgccgttatctggtggtcaattgaatggtgctctgggtataggaacatccagtgctcttggcggtaattcga ttgttttgggtgataatgacacgggctttaaacaaaatggtgatggtaatctggatgtttatgctaatagcgtccatgttatgcgctt gtctccggaagcgttcaaagtaataaaaccataaatattacggggcgtgttaatccctcggattacggtaactttgattcccgctatgt gagagatgtcagacttggcacacgtgttgtccagaccatgcagaaaggggtgatgtatgagaaagcagggcacgtaattaccgggcttg gtattgtcggtgaagtcgatggtgatgaccccgcagtattcagaccaatacaaaaatacatcaatggcacatggtataacgtcgcacag gtg
```

STF-20-AP1

(SEQ ID NO: 88)

```
atgcagcatttaaaaaatattactgcgggtaatccaaaaactgttgcccaatatcaactgacaaaaaattttgatgttatctggttatg gtccgaagagggaaaaaactggtatgaggaagtaagtaattttcaggaagacacgataaagattgtttacgatgagaataatataattg tcggcatcaccagagatgcttcaacgctcaaccctgaaggttttagcgttgtcgaggttcctgatattaccgccaaccgacgtgctgat
```

-continued gactcaggtaaatggatgtttaaggatggtgccgtgattaagcggatttatacggcagacgaacagctgcaactggcggaattacagaa gtcagctttgctttccgaagctgaaactatcattcagccactggaacgtctgtcagactgaatatggcaacagatgatgagcgtagcc gactggaagcatgggaacgctacagtgttctggtcagccgtgtggatcctgcaaatcctgaatggccggaaatgccgcaa

STF-23

(SEQ ID NO: 89)

ATGGCAGTAAAGATTTCAGGAGTCCTGAAAGACGGCACAGGAAAACCGGTACAGAACTGCACCATTCAGCTGAAAGCCAGACGTAACAG

CACCACGGTGGTGGTGAACACGGTGGGCTCAGAGAATCCGGATGAAGCCGGGCGTTACAGCATGGATGTGGAGTACGGTCAGTACAGTG

TCATCCTGCAGGTTGACGGTTTTCCACCATCGCACGCCGGGACCATCACCGTGTATGAAGATTCACAACCGGGGACGCTGAATGATTTT

CTCTGTGCCATGACGGAGGATGATGCCCGGCCGGAGGTGCTGCGTCGTCTTGAACTGATGGTGGAAGAGGTGGCGCGTAACGCGTCCGT

GGTGGCACAGAGTACGGCAGACGCGAAGAAATCAGCCGGCGATGCCAGTGCATCAGCTGCTCAGGTCGCGGCCCTTGTGACTGATGCAA

CTGACTCAGCACGCGCCGCCAGCACGTCCGCCGGACAGGCTGCATCGTCAGCTCAGGAAGCGTCCTCCGGCGCAGAAGCGGCATCAGCA

AAGGCCACTGAAGCGGAAAAAAGTGCCGCAGCCGCAGAGTCCTCAAAAAACGCGGCGGCCACCAGTGCCGGTGCGGCGAAAACGTCAGA

AACGAATGCTGCAGCGTCACAACAATCAGCCGCCACGTCTGCCTCCACCGCGGCCACGAAAGCGTCAGAGGCCGCCACTTCAGCACGAG

ATGCGGTGGCCTCAAAAGAGGCAGCAAAATCATCAGAAACGAACGCATCATCAAGTGCCGGTCGTGCAGCTTCCTCGGCAACGGCGGCA

GAAAATTCTGCCAGGGCGGCAAAAACGTCCGAGACGAATGCCAGGTCATCTGAAACAGCAGCGGAACGGAGCGCCTCTGCCGCGGCAGA

CGCAAAAACAGCGGCGGCGGGGAGTGCGTCAACGGCATCCACGAAGGCGACAGAGGCTGCGGGAAGTGCGGTATCAGCATCGCAGAGCA

AAAGTGCGGCAGAAGCGGCGGCAATACGTGCAAAAAATTCGGCAAAACGTGCAGAAGATATAGCTTCAGCTGTCGCGCTTGAGGATGCG

GACACAACGAGAAAGGGGATAGTGCAGCTCAGCAGTGCAACCAACAGCACGTCTGAAACGCTTGCTGCAACGCCAAAGGCGGTTAAGGT

GGTAATGGATGAGACTAATCGTaaagccccattaaacagcccggcgctgaccggaacgccaacaacaccaactgcgcgacagggaacga ataatacccaaatcgcaagcacggctttcgttatggctgcgattgccgcccttgtagattcgtcacctgatgcactgaacacgctgaac gagctggctgcggcgttgggcaacgacccgaattttgcgaccaccatgactaacgcgcttgcgggtaagcaaccgaaagatgccaccct gacggcgctggccgggcttgctactgcggcagacaggtttccgtatttttacggggaatgatgtcgccagcctggcaaccctgacaaaag tcgggcgggatattcttgcgaaatcgaccgttgctgccgttatcgaatacctcggtttacgagaactcggcacaagcggggagaaaata ccgttactcagtacagcgaatacctggaccaatcgacaaacattcagcggtggccttctgggggactgtccggcaatgccgctactgc aacaaagctgaaaacagcacgaaaaattgctggagttggttttgatggttctagcgatatttcaattagtgccaaaaatgtcaatgcat ttgcactccgacaaacaggtaatactgttaatggtgatacatccgttggatggaattgggatagtggtgcatataacgccctgattggt ggtgcatctgcattaattcttcactttaatataaatgctggtagctgtcctgccgtacaattccgtgtgaattataaaaatggtggcat ttcctacaggtcggctcgtgatggttatgggtttgaattaggttggtcagatttctataccacgacacgaaaaccttcagcgggagatg ttggtgcatatacgcgggcagaatgtaactcaaggtttattacaggtattcgccttggcggtctgtcatctgttcagacatggaatggt cccggctggtctgacaggtcaggttatgtcgttacggggttcagttaacggaaaccgtgatgaattaattgatacaacacaggcaaggcc aattcagtattgcattaatgggacgtggtataacgcggggagtatttaa

STF-23-AP1

(SEQ ID NO: 90)

atgatgcacttaaaaaacattactgctggcaaccctaaaacaaaagagcaataccagctaacaaagcaatttaacatcaaatggcttta ttcagatgatggaaaaaactggtatgaggaacaaaagaatttccagccagacactttgaaaatggtctatgaccataacggcgttatta tttgtattgaaaaggatgtttcagcaattaatccggaaggcgcaagcgtcgttgaattacctgatattacagcaaatcgccgggctgat atttcggggaaatggttgttcaaagatggcgtagtgataaagcgaacttataccgaggaagagcagaggcaacaagcggaaaatgaaaa gcaaagcctgttgcaacttgtcagggataaaacccagctatgggactcacagctacggctgggcatcatttccgacgagaataaacaaa aattaaccgagtggatgctctatgcgcagaaagtcgaatctacagacacctccagcctgccagtaacgtttccgaacaaccagaa

STF-24

(SEQ ID NO: 91)

ATGGCAGTAAAGATTTCAGGAGTCCTGAAAGACGGCACAGGAAAACCGGTACAGAACTGCACCATTCAGCTGAAAGCCAGACGTAACAG

CACCACGGTGGTGGTGAACACGGTGGGCTCAGAGAATCCGGATGAAGCCGGGCGTTACAGCATGGATGTGGAGTACGGTCAGTACAGTG

TCATCCTGCAGGTTGACGGTTTTCCACCATCGCACGCCGGGACCATCACCGTGTATGAAGATTCACAACCGGGGACGCTGAATGATTTT

```
CTCTGTGCCATGACGGAGGATGATGCCCGGCCGGAGGTGCTGCGTCGTCTTGAACTGATGGTGGAAGAGGTGGCGCGTAACGCGTCCGT

GGTGGCACAGAGTACGGCAGACGCGAAGAAATCAGCCGGCGATGCCAGTGCATCAGCTGCTCAGGTCGCGGCCCTTGTGACTGATGCAA

CTGACTCAGCACGCGCCGCCAGCACGTCCGCCGGACAGGCTGCATCGTCAGCTCAGGAAGCGTCCTCCGGCGCAGAAGCGGCATCAGCA

AAGGCCACTGAAGCGGAAAAAAGTGCCGCAGCCGCAGAGTCCTCAAAAAACGCGGCGGCCACCAGTGCCGGTGCGGCGAAAACGTCAGA

AACGAATGCTGCAGCGTCACAACAATCAGCCGCCACGTCTGCCTCCACCGCGGCCACGAAAGCGTCAGAGGCCGCCACTTCAGCACGAG

ATGCGGTGGCCTCAAAAGAGGCAGCAAATCATCAGAAACGAACGCATCATCAAGTGCCGGTCGTGCAGCTTCCTCGGCAACGGCGGCA

GAAAATTCTGCCAGGGCGGCAAAAACGTCCGAGACGAATGCCAGGTCATCTGAAACAGCAGCGGAACGGAGCGCCTCTGCCGCGGCAGA

CGCAAAAACAGCGGCGGCGGGGAGTGCGTCAACGGCATCCACGAAGGCGACAGAGGCTGCGGGAAGTGCGGTATCAGCATCGCAGAGCA

AAAGTGCGGCAGAAGCGGCGGCAATACGTGCAAAAAATTCGGCAAAACGTGCAGAAGATATAGCTTCAGCTGTCGCGCTTGAGGATGCG

GACACAACGAGAAAGGGGATAGTGCAGCTCAGCAGTGCAACCAACAGCACGTCTGAAACGCTTGCTGCAACGCCAAAGGCGGTTAAGGT

GGTAATGGATGAGACTAATCGTcgtcttcagaaagatcagaacggtgcggatattcctgataaagattattcctgcgcaatattggag caacaaattcaacaaccatgtcttttagtggtggtacaggatggttcaggctggcaactgtaaccatgccccaggccagttccgtggtt tacataagcctgattggtggtgccggatataatgttaatcccctatgcaggctggtatatctgaacttgttcttcgtgcgggaaatgga aatccaaaaggtcttactggtgcgttatggcgacggacatcggttggatttactaattttgcatgggtgaatacatccggtgatacccta tgatgtttatgttgaaataggtaattacgccacaggtgttaatattcagtgggattataccagtaacgccagcgtaacgattcatacat caccaacttatacagcgaataaaccaacaggcctgacagatggaactgtatatgtaatttacagttcgtacattaaaccgactgctgct gatgttgggcgttatcattatctggtggtcaattgaatggtgctctgggtataggaacatccagtgctcttggcggtaattcgattgt tttgggtgataatgacacgggctttaaacaaaatggtgatggtaatctggatgtttatgctaatagcgtccatgttatgcgctttgtct ccggaagcgttcaaagtaataaaaccataaatattacggggcgtgttaatccctcggattacggtaactttgattcccgctatgtgaga gatgtcagacttggcacacgtgttgtccagaccatgcagaaaggggtgatgtatgagaaagcagggcacgtaattaccgggcttggtat tgtcggtgaagtcgatggtgatgaccccgcagtattcagaccaatacaaaaatacatcaatggcacatggtataacgtcgcacaggtg
```

STF-24-AP1

```
                                                                                         (SEQ ID NO: 92)
atgcagcatttaaaaaatattactgcgggtaatccaaaaactgttgcccaatatcaactgacaaaaaattttgatgttatctggttatg gtccgaagagggaaaaaactggtatgaggaagtaagtaattttcaggaagacacgataaagattgtttacgatgagaataatataattg tcggcatcaccagagatgcttcaacgctcaaccctgaaggttttagcgttgtcgaggttcctgatattaccgccaaccgacgtgctgat gactcaggtaaatggatgtttaaggatggtgccgtgattaagcggatttatacggcagacgaacagctgcaactggcggaattacagaa gtcagctttgctttccgaagctgaaactatcattcagccactggaacgctctgtcagactgaatatggcaacagatgaggagcgtagcc gactggaagcatgggaacgctacagtgttctggtcagccgtgtggatcctgcaaatcctgaatggccggaaatgccgcaataa
```

O111-2.0

```
                                                                                         (SEQ ID NO: 93)
ATGGCAGTAAAGATTTCAGGAGTCCTGAAAGACGGCACAGGAAAACCGGTACAGAACTGCACCATTCAGCTGAAAGCCAGACGTAACAG

CACCACGGTGGTGGTGAACACGGTGGGCTCAGAGAATCCGGATGAAGCCGGGCGTTACAGCATGGATGTGGAGTACGGTCAGTACAGTG

TCATCCTGCAGGTTGACGGTTTTCCACCATCGCACGCCGGGACCATCACCGTGTATGAAGATTCACAACCGGGGACGCTGAATGATTTT

CTCTGTGCCATGACGGAGGATGATGCCCGGCCGGAGGTGCTGCGTCGTCTTGAACTGATGGTGGAAGAGGTGGCGCGTAACGCGTCCGT

GGTGGCACAGAGTACGGCAGACGCGAAGAAATCAGCCGGCGATGCCAGTGCATCAGCTGCTCAGGTCGCGGCCCTTGTGACTGATGCAA

CTGACTCAGCACGCGCCGCCAGCACGTCCGCCGGACAGGCTGCATCGTCAGCTCAGGAAGCGTCCTCCGGCGCAGAAGCGGCATCAGCA

AAGGCCACTGAAGCGGAAAAAAGTGCCGCAGCCGCAGAGTCCTCAAAAAACGCGGCGGCCACCAGTGCCGGTGCGGCGAAAACGTCAGA

AACGAATGCTGCAGCGTCACAACAATCAGCCGCCACGTCTGCCTCCACCGCGGCCACGAAAGCGTCAGAGGCCGCCACTTCAGCACGAG

ATGCGGTGGCCTCAAAAGAGGCAGCAAATCATCAGAAACGAACGCATCATCAAGTGCCGGTCGTGCAGCTTCCTCGGCAACGGCGGCA

GAAAATTCTGCCAGGGCGGCAAAAACGTCCGAGACGAATGCCAGGTCATCTGAAACAGCAGCGGAACGGAGCGCCTCTGCCGCGGCAGA

CGCAAAAACAGCGGCGGCGGGGAGTGCGTCAACGGCATCCACGAAGGCGACAGAGGCTGCGGGAAGTGCGGTATCAGCATCGCAGAGCA
```

-continued

AAAGTGCGGCAGAAGCGGCGGCAATACGTGCAAAAAATTCGGCAAAACGTGCAGAAGATATAGCTTCAGCTGTCGCGCTTGAGGATGCG
GACACAACGAGAAAGGGGATAGTGCAGCTCAGCAGTGCAACCAACAGCACGTCTGAAACGCTTGCTGCAACGCCAAAGGCGGTTAAGGT
GGTAATGGATGAGACTAATCGTAAGGCTCCTCTGAACTCTCCGGCCCTGACTGGCACGCCTACTACTCCGACTGCGCCGCAAGGGACCA
ACTCTACCCAGATTGCGTCCACGGCATTCGTTATGGCTGCTATTGCAGCACTGGTAGATTCCTCGCCGGACGCTCTGAACACTCTGTCG
GAACTGGCGGCTGCACTCGGAAATGATCCGAACTTCGCCACCACCATGACTAACGCTCTGGCCGGCAAACAGCCGAAAGATGCTACCCT
GACCGCCCTGGCAGGTCTCGTGACCGCTGCGGACCGCTTCCCGTATTTCACAGGCAATGACGTTGCCTCCCTGGCTACCCTGACCGAGG
TTGGTCGTGACATCCTGGCGAAGTCTACCGTTGCGGCCGTGATTGAATATCTGGGTCTGCAGGAAACTGTTAACCAGGCATCAGGTGCA
TTACAGAAGAATCAAAACGGTGCAGACATTCCGGGCAAAGATACCTTTACCAAGAATATCGGTGCTTGTCGTGCTTATTCGGCATGGCT
TAATATCGGAGGTGATTCTCAGGTATGGACTACGGCTCAGTTTATCTCTTGGCTCGAGAGTCAGGGTGCGTTTAATCATCCGTACTGGA
TGTGCAAAGGCTCTTGGGCGTACGCGAACAACAAAGTCATCACCGACACTGGTTGTGGTAACATCTGTCTGGCGGGTGCAGTAGTGGAA
GTTATCGGTACGCGCGGTGCGATGACGATCCGTGTAACTACTCCATCTACCTCCTCCGGTGGCGGTATCACCAACGCCCAGTTCACTTA
CATTAACCACGGCGATGCCTATGCTCCGGGCTGGCGCCGTGATTACAACACTAAAAACCAACAACCTGCGTTTGCACTGGGTCAGACGG
GTAGTCGTGTGGCGAACGATAAAGCGGTCGGTTGGAATTGGAACTCTGGTGTGTACAACGCTGATATTAGTGGAGCTTCTACTCTGATC
CTTCATTTTAACATGAATGCTGGAAGTTGTCCGGCAGTGCAGTTTCGTGTTAACTATCGTAATGGAGGAATCTTTTACCGCTCTGCACG
TGACGGCTACGGCTTCGAAGCGAACTGGAGTGAATTTTACACGACCACTCGTAAGCCGAGTGCTGGAGATGTGGGAGCTTATACTCAGG
CAGAATGCAATTCGCGTTTCATTACTGGTATTCGTCTGGGAGGTTTAAGTTCCGTGCAGACTTGGAACGGTCCAGGTTGGAGTGATCGT
AGTGGCTATGTTGTGACAGGCAGTGTTAACGGCAACCGTGACGAACTGATCGACACTACTCAAGCGCGTCCGATCCAGTACTGCATTAA
CGGAACTTGGTATAACGCGGGAAGTATCTAA

O111-2.0-AP1
(SEQ ID NO: 94)
atgatgcacttaaaaaacattactgctggcaaccctaaaacaaaagagcaataccagctaacgaaacaatttaacatcaaatggcttta
ttcagaggatggaaaaaactggtatgaggaacaaaagaatttccagccagacacttttgaaaatggtttatgaccataacggcgttatta
tttgtattgaaaaggatgtttcagcaattaatccggaaggcgcaagcgtcgttgaattacctgatattacagcaaatcgccgtgctgac
atttcgggtaaatggatgttcaaagatggcgtagtggtaaagcgtacttacacagaagaagagcaacgtcaacaggcggaaaatgaaaa
gcaaagcctgctacagctcgtcagggataaaaacccagctatgggacagtcagctacggctgggcatcatttccgacgagaataaacaaa
aattaacagagtggatgctctttgcgcagaaagtcgaatctacagacacttccagcctgccagtaacgtttcccgaacaaccagaatga STF-74
(SEQ ID NO: 95)
ATGGCAGTAAAGATTTCAGGAGTCCTGAAAGACGGCACAGGAAAACCGGTACAGAACTGCACCATTCAGCTGAAAGCCAGACGTAACAG
CACCACGGTGGTGGTGAACACGGTGGGCTCAGAGAATCCGGATGAAGCCGGGCGTTACAGCATGGATGTGGAGTACGGTCAGTACAGTG
TCATCCTGCAGGTTGACGGTTTTCCACCATCGCACGCCGGGACCATCACCGTGTATGAAGATTCACAACCGGGGACGCTGAATGATTTT
CTCTGTGCCATGACGGAGGATGATGCCCGGCCGGAGGTGCTGCGTCGTCTTGAACTGATGGTGGAAGAGGTGGCGCGTAACGCGTCCGT
GGTGGCACAGAGTACGGCAGACGCGAAGAAATCAGCCGGCGATGCCAGTGCATCAGCTGCTCAGGTCGCGGCCCTTGTGACTGATGCAA
CTGACTCAGCACGCGCCGCCAGCACGTCCGCCGGACAGGCTGCATCGTCAGCTCAGGAAGCGTCCTCCGGCGCAGAAGCGGCATCAGCA
AAGGCCACTGAAGCGGAAAAAAGTGCCGCAGCCGCAGAGTCCTCAAAAAACGCGGCGGCCACCAGTGCCGGTGCGGCGAAAACGTCAGA
AACGAATGCTGCAGCGTCACAACAATCAGCCGCCACGTCTGCCTCCACCGCGGCCACGAAAGCGTCAGAGGCCGCCACTTCAGCACGAG
ATGCGGTGGCCTCAAAAGAGGCAGCAAAATCATCAGAAACGAACGCATCATCAAGTGCCGGTCGTGCAGCTTCCTCGGCAACGGCGGCA
GAAAATTCTGCCAGGGCGGCAAAAACGTCCGAGACGAATGCCAGGTCATCTGAAACAGCAGCGGAACGGAGCGCCTCTGCCGCGGCAGA
CGCAAAAACAGCGGCGGCGGGGAGTGCGTCAACGGCATCCACGAAGGCGACAGAGGCTGCGGGAAGTGCGGTATCAGCATCGCAGAGCA
AAAGTGCGGCAGAAGCGGCGGCAATACGTGCAAAAAATTCGGCAAAACGTGCAGAAGATATAGCTTCAGCTGTCGCGCTTGAGGATGCG
GACACAACGAGAAAGGGGATAGTGCAGCTCAGCAGTGCAACCAACAGCACGTCTGAAACGCTTGCTGCAACGCCAAAGGCGGTTAAGGT
GGTAATGGATGAGACTAATCGTAAATATACGGCTCAGGACGCGAGCACGGCCAGAAAGGTCTGGTGAAACTGAGCAGCGCCACCGACA
GCACATCTGAGACCCTCGCCGCGACACCGAAAGCGGTTAAGGCGGTGAATGATAATGCGAATGGTCGCGTCCCGTCTGAGCGAAAAGTT -continued AACGGACATTCGCTGGCCGGTGATATCAGTGTCACCTCACAGGATATTTTTGACGGTCAGTGTGTTGAAATTGGTCCGGGTCAGGATCT
GGATAATTACCAGACGCCGGGTCTGTATTTTCAGCCCGCAAATGCCAATACCAGTGCTGCTCTGCATTACCCGGAAAATAATGCCGGTT
CCCTGATGGTTTTAAGAAGCGCAGGGATAACGCAGGTTTATCGCGTGTACAGCGGTTCGCGAAGTTATTTGCGGAGCAAATATTCCACG
CAGCCATGGACGACGTGGACACCCGATGATGCTTTTCCTGTCGGCGCGCCGATTCCGTGGCCATCTGACATCGCCCCGCCCGCTTACGC
CTTAATGCAGGGGCAGTCATTTGATAAATCTGCATATCCATTGCTTGCTGTAGCGTATCCCTCTGGTGTTATCCCGGATATGCGTGGTC
AGACGATAAAGGGCAAGCCGGACGGACGAGCGGTACTCTCGTATGAACAGGACGGTATTAAATCGCACGCTCATACAGCCAGTATTTCC
GATACCGATTTGGGAACGAAATATACCAACTCTTTTGATTATGGTTCAAAACCAACAACCAGTTTTGACTACGGCAATAAGTCCTCCAC
TGAGGGGGGATGGCACGTACATAACTTTCGTTATTGTGCTACGTCTGCATACCGGGATACTCCTGGCTCAGGGCTGGGGATGCACTCGT
CGAATATTTCGTGGTCAGCCGGGGATCGCATTGAGGGGAGTGGTAATCATGCACATGTTACGTGGATTGGTCCCCATGATCACTGGGTT
GGTATCGGTGAGCATAACCATTATGTGGTTATGGGGTATCACGGACATACAGCGACCGTTCATGCAACCGGGAATACAGAAAACACCGT
TAAAAATATTGCGTTTAACTACATTGTGAGGCTTGCATAA

STF-74-AP1

(SEQ ID NO: 96)
ATGGCTTTTGAAATGACCGGAGAAAACCGGACAATTATTCTTTATAACCTTCGTTCAGATACAAATGAATTTATTGGGAAATCTGATGG
GTTTATCCCTGCTAATACGGGCTTGCCTGCTTACAGTACCGATATCGCGCCCCAAAAGTGACGGCAGGTTTTGTGGCTGTTTTCGATG
CACAGACGAATAAATGGTCGCGGGTGGAGGACTACCGCGGGACAACCGTCTATGACATCAGCACCGGTAAGCCCGCTGTTATTGAAAAA
CTTGGCGCTCTGCCTGATAACGTTGTGTCGGTTGCTCCTGACGGGGAGTATGTAAAATGGGATGGCGCTAAGTGGATCCACGATGCCGA
AGCGGAAAAACATTTCGTCAGGGGCAGGCGGCGCAGGAAAAATCAAACCTGCTGATGATTGCAACATCGGCTATTGCCCCCCTGCAGG
ATGCCGTTGATCTGGATATGGCAACGGAAGACGAAGCGACCGCGCTTAATGAATGGAAAAAATACCGGGTCATGCTCAACAGAGTCAAA
CCCGAAGATGCCCCCGATATCACATGGCCGGAACTGCCCGCATAA

STF86

(SEQ ID NO: 97)
ATGGCAGTAAAGATTTCAGGAGTCCTGAAAGACGGCACAGGAAAACCGGTACAGAACTGCACCATTCAGCTGAAAGCCAGACGTAACAG
CACCACGGTGGTGGTGAACACGGTGGGCTCAGAGAATCCGGATGAAGCCGGGCGTTACAGCATGGATGTGGAGTACGGTCAGTACAGTG
TCATCCTGCAGGTTGACGGTTTTCCACCATCGCACGCCGGGACCATCACCGTGTATGAAGATTCACAACCGGGGACGCTGAATGATTTT
CTCTGTGCCATGACGGAGGATGATGCCCGGCCGGAGGTGCTGCGTCGTCTTGAACTGATGGTGGAAGAGGTGGCGCGTAACGCGTCCGT
GGTGGCACAGAGTACGGCAGACGCGAAGAAATCAGCCGGCGATGCCAGTGCATCAGCTGCTCAGGTCGCGGCCCTTGTGACTGATGCAA
CTGACTCAGCACGCGCCGCCAGCACGTCCGCCGGACAGGCTGCATCGTCAGCTCAGGAAGCGTCCTCCGGCGCAGAAGCGGCATCAGCA
AAGGCCACTGAAGCGGAAAAAAGTGCCGCAGCCGCAGAGTCCTCAAAAAACGCGGCGGCCACCAGTGCCGGTGCGGCGAAAACGTCAGA
AACGAATGCTGCAGCGTCACAACAATCAGCCGCCACGTCTGCCTCCACCGCGGCCACGAAAGCGTCAGAGGCCGCCACTTCAGCACGAG
ATGCGGTGGCCTCAAAAGAGGCAGCAAAATCATCAGAAACGAACGCATCATCAAGTGCCGGTCGTGCAGCTTCCTCGGCAACGGCGGCA
GAAAATTCTGCCAGGGCGGCAAAAACGTCCGAGACGAATGCCAGGTCATCTGAAACAGCAGCGGAACGGAGCGCCTCTGCCGCGGCAGA
CGCAAAAACAGCGGCGGCGGGGAGTGCGTCAACGGCATCCACGAAGGCGACAGAGGCTGCGGGAAGTGCGGTATCAGCATCGCAGAGCA
AAAGTGCGGCAGAAGCGGCGGCAATACGTGCAAAAAATTCGGCAAAACGTGCAGAAGATATAGCTTCAGCTGTCGCGCTTGAGGATGCG
GACACAACGAGAAAGGGGATAGTGCAGCTCAGCAGTGCAACCAACAGCACGTCTGAAACGCTTGCTGCAACGCCAAAGGCGGTTAAGGT
GGTAATGGATGAGACTAATCGTCGCGTTCCGGCATCACGAAAAGTGAACGGCCATGCCCTGAATGGAGATATCAATGTCACTTCACGGG
ATATTTTTGACGGCCAGGTTATAGCGATTGGTGCAAATAAGAATCTGGATGATTACCAGGTACCGGGGCTTTATTTTCAGGAAGCGAAC
AACAATACCAGTGCAGCAATGAATTACCCGGAGAATAGCGCGGGTTCTCTGATGGTACTGAGAGGTGCCGGAGTCACTCAGGTTTATCG
TGTGTACAACAGCTCGCGCAGTTATTCGCGCAGCAAGTATTCAACGCTGGCATGGACGCCGTGGATGCCAGAAGATTCTTACCCTGTCG
GCGCACCTATCCCCTGGCCATCGGATGTTACCCCGACAGGGTACGCCTTAATGCAGGGGCAGCCCTTTGATAAAGCGGTCTATCCATTG
CTAGCGATTGCCTATCCTGCGGGGATTATCCCGGACATGCGAGGCCAGACGATTAAGGGTAAACCGAACGGTCGCGCGGTACTCTCGTA
TGAACAGGATGGTGTTATATCGCATACCCACGGAGCCAGTATTTCCGATACCGATTTGGGGACGAAATACACCAGCTCTTTTGATTATG

-continued

```
GTTCAAAACCAACAACCAGTTTTGACTACGGCAATAAATCCTCCACTGAGGGTGGGTGGCACGCACATAACTTTCGTTATTGCGCAACG
TCTGCATACCGGGATACCCCCGGTCAGGGGCTGGGGATGCATTCGTCTAATGTTTCATGGGCGGCGGGAGATCGCATTGAGGGAAGCGG
TAATCATGCTCATGTGACATGGATCGGCCCTCATGATCACTGGGTGGGTATTGGTGCGCATAACCATTATGTGGTTATGGGCTATCACG
GACATACAGCGACCGTTCATGCCGCAGGAAATGCGGAAAATACCGTTAAAAATATTGCGTTTAACTACATTGTGAGGCTTGCCTGA
```

ATF86-AP1
(SEQ ID NO: 98)
```
ATGACTTTTGAAATGACCGGAGAAAACCGGACAATTACCATCTATAACCTGCGTGCTGATACAAATGAATTTATCGGGAAAAGTGATGG
GTTTATCCCTGCTAATACCGGTTTGCCTGCTAACAGTACCAATATTGCGCCACCGCCGATGAAAGCCGGTTTTGTCGCTGTATTTAATT
CTGCGTCAGAAAAATGGTCACTTGTTGAAGACCATCGCGGGAAAATTGTTTACGACATTCTCACCGGGAAATCCATCACGATTGATGAA
TTAGGTCAGTTACCTGACGACGTTGTTTCCGTTGCGCCGGAAGGCCATTTTGTTAAATGGAATGGTAAAAAATGGGTGCATGATGCTGA
CGCAGAAAAAACGGCACAGATTACACAGGCTACACAGCAAAAAGACAGTCTTCTGGCGCTGGCTGCATCAAAAATTGCCCCATTACAGG
ATGCTGTTGATCTGGATATTGCAACGGAAGAGGAAACAGCGCTTTTGCTGGCGTGGAAAAAATACAGGGTTTTGATTAATCGTATTAAG
CCAGAAGATGCGCCAGATATTGACTGGCCGGAGGTTCCGGGCGATGTGGCGTGA
```

STF84
(SEQ ID NO: 99)
```
ATGGCAGTAAAGATTTCAGGAGTCCTGAAAGACGGCACAGGAAAACCGGTACAGAACTGCACCATTCAGCTGAAAGCCAGACGTAACAG
CACCACGGTGGTGGTGAACACGGTGGGCTCAGAGAATCCGGATGAAGCCGGGCGTTACAGCATGGATGTGGAGTACGGTCAGTACAGTG
TCATCCTGCAGGTTGACGGTTTTCCACCATCGCACGCCGGGACCATCACCGTGTATGAAGATTCACAACCGGGGACGCTGAATGATTTT
CTCTGTGCCATGACGGAGGATGATGCCCGGCCGGAGGTGCTGCGTCGTCTTGAACTGATGGTGGAAGAGGTGGCGCGTAACGCGTCCGT
GGTGGCACAGAGTACGGCAGACGCGAAGAAATCAGCCGGCGATGCCAGTGCATCAGCTGCTCAGGTCGCGGCCCTTGTGACTGATGCAA
CTGACTCAGCACGCGCCGCCAGCACGTCCGCCGGACAGGCTGCATCGTCAGCTCAGGAAGCGTCCTCCGGCGCAGAAGCGGCATCAGCA
AAGGCCACTGAAGCGGAAAAAAGTGCCGCAGCCGCAGAGTCCTCAAAAAACGCGGCGGCCACCAGTGCCGGTGCGGCGAAAACGTCAGA
AACGAATGCTGCAGCGTCACAACAATCAGCCGCCACGTCTGCCTCCACCGCGGCCACGAAAGCGTCAGAGGCCGCCACTTCAGCACGAG
ATGCGGTGGCCTCAAAAGAGGCAGCAAAATCATCAGAAACGAACGCATCATCAAGTGCCGGTCGTGCAGCTTCCTCGGCAACGGCGGCA
GAAAATTCTGCCAGGGCGGCAAAAACGTCCGAGACGAATGCCAGGTCATCTGAAACAGCAGCGGAACGGAGCGCCTCTGCCGCGGCAGA
CGCAAAAACAGCGGCGGCGGGGAGTGCGTCAACGGCATCCACGAAGGCGACAGAGGCTGCGGGAAGTGCGGTATCAGCATCGCAGAGCA
AAAGTGCGGCAGAAGCGGCGGCAATACGTGCAAAAAATTCGGCAAAACGTGCAGAAGATATAGCTTCAGCTGTCGCGCTTGAGGATGCG
GACACAACGAGAAAGGGGATAGTGCAGCTCAGCAGTGCAACCAACAGCACGTCTGAAACGCTTGCTGCAACGCCAAAGGCGGTTAAGGT
GGTAATGGATGAGACTAATCGTAAATACACCGCACAGGATGCAACGACAGCACAGAAAGGGATAGTTCAGCTTAGCAACGCGACCAACA
GCACATCTGAAATGCTGGCGGCAACGCCAAAGTCGGTAAAGGCAGCCTATGACCTTGCTAACGGGAAATATACTGCTCAGGACGCTACG
ACAGCACAAAAAGGAATTGTCCAGCTCAGTAGTGCAACCAACAGCGCATCTGAAACGCTTGCCGCGACACCGAAAGCAGCTAATGATAA
TGCGAATGGTCGGGTACCTTCTGCCCGTAAGGTGAATGGTAAGGCGCTTTCAGCGGATATAACACTGACGCCGAAAGATATTGGTACGC
TTAACTCAACAACAATGTCATTCAGCGGTGGTGCTGGTTGGTTCAAATTAGCAACGGTAACCATGCCACAGGCGAGTTCTGTTGTTTCA
ATTACGTTGATTGGTGGCGCGGGATTTAACGTGGGGTCACCTCAACAGGCAGGTATATCTGAACTTGTTTTGCGTGCAGGTAATGGTAA
TCCGAAGGGGATTACTGGTGCTTTATGGCAGCGCACATCGACAGGGTTTACAAATTTTGCCTGGGTCAATACATCTGGTGATACTTACG
ATATTTACGTTGCAATCGGAAATTATGCGACTGGTGTAAATATTCAATGGGATTATACCAGTAATGCCAGCGTGACGATTCATACGTCA
CCAGCATATTCTGCTAATAAGCCGGAAGGGTTAACGGACGGTACAGTTTATTCACTCTATACGCCATCAGGGCAGTTTTATCCGCCTGG
CGCACCAATCCCGTGGCCATCAGATACCGTTCCGTCTGGTTATGCCCTGATGCAGGGGCAGACTTTTGACAAATCTGCTTACCCGAAAC
TCGCAGCCGCTTATCCGTCAGGCGTGATCCCTGATATGCGTGGCTGGACGATTAAGGGCAAACCTGCCAGTGGTCGTGCCGTATTGTCT
CAGGAACAGGACGGCATTAAATCGCACACCCACAGCGCCAGCGCATCCAGTACGGATTTGGGGACGAAAACCACATCGTCGTTTGATTA
CGGCACTAAATCCACGAATAACACCGGGGCGCATACGCACAGTGTGAGCGGTACAGCCGCAAGTGCCGGAAACCATACTCATAGTGTCA
CAGGCGCATCAGCAGTCAGCCAGTGGTCACAAAATGGGTCAGTACATAAGGTAGTGTCTGCGGCCAGTGTGAATACAAGTGCTGCAGGA
GCGCACACTCATAGTGTCAGCGGCACAGCCGCATCTGCAGGTGCTCACGCACATACTGTCGGTATTGGTGCTCATACGCACTCTGTTGC
```

GATTGGCTCACATGGACACACCATCACCGTTAACGCTGCTGGTAACGCGGAAAACACCGTCAAAAACATCGCATTTAACTACATTGTGA

GGCTTGCATAA

STF84-AP1

(SEQ ID NO: 100)

ATGGCATTCAGAATGAGTGAACAACCACGGACCATAAAAATTTATAATCTGCTGGCCGGAACTAATGAATTTATTGGTGAAGGTGACGC

ATATATTCCGCCTCATACAGGTCTGCCAGCAAACAGTACCTATATTGCACCGCCAGATATTCCTGCTGGCTTTGTGGCCGTTTTCAACA

GTGATGAGGGATCGTGGCATCTCGTTGAAGACCATCGGGGAAAAACCGTCTATGACGTGGCTTCCGGCGACGCGTTATTTATTTCTGAA

CTTGGCCCATTACCGGAAAATGTCACCTGGTTATCCCCGGAAGGGGAGTTTCAGAAGTGGAACGGCACAGCCTGGGTGAAAGATGCAGA

AGCAGAAAAACTGTTCCGGATCCGGGAGGCGGAAGAAACAAAAAACAGCCTGATGCAGGTAGCCAGTGAGCATATTGCGCCACTTCAGG

ATGCTGTAGATCTGGAAATCGCAACGGAGGAAGAAACCTCATTGCTGGAAGCCTGGAAAAAGTATCGGGTGTTGCTGAACCGTGTTGAT

ACATCAACTGCACCTGATATTGAGTGGCCTACGAACCCTGTCAGGGAGTAA

STF-93

(SEQ ID NO: 101)

ATGGCAGTAAAGATTTCAGGAGTCCTGAAAGACGGCACAGGAAAACCGGTACAGAACTGCACCATTCAGCTGAAAGCCAGACGTAACAG

CACCACGGTGGTGGTGAACACGGTGGGCTCAGAGAATCCGGATGAAGCCGGGCGTTACAGCATGGATGTGGAGTACGGTCAGTACAGTG

TCATCCTGCAGGTTGACGGTTTTCCACCATCGCACGCCGGGACCATCACCGTGTATGAAGATTCACAACCGGGGACGCTGAATGATTTT

CTCTGTGCCATGACGGAGGATGATGCCCGGCCGGAGGTGCTGCGTCGTCTTGAACTGATGGTGGAAGAGGTGGCGCGTAACGCGTCCGT

GGTGGCACAGAGTACGGCAGACGCGAAGAAATCAGCCGGCGATGCCAGTGCATCAGCTGCTCAGGTCGCGGCCCTTGTGACTGATGCAA

CTGACTCAGCACGCGCCGCCAGCACGTCCGCCGGACAGGCTGCATCGTCAGCTCAGGAAGCGTCCTCCGGCGCAGAAGCGGCATCAGCA

AAGGCCACTGAAGCGGAAAAAAGTGCCGCAGCCGCAGAGTCCTCAAAAAACGCGGCGGCCACCAGTGCCGGTGCGGCGAAAACGTCAGA

AACGAATGCTGCAGCGTCACAACAATCAGCCGCCACGTCTGCCTCCACCGCGGCCACGAAAGCGTCAGAGGCCGCCACTTCAGCACGAG

ATGCGGTGGCCTCAAAAGAGGCAGCAAAATCATCAGAAACGAACGCATCATCAAGTGCCGGTCGTGCAGCTTCCTCGGCAACGGCGGCA

GAAAATTCTGCCAGGGCGGCAAAAACGTCCGAGACGAATGCCAGGTCATCTGAAACAGCAGCGGAACGGAGCGCCTCTGCCGCGGCAGA

CGCAAAAACAGCGGCGGCGGGGAGTGCGTCAACGGCATCCACGAAGGCGACAGAGGCTGCGGGAAGTGCGGTATCAGCATCGCAGAGCA

AAAGTGCGGCAGAAGCGGCGGCAATACGTGCAAAAAATTCGGCAAAACGTGCAGAAGATATAGCTTCAGCTGTCGCGCTTGAGGATGCG

GACACAACGAGAAAGGGGATAGTGCAGCTCAGCAGTGCAACCAACAGCACGTCTGAAACGCTTGCTGCAACGCCAAAGGCGGTTAAGGT

GGTAATGGATGAGACTAATCGTAGGGTGCCATCTAACCGAAAAGTTAACGGTAAAGCACTGACTGCGGATATCACATTAACGCCGAAAG

ATATTGGTACTTTAAATTCAGTAACGATGTCTTTCTCTGGCGGGGCTGGGTGGTTCAAACTGGCTACGGTTACCATGCCACAAGCGAGT

TCCATCGTTTACATCGCATTGATTGGTGGCGCTGGTTACAACGTCGGCTCCCCACATCAGGCAGGCATTTCAGAACTGGTTCTACGAGC

AGGCAATGGAAACCCCAAAGGGATTACCGGTGCTTTGTGGAAGCGTACAGCCGTCGGATTAACGAATTTCGCCTGGATCAACACATCCG

GCGATACATATGATATTTACGTTGAGATTGGCAATTATGCGACTAGTGTAAATATCCATTGGGATTGTACTGCAAATGCGACAGTTTCT

ATTTATACATCGCCAACATATTCAGCGAGTAAGCCTTCCAGCGTTACCGATGGTGTTGTTTATACGATGTATAGCACACATCAGAAACC

GACGCCGTTAGATATTGGAGCACTGCCAACAACCGGAGGAACAGTTTCAGGTCCGTTGTCTGTTACTGGTGGGATCACCGGAACATTAA

ATGGTAATGCAAGTACAGCAACGAAATTGCAGACGGCAAGATCTATCGGTGGAGTTGGTTTCGACGGTTCTGCAAATATCAACCTTCCA

GGTGTAAATACTACGGGTAATCAGAACACCACTGGTAATGCTGCAACTGCTACAAAACTTCAGACGGCAAGAACTATCGGCGGCGTGAG

CTTTGATGGTACTGCGAATATTAATTTGCCAGGTGTTAATACGACTGGTAATCAGAATACAACGGGCAACGCGGCTACTGCTACGAAGT

TGCAGACTGCGCGTACTATCAATGGGGTGTCGTTTGACGGCTCGGCAAATATTTCCTTGTCGCCAGCAAATATAGGTTGCCCGGCATCT

CCTACTGGTTGGTTAACTACAGGAAGTAATGGCGGAGCAATAACAACAGCACAGTTAGTGACGTTATTGCAAAATAATGGAGCATTTAA

CACAAAGTCATGGATTGCTCGATGTGCGTGGGCCTATGCCAATAGTGCAACCATACCAAATAGTGAAACTGGTTGTGGCGTTATTCCAT

TGGCAGGAGCTGTTATAGAGGTATTTAATAACGGTAGTAGCTCAAACAATTATACGATCCGTATAACAACGGCCACAACGACGAGTGTC

TCTGGTGCTCTCACTAATGCGGAGTTTATCTATGTATTTAATGGCACAGATTATTCTCCGGGATGGCGAAGAGTATATAACACGAAAAA

CAAACCAACAGCCTCTGATGTCGGTGCATTACCTCTTACCGGTGGTACATTATCTGGAGGTTTGACATCTTCTGGCGAGATCATTTCAA

-continued

AATATGCAAATGGTTTCCGCATTGCTTACGGTAGCTTTGGGTTCTTTATCCGTAATGATGGATCGAACACATATTTCATGCTAACAGCA
TCAGGAGACACATTAGGTTCATGGAACGGTTTGCGACCTATTACAATTAATAATACCAGCGGTGCGGTATCAATTGGTAATGGACTAAA
TGTGACTGGTGGCGTAAATGGTAGTTTGAACGGTAATGCTTCAACAGCTACGAAGTTGCAAACAGCGAGAAACATCAATGGTGTTAAGT
TTGATGGCTCAGGCGATATCAACATTAATACACTGGTATCTCGTGGCCGAGTTACGGCATTAAGCGGCTCTACTCAAGGCACTGCTGGC
ATTCAAATGTACGAGGCGTACAACAATAGCTACCCGACCACGTATGGCAACGTATTGCACATGAAAGGTGCGAGTGCTGCTGGTGAGGG
CGAGTTGCTTATTGGCTGGAGTGGTACGAGCGGTGCACATGCGCCAGTTTTCATTCGCTCACGAAGAGATACCACAGATGCGGCATGGT
CAGCGTGGGCGCAGCTATATACTGCTAAGGATTCAATCCCTGGTGTGAATACAACCGGTAATCAGAATACTACTGGTAATGCCGCAACA
GCCACAAAATTGCAGACAGCAAGGAAAATTGCTGGTGTGGCGTTTGATGGCTCTGCCGATATTACTTTGACTGCGGCTAACCTTAATGC
TTATACGAAAACAGAGGTAACAAACCTTCTAAGTTCCTATGCAAGCAGATCATCACTGACAGGCTATAGTGGCAACCTGGATATTATTG
CTGAAACACTGGTTGTCAAATCAGGCGGTAGTGGAGGGTTTGCTATATGGGATATTGGCACAACTACTAGCGGTGCCAATATGTACATT
GATCCAAACCCTGGTATCAATACAGTTTGGCGTTCAACATCTTCAAGGCGCTATAAAAAGGATATTGAAACATTACAAGATCGATATGC
TGATGAACTTTTGTCATTAAGACCTGTTTGGTATCGTTCAATTTGTCGAGGTGACCGAAAGGATTGGGGGTATTACGGCCTTATTGCTG
AAGAGGTTGGTGAGATTGCCCCGCAATATGTCCATTGGCGTGAACCAACAAATAATGATTCTCCAGAAGATATTTCCTCAAATGGTATG
GTCGCTGAAGGGGTGATGTATGAGCGTTTGGTTGTACCACTCATTCATCATATTCAGCAATTGACCAAAAGGGTTGAGGAGCTTGAAAC
GAAGTTAAATTCACCTAAAGAA

STF-95

(SEQ ID NO: 102)
ATGGCAGTAAAGATTTCAGGAGTCCTGAAAGACGGCACAGGAAAACCGGTACAGAACTGCACCATTCAGCTGAAAGCCAGACGTAACAG
CACCACGGTGGTGGTGAACACGGTGGGCTCAGAGAATCCGGATGAAGCCGGGCGTTACAGCATGGATGTGGAGTACGGTCAGTACAGTG
TCATCCTGCAGGTTGACGGTTTTCCACCATCGCACGCCGGGACCATCACCGTGTATGAAGATTCACAACCGGGGACGCTGAATGATTTT
CTCTGTGCCATGACGGAGGATGATGCCCGGCCGGAGGTGCTGCGTCGTCTTGAACTGATGGTGGAAGAGGTGGCGCGTAACGCGTCCGT
GGTGGCACAGAGTACGGCAGACGCGAAGAAATCAGCCGGCGATGCCAGTGCATCAGCTGCTCAGGTCGCGGCCCTTGTGACTGATGCAA
CTGACTCAGCACGCGCCGCCAGCACGTCCGCCGGACAGGCTGCATCGTCAGCTCAGGAAGCGTCCTCCGGCGCAGAAGCGGCATCAGCA
AAGGCCACTGAAGCGGAAAAAAGTGCCGCAGCCGCAGAGTCCTCAAAAAACGCGGCGGCCACCAGTGCCGGTGCGGCGAAAACGTCAGA
AACGAATGCTGCAGCGTCACAACAATCAGCCGCCACGTCTGCCTCCACCGCGGCCACGAAAGCGTCAGAGGCCGCCACTTCAGCACGAG
ATGCGGTGGCCTCAAAAGAGGCAGCAAAATCATCAGAAACGAACGCATCATCAAGTGCCGGTCGTGCAGCTTCCTCGGCAACGGCGGCA
GAAAATTCTGCCAGGGCGGCAAAAACGTCCGAGACGAATGCCAGGTCATCTGAAACAGCAGCGGAACGGAGCGCCTCTGCCGCGGCAGA
CGCAAAAACAGCGGCGGCGGGGAGTGCGTCAACGGCATCCACGAAGGCGACAGAGGCTGCGGGAAGTGCGGTATCAGCATCGCAGAGCA
AAAGTGCGGCAGAAGCGGCGGCAATACGTGCAAAAAATTCGGCAAAACGTGCAGAAGATATAGCTTCAGCTGTCGCGCTTGAGGATGCG
GACACAACGAGAAAGGGATAGTGCAGCTCAGCAGTGCAACCAACAGCACGTCTGAAACGCTTGCTGCAACGCCAAAGGCGGTTAAGGT
GGTAATGGATGAGACTAATCGTCGGGTACCTTCTGCCCGTAAGGTGAATGGTAAGGCGCTTTCAGCGGATATAACACTGACGCCGAAAG
ATATTGGTACGCTTAACTCAACAACAATGTCATTCAGCGGTGGTGCTGGTTGGTTCAAATTAGCAACGGTAACCATGCCACAGGCGAGT
TCTGTTGTTTCAATTACGTTGATTGGTGGTGCGGGATTTAACGTGGGGTCACCTCAACAGGCAGGTATATCTGAACTTGTTTTGCGTGC
AGGTAATGGTAATCCGAAGGGGATTACTGGTGCTTTATGGCAGCGCACATCGACAGGGTTTACAAATTTTGCCTGGGTCAATACATCTG
GTGATACTTACGATATTTACGTTGCAATCGGAAATTATGCGACTGGTGTAAATATTCAATGGGATTATACCAGTAATGCCAGCGTGACG
ATTCATACGTCACCAGCATATTCTGCTAATAAGCCGGAAGGGTTAACGGACGGTACAGTTTATTCACTCTATACGCCATCAGAGCAGTT
TTATCCGCCTGGCGCACCAATCCCGTGGCCATCAGATACCGTTCCGTCTGGCTATGCCCTGATGCAGGGGCAGACTTTTGACAAATCTG
CATACCCGAAACTTGCAGCCGCTTATCCGTCAGGCGTGATCCCTGATATGCGTGGCTGGACGATTAAGGGCAAACCCGCCAGTGGTCGT
GCCGTATTGTCTCAGGAACAGGACGGCATTAAATCGCACACCCACAGCGCCAGCGCATCCAGTACGGATTTGGGGACGAAAAACACATC
GTCGTTTGATTACGGAACCAAATCCACGAATAACACCGGGGCGCATACGCACAGTCTGAGTGGCTCTACGGGGTCTGCCGGTGATCATA
CTCATGGTAATGGTATTCGTTGGCCAGGAGGCGGCGGTTCTGCGTTAGCATTTTATGATGGCGGTGGGTTCACTTATGTCCAGGATTCA
CAGTATCAAGTAAGCCCGGGGACTTCTTCCCGTAGATCGTATTATCAACGTATTCAGACACAGTCAGCAGGTGCTCATACCCACTCGCT

-continued

GTCTGGTACTGCAGCAAGTTCTGGCGCACATGCACATACTGTAGGTATTGGTGCGCATACGCACTCCGTTGCGATTGGTTCACATGGAC

ACACCATCACCGTTAACGCTGCTGGTAACGCGGAAAACACCGTCAAAAACATCGCATTTAACTATATTGTGAGGCTTGCATAA

STF-95-AP1

(SEQ ID NO: 103)
ATGGCATTCAGAATGAGTGAACAAGCACGGACCATAAAAATTTATAATCTGCTGGCCGGAACTAATGAATTTATTGGTGAAGGTGACGC

ATATATTCCGCCTCATACAGGTCTGCCAGCAAACAGTACCGATATTGCACCACCAGATATTCCTGCTGGCTTTGTGGCTGTTTTCAACA

GTGATGAGGCATCGTGGCATCTCGTTGAAGACCATCGGGGTAAAACGGTTTATGACGTAGCGTCAGGGGACGAGTTATTTATTTCTGAA

CTCGGTCCGTTACCGGAAAATGTTACCTGGTTATCGCCGGAAGGGGAGTTTCAGAAGTGGAACGGCACAGCCTGGGTGAAGGATACGGA

AGCAGAAAAAATGTTCCGGATCCGGGAGGCGGAAGAAACAAAAAACAACCTGATGCAGGTAGCCAGTGAGCATATTGCGCCGCTTCAGG

ATGCTGCAGATCTGGAAATTGCAACGGAGGAAGAAACCTCATTGCTGGAAGCCTGGAAAAAGTATCGGGTGTTGCTGAACCGTGTTGAT

ACATCAACTGCACCTGATATTGAGTGGCCTACGAACCCTGTCAGGGAGTAA

STF-132

(SEQ ID NO: 104)
ATGGCAGTAAAGATTTCAGGAGTCCTGAAAGACGGCACAGGAAAACCGGTACAGAACTGCACCATTCAGCTGAAAGCCAGACGTAACAG

CACCACGGTGGTGGTGAACACGGTGGGCTCAGAGAATCCGGATGAAGCCGGGCGTTACAGCATGGATGTGGAGTACGGTCAGTACAGTG

TCATCCTGCAGGTTGACGGTTTTCCACCATCGCACGCCGGGACCATCACCGTGTATGAAGATTCACAACCGGGGACGCTGAATGATTTT

CTCTGTGCCATGACGGAGGATGATGCCCGGCCGGAGGTGCTGCGTCGTCTTGAACTGATGGTGGAAGAGGTGGCGCGTAACGCGTCCGT

GGTGGCACAGAGTACGGCAGACGCGAAGAAATCAGCCGGCGATGCCAGTGCATCAGCTGCTCAGGTCGCGGCCCTTGTGACTGATGCAA

CTGACTCAGCACGCGCCGCCAGCACGTCCGCCGGACAGGCTGCATCGTCAGCTCAGGAAGCGTCCTCCGGCGCAGAAGCGGCATCAGCA

AAGGCCACTGAAGCGGAAAAAAGTGCCGCAGCCGCAGAGTCCTCAAAAAACGCGGCGGCCACCAGTGCCGGTGCGGCGAAAACGTCAGA

AACGAATGCTGCAGCGTCACAACAATCAGCCGCCACGTCTGCCTCCACCGCGGCCACGAAAGCGTCAGAGGCCGCCACTTCAGCACGAG

ATGCGGTGGCCTCAAAAGAGGCAGCAAAATCATCAGAAACGAACGCATCATCAAGTGCCGGTCGTGCAGCTTCCTCGGCAACGGCGGCA

GAAAATTCTGCCAGGGCGGCAAAAACGTCCGAGACGAATGCCAGGTCATCTGAAACAGCAGCGGAACGGAGCGCCTCTGCCGCGGCAGA

CGCAAAAACAGCGGCGGCGGGGAGTGCGTCAACGGCATCCACGAAGGCGACAGAGGCTGCGGGAAGTGCGGTATCAGCATCGCAGAGCA

AAAGTGCGGCAGAAGCGGCGGCAATACGTGCAAAAAATTCGGCAAAACGTGCAGAAGATATAGCTTCAGCTGTCGCGCTTGAGGATGCG

GACACAACGAGAAAGGGGATAGTGCAGCTCAGCAGTGCAACCAACAGCACGTCTGAAACGCTTGCTGCAACGCCAAAGGCGGTTAAGGT

GGTAATGGATGAGACTAATCGTGCCGTTCAGCGTGATGGTGACACCATGACCGGGGAACTGAAAATCCGTGGTGTTAATGCGCTGAGGA

TTTTCAACGACGCCTTTGGTCTGATTTTTCGTCGTTCAGAAGAGTGCCTGCACCTTATCCCTACCAGTGAAGGTCAGGGCGAGAATGGC

GATATTGGTCCACTTCGCCCCGTTCACTATTAATCTGCGGACGGGTGAAATATCCATGTCGCATAAAGTGTCTGTTGGCGGCGGTTCTCA

GGTCAATGGTGCGCTGGGTATCGGCGTTCAGAACGCGCTGGGCGGAAACTCAATTGCTTTCGGGGATAACGATACAGGTATAAAACAAA

ACGGCGACGGCATTCTGGATGTTTATGCGAATGGACAGCACGTATTCCGTTTTCAGAATGGCGCGTTACAAAGTCACCGGGCAGTGAAT

GTTTCAGGGCGGGTAACACCAACTGATTATGGCAATTTCGATGAACGCTACCAGACCAAAACAGGCGGCGTGCAGAATTTTCAGTACAC

CAGTGAGGTGTTTCACAAGCCAGCCGGTAATGAGGTTTCCTGGGTTTTTCGGGCGCCGTCAGGTTGCACTCTTTCTGGGATTAATGTGC

AGGAGACCGGTAGTAACTCTGCGGATAATATCGGTGGTGTGTATTACAAACAGGCCCAGATTTATATAAATGGCGCATGGCGCTCAGTA

TCAGGTTAA

STF-132-AP1

(SEQ ID NO: 105)
ATGGCGCTCAGTATCAGGTTAATTAAGGCAAAAATAATGGAACTCAGAAATGTCACGCGTTATTACCCGGAAAACATGCCTTATGGTGA

AGGTGTTCAGTATTTCCGTAGTGAAGACGGGCAGGATTTTTATGAATCACTGGATAAATTCGCGAAGAAATACAAGCTGTGCACGCATC

CTGAAACCGGTGTTATTTATTCAATGGCGGAAGACGTATCCCGGCTTTATCCGGCAGGTTTCACCATTGTGGAAGTGGATGAACTACCG

GATGGCTTTTGTATAGAGGCGCGCTGGTATTATAAAGACGGTGAAGTACTGCCGGTTCCTGTTGATTACAGACTGCTGGCTGAGTCGGA

ACGAGCACGTCTTACGGCGATTGCTGAACGGGAAATATCCGACAAGAAAACAGATTTACTTCTGGGAATAATTAATAATGGGGAAAAAG

-continued

```
AAATGCTGAAATTATGGCGGATGTACATCAGAAATTTAAAGAATATTGATTTTAATCACATTCATGATAAATCGTCATTTGATAGTATT
AAATGGCCTTGTGATCCTGAGAATTCACATTAA
```

4) Insertion Point GAGENS

K1F
(SEQ ID NO: 106)
```
ATGGCAGTAAAGATTTCAGGAGTCCTGAAAGACGGCACAGGAAAACCGGTACAGAACTGCACCATTCAGCTGAAAGCCAGACGTAACA
GCACCACGGTGGTGGTGAACACGGTGGGCTCAGAGAATCCGGATGAAGCCGGGCGTTACAGCATGGATGTGGAGTACGGTCAGTACAG
TGTCATCCTGCAGGTTGACGGTTTTCCACCATCGCACGCCGGGACCATCACCGTGTATGAAGATTCACAACCGGGGACGCTGAATGAT
TTTCTCTGTGCCATGACGGAGGATGATGCCCGGCCGGAGGTGCTGCGTCGTCTTGAACTGATGGTGGAAGAGGTGGCGCGTAACGCGT
CCGTGGTGGCACAGAGTACGGCAGACGCGAAGAAATCAGCCGGCGATGCCAGTGCATCAGCTGCTCAGGTCGCGGCCCTTGTGACTGA
TGCAACTGACTCAGCACGCGCCGCCAGCACGTCCGCCGGACAGGCTGCATCGTCAGCTCAGGAAGCGTCCTCCGGCGCAGAAGCGGCA
TCAGCAAAGGCCACTGAAGCGGAAAAAAGTGCCGCAGCCGCAGAGTCCTCAAAAAACGCGGCGGCCACCAGTGCCGGTGCGGCGAAAA
CGTCAGAAACGAATGCTGCAGCGTCACAACAATCAGCCGCCACGTCTGCCTCCACCGCGGCCACGAAAGCGTCAGAGGCCGCCACTTC
AGCACGAGATGCGGTGGCCTCAAAAGAGGCAGCAAAATCATCAGAAACGAACGCATCATCAAGTGCCGGTCGTGCAGCTTCCTCGGCA
ACGGCGGCAGAAAATTCTGCCAGGGCGGCAAAAACGTCCGAGACGAATGCCAGGTCATCTGAAACAGCAGCGGAACGGAGCGCCTCTG
CCGCGGCAGACGCAAAAACAGCGGCGGCGGGGAGTGCGTCAACGGCATCCACGAAGGCGACAGAGGCTGCGGGAAGTGCGGTATCAGC
ATCGCAGAGCAAAGTGCGGCAGAAGCGGCGGCAATACGTGCAAAAAATTCGGCAAAACGTGCAGAAGATATAGCTTCAGCTGTCGCG
CTTGAGGATGCGGACACAACGAGAAAGGGGATAGTGCAGCTCAGCAGTGCAACCAACAGCACGTCTGAAACGCTTGCTGCAACGCCAA
AGGCGGTTAAGGTGGTAATGGATCTGGACAGTCCGGCACTGACCGGAACGCCAACAGCACCAACCGCGCTCAGGGGAACAAACAATAC
CCAGATTGCGAACACCGCTTTTGTACTGGCCGCGATTGCAGATGTTATCGACGCGTCACCTGACGCACTGAATACGCTGAATGAACTG
GCCGCAGCGCTCGGGAATGATCCAGATTTTGCTACCACCATGACTAACGCGCTTGCGGGTAAACAACCGAAGAATGCGACACTGACGG
CGCTGGCAGGGCTTTCCACGGCGAAAAATAAATTACCGTATTTTGCGGAAAATGATGCCGCCAGCCTGACTGAACTGACTCAGGTTGG
CAGGGATATTCTGGCAAAAAATTCCGTTGCAGATGTTCTTGAATACCTTGGGGCCGGTGAGAATTCGGGTGCGAAGGGCGATGGCGTT
ACCGACGACACTGCAGCGCTGACTTCCGCCCTGAACGATACTCCGGTGGGTCAGAAAATCAACGGTAACGGTAAAACTTATAAAGTTA
CGTCCCTGCCGGACATCTCCCGCTTTATCAACACCCGTTTCGTGTATGAACGTATCCCAGGCCAGCCGCTGTACTACGCATCGGAAGA
GTTCGTTCAGGGTGAGCTTTTTAAAATCACCGACACTCCGTATTATAACGCCTGGCCACAGGATAAGGCTTTCGTGTACGAAAACGTT
ATCTATGCTCCGTACATGGGTTCCGACCGTCACGGTGTCAGCCGACTGCACGTAAGCTGGGTGAAATCGGGCGACGATGGTCAGACCT
GGAGCACGCCTGAGTGGCTGACCGACCTTCATCCGGACTATCCGACCGTTAACTATCACTGCATGAGCATGGGCGTCTGTCGCAACCG
TCTGTTCGCAATGATCGAAACCCGTACGCTGGCAAAAAACGCTCTGACTAACTGCGCCCTGTGGGATCGTCCAATGAGCCGCTCTCTG
CACCTGACGGGTGGTATTACCAAAGCAGCGAACCAGCGTTACGCCACCATTCACGTACCGGATCATGGTCTGTTCGTTGGTGACTTTG
TAAATTTCTCTAATTCTGCAGTTACCGGTGTGTCTGGCGACATGACCGTTGCGACCGTAATCGATAAGGACAATTTCACCGTCCTGAC
CCCGAACCAGCAAACCTCTGATCTTAACAACGCTGGCAAGAACTGGCACATGGGCACTAGCTTTCACAAATCTCCGTGGCGTAAAACC
GATCTGGGCCTGATCCCGTCTGTAACTGAAGTGCACTCCTTCGCGACCATTGATAACAACGGTTTCGCTATGGGTTATCACCAAGGTG
ATGTTGCACCGCGTGAAGTCGGCCTCTTTTATTTTCCGGACGCATTCAACAGCCCGTCCAACTACGTGCGCCGTCAGATTCCGTCTGA
ATATGAACCGGACGCCTCCGAGCCGTGCATTAAGTACTATGACGGTGTGCTGTACCTGATTACCCGTGGCACCCGTGGTGATCGTCTG
GGTTCATCTCTGCATCGCTCCCGCGACATTGGTCAGACGTGGGAAAGTCTGCGCTTCCCGCACAATGTTCATCACACCACCCTGCCGT
TCGCGAAAGTCGGCGATGACCTGATCATGTTTGGCTCCGAACGTGCTGAAAACGAATGGGAAGCGGGCGCCCCAGACGATCGCTACAA
GGCATCTTACCCGCGCACCTTCTACGCGCGTCTGAACGTGAACAACTGGAACGCAGACGATATCGAATGGGTAAACATCACCGACCAG
ATCTACCAGGGTGGTATCGTGAACTCTGGTGTGGGCGTTGGTTCCGTTGTAGTTAAAGATAACTACATCTATTATATGTTCGGCGGCG
AAGACCACTTCAACCCGTGGACTTACGGCGATAACTCCGCGAAAGACCCGTTCAAATCCGATGGTCACCCTTCTGACCTCTATTGTTA
```

-continued

```
CAAAATGAAAATCGGTCCGGACAACCGTGTTTCCCGCGATTTTCGCTACGGCGCTGTTCCAAACCGTGCAGTTCCGGTATTCTTCGAC

ACGAACGGCGTGCGTACCGTTCCGGCTCCGATGGAATTCACCGGCGACCTGGGTCTGGGCCACGTAACCATTCGTGCCTCCACCAGCT

CTAACATCCGTTCCGAAGTACTCATGGAAGGTGAATACGGCTTTATCGGTAAGTCTATCCCGACGGACAACCCGGCAGGTCAGCGTAT

CATCTTCTGCGGCGGTGAGGGTACCTCTAGCACCACCGGCGCGCAAATCACCCTGTACGGCGCTAACAACACCGACTCTCGTCGTATC

GTATACAACGGTGATGAACATCTGTTCCAGTCCGCAGACGTGAAACCGTACAACGACAACGTCACCGCACTGGGTGGTCCATCCAACC

GTTTCACCACTGCGTACCTGGGTTCCAACCCGATCGTTACTAGCAATGGTGAACGCAAAACTGAACCGGTAGTGTTTGACGACGCTTT

TCTGGACGCATGGGGCGATGTTCATTACATCATGTATCAGTGGCTGGATGCCGTGCAGCTGAAAGGTAACGACGCGCGTATCCACTTT

GGTGTGATCGCACAGCAGATTCGCGATGTCTTCATCGCACACGGTCTGATGGATGAAAATAGTACTAACTGTCGCTATGCGGTGCTGT

GCTATGACAAATACCCGCGTATGACCGACACCGTGTTCTCGCACAATGAGATTGTTGAACATACCGATGAAGAAGGTAACGTGACTAC

TACCGAAGAACCGGTTTATACCGAAGTGGTTATTCACGAAGAAGGTGAAGAATGGGGCGTGCGTCCTGATGGTATCTTTTTCGCGGAG

GCAGCGTACCAGCGTCGCAAACTGGAACGCATCGAAGCTCGTCTGTCGGCACTGGAACAGAAA
```

K5

(SEQ ID NO: 107)
```
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAAGGCACCTCTGGACAGTCCGGCACTGACCGGAACGCCAACAGCACCAACCGC

GCTCAGGGGAACAAACAATACCCAGATTGCGAACACCGCTTTTGTACTGGCCGCGATTGCAGATGTTATCGACGCGTCACCTGACGCA

CTGAATACGCTGAATGAACTGGCCGCAGCGCTCGGGAATGATCCAGATTTTGCTACCACCATGACTAACGCGCTTGCGGGTAAACAAC

CGAAGAATGCGACACTGACGGCGCTGGCAGGGCTTTCCACGGCGAAAAATAAATTACCGTATTTTGCGGAAAATGATGCCGCCAGCCT

GACTGAACTGACTCAGGTTGGCAGGGATATTCTGGCAAAAAATTCCGTTGCAGATGTTCTTGAATACCTTGGGGCCGGTGAGAATTCG

CCTAAAACCGAAGGTATCCTCCATAAAGGTCAGAGCTTATACGAATATCTGGATGCCCGTGTTCTTACTTCTAAGCCATTCGGTGCAG

CGGGTGATGCAACGACCGACGACACGGAGGTTATCGCTGCGAGCCTGAACAGCCAGAAAGCTGTTACCATCTCTGACGGCGTTTTCAG

TTCTTCTGGCATCAACTCCAACTACTGTAACCTGGATGGTCGCGGATCCGGTGTGCTCAGCCACCGTAGCTCTACTGGTAATTACCTG

GTGTTTAACAATCCGCGTACTGGTCGTCTGAGCAATATCACTGTTGAATCTAACAAAGCGACCGATACCACTCAGGGCCAACAGGTGT

CCCTGGCAGGTGGCAGTGACGTGACCGTGTCAGATGTCAACTTCTCCAACGTGAAAGGCACTGGTTTTAGCCTGATTGCCTACCCAAA

CGATGCTCCGCCGGATGGCCTGATGATCAAAGGCATTCGCGGATCTTACAGCGGTTACGCGACCAACAAAGCAGCTGGTTGCGTCCTG

GCGGATAGCTCCGTTAACAGCCTGATCGACAATGTGATCGCTAAGAATTACCCGCAATTCGGTGCTGTTGAATTAAAGGGCACTGCAA

GCTACAACATTGTATCGAACGTTATCGGTGCGGATTGTCAGCACGTGACTTACAACGGCACTGAGGGACCGATCGCTCCTAGTAACAA

TCTGATCAAGGGCGTTATGGCGAACAACCCGAAATACGCGGCAGTTGTGGCGGGTAAAGGCTCGACGAATCTGATCTCTGATGTACTG

GTAGACTATTCTACCAGCGATGCTCGTCAGGCGCATGGTGTTACCGTCGAAGGATCTGATAACGTGATTAACAACGTACTGATGTCCG

GTTGCGACGGAACTAATTCCCTGGGTCAGCGTCAAACCGCAACTATCGCGCGTTTCATCGGTACTGCAAATAACAACTATGCTAGCGT
```

-continued

```
GTTCCCATCCTATTCTGCCACTGGTGTGATCACGTTTGAGTCTGGCAGTACCCGTAACTTCGTCGAGGTTAAGCATCCGGGCCGTCGC

AACGATCTTCTGTCATCGGCAAGCACGATTGACGGCGCTGCGACCATCGACGGGACTTCTAACTCTAACGTAGTACACGCGCCTGCTC

TGGGCCAATACATTGGCTCCATGAGTGGTCGCTTTGAATGGCGTATTAAGTCAATGAGCCTGCCGTCCGGCGTACTCACTAGCGCGGA

TAAATACCGTATGCTGGGTGACGGTGCTGTTAGCCTTGCTGTTGGCGGAGGAACTAGCAGTCAGGTGCGCTTGTTCACCTCAGACGGT

ACTTCTCGCACTGTTTCTCTGACCAATGGTAACGTGCGCCTGAGCACGTCCTCTACTGGCTATTTACAGCTGGGTGCAGACGCAATGA

CTCCGGACTCCACTGGTACTTACGCGTTAGGCTCCGCATCTCGTGCTTGGAGTGGCGGATTCACTCAGGCAGCATTCACCGTTACTTC

TGACGCACGTTGCAAAACTGAGCCTTTAACCATCTCTGACGCTTTACTGGATGCTTGGAGTGAAGTGGACTTTGTCCAGTTCCAGTAT

CTGGATCGTGTTGAAGAGAAAGGTGCTGACTCCGCGCGTTGGCATTTCGGAATCATCGCCCAGCGTGCTAAAGAGGCATTCGAACGTC

ACGGCATCGATGCGCATCGTTACGGTTTCTTATGCTTTGACTCTTGGGACGATGTGTACGAAGAGGATGCAAATGGATCTCGCAAACT

GATCACTCCGGCGGGTAGTCGCTATGGTATTCGCTATGAGGAAGTTCTGATCCTCGAAGCAGCGCTGATGCGTCGCACGATCAAGCGC

ATGCAGGAAGCACTGGCTGCGTTACCGAAG
```

STF-37
(SEQ ID NO: 108)

```
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAAGGCACCTCTGGACAGTCCGGCACTGACCGGAACGCCAACAGCACCAACCGC

GCTCAGGGGAACAAACAATACCCAGATTGCGAACACCGCTTTTGTACTGGCCGCGATTGCAGATGTTATCGACGCGTCACCTGACGCA

CTGAATACGCTGAATGAACTGGCCGCAGCGCTCGGGAATGATCCAGATTTTGCTACCACCATGACTAACGCGCTTGCGGGTAAACAAC

CGAAGAATGCGACACTGACGGCGCTGGCAGGGCTTTCCACGGCGAAAATAAATTACCGTATTTTGCGGAAAATGATGCCGCCAGCCT

GACTGAACTGACTCAGGTTGGCAGGGATATTCTGGCAAAAAATTCCGTTGCAGATGTTCTTGAATACCTTGGGGCCGGTGAGAATTCG

GAGTTATCTGGAGAGCACGGGTCGTTTTTGATTGGCGGAGTAATTGATTGTTACTCAACCGTTTCAGATCTTATTTCTTCCTCCCCAT

CCGTTGGTAGAGTATGCAGGACTATAGGGTATTACAGCCCAGGTGATGGAGGTGGGCAGATTACATAATTAGTATTGGAACTCCGAT

GCAAGATTTTAGCGATTCTGGTTCTATAGTTATAGATGAATGCAAGTTCGCTAAATTAATCCAGCAAAGCCAATATGATTTAAAGCAG

TTTGGAGTAAAACCATCTGACCCGTCTTATGCAGAAAAAAACGACATATTTATCTCGCAAGCCATTACTAGGTCTAGAGTTGGAAGAT

GCAAGATTATTATAAGCGATGTTATATATCATAAAAAACCTTTAATTTTTGATTATTACAATCATATGGAAGGAAGTTGTATTGGTAG

TGACCCGGAATTTACTCCTAGGTTTATAAAAATAGATAATACAACTAGCGGTTTGCCAGATATGGGATACCCTGGTGTTGCTGATGTT

GTATCTTACGATGTTGATGCAGGAATAATAATTAAAAGACAGAATTCTGGCACAAGTTTTGCCAGAGGTTTCATAATTAAGGGGTTTC

TTCTTCAGTCGGAGAAGAAATCAGCATGGGCAATTTACGCGCCGCATATGGCGGATTTTGATATAGACATTGATAGTCGTGGGTTTAA

TGGAGGAATCAGATGGTTTGTTAATTTTCTTGGAAGAATGGCAGGAAGACATATAGGTCTTGGTGCAAACTCATCAGATCCAACATTA

TCTATAGGTGCGTGGTGTTCGAAATTCTCTACAATACCTGATTGTGGTAATTCCGTTGTATTCAGATTGTCATTCAATGGATTTAACA
```

-continued

GAGGTATGCAAATGGAGTATTTTGGTAATGGGGTTTTAGATAGAGTAACTCTTGAAAATATTTCAAAACCAACACCTACGTCGCCAAC

AACACATGGAATATATGCAACTGATACATGGTTAACTGGCCAGGTGTCATGTGAAAGTTCTTCAACCTGCATCATCCGTGCTGGCAAT

AACGCGAACTTCGATATTACCCTTAGTGCGGTATTCCATGTTACGCAAGATGATCCTTCCGAGGGTATTGTTCATGTATTAAATGGAG

GCCGCCTAACTCTGCGTTCATCTACAATTCTTGCTGATTTGGCAGATACAAAAATCATTAATGAGAATGGAGGTTATCTCGATATTGC

CGCAAATACCAGAACAGGAAATATTGTTTATTCCAATAGTGATAATTACAGATTCAAAGACAGAACCATTGGTTTTGGTCAGACTGCG

GCAACTACAAAAACAAGCTTCTCTTCTGGTGAAGAGATTACATTTTCACTACTAAACGGAACGCCAAAAGCGAATCTATCTGGCGGAA

CGATCCAGTTTAACTCTCCATGCCTGATTAAAATCACTGTGCAGGGGAGGGGTATAACATCAGGAGCACTTACTTTTGGGATAAATGG

AGAATCTTCAGAGAGCGTGAGTCAGGGACAGCAGGTTTCTATGGTTGTCGGAGTGGTATCCGGTGACATTCTTAACCTGAAGGCAACC

TCATCACTGACGCTGGGTAGTGCAGGAGGGGTGCGGGTACTTCTTGAGCCTGTAAAC

1JL (SEQ ID NO: 109)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAAGGCACCTCTGGACAGTCCGGCACTGACCGGAACGCCAACAGCACCAACCGC

GCTCAGGGGAACAAACAATACCCAGATTGCGAACACCGCTTTTGTACTGGCCGCGATTGCAGATGTTATCGACGCGTCACCTGACGCA

CTGAATACGCTGAATGAACTGGCCGCAGCGCTCGGGAATGATCCAGATTTTGCTACCACCATGACTAACGCGCTTGCGGGTAAACAAC

CGAAGAATGCGACACTGACGGCGCTGGCAGGGCTTTCCACGGCGAAAAATAAATTACCGTATTTTGCGGAAAATGATGCCGCCAGCCT

GACTGAACTGACTCAGGTTGGCAGGGATATTCTGGCAAAAAATTCCGTTGCAGATGTTCTTGAATACCTTGGGGCCGGTGAGAATTCG ggctacaaagttcagagcttagcaattctgtccgacacccaagctgtccacgatgctactaacaccattaaaacccagacggacaaga tcaaggcagacacgcaggcaatcaaaactcaaacaaatcaaattaaaaccgaaacgggcgtaattcgtgataaagcgaacactgcgaa aactgatgcgcaggccgcgagcgccgccgcacaaggcttccgtgatcaggcgaaggagtgggcacaaagtgtaaacgctgataactta ttaaccaaaacgggcaacttagctggcctgactgacaagagcgcggcacgttctaatttagggctaggAAGCGTAGCAACGGAAAACA CCGTTCCAATTAAGAAAGGCGGCACTgcggcaacgaccgtcgcggcggcacgctccaatttagggctgggtagcgttgcaacggagaa cactgtcccaattgaaaaggggggactgcggcgacaaccgccgcgaaagcgcgtagcaatctgggtttaggtagcgtagctacggag aataccgtgccgattgaaaagggcggcacggcggcgaccactgccgctaaagcccgttcgaacttcggcttaggcgataacaacaaag taaaacttggtacactgcgcctgaacgggggtgaatctctggttttcaacgatgtggaacgcaatggcctgattatcagcaacgccag cttcggtatcgatagctgggttggtcaaaccatgcacaaatggtataccgattggacgcgtgctggcttagtgcgtgcaggtgacgcg catctgagcgattatcgtgtgcatgtttggaaagacggtttcaccgaagccctgtttcgtttcctgccgacgggcgcttgatttccg gcaactccggtaatccgtctgttaacgaatttcaaaaagccccgctgtctgatcgtgacctgaaaaaagaaatcaagtacactgatgg cgaagaatcctataaccgtgttcgccaatggcttccggctatgttcaaatacaaagagagcgacgttcagcgttacggcctgattgca caagatctggcacgtattgatccggaatacgttcacttattaccgggctatgcaatctacgaagacgttaagggtgtagacgaagagg gcaatgaggttgttgtggatcgtaaagagatcggctataccgacgatgtgttatctctggattctaacgtcttattaatggatttatg cgcggcattcgtgcatttattacataaagttgaaaaattggaaggcaaa

STF-48

(SEQ ID NO: 110)

ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAAGGCACCTCTGGACAGTCCGGCACTGACCGGAACGCCAACAGCACCAACCGC

GCTCAGGGGAACAAACAATACCCAGATTGCGAACACCGCTTTTGTACTGGCCGCGATTGCAGATGTTATCGACGCGTCACCTGACGCA

CTGAATACGCTGAATGAACTGGCCGCAGCGCTCGGGAATGATCCAGATTTTGCTACCACCATGACTAACGCGCTTGCGGGTAAACAAC

CGAAGAATGCGACACTGACGGCGCTGGCAGGGCTTTCCACGGCGAAAAATAAATTACCGTATTTTGCGGAAAATGATGCCGCCAGCCT

GACTGAACTGACTCAGGTTGGCAGGGATATTCTGGCAAAAAATTCCGTTGCAGATGTTCTTGAATACCTTGGGGCCGGTGAGAATTCG

CAGTTAGAAAGCGATGCTGATGGAATGGGAGATGCACTAGTTGCAGTTAAGCAGCCATATATCGGCTCAATAGCTTTAACTCAACATG

ATAAAAATACCAACTTCATTTCAGCCAAGGATTTCGGTGCAACAGCTGACGGAACTCTGCATCCACTCAGCGAGAAATTCTCCACACT

ATCAGCGGCGCAGGCTGTTTATCCATTCGTAACATCACTAACTCAGTCTCTTGACTATGCAGGCATACAGGCCGCAATTAATACAGGG

CGGAATGTATTATTGACATCTGGAACTTACTTCGTAAATGCAACGATAGAGATGAATTCAAACTGCACAATAAATGGCGAAACAAACA

GCAACATAAATAGGCCGGAAACTTTCATAGCAGTAATAGGAAATATAGCTTGTTTCCATTACCACGCAGCGTTTAATACAATAAATAT

TGAAAATGTCTATATTTTTTACGATGGAGGACGCCCTACATCACCTACTGGCAATGATGGTAAAATTGGCATTCTAATTGATGGAGGA

ACTACTTCACCAGGCGTTATGCACATTAAAAATGTTGAGGTTGATGGTGCATGGTGGGCCATATATGATGACTCTGGAAATTACCTAA

CAAAGTATACCCAGGTATGGGCGAGGAGAGTTGCGCATGGTTTCTATAAGGCGAACGGAACGACAATACAGTGGGATACATGTTATGT

GCTGGATGCAGCACAGGCATGGTATGTTGTAAATTGCCTGTCTCCTCAGCTAATAAACTGTGCAGGAGACCAGATCACAGTTGACGGG

TCGCAATATACATTTGATTCCTCAGGGTTATATTTTTCTGGATGTAAGTGTCTTACTATTACAGGGTATGATGGTGAGTCTAATATAA

TAAAAAATACAAATGGAATTACTGCGTCGTATATAAAACTTAATGATACTATTGCCCATATATCAGGATTGGCCGGGCATGGAAACTC

AATGCAAACAACGGGGAGTGGGACAGCAGCATTTATCTTTGCAACAGGCACAAGCATTGTTAACATAAAATCAAGTACCGATAGCTTC

CTTGATAGCGAATCAATAACCTACACTGGCTCTGGATACCCAAACACATTGCTGACAGACTCAACAGCAAAATAATTGCTGAGGGAT

GCCGGTTTAAGGCTCCGACTGGTGGGACTCCTGTAATATCAACTTACAGCACAGGGAATGGAGTATTTACTGACTGCTCATTAACTGG

GACGCAAACTTCAGGCTCATATGTTGAATCACGAAGCTCTGCAGGTAATCAGTTGCCAGCAGTGTACACAGCGAAAGGAACTCAGGCT

GTTGCAGCTAACGTAGCAACTACGTTGTTTGAACTGCCAAATAGCCAAGGGATGTACCTGATAAGCGTTTGGGCAGAAAGCAGTGGAA

CAAATTTCTCTTCGCTTCAGCTTGCCATGTGGGACGGAACAACACACTTACTTTAACTCCGCTTAAGTCAGGAGGGTTGATATCATTTAC

AGTGACAGGAAGGATTGTAACCATCACAAGCCAGGGAACAACAACATTTAACTGGACATACACCAAGGCAGGG

STF-49

(SEQ ID NO: 111)

ATGGCAGTAAAGATTTCAGGAGTCCTGAAAGACGGCACAGGAAAACCGGTACAGAACTGCACCATTCAGCTGAAAGCCAGACGTAACA
GCACCACGGTGGTGGTGAACACGGTGGGCTCAGAGAATCCGGATGAAGCCGGGCGTTACAGCATGGATGTGGAGTACGGTCAGTACAG
TGTCATCCTGCAGGTTGACGGTTTTCCACCATCGCACGCCGGGACCATCACCGTGTATGAAGATTCACAACCGGGGACGCTGAATGAT
TTTCTCTGTGCCATGACGGAGGATGATGCCCGGCCGGAGGTGCTGCGTCGTCTTGAACTGATGGTGGAAGAGGTGGCGCGTAACGCGT
CCGTGGTGGCACAGAGTACGGCAGACGCGAAGAAATCAGCCGGCGATGCCAGTGCATCAGCTGCTCAGGTCGCGGCCCTTGTGACTGA
TGCAACTGACTCAGCACGCGCCGCCAGCACGTCCGCCGGACAGGCTGCATCGTCAGCTCAGGAAGCGTCCTCCGGCGCAGAAGCGGCA
TCAGCAAAGGCCACTGAAGCGGAAAAAAGTGCCGCAGCCGCAGAGTCCTCAAAAAACGCGGCGGCCACCAGTGCCGGTGCGGCGAAAA
CGTCAGAAACGAATGCTGCAGCGTCACAACAATCAGCCGCCACGTCTGCCTCCACCGCGGCCACGAAAGCGTCAGAGGCCGCCACTTC
AGCACGAGATGCGGTGGCCTCAAAAGAGGCAGCAAAATCATCAGAAACGAACGCATCATCAAGTGCCGGTCGTGCAGCTTCCTCGGCA
ACGGCGGCAGAAAATTCTGCCAGGGCGGCAAAAACGTCCGAGACGAATGCCAGGTCATCTGAAACAGCAGCGGAACGGAGCGCCTCTG
CCGCGGCAGACGCAAAAACAGCGGCGGCGGGGAGTGCGTCAACGGCATCCACGAAGGCGACAGAGGCTGCGGGAAGTGCGGTATCAGC
ATCGCAGAGCAAAAGTGCGGCAGAAGCGGCGGCAATACGTGCAAAAAATTCGGCAAAACGTGCAGAAGATATAGCTTCAGCTGTCGCG
CTTGAGGATGCGGACACAACGAGAAAGGGGATAGTGCAGCTCAGCAGTGCAACCAACAGCACGTCTGAAACGCTTGCTGCAACGCCAA
AGGCGGTTAAGGTGGTAATGGATGAGACTAATCGTAAGGCACCTCTGGACAGTCCGGCACTGACCGGAACGCCAACAGCACCAACCGC
GCTCAGGGGAACAAACAATACCCAGATTGCGAACACCGCTTTTGTACTGGCCGCGATTGCAGATGTTATCGACGCGTCACCTGACGCA
CTGAATACGCTGAATGAACTGGCCGCAGCGCTCGGGAATGATCCAGATTTTGCTACCACCATGACTAACGCGCTTGCGGGTAAACAAC
CGAAGAATGCGACACTGACGGCGCTGGCAGGGCTTTCCACGGCGAAAAATAAATTACCGTATTTGCGGAAAATGATGCCGCCAGCCT
GACTGAACTGACTCAGGTTGGCAGGGATATTCTGGCAAAAAATTCCGTTGCAGATGTTCTTGAATACCTTGGGGCCGGTGAGAATTCG
GGGGCTATTGGTGATGGTGTTCATGATGATACATCAGCTCTATCAGAATTACTTTCTGTTGCAACAGGTGGTGAAAAGATAGATGGGC
GAGGGCTTACTTTTAAAGTATCAACTCTTCCAGATGTCAGTCGATTTAAAAATGCTCGTTTTTATTTGAGAGAATACCGGGTCAGCC
TCTTTTTTATGCTTCTGAAGATTTTATCCAGGGAGAGTTATTTAAAATTACAGATACACCGTGGTACAACGCCTGGACGCAGGATAAA
ACGTTTGTATATGACAATGTCATCTATGCGCCTTTTATGGCTGGAGACCGCCATGGTGTAAATAACCTCCATGTTGCATGGGTTCGCT
CAGGAGATGACGGGAGGACCTGGACAACGCCGGAATGGCTTACAGATTTACATGAAAACTATCCCACAGTTAACTATCACTGCATGAG
TATGGGGGTTGTCAGAAATCGCCTTTTTGCTGTAATTGAGACGCGGACCGTGAGCGGAAATAAACTGCAGGTTGCAGAGTTGTGGGAT
CGCCCAATGAGTCGCAGCCTTCGCGCTTATGGTGGTATAACGAAAGCAGCAAATCAGCAAGTCGCTTATATTCGCATTACTGATCACG
GATTATTTGCTGGTGATTTTGTCAACTTCTCAAACTCTGGTGTTACAGGTGTTACCGGGAATATGACGGTGACTACTGTTATTGATAA
AAATACTTTTACAGTTACGACGCAAAATACCCAGGATGTGGATCAGAATAACGAGGGTAGATACTGGAGTTTTGGTACATCATTTCAC
TCGTCACCATGGAGAAAAACCAGTCTTGGAACTATTCCTTCTTTTGTTGACGGAAGCACTCCTGTTACTGAGATTCACAGTTTTGCGA
CGATTAGCGATAACAGTTTTGCTGTTGGCTACCATAATGGTGATATTGGTCCACGCGAGCTTGGGATACTCTATTTCTCTGATGCTTT
CGGTTCTCCTGGTAGCTTTGTTCGCAGACGCATACCTGCAGAATATGAGGCGAATGCATCTGAGCCATGTGTAAAATATTATGATGGC
ATTCTGTATCTGACGACCAGGGGGACATTAAGTACTCAACCCGGTAGTTCATTGCACAGAAGCTCTGATTTAGGTACATCATGGAATT
CTCTTCGCTTCCCAAATAATGTTCATCACTCAAACCTTCCTTTTGCCAAAGTTGGCGATGAGCTGATTATTTTTGGCAGTGAGCGCGC
ATTTGGTGAGTGGGAAGGAGGAGAACCTGATAACCGTTATGCAGGAAACTATCCAAGAACATTTATGACCAGAGTTAACGTCAATGAG
TGGAGTCTGGATAATGTAGAGTGGGTTAATGTTACTGATCAGATTTATCAGGGCGGAATAGTTAACTCTGCGGTTGGTGTTGGTTCAG
TTTGTATCAAAGACAACTGGCTGTACTACATTTTCGGTGGGAAGACTTTCTAAACCCATGGAGCATAGGGGATAACAACAGAAAATA
TCCTTATGTTCACGATGGTCACCCGGCTGATTTGTATTGTTTCAGGGTGAAAATTAAACAGGAAGAATTTGTTTCAAGGGATTTTGTC
TACGGAGCCACTCCTAACAGAACGCTTCCTACTTTTATGTCGACGTCAGGCGTGAGGACGGTTCCTGTACCCGTTGATTTCACAGATG
ATGTTGCCGTCCAGTCACTGACTGTCCATGCAGGTACATCAGGACAAGTTCGCGCGAAGTCAAACTTGAGGGTAATTACGCCATTAT
TGCGAAGAAAGTACCGTCTGATGATGTTACCGCTCAGAGATTAATCGTTAGCGGCGGTGAAACAACGTCTTCAGCAGATGGTGCAATG

-continued

ATAACGTTGCATGGTTCCGGAAGCAGTACTCCTCGTCGCGCGGTATATAACGCACTCGAACATCTTTTTGAGAACGGAGATGTTAAAC
CTTATCTTGATAATGTAAATGCTCTTGGTGGTCCGGGAAACAGGTTCTCGACAGTTTATCTTGGCTCCAATCCTGTGGTTACCAGTGA
CGGAACATTAAAGACAGAGCCGGTCTCTCCTGACGAAGCATTGCTGGATGCCTGGGGTGACGTCAGGTATATCGCTTATAAATGGCTG
AACGCTGTCGCTATAAAGGGGGAAGAAGGGGCGAGGATACATCATGGTGTAATCGCGCAGCAACTTCGTGATGTTCTTATTTCTCACG
GACTCATGGAAGAAGAAAGCACAACATGCCGCTATGCGTTTCTTTGCTATGACGATTATCCCGCAGTATATGATGACGTCATTACTGG
CCAAAGGGAAATGCCGCTGACTGATAATGACGGGAGCATCATTGTTGATGAGGATGATAATCCAGTGATGGTAATGGAAGACATCATT
GAGCGCGTTGAAATAACGCCAGCAGGATCTAGATGGGGGTCAGACCTGATCTCTTATTCTATATCGAGGCGGCATGGCAGCGCAGAG
AAATAGAAGAATAAAAGCTAGGTTAGACTTAATAGAAGGGAAGCAC

STF-52

(SEQ ID NO: 112)

ATGGCAGTAAAGATTTCAGGAGTCCTGAAAGACGGCACAGGAAAACCGGTACAGAACTGCACCATTCAGCTGAAAGCCAGACGTAACA
GCACCACGGTGGTGGTGAACACGGTGGGCTCAGAGAATCCGGATGAAGCCGGGCGTTACAGCATGGATGTGGAGTACGGTCAGTACAG
TGTCATCCTGCAGGTTGACGGTTTTCCACCATCGCACGCCGGGACCATCACCGTGTATGAAGATTCACAACCGGGGACGCTGAATGAT
TTTCTCTGTGCCATGACGGAGGATGATGCCCGGCCGGAGGTGCTGCGTCGTCTTGAACTGATGGTGGAAGAGGTGGCGCGTAACGCGT
CCGTGGTGGCACAGAGTACGGCAGACGCGAAGAAATCAGCCGGCGATGCCAGTGCATCAGCTGCTCAGGTCGCGGCCCTTGTGACTGA
TGCAACTGACTCAGCACGCGCCGCCAGCACGTCCGCCGGACAGGCTGCATCGTCAGCTCAGGAAGCGTCCTCCGGCGCAGAAGCGGCA
TCAGCAAAGGCCACTGAAGCGGAAAAAAGTGCCGCAGCCGCAGAGTCCTCAAAAAACGCGGCGGCCACCAGTGCCGGTGCGGCGAAAA
CGTCAGAAACGAATGCTGCAGCGTCACAACAATCAGCCGCCACGTCTGCCTCCACCGCGGCCACGAAAGCGTCAGAGGCCGCCACTTC
AGCACGAGATGCGGTGGCCTCAAAAGAGGCAGCAAAATCATCAGAAACGAACGCATCATCAAGTGCCGGTCGTGCAGCTTCCTCGGCA
ACGGCGGCAGAAAATTCTGCCAGGGCGGCAAAAACGTCCGAGACGAATGCCAGGTCATCTGAAACAGCAGCGGAACGGAGCGCCTCTG
CCGCGGCAGACGCAAAAACAGCGGCGGCGGGGAGTGCGTCAACGGCATCCACGAAGGCGACAGAGGCTGCGGGAAGTGCGGTATCAGC
ATCGCAGAGCAAAAGTGCGGCAGAAGCGGCGGCAATACGTGCAAAAAATTCGGCAAAACGTGCAGAAGATATAGCTTCAGCTGTCGCG
CTTGAGGATGCGGACACAACGAGAAAGGGGATAGTGCAGCTCAGCAGTGCAACCAACAGCACGTCTGAAACGCTTGCTGCAACGCCAA
AGGCGGTTAAGGTGGTAATGGATGAGACTAATCGTAAGGCACCTCTGGACAGTCCGGCACTGACCGGAACGCCAACAGCACCAACCGC
GCTCAGGGGAACAAACAATACCCAGATTGCGAACACCGCTTTTGTACTGGCCGCGATTGCAGATGTTATCGACGCGTCACCTGACGCA
CTGAATACGCTGAATGAACTGGCCGCAGCGCTCGGGAATGATCCAGATTTTGCTACCACCATGACTAACGCGCTTGCGGGTAAACAAC
CGAAGAATGCGACACTGACGGCGCTGGCAGGGCTTTCCACGGCGAAAAATAAATTACCGTATTTTGCGGAAAATGATGCCGCCAGCCT
GACTGAACTGACTCAGGTTGGCAGGGATATTCTGGCAAAAAATTCCGTTGCAGATGTTCTTGAATACCTTGGGGCCGGTGAGAATTCG
CAGCTAGCAAGCTCAGAAGATGGAATGGGTGACGCACTAGTTGCAGTTAAGCAGCCATATATCGGCTCAATAGCTTTAACTCAACATG
ATAAAAATACCAACTTCATTTCAGCCAAGGATTTCGGTGCAACAGCTGACGGAACTCTGCATCCACTCAGCGAGAAATTCTCCACACT
ATCAGCGGCGCAGGCTGTTTATCCATTCGTAACATCACTAACTCAGTCTCTTGACTATGCAGGCATACAGGCCGCAATTAATACAGGG
CGGAATGTATTATTGACATCTGGAACTTACTTCGTAAATGCAACGATAGAGATGAATTCAAACTGCACAATAAATGGCGAAACAAACA
GCAACATAAATAGGCCGGAAACTTTCATAGCAGTAATAGGAAATATAGCTTGTTTCCATTACCACGCAGCGTTTAATACAATAAATAT
TGAAAATGTCTATATTTTTACGATGGAGGACGCCCTACATCACCTACTGGCAATGATGGTAAAATTGGCATTCTAATTGATGGAGGA
ACTACTTCACCAGGCGTTATGCACATTAAAAATGTTGAGGTTGATGGTGCATGGTGGGCCATATATGATGACTCTGGAAATTACCTAA
CAAAGTATACCCAGGTATGGGCGAGGAGAGTTGCGCATGGTTTCTATAAGGCGAACGGAACGACAATACAGTGGGATACATGTTATGT
GCTGGATGCAGCACAGGCATGGTATGTTGTAAATTGCCTGTCTCCTCAGCTAATAAACTGTGCAGGAGACCAGATCACAGTTGACGGG
TCGCAATATACATTTGATTCCTCAGGGTTATATTTTTCTGGATGTAAGTGTCTTACTATTACAGGGTATGATGGTGAGTCTAATATAA
TAAAAAATACAAATGGAATTACTGCGTCGTATATAAAACTTAATGATACTATTGCCCATATATCAGGATTGGCCGGGCATGGAAACTC
AATGCAAACAACGGGAGTGGGACAGCAGCATTTATCTTTGCAACAGGCACAAGCATTGTTAACATAAAATCAAGTACCGATAGCTTC
CTTGATAGCGAATCAATAACCTACACTGGCTCTGGATACCCAAACACATTGCTGACAGACTCAACAGCAAAATAATTGCTGAGGGAT
GCCGGTTTAAGGCTCCGACTGGTGGGACTCCTGTAATATCAACTTACAGCACAGGGAATGGAGTATTTACTGACTGCTCATTAACTGG

-continued

GACGCAAACTTCAGGCTCATATGTTGAATCACGAAGCTCTGCAGGTAATCAGTTGCCAGCAGTGTACACAGCGAAAGGAACTCAGGCT

GTTGCAGCTAACGTAGCAACTACGTTGTTTGAACTGCCAAATAGCCAAGGGATGTACCTGATAAGCGTTTGGGCAGAAAGCAGTGGAA

CAAATTTCTCTTCGCTTCAGCTTGCCATGTGGGACGGAACAACACTTACTTTAACTCCGCTTAAGTCAGGAGGGTTGATATCATTTAC

AGTGACAGGAAGGATTGTAACCATCACAAGCCAGGGAACAACAACATTTAACTGGACATACACCAAGGCAGGG

1AR (SEQ ID NO: 113)

ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAAGGCACCTCTGGACAGTCCGGCACTGACCGGAACGCCAACAGCACCAACCGC

GCTCAGGGGAACAAACAATACCCAGATTGCGAACACCGCTTTTGTACTGGCCGCGATTGCAGATGTTATCGACGCGTCACCTGACGCA

CTGAATACGCTGAATGAACTGGCCGCAGCGCTCGGGAATGATCCAGATTTTGCTACCACCATGACTAACGCGCTTGCGGGTAAACAAC

CGAAGAATGCGACACTGACGGCGCTGGCAGGGCTTTCCACGGCGAAAAATAAATTACCGTATTTTGCGGAAAATGATGCCGCCAGCCT

GACTGAACTGACTCAGGTTGGCAGGGATATTCTGGCAAAAAATTCCGTTGCAGATGTTCTTGAATACCTTGGGGCCGGTGAGAATTCG atcgctacccgcgtgtccaaagaaggtgacactatgactggtaagctgactctgtctgcgggtaacgatgcgctggtgctgactgcgg gcgagggcgcgtcctcgcacattcgctctgacgtgggcgggacgaacaactggtatatcggtaaaggcagtggggataacggtttagg cttctactcatacatcactcagggcggggtgtatattaccaacaacggggaaatcgctttaagcccgcagggtcagggtacgtttaac ttcaaccgtgatcgtctgcacatcaacggcacgcaatggacggcacatcaaggcggtggctggaaaaccagtggaatcaggaagcgcc gattttattgatttcggcaacgtgggcaatgatagctactacccgattatcaaaggtaagtccggcattaccaacgaaggttatatt tctggcgtggacttcggtatgcgtcggattactaacacgtgggcgcagggtattatccgcgtaggcaatcaggaaaacggtagcgatc cgcaggccatctacgagttccatcataatggcgtactgtacgttcctaatatggtaaaaacgggtgcgcgtctgagcgcaggtggggg ggatccggtatggcagggtgcatgtgttgttatcggtgacaatgacacgggcttagtgcatggtggcgatggtcgcatcaatatggtt gcaaacggtatgcacattgcgtcttggagttccgcgtatcatttacatgagggtttatgggatactacgggcgcgttatggacggagc aagggcgtgcaattatcagcttcggtcatctggtacaacaaagcgatgcctattccacctttgtccgtgatgtatacgttcgttcgga tattcgcgttaaaaaagatctggtgaaattcgaaaacgctagcgaaaaactgtccaaaatcaacggttatacttatatgcagaaacgc gggttagacgaagaaggtaatcagaaatgggagcctaacgccggattaatcgcgcaggaagtgcaggcgattctgccggaactggtag aaggcgatccggacggtgaagcattattacgtctgaactacaatggcgtgatcggcctgaatactgcggcgattaatgaacatacggc agagatcgcggagctgaaaagcgagattgaagaactgaaaaaaattgtcaaaagcctgttaaag

1AR-AP1

(SEQ ID NO: 114)

atggcagtaacaggaccgtgggtaggatcgtctgcagtagttaatacaggacaaaattggatggtcggcgcggcccaacgattaagaa tgggtgctccgttctggatgagcaacatgattgggcgctctgttgaagtgattcatacgttaggcgcagatcataattttaatggtca -continued atggtttcgtgaccgttgctttgaggcgggcagtgcgccgatcgtgtttaacatcactggcgatttagtttcttactcccgtgacgtt ccgctgtttttcatgtatggtgacacgccgaacgagtatgtacaattaaacattcacggtgtcacgatgtacgggcgcggggcaacg gttgggcggcgggtgcaatcggtgcgagcgatggcggggtgtgcatccagaatgatattggaggccgactgcgtatcaacaatggtgg ggcaatcgcgggcggtggcggtggtgggggtggttattctcaggctaacaattgggcaggtaagtacgtttgcggtggcggtggcggt cgtccgttcggcttaggtggcaacaacggtgcgcgttggcctgggggcaacgctagcctgacctcgccgggcgcaggtgggaacactg gcacgcgttattacgctggcggggggaggtgaggttggtcagccgggtcagtatgcaaacccggcgcgggttactccaccccaccaac gtcgccgggcgcggcagttgcaggtagtgcgccaacttggcaaaacgtgggcgctatttatggcccgcgtgtttaa 1AR-AP2
(SEQ ID NO: 115)
ATGAGTGAACAGACCATCGAACAAAAATTAAGCGCGGAAATCGTGACTCTGAAAAGTCGCATTCTGGATACTCAGGACCAGGCAGCAC GTCTGATGGAAGAGTCTAAAATCTTGCAGGGCACTCTGGCAGAAATTGCCCGTGCGGTGGGTATCACAGGCGACACGATCAAAGTAGA

AGAAATTGTGGAGGCCGTAAAGAATCTCACAGCGGAGAGCACCGATGAAGCAAAAGACGAAGAATAA 13-13.0
(SEQ ID NO: 116)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAAGGCACCTCTGGACAGTCCGGCACTGACCGGAACGCCAACAGCACCAACCGC

GCTCAGGGGAACAAACAATACCCAGATTGCGAACACCGCTTTTGTACTGGCCGCGATTGCAGATGTTATCGACGCGTCACCTGACGCA

CTGAATACGCTGAATGAACTGGCCGCAGCGCTCGGGAATGATCCAGATTTTGCTACCACCATGACTAACGCGCTTGCGGGTAAACAAC

CGAAGAATGCGACACTGACGGCGCTGGCAGGGCTTTCCACGGCGAAAAATAAATTACCGTATTTTGCGGAAAATGATGCCGCCAGCCT

GACTGAACTGACTCAGGTTGGCAGGGATATTCTGGCAAAAAATTCCGTTGCAGATGTTCTTGAATACCTTGGGGCCGGTGAGAATTCG

ATCATCCAGTTAGAAGATAGTCAAGGCGCCCATTTTTCCACTGAACGTACTTTAGCGACAGGTGCAATTAAAACTCGTTTCTTTGGCG

AAACATTTACTGATGGTACATTATACCTAAATCAGATGAATAATAGTTCTGAACGATTCTCTATTAATAATTGGGGAAATTCAGAAGT

TGGTCGCCCGGCAGTGTTGGAAGTCGGTGATTCCAAAGGTTATCACTTCTATACGGAACGCGGGACAGATAAACAGTTTGAATTTTGAT

GTTGCTGGCAATTTTACTGTGCATGGACCTTCCGGGATTACTATCAAAACCTCTACTGGTGCTCGCCATATCTGGTTTAGAGATGATA

GCGATGCAGAAAAGGCTGTTATCTGGGCTACAGATGAGGGTATTTTACATATACGAAATAATTATGGGGGTTCATTTAGTCATCACTT

CCAGGGTGCAATGATTCTAGCGGGAGAGCGTGTTCCATATAATAGTGAATACGCTCTTATCCGTGGTAATATTTCCGGTGGTGCATGG

GTAGACTGGCGAGGTCGTCCGGCTGGATTGTTGGTAGACTGTCAGGACTCACGAAATCAAGCATATAACATTTGGAAAGCTACTCATT

GGGGCGACCAGCACCTTGCGGCGATGGGTGTTCATGCTGGCGGTGGTAATCCTCAGGTTGTATTGCATGTGGGTGGGAATGATTATGC

ATTTGCATCTAACGGTGATTTTACTGCTGGTGCTGCTGTATATTGTAACGACGTTTATATTCGTTCTGACCGTCGTCTGAAAATTAAT

GTTAAAGACTACGAAGAGAATGCGGTGGATAAGGTAAATAAACTCAAAGTTAAAACCTATGATAAAGTTAAATCTCTTTCTGACCGCG

AAGTTATCGGCCATGAGATTGGTATTATCGCACAGGATTTGCAAGAAGTATTACCGGAAGCTGTTAGCACTTCTAGTGTCGGATCTCA

-continued

GGATAACCCAGAAGAAATTTTAACAATTTCTAACTCTGCTGTGAACGCGCTTTTAATTAAGGCTATTCAGGAAATGAGTGAAGAAATT

AAAGAATTGAAAACGCCTCTCTTTACTAAAATTGCTCGCAAAATTAGTAAATATTTTAAATTCTAA 13-13.0-AP1

(SEQ ID NO: 117)

ATGGCAGTAGTTGGAGTTCCTGGCTGGATTGGAAGTTCAGCCGTAAATGAAACGGGTCAGCGCTGGATGAGTCAAGCAGCTGGTCAAT

TAAGATTGGGTGTTCCTTGCTGGATGAGTCAATTTGCAGGTCGCTCAAGAGAAATTATTCATACACTTGGAGCAGACCATAACTTCAA

TGGTCAATGGTTCCGAGATAGATGTTTTGAGGCAGGTAGTACACCTATAGTGTTTAATATCACTGGAGATTTAGTATCATATTCTAAA

GATGTTCCTTTATTCTTCATGTACGGAGATACACCGAATGAATATGTTCAACTGAATATACACGGCGTAACGATGTATGGACGTGGCG

GTAATGGCGGTAGCAATAGTCCTGGTTCAGCTGGAGGTCATTGTATTCAAAACGATATTGGTGGGAGACTAAGAATTAATAACGGTGG

AGCTATTGCCGGCGGCGGCGGTGGCGGCGGTGGCGGTAGATATGGCAGACTATCATTTGGTGGTGGCGGTGGTCGCCCATTCGGTGCT

GGCGGGTCTTCCTCTCATATGAGTTCCGGTGCAACTGCTGGCACCATTTCCGCTCCGGGTGCAGGATCTGTCGGTGAGGGaTCTCTTT

GGGTATATACAGGCGGTTCGGGTGGTAATGTCGGTGCTGCTGGAGGAAGATGTAATATTCAAGGTAACGGTACAGAATATGATGGCGG

TGCTGCTGGTTATGCTGTTATAGGGTCTGCTCCAACTTGGATAAATGTTGGAGCAATATATGGTCCAAGAGTATAA 13-13.0-AP2

(SEQ ID NO: 118)

ATGTCTGAACAAACTATTGAACAAAAACTGTCTGCTGAAATCGTAACTCTGAAGTCTCGTATCCTTGATACGCAGGACCAAGCGGCTC

GTCTGATGGAAGAATCCAAAATTCTGCAAGGAACTTTGGCTGAAATTGCTCGTGCAGTAGGTATCACTGGCGATACTATCAAAGTTGA

AGAAATCGTTGAAGCTGTCAAGAATCTTACTGCTGAATCTGCAGATGAAGCAAAAGATGAAGAATGA

5) Insertion Point SAGDAS 13-14.3

(SEQ ID NO: 119)

ATGGCAGTAAAGATTTCAGGAGTCCTGAAAGACGGCACAGGAAAACCGGT

ACAGAACTGCACCATTCAGCTGAAAGCCAGACGTAACAGCACCACGGTGG

TGGTGAACACGGTGGGCTCAGAGAATCCGGATGAAGCCGGGCGTTACAGC

ATGGATGTGGAGTACGGTCAGTACAGTGTCATCCTGCAGGTTGACGGTTT

TCCACCATCGCACGCCGGGACCATCACCGTGTATGAAGATTCACAACCGG

GGACGCTGAATGATTTTCTCTGTGCCATGACGGAGGATGATGCCCGGCCG

GAGGTGCTGCGTCGTCTTGAACTGATGGTGGAAGAGGTGGCGCGTAACGC

GTCCGTGGTGGCACAGAGTACGGCAGACGCGAAGAAATCAGCCGGCGATG

CCAGTATTTCTGATGATATTGGATGGATGCATTATATTCAACGAAATAAA

GATAATACAGTTGAAGCCGTATTAAATGGTCAACAGACAATTAACGAAAA

TATTATTGCGAAAAAGGATATTTGGGTTGACCGAGCAGTTCACACCCTTG

GCGAAATCACTACAAATGCTGTTAATGGTCTTCGTATTTGGAATAATGAT

TATGGAGTCATTTTTAGACGTTCAGAAGGAAGTCTTCATATTATTCCTAC

CGCATTTGGTGAAGGAGAAACCGGTGATATTGGACCTTTACGTCCTCTCA

GTATAGCTTTAGATACCGGTAAAGTTACTATTCCGGATTTACAATCAAGT

TACAATACGTTCGCTGCTAACGGTTATATTAAATTTGTTGGTCATGGAGC

GGGGGCCGGCGGTTATGACATTCAATATGCTCAAGCGGCTCCTATTTTCC

AGGAAATCGATGATGATGCTGTAAGCAAATATTATCCTATTGTTAAACAG

AAGTTTTTAAACGGTAAATCCGTTTGGTCTTTAGGTACCGAAATTGAATC

AGGTACATTCGTTATTCATCATCTGAAAGAAGATGGTTCACAAGGCCATG

CGTCTCGTTTTAATCAAGACGGTACTGTTAACTTCCCGGATAACGTTCTG

-continued

GTCGGCGGTGATATTAACATGAAAGGCATGATGACTTTTGACGCCGGACG

TTTAGGATCACGAGATTATTTTAAATTTAACCATTGGGGTGATAGTAATA

ATGGTCGTGATAACATCATCCAGTTAGAAGATAGTCAAGGCGCCCATTTT

TCCACTGAACGTACTTTAGCGACAGGTGCAATTAAAACTCGTTTCTTTGG

CGAAACATTTACTGATGGTACATTATACCTAAATCAGATGAATAATAGTT

CTGAACGATTCTCTATTAATAATTGGGGAAATTCAGAAGTTGGTCGCCCG

GCAGTGTTGGAAGTCGGTGATTCCAAAGGTTATCACTTCTATACGGAACG

CGGGACAGATAACAGTTTGAATTTTGATGTTGCTGGCAATTTTACTGTGC

ATGGACCTTCCGGGATTACTATCAAAACCTCTACTGGTGCTCGCCATATC

TGGTTTAGAGATGATAGCGATGCAGAAAAGGCTGTTATCTGGGCTACAGA

TGAGGGTATTTTACATATACGAAATAATTATGGGGGTTCATTTAGTCATC

ACTTCCAGGGTGCAATGATTCTAGCGGGAGAGCGTGTTCCATATAATAGT

GAATACGCTCTTATCCGTGGTAATATTTCCGGTGGTGCATGGGTAGACTG

GCGAGGTCGTCCGGCTGGATTGTTGGTAGACTGTCAGGACTCACGAAATC

AAGCATATAACATTTGGAAAGCTACTCATTGGGGCGACCAGCACCTTGCG

GCGATGGGTGTTCATGCTGGCGGTGGTAATCCTCAGGTTGTATTGCATGT

GGGTGGGAATGATTATGCATTTGCATCTAACGGTGATTTTACTGCTGGTG

CTGCTGTATATTGTAACGACGTTTATATTCGTTCTGACCGTCGTCTGAAA

ATTAATGTTAAAGACTACGAAGAGAATGCGGTGGATAAGGTAAATAAACT

CAAAGTTAAAACCTATGATAAAGTTAAATCTCTTTCTGACCGCGAAGTTA

TCGGCCATGAGATTGGTATTCGCACAGGATTTGCAAGAAGTATTACCG

GAAGCTGTTAGCACTTCTAGTGTCGGATCTCAGGATAACCCAGAAGAAAT

-continued
TTTAACAATTTCTAACTCTGCTGTGAACGCGCTTTTAATTAAGGCTATTC
AGGAAATGAGTGAAGAAATTAAAGAATTGAAAACGCCTCTCTTTACTAAA
ATTGCTCGCAAAATTAGTAAATATTTTAAATTC 13-14.3-AP1
(SEQ ID NO: 120)
ATGGCAGTAGTTGGAGTTCCTGGCTGGATTGGAAGTTCAGCCGTAAATGA
AACGGGTCAGCGCTGGATGAGTCAAGCAGCTGGTCAATTAAGATTGGGTG
TTCCTTGCTGGATGAGTCAATTTGCAGGTCGCTCAAGAGAAATTATTCAT
ACACTTGGAGCAGACCATAACTTCAATGGTCAATGGTTCCGAGATAGATG
TTTTGAGGCAGGTAGTACACCTATAGTGTTTAATATCACTGGAGATTTAG
TATCATATTCTAAAGATGTTCCTTTATTCTTCATGTACGGAGATACACCG
AATGAATATGTTCAACTGAATATACACGGCGTAACGATGTATGGACGTGG
CGGTAATGGCGGTAGCAATAGTCCTGGTTCAGCTGGAGGTCATTGTATTC
AAAACGATATTGGTGGGAGACTAAGAATTAATAACGGTGGAGCTATTGCC
GGCGGCGGCGGTGGCGGCGGTGGCGGTAGATATGGCAGACTATCATTTGG
TGGTGGCGGTGGTCGCCCATTCGGTGCTGGCGGGTCTTCCTCTCATATGA
GTTCCGGTGCAACTGCTGGCACCATTTCCGCTCCGGGTGCAGGATCTGTC
GGTGAGGGaTCTCTTTGGGTATATACAGGCGGTTCGGGTGGTAATGTCGG
TGCTGCTGGAGGAAGATGTAATATTCAAGGTAACGGTACAGAATATGATG
GCGGTGCTGCTGGTTATGCTGTTATAGGGTCTGCTCCAACTTGGATAAAT
GTTGGAGCAATATATGGTCCAAGAGTA 13-14.3-AP2
(SEQ ID NO: 122)
ATGTCTGAACAAACTATTGAACAAAAACTGTCTGCTGAAATCGTAACTCT
GAAGTCTCGTATCCTTGATACGCAGGACCAAGCGGCTCGTCTGATGGAAG
AATCCAAAATTCTGCAAGGAACTTTGGCTGAAATTGCTCGTGCAGTAGGT
ATCACTGGCGATACTATCAAAGTTGAAGAAATCGTTGAAGCTGTCAAGAA
TCTTACTGCTGAATCTGCAGATGAAGCAAAAGATGAAGAA T4-like SEQUENCES (underlined are the DTF insertion
sites used in the fusions described above):

WW13
(SEQ ID NO: 123)
MATLKQIQFKRSKTAGARPAASVLAEGELAINLKDRVLFTKDDQGNIIDL
GFAKGGSIDGNVIHIGNYNQTGDYTLNGTFTQTGNFNLTGIARVTRDIIA
AGQIMTEGGELITKSSGTAHVRFFDGNSRERGIIYAPANDGLTTQVLNIR
VQDYAAGSESTYAFSGSGLFTSPEVSAWKSMSTPQILTDKVITNGKKTGD
YDIYSLSNNTPLAESETAINHLRVMRNAVGAGIFHEVNVNDGITWYSGDG
LDTYLWSFNWAGGLKAGHSISVGLPGGSKGYSELGTASIALGDNDTGFKW
HQDGYFHTVNNGTRTFIYGPAETQSLRKMVMGYSPDGILMTTPPTENYAL
ATVVTYHDNNAFGDGQTLLGYYQGGNYHHYFRGKGTTNINTHGGLLVTPG
NIDVIGGSVNIDGRNNSTLMFKGYTMGQSSVDNMYIAVWGNTFTNPSEG
TRKNVMEISDDIGWMHYIQRNKDNTVEAVLNGQQTINENIIAKKDIWVDR
AVHTLGEITTNAVNGLRIWNNDYGVIFRRSEGSLHIIPTAFGEGETGDIG

-continued
PLRPLSIALDTGKVTIPDLQSSYNTFAANGYIKFVGHGAGAGGYDIQYAQ
AAPIFQEIDDDAVSKYYPIVKQKFLNGKSVWSLGTEIESGTFVIHHLKED
GSQGHASRFNQDGTVNFPDNVLVGGDINMKGMMTFDAGRLGSRDYFKFNH
WGDSNNGRDNIIQLEDSQGAHFSTERTLATGAIKTRFFGETFTDGTLYLN
QMNNSSERFSINNWGNSEVGRPAVLEVGDSKGYHFYTERGTDNSLNFDVA
GNFTVHGPSGITIKTSTGARHIWFRDDSDAEKAVIWATDEGILHIRNNYG
GSFSHHFQGAMILAGERVPYNSEYALIRGNISGGAWVDWRGRPAGLLVDC
QDSRNQAYNIWKATHWGDQHLAAMGVHAGGGNPQVVLHVGGNDYAFASNG
DFTAGAAVYCNDVYIRSDRRLKINVKDYEENAVDKVNKLKVKTYDKVKSL
SDREVIGHEIGIIAQDLQEVLPEAVSTSSVGSQDNPEEILTISNSAVNAL
LIKAIQEMSEEIKELKTPLFTKIARKISKYFKF PP-1
(SEQ ID NO: 124)
MATLKQIQFKRSKTAGQRPAASVLAEGELAINLKDRVLFTKDDQGNIIDL
GFAKGGSIDGNVIHKGNYNQTGDYTLNGTFTQTGNFNLTGIARVTRDIIA
AGQIMTEGGELITKSSGTAHVRFHDSADRERGIIFSPANDGLTTQVVNIR
VQDYKASSESTFAFNGNGLFSSPEVFGWKSVSTPVIYTNKVITNKKVKDD
YDIYSMADNVPLSEITTAINHLRVMRNAVGSGIFHEVKDNDGITWYSGDG
LDAYLWSFTWSGGIKSSHSISIGLTPGPKDYSILGPSSIALGDNDTGFKW
HQDGYYFSVNNGTKTFLFSPSETTSLRKFVAGYSTNGTDLTTPPTENYAL
ATVVTYHDNNAFGDGQTLLGYYQGGNYHHYFRGKGTTNINTHGGLLVTPG
NIDVIGGSVNIDGRNNASTAMFKGNTTGSSSVDNMTISVWGNTFTNPSEG
NRKNVMEISDATSVVMSYIQRLTTGEVEMNVNGSFESSGVTAGNRGVHTT
GEISSGAVNALRIWNADYGVIFRRSEGSLHIIPTAYGEGKNGDIGPLRPF
SIALDTGKVVIPDLESSYNTFAANGYIKFAGHGAGAGGYDIQYSQAAPIF
QEIDDAAVSKYYPIVKQKFLNGKAVWSLGTEINSGTFVLHHLKEDGSQGH
TSRFNADGTVNFPDNVQVGGGEATIARNGNIFSDIWKTFTSAGETTNIRD
AIATRVSKEGDTMTGKLTLSAGNDALVLTAGEGASSHIRSDVGGTNNWYI
GKGSGDNGLGFYSYITQGGVYITNNGEIALSPQGQGTFNFNRDRLHINGT
QWTAHQGGGWENQWNQEAPIFIDFGNVGNDSYYPIIKGKSGITNEGYISG
VDFGMRRITNTWAQGIIRVGNQENGSDPQAIYEFHHNGVLYVPNMVKTGA
RLSAGGGDPVWQGACVVIGDNDTGLVHGGDGRINMVANGMHIASWSSAYH
LHEGLWDTTGALWTEQGRAIISFGHLVQQSDAYSTFVRDVYVRSDIRVKK
DLVKFENASEKLSKINGYTYMQKRGLDEEGNQKWEPNAGLIAQEVQAILP
ELVEGDPDGEALLRLNYNGVIGLNTAAINEHTAEIAELKSEIEELKKIVK
SLLK WW55
(SEQ ID NO: 125)
MADLSRIQFKRTSTKGRRPDASTMNPGELAINLADQYLLTKNDSGAIINL
SCPPVYDRDVTMAGKVKGNNYILSKTANYLEDQTARDLNYFGAFRTNGLD
GLLELTLNVPHSSGVQHGRGFTFQYGHTGSRVETYGYNKEGQKAFSYKMY
HEGDKPTPGELNVYSKQEIDRMFVKNVKMVVPSGGATRGYFKIASAMIPQ
SGRMAFLRIYGGNGYNVNSYDQVDFLEIVIRSGNNNPKGVSIAAYRRNSL NVHEVFAINTSGDNYDIYVNYGRFTDNVIVEFGKTVDVALTVHDVPEFSA
TKPETGTKFDARVITMFNTENKAGTLMFDNNNQLTYDIVSLSNGPDDVRN
YLRKFRSKAGEMIWHETVQGAVYRLATGTTDSTEVLRVDSNSALPGSYKG
YVITGKMELHGSGSAMNLHRQTGQAAYMAWWDRRDGKNQRSGYIGHADGT
TDGFVWRNDVGANSFDLESSGQVNLTTGKTKIVYTNGQYYSANSDAFRMI
YGNYGAFWRNDGGKVYLLSTAENDRFGGWNGNRPFIYDLSTGKVTLGGDG
NEGALVLERDSRAARFSNSVFLEKGLLTFSAGGNQSMDSFTINHWGNSNA
GRYNVLQFEDTKGTHFTTERNADGGLLAHFRGDLTTEGKLTWGKGTATSS
FNIRAWGNSDSRKQVFECVDESGWHWYTQRPGGPGTSAIEFAINGTVKPQ
AIHTGGNILLNGADIEFRRTGNKHLWFRDPNGLELGLIYCDDNGVIRFRG
QKQGQDWVFANKMIQLGTASTVGGSGNGLIRGQVQGGAWAQWRDAAGIL
VDCQQSTDSAHNIWKATHWGKYHIAAMGVHVPSGTIGNAMARLNVNDANF
DFSASGDMSAGRNGSFNDVYIRSDARLKINKEEYKENATDKVNRLTVYTY
DKVKSLTDRTVIAHEVGIIAQDLEKELPEAVTTSKIGDPDKPEEILTISN
SAVNALLIKAFQEMSEELKAVKAELAELKK WW34 (SEQ ID NO: 126)
MADLSRIQFKRTSTKGRRPDAGTMNPGELAINLADQYLLTKNDSGAIINL
SCPPVYDSDVTMAGKVKGNNYILSKTANYFEDQTARDLNYFGAFRPNNAD
DWSNLILNIPHPSGKAHGRGFEFQYGSSSSQVKTYGFDKDGNKRFSFRMY
HEGDKPTPGELNVYSKQEIDRMFVKNVKMSTPSGEATRGYFKIASAMIPQ
SGRMAFLRIYGGNGFNVNSYDQVDFLEIVIRSGNNNPKGVSIAAYRRNSL
NVHEVFAINTSGDNYDIYVNYGRFTDNVIVEFGKTVDVALTVHDVPEFSA
TKPETGTKFDARVITMFNTENKAGTLMFDNNNQLTYDIVSLSNGPDDVRN
YLRKFRSKAGEMIWHETVQGAVYRLATGTTDSTEVLRVDSNSAIPGSYKG
YVITGKMELHGSGNSMILHRQTAQAAYMSWWDRRDGKNQRSGYIGHADGT
SDAIVWNNDIGQNSAVLETSGQISFRTGATKIVYTNGQYYSANSDAYRMI
FGNYGAFWRNDGTKVYLLSTAENDKYGGWNAYRPFIYDLTSGNVQLGGDG
NEDALTLECASRAARFSNDVYIKKGLLTFDAGRAGSRDYIRFNHWGDSNN
ARDNVLCIEDSQGRHFSTERAMGTGALKAYFLGDLEVGGKFTWGKNTATS
SFNIRAWGNSDSRKQVLECADESGWHWYTQRTGGPDTSAIDFAINGTVRPQ
AIHTGGNITINGADIEFKRTGNKHIWFRDPNGLELGLMYCDDAGAIRFRG
QKQAQAWKFADKMIQLESGTVSGGGNGLIRGEVAGGSWASWRDAAGLMV
GCPQSTNSAHNVWKATHWGKYHIAAMAVHVPDGTITNALARLNVHDANFD
FSASGDLSAGRNGSFNDVYIRSDARLKINKEEYKENATDKVNRLTVYTYD
KVKSLTDRTVIAHEVGIIAQDLEKELPEAVTTSKIGDPDKPEEILTISNS
AVNALLIKAFQEMSEELKAVKAELAELKKN WW14 (SEQ ID NO: 127)
MATLKAIQFKRSKTPGAKPTVDQLVEGELAINLRDRTIFTKSDQNQIIDL
GFAKGGQVDGDVTINGTLNLNGPEIVASGGYIEFNYRTTGSGSWAGQHAA
KAPIFVDLSAALSTSEYNPLFKQRYKDGTFSAGTLVTEGSFKFHYINEAG DSKYWTFNRNGNFQVDTGSLFVSGGNISASGNINSASGFVSAPQINTKNI
ILDTKAFGQYDSQSLVNYVYPGTGETNGVNYLRKVRAKSGGTMWHELCTA
QLGQADEMSWWTGNTPQSKQYGVRNDGRLIGRNSLALGTMTTDFPSSDYG
NTGAMGDKYLVLGDTATGLKYIKQGNFDLVGGGYSVASITTDGFRGTSKT
LFGRSNDQGLTWLLPGQNSAMVSIRTEIDGNNSGDGQTHLGYNSNGKLYH
YFRGTGRVAISMAEGMIIEPGILNIKTGVNELNLRADGTVSTTQRLMVNN
GLVLNANNNTSALALTAPTGVDGTKTINWDAGTRNGQNKNTVTMKAWGNS
FNAGGGNRETVFEVSDSQGYYFYGQRTNPASGETVGPINFKFNGSVETGH
FSSLGNISASGTGSFGGNVTMTNGLFVQGGASINGQVKMGGTADALRIWN
AEYGMIFRRSETGSSASFHLIPTLQNAGENGGISDLRPLSINLASGTVIM
GNKSTGGPLFTVDNVSKFVQTDCRLRVNMDSDGIVLNASSQAASNFIQGR
KADVTKWYLGIGDGGNVVRMHNYTYSHGIALNSDTVDITKPLKIGSDIRI
GTDGNIIGSATLDNFKNLNTTLDHKVNMGGWSGGATTGWYKFATVEIPQA
TGTASFKIFGGSGFNFKSYGQASIAEIILRTGNNNPKGLNATLWNRTSEA
ISQIASVNTSEDIYDIYVYLGGYSNSLVVEYTCSSNSKVTVVGMDGGVQP
LVETLPEGHVVGKSVRMLNNLDGMFAAGESDIVTRGEYVTNNQKGMRIKS
KGNDLDSNAALLRNDGGSFYILATDKNTTEKPDAANGDWNGLRPFSINMA
DGRVGMNHGLNITGGGLNVTGGNTNLGNITSRVVSSARAGSGWGDNSDAM
KSKITFMADHGDLSNSGSYYPIVGAYSNYGSAGYRQTFEFGWVGSGSTAN
WREGIIRIRGDNANGQQARWRFTMDGILGCPGKVEMPETSAFGINTTNGF
GGNSIVIGDSDTGFRQVGDGLLEVWTNASRRMRFQGGDTYSDMNINAPNV
YIRSDIRLKSNFKPIENALDKVEQLDGLIYDKADYIGGEVVHTEAGVIAQ
SLEKVLPEAVREVDDIKGNKVLTVSTQAQVALLIEAVKTLSAKVKELEAK
LN WW170 (SEQ ID NO: 128)
MADLSRIQFKRTSTKGRRPDASTMNPGELAINLADQYLLTKNDSGAIINL
SCPPVYDRDVTMAGKVKGNNYILSKTANYLEDQTARDLNYFGAFRTNGQD
GLLDLTLNVPHSAGVNHGRGFTFRYATGGSRVETYGYNAQGQKAFSYKMY
HEGDKPTPSELNVYSKQEVDRMFVKTVKLATVPVDIVDGYFKLATAMIPQ
NGRSVFFRIHGGNGYNVTAYDQVDIVEIVIRSGNNRPKGVNVIAYRRNTN
KAFDVLAVNTSGDNYDIYVKYQRYTDNVIVEFGKSVDVDLVVHDVPDFVV
DRPVGDNVIGGRAVTLFNTENKRGVLSFDDNTQNSYDIVHLSNDRGTGRK
YIRKFRSNYNEMIWHETVQGSTYRLATGSTDAQEILSVESSSSIAGTHKG
NILSGRMMLGGGSNVITLRRPAGQSNHIAFQDNRTGSITRQGWIGYGNAD
TNVFEWYSDVGGTSIRHHIDGQIELATGNTKRVYTNAQFISMNSDAYRMI
FGNYGAFWRNDGTKVYLLSTAEDDKFGGWNGNRPFIYDLTNGKVTLGGDG
NEGALVLERDSRAARFAGDVYVEKGFLHFSSGRQGASGFMKINHLGDIAS
GRHNILQIEDPTGIHFSTERNDETGNITARFKGFVRVEAGEIAFDANRGS
QSQFTLHTWGNEQRKQVFECKDATGYHWYTERTQGGTGNVLFSMAGSLNV
TSNITTTGADITFKRAGNKHIWFRDPDGLELGLMYCDDAGAIRFRGQKQA
QAWKFADKMIQLESGTVSGGGNGLIRGEVAGGSWSSWRDAAGLMVGCPQ -continued STNSAHNVWKATHWGKYHIAAMGIHVPDGTIGNALARLHVHDTNFDFSAS
GDMTAGRNGSFNDVYIRSDARLKINKEEYKENATDKINRLTVYTYDKVKS
LTDRTVIAHEVGIIAQDLEKELPEAVTTSKVGDPDKPEEILTISNSAVNA
LLIKAFQEMSEELKAVKAELAELKKN

WW202
(SEQ ID NO: 129)

MADLNRIQFKRTSTAGRKPDAGTMNPGELAINLADQYLLTKNDD<u>GQIVNL</u>
SCPPVYDKGFDVRGRVVVDDLVWSNTANYFDDPTARNLDKFGAFRTNDMD
GHLAFALHIPHPSGINHARGFDFTYGSNVVPTVKTYGYNADGVLAYSYRM
YHEGDKPSPSELNVYSKQEVDRMFQKTINFGVETGWFKIATAFIPQNDGR
SLKIRLVGGNGWNVGQTGQCNIIELVIRTSNGSPKGINFVAYHHVSGYEN
QFCAINTGDDTYDIYAYYYEFTNMVMAEYQASSDVNLTVFDRPEYVGEKP
VAEHIFDAYTIHSFNSFSNRGTLNFAGNHQGQYDIEHMNEQPTNAKKMLR
RFRSSASATIWHETVDDQNYRLATGGTDSVQQLLLSSGTGLHIRRLTIDG

-continued

GLGSGSNAGIDIRRGPNESSHFNFMDYRTGQDVRNGWFGFGDLTTKDFIV
WVNDNGQNSINLIENGELHITGGRGQKIVMNSEVALSENARLAVKGGNYG
LILRNDGTGFHILTTDLKDSFGSWNNRRPFSYNFADGGLYLGGTETARCL
HLGIDGSTRLEDNLFFKAGSRQSMDYMELVHWGASNTGRNNVLSLRDSKG
FLAEFERVGGTDGVKTRFFGETFTDGTLYLNQMNNSSERFSINNWGNSEV
GRAAVMEVGDSKGYHFYAERRTDDTVLFDVSGALTVHGPNGITVKNSTGA
RHIWFRDDSDTEKAVIWATDDGMLHIRNNHEGSFAHHFQGAMIKLEGRVP
YGAAKGLIRGEVDGGAYVAWRDRPAGLLVDCQKSIDSAHAVWKAVDWGRQ
YIAAMDVHCPGDGNNTAAAVLHVQAADYQFHASGEFHASGNGNFNDVYIR
SDRRLKDNIEDYTGNALSLIGKLKVKTYDKVKSLKDREIIGHEIGIIAQD
LQEILPEAVKSSKVGNLDNPDDVLTISNSAVNALLIKAIQEMSEEIKELK
TPFFTKIARKISKYFKF

Chimeras SEQUENCES (underlined are the sites used in the fusions shown above): In italics: Lambda N-terminal part and Underlined: T4-like DTF part

WW13 13.0 (FIG. 8)
(SEQ ID NO: 130)

*MAVKISGVLKDGTGKPVQNCTIQLKARRNSTTVVVNTVGSENPDEAGRYSMDVEYGQYSVILQVDGFPPSHAG*
*TITVYEDSQPGTLNDFLCAMTEDDARPEVLRRLELMVEEVARNSASVVAQSTADAKKSAGDASASAAQVAALV*
*TDATDSARAASTSAGQAASSAQEASSGAEAASAKATEAEKSAAAAESSKNAAATSAGAAKTSETNAAASQQSA*
*ATSASTAATKASEAATSARDAVASKEAAKSSETNASSSAGRAASSATAAENSARAAKTSETNARSSETAAERS*
*ASAAAADAKTAAAGSASTASTKATEAAGSAVSASQSKSAAEAAAIRAKNSAKRAEDIASAVALEDADTTRKGIV*
*QLSSATNSTSETLAATPKAVKVVMDETNRKAPLDSPALTGTPTAPTALRGTNNITQIANTAFVLAAIADVIDA*
*SPDALNTLNELAAALGNDPDFATTMTNALAGKQPKNATLTALAGLSTAKNKLPYFAENDAASLTELTQVGRDI*
*LAKNSVADVLEYLGAGENS*<u>IIQLED</u>SQGAHFSTERTLATGAIKTRFFGETFTDGTLYLNQMNNSSERFSINNW
GNSEVGRPAVLEVGDSKGYHFYTERGTDNSLNFDVAGNFTVHGPSGITIKTSTGARHIWFRDDSDAEKAVIWA
TDEGILHIRNNYGGSFSHHFQGAMILAGERVPYNSEYALIRGNISGGAWVDWRGRPAGLLVDCQDSRNQAYNI
WKATHWGDQHLAAMGVHAGGGNPQVVLHVGGNDYAFASNGDFTAGAAVYCNDVYIRSDRRLKINVKDYEENAV
DKVNKLKVKTYDKVKSLSDREVIGHEIGIIAQDLQEVLPEAVSTSSVGSQDNPEEILTISNSAVNALLIKAIQ
EMSEEIKELKTPLFTKIARKISKYFKF

WW13 10.0
(SEQ ID NO: 131)

*MAVKISGVLKDGTGKPVQNCTIQLKARRSNSTTVVVNTVGSENPDEAGRYSMDVEYGQYSVILQVDGFPPSHA*
*GTITVYEDSQPGTLNDFLCAMTEDDARPEVLRRLELMVEEVARNASVVAQSTADAKKSAGDASASAAQVAALV*
*TDATDSARAASTSAGQAASSAQEASSGAEAASAKATEAEKSAAAAESSKNAAATSAGAAKTSETNAAASQQSA*
*ATSASTAATKASEAATSARDAVASKEAAKSSETNASSSAGRAASSATAAENSARAAKTSETNARSSETAAERS*
*ASAAAADAKTAAAGSASTASTKATEAAGSAVSASQSKSAAEAAAIRAKNSAKRAEDIASAVALEDADTTRKGIV*
*QLSSATNSTSETLAATPKAVKVVMDETNR*<u>VDRAVH</u>TLGEITTNAVNGLRIWNNDYGVIFRRSEGSLHIIPTAF
GEGETGDIGPLRPLSIALDTGKVTIPDLQSSYNTFAANGYIKFVGHGAGAGGYDIQYAQAAPIFQEIDDDAVS
KYYPIVKQKFLNGKSVWSLGTEIESGTFVIHHLKEDGSQGHASRFNQDGTVNFPDNVLVGGDINMKGMMTFDA
GRLGSRDYFKFNHWGDSNNGRDNIIQLEDSQGAHFSTERTLATGAIKTRFFGETFTDGTLYLNQMNNSSERFS
INNWGNSEVGRPAVLEVGDSKGYHFYTERGTDNSLNFDVAGNFTVHGPSGITIKTSTGARHIWFRDDSDAEKA

VIWATDEGILHIRNNYGGSFSHHFQGAMILAGERVPYNSEYALIRGNISGGAWVDWRGRPAGLLVDCQDSRNQ
AYNIWKATHWGDQHLAAMGVHAGGGNPQVVLHVGGNDYAFASNGDFTAGAAVYCNDVYIRSDRRLKINVKDYE
ENAVDKVNKLKVKTYDKVKSLSDREVIGHEIGIIAQDLQEVLPEAVSTSSVGSQDNPEEILTISNSAVNALLI
KAIQEMSEEIKELKTPLFTKIARKISKYFKF

WW13-G8 (FIG. 10) (SEQ ID NO: 132)
MAVKISGVLKDGTGKPVQNCTIQLKARRNSTTVVVNTVGSENPDEAGRYSMDVEYGQYSVILQVDGFPPSHAG
TITVYEDSQPGTLNDFLCAMTEDDARPEVLRRLELMVEEVARNASVVAQSTADAKKSAGDASASAAQVAALVT
DATDSARAASTSAGQAASSAQEASSGAEAASAKATEAEKSAAAAESSKNAAATSAGAAKTSETNAAASQQSAA
TSASTAATKASEAATSARDAVASKEAAKSSETNASSSARGRAASSATAAENSARAAKTSETNARSSETAAERS
ASAAAADAKTAAAGSASTASTKATEAAGSAVSASQSKSAAEAAAIRAKNSAKRAEDIASAVALEDADTTRKGIV
QLSSATNSTSETLAATPKAVKVVMDETNRGNIIDLGFAKGGSIDGNVIHIGNYNQTGDYTLNGTFTQTGNFNL
TGIARVTRDIIAAGQIMTEGGELITKSSGTAHVRFFDGNSRERGIIYAPANDGLTTQVLNIRVQDYAAGSEST
YAFSGSGLFTSPEVSAWKSMSTPQILTDKVITNGKKTGDYDIYSLSNNTPLAESETAINHLRVMRNAVGAGIF
HEVNVNDGITYWYSGDGLDTYLWSFNWAGGLKAGHSISVGLPGGSKYSELGTASIALGDNDTGFKWHQDGYFH
TVNNGTRTFIYGPAETQSLRKMVMGYSPDGILMTTPPTENYALATVVTYHDNNAFGDGQTLLGYYQGGNYHHY
FRGKGTTNINTHGGLLVTPGNIDVIGGSVNIDGRNNNSTLMFKGYTMGQSSVDNMYIAVWGNTFTNPSEGTRK
NVMEISDDIGWMHYIQRNKDNTVEAVLNGQQTINENIIAKKDIWVDRAVHTLGEITTNAVNGLRIWNNDYGVI
FRRSEGSLHIIPTAFGEGETGDIGPLRPLSIALDTGKVTIPDLQSSYNTFAANGYIKFVGHGAGAGGYDIQYA
QAAPIFQEIDDDAVSKYYPIVKQKFLNGKSVWSLGTEIESGTFVIHHLKEDGSQGHASRFNQDGTVNFPDNVL
VGGDINMKGMMTFDAGRLGSRDYFKFNHWGDSNNGRDNIIQLEDSQGAHFSTERTLATGAIKTRFFGETFTDG
TLYLNQMNNSSERFSINNWGNSEVGRPAVLEVGDSKGYHFYTERGTDNSLNFDVAGNFTVHGPSGITIKTSTG
ARHIWFRDDSDAEKAVIWATDEGILHIRNNYGGSFSHHGQGAMILAGERVPYNSEYALIRGNISGGAWVDWRG
RPAGLLVDCQDSRNQAYNIWKATHWGDQHLAAMGVHAGGGNPQVVLHVGGNDYAFASNGDFTAGAAVYCNDVY
IRSDRRLKINVKDYEENAVDKVNKLKVKTYDKVKSLSDREVIGHEIGIIAQDLQEVLPEAVSTSSVGSQDNPE
EILTISNSAVNALLIKAIQEMSEEIKELKTPLFTKIARKISKYFKF

WW13 gp38 (SEQ ID NO: 133)
MAVVGVPGWIGSSAVNETGQRWMSQAAGQLRLGVPCWMSQFAGRSREIIHTLGADHNFNGQWFRDRCFEAGST
PIVFNITGDLVSYSKDVPLFFMYGDTPNEYVQLNIHGVTMYGRGGNGGSNSPGSAGGHCIQNDIGGRLRINNG
GAIAGGGGGGGGRYGRLSFGGGGGRPFGAGGSSSHMSSGATAGTISAPGAGSVGEGSLWVYTGGSGGNVGAA
GGRCNIQGNGTEYDGGAAGYAVIGSAPTWINVGAIYGPRV

WW13 gp57A (SEQ ID NO: 134)
MSEQTIEQKLSAEIVTLKSRILDTQDQAARLMEESKILQGTLAEIARAVGITGDTIKVEEIVEAVKNLTAESA
DEAKDEE

PP-1 (FIG. 8) (SEQ ID NO: 135)
MAVKISGVLKDGTGKPVQNCTIQLKARRNSTTVVVNTVGSENPDEAGRYSMDVEYGQYSVILQVDGFPPSHAG
TITVYEDSQPGTLNDFLCAMTEDDARPEVLRRLELMVEEVARNASVVAQSTADAKKSAGDASASAAQVAALVT
DATDSARAASTSAGQAASSAQEASSGAEAASAKATEAEKSAAAAESSKNAAATSAGAAKTSETNAAASQQSAA
TSASTAATKASEAATSARDAVASKEAAKSSETNASSSAGRAASSATAAENSARAAKTSETNARSSETAAERSA
SAAAADAKTAAAGSASTASTKATEAAGSAVSASQSKSAAEAAAIRAKNSAKRAEDIASAVALEDADTTRKGIVQ
LSSATNSTSETLAATPKAVKVVMDETNRKAPLDSPALTGTPTAPTALRGTNNTQIANTAFVLAAIADVIDASP
DALNTLNELAAALGNDPDFATTMTNALAGKQPKNATLTALAGLSTAKNKLPYFAENDAASLTELTQVGRDILA

-continued

KNSVADVLEYLGAGENSIATRVSKEGDTMTGKLTLSAGNDALVLTAGEGASSHIRSDVGGTNNWYIGKGSGDN
GLGFYSYITQGGVYITNNGEIALSPQGQGTFNFNRDRLHINGTQWTAHQGGGWENQWNQEAPIFIDFGNVGND
SYYPIIKGKSGITNEGYISGVDFGMRRITNTWAQGIIRVGNQENGSDPQAIYEFHHNGVLYVPNMVKTGARLS
AGGGDPVWQGACVVIGDNDTGLVHGGDGRINMVANGMHIASWSSAYHLHEGLWDTTGALWTEQGRAIISFGHL
VQQSDAYSTFVRDVYVRSDIRVKKDLVKFENASEKLSKINGYTYMQKRGLDEEGNQKWEPNAGLIAQEVQAIL
PELVEGDPDGEALLRLNYNGVIGLNTAAINEHTAEIAELKSEIEELKKIVKSLLK

PP-1 gp38
(SEQ ID NO: 136)
MAVTGPWVGSSAVVNTGQNWMVGAAQRLRMGAPFWMSNMIGRSVEVIHTLGADHNFNGQWFRDRCFEAGSAPI
VFNITGDLVSYSRDVPLFFMYGDTPNEYVQLNIHGVTMYGRGGNGWAAGAIGASDGGVCIQNDIGGRLRINNG
GAIAGGGGGGGYSQANNWAGKYVCGGGGGRPFGLGGNNGARWPGGNASLTSPGAGGNTGTRYYAGGGGEVGQ
PGQYANPGAGYSTPPTSPGAAVAGSAPTWQNVGAIYGPRV

PP-1 gp57A
(SEQ ID NO: 137)
MSEQTIEQKLSAEIVTLKSRILDTQDQAARLMEESKILQGTLAEIARAVGITGDTIKVEEIVEAVKNLTAEST
DEAKDEE

>WW55 3.0 (FIG. 9)
(SEQ ID NO: 138)
*MAVKISGVLKDTGKPVQNCTIQLKARRNSTTVVVNTVGSENPDEAGRYSMDVEYGQYSVILQVDGFPPSHAG*
*TIVYEDSQPGTLNDFLCAMTEDDARPEVLRRLELMVEEVARNASVVAQSTADAKKSAGDASASAAQVAALVTD*
*ATDSARAASTSAGQAASSAQEASSGAEAASAKATEAEKSAAAAESSKNAAATSAGAAKTSETNAAASQQSAAT*
*SASTAATKASEAATSARDAVASKEAAKSSETNASSSAGRAASSATAAENSARAAKTSETNARSSETAAERSAS*
*AAADAKTAAAGSASTASTKATEAAGSAVSASQSKSAAEAAAIRAKNSAKRAEDIASAVALEDADTTRKGIVQL*
*SSATNSTSETLAATPKAVKVVMDETNRTPGELNVYSKQEIDRMFVKNVKMVVPSGGATRGYFKIASAMIPQSG*
*RMAFLRIYGGNGYNVNSYDQVDFLEIVIRSGNNNPKGVSIAAYRRNSLNVHEVFAINTSGDNYDIYVNYGRFT*
*DNVIVEFGKTVDVALTVHDVPEFSATKPETGTKFDARVITMFNTENKAGTLMFDNNNQLTYDIVSLSNGPDDV*
*RNYLRKFRSKAGEMIWHETVQGAVYRLATGTTDSTEVLRVDSNSALPGSYKGYVITGKMELHGSGSAMNLHRQ*
*TGQAAYMAWWDRRDGKNQRSGYIGHADGTTDGFVWRNDVGANSFDLESSGQVNLTTGKTKIVYTNGQYYSANS*
*DAFRMIYGNYGAFWRNDGGKVYLLSTAENDRFGGWNGNRPFIYDLSTGKVTLGGDGNEGLAVLERDSRAARFS*
*NSVFLEKGLLTFSAGGNQSMDSFTINHWGNSNAGRYNVLQFEDTKGTHFTTERNADGGLLAHFRGDLTTEGKL*
*TWGKGTATSSFNIRAWGNSDSRKQVFECVDESGWHWYTQRPGGPGTSAIEFAINGTVKPQAIHTGGNILLNGA*
*DIEFRRTGNKHLWFRDPNGLELGLIYCDDNGVIRFRGQKQGQDWVFANKMIQLGTASTVGGSGNGLIRGQVQG*
*GAWAQWRDRAAGILVDCQQSTDSAHNIWKATHWGKYHIAAMGVHVPSGTIGNAMARLNVNDANFDFSASGDMS*
*AGRNGSFNDVYIRSDARLKINKEEYKENATDKVNRLTVYTYDKVKSLTDRTVIAHEVGIIAQDLEKELPEAVT*
*TSKIGDPDKPEEILTISNSAVNALLIKAFQEMSEELKAVKAELAELKK*

>WWGG-G8 (FIG. 10)
(SEQ ID NO: 139)
*MAVKISGVLKDTGKPVQNCTIQLKARRNSTTVVVNTVGSENPDEAGRYSMDVEYGQYSVILQVDGFPPSHAG*
*TITVYEDSQPGTLNDFLCAMTEDDARPEVLRRLELMVEEVARNASVVAQSTADAKKSAGDASASAAQVAALVT*
*DATDSARAASTSAGQAASSAQEASSGAEAASAKATEAEKSAAAAESSKNAAATSAGAAKTSETNAAASQQSAA*
*TSASTAATKASEAATSARDAVASKEAAKSSETNASSSAGRAASSATAAENSARAAKTSETNARSSETAAERSA*
*SAAADAKTAAAGSASTASTKATEAAGSAVSASQSKSAAEAAAIRAKNSAKRAEDIASAVALEDADTTRKGIVQ*
*LSSATNSTSETLAATPKAVKVVMDETNRGAIINLSCPPVYDRDVTMAGKVKGNNYILSKTANYLEDQTARDLN*
YFGAFRTNGLDGLLELTLNVPHSSGVQHGRGFTFQYGHTGSRVETYGYNKEGQKAFSYKMYHEGDKPTPGELN

-continued

VYSKQEIDRMFVKNVKMVVPSGGATRGYFKIASAMIPQSGRMAFLRIYGGNGYNVNSYDQVDFLEIVIRSGNN

NPKGVSIAAYRRNSLNVHEVFAINTSGDNYDIYVNYGRFTDNVIVEFGKTVDVALTVHDVPEFSATKPETGTK

FDARVITMFNTENKAGTLMFDNNNQLTYDIVSLSNGPDDVRNYLRKFRSKAGEMIWHETVQGAVYRLATGTTD

STEVLRVDSNSALPGSYKGYVITGKMELHGSGSAMNLHRQTGQAAYMAWWDRRDGKNQRSGYIGHADGTTDGF

VWRNDVGANSFDLESSGQVNLTTGKTKIVYTNGQYYSANSDAFRMIYGNYGAFWRNDGGKVYLLSTAENDRFG

GWNGNRPFIYDLSTGKVLTGGDGNEGALVLERDSRAARFSNSVFLEKGLLTFSAGGNQSMDSFTINHWGNSNA

GRYNVLQFEDTKGTHFTTERNADGGLLAHFRGDLTTEGKLTWGKGTATSSFNIRAWGNSDSRKQVFECVDESG

WHWYTQRPGGPGTSAIEFAINGTVKPQAIHTGGNILLNGADIEFRRTGNKHLWFRDPNGLELGLIYCDDNGVI

RFRGQKQGQDWVFANKMIQLGTASTVGGSGNGLIRGQVQGGAWAQWRDRAAGILVDCQQSTDSAHNIWKATHW

GKYHIAAMGVHVPSGTIGNAMARLNVNDANFDFSASGDMSAGRNGSFNDVYIRSDARLKINKEEYKENATDKV

NRLTVYTYDKVKSLTDRTVIAHEVGIIAQDLEKELPEAVTTSKIGDPDKPEEILTISNSAVNALLIKAFQEMS

EELKAVKAELAELKKN

>WW55 gp38
(SEQ ID NO: 140)
MAISSGWVGSSAVSETGQRWMSAAMQAVRLGRPAYMSAMVGRSKEIHYSIGASNSYNKDTLINWMKAQGSTPV

VITITGNIVSQSTGVPCLDFPSSLTNEYVTLIINSGVHVLGRGGNGGSNSAGGAGGNAINNGIGTRLRINNNG

IIGGGGGGAGARYNPFPQMDMKFGGGGGRPFGAAGAAGGGAAAASAGTISAPGKGTVSGVHYGGDGGDLGAA

GKSSYIKGGTGGTVHSGGAAGKAVTGNAPRWDKVGTIYGARV

WW55 gp57A
(SEQ ID NO: 141)
MSNQHEQMINVLKVRLFDTQEKAAFLEGQLKDRERVLMELVRILGIQPDENGTVSLDAIVEEVKALLPKDEAA

EDAEEEVELITEA

WW34 3.0
(SEQ ID NO: 142)
*MAVKISGVLKDGTGKPVQNCTIQLKARRNSTTVVVNTVGSENPDEAGRYSMDVEYGQYSVILQVDGFPPSHA*

*GTITVYEDSQPGTLNDFLCAMTEDDARPEVLRRLELMVEEVARNASVVAQSTADAKKSAGDASASAAQVAAL*

*VTDATDSARAASTSAGQAASSAQEASSGAEAASAKATEAEKSAAAAESSKNAAATSAGAAKTSETNAAASQQ*

*SAATSASTAATKASEAATSARDAVASKEAAKSSETNASSSAGRAASSATAAENSARAAKTSETNARSSETAA*

*ERSASAAADAKTAAAGSASTASTKATEAAGSAVSASQSKSAAEAAAIRAKNSAKRAEDIASAVALEDADTTR*

*KGIVQLSSATNSTSETLAATPKAVKVVMDETNR*TPGELNVYSKQEIDRMFVKNVKMSTPSGEATRGYFKIAS

AMIPQSGRMAFLRIYGGNGFNVNSYDQVDFLEIVIRSGNNNPKGVSIAAYRRNSLNVHEVFAINTSGDNYDI

YVNYGRFTDNVIVEFGKTVDVALTVHDVPEFSATKPETGTKFDARVITMFNTENKAGTLMFDNNNQLTYDIV

SLSNGPDDVRNYLRKFRSKAGEMIWHETVQGAVYRLATGTTDSTEVLRVDSNSAIPGSYKGYVITGKMELHG

SGNSMILHRQTAQAAYMSWWDRRDGKNQRSGYIGHADGTSDAIVWNNDIGQNSAVLETSGQISFRTGATKIV

YTNGQYYSANSDAYRMIFGNYGAFWRNDGTKVYLLSTAENDKYGGWNAYRPFIYDLTSGNVQLGGDGNEDAL

TLECASRAARFSNDVYIKKGLLTFDAGRAGSRDYIRFNHWGDSNNARDNVLCIEDSQGRHFSTERAMGTGAL

KAYFLGDLEVGGKFTWGKNTATSSFNIRAWGNDSRKQVLECADESGWHWYTQRTGGPDTSAIDFAINGTVRP

QAIHTGGNITINGADIEFKRTGNKHIWFRDPNGLELGLMYCDDAGAIRFRGQKQAQAWKFADKMIQLESGTV

SGGGGNGLIRGEVAGGSWASWRDRAAGLMVGCPQSTNSAHNVWEKATHWGKYHIAAMAVHVPDGTITNALARL

NVHDANFDFSASGDLSAGRNGSFNDVYIRSDARLKINKEEYKENATDKVNRLTVYTYDKVKSLTDRTVIAHE

VGIIAQDLEKELPEAVTTSKIGDPDKPEEILTISNSAVNALLIKAFQEMSEELKAVKAELAELKKN

WW34 gp38
(SEQ ID NO: 143)
MAISSGWGSSAVSETGQRWMSAAMQAVRLGRPAYMSAMVGRSKEIHYSIGASNSYNKDTLINWMKAQGSTP

VVITITGNIVSQSTGVPCLDQFPSSLTNEYVTLIINPGVHVWGRGGNGGNNSAGGAGGNAINNGIGTRLRI

-continued

```
TNNGAICGGGGGGGGGYYSPFSQMRLTFGGGGGRPFGAAGGSANMEQGATAGTISAPGKGSVNGVYNGGNG

GDAGGAGGEKCNIRGQGSEYNGGAAGKAVTGNAPRWDKVGTIYGARV
```

WW34 gp57A (SEQ ID NO: 144)

```
MSNQHEQMINVLKVRLFDTQEKAAFLEGQLKDRERVLMELVRILGIQPDENGTVSLDAIVEEVKALLPKDEA

AEDAEEEVELITEA
```

WW14-G8

(SEQ ID NO: 145)

*MAVKISGVLKDGTGKPVQNCTIQLKARRNSTTVVVNTVGSENPDEAGRYSMDVEYGQYSVILQVDGFPPSHAG*

*TITVYEDSQPGTLNDFLCAMTEDDARPEVLRRLELMVEEVARNSASVVAQSTADAKKSAGDASASAAQVAALV*

*TDATDSARAASTSAGQAASSAQEASSGAEAASAKATEAEKSAAAAESSKNAAATSAGAAKTSETNAAASQQSA*

*ATSASTAATKASEAATSARDAVASKEAAKSSETNASSSAGRAASSATAAENSARAAKTSETNARSSETAAERS*

*ASAAADAKTAAAGSASTASTKATEAAGSAVSASQSKSAAEAAAIRAKNSAKRAEDIASAVALEDADTTRKGIV*

*QLSSATNSTSETLAATPKAVKVVMDETNR*__NQIIDLG__*FAKGGQVDGDVTINGTLNLNGPEIVASGGYIEFNYRT*

*TGSGSWAGQHAAKAPIFVDLSAALSTSEYNPLFKQRYKDGTFSAGTLVTEGSFKFHYINEAGDSKYWTFNRNG*

*NFQVDTGSLFVSGGNISASGNINSASGFVSAPQINTKNIILDTKAFGQYDSQSLVNYVYPGTGETNGVNYLRK*

*VRAKSGGTMWHELCTAQLGQADEMSWWTGNTPQSKQYGVRNDGRLIGRNSLALGTMTTDFPSSDYGNTGAMGD*

*KYLVLGDTATGLKYIKQGNFDLVGGGYSVASITTDGFRGTSKTLFGRSNDQGLTWLLPGQNSAMVSIRTEIDG*

*NNSGDGQTHLGYNSNGKLYHYFRGTGRVAISMAEGMIIEPGILNIKTGVNELNLRADGTVSTTQRLMVNNGLV*

*LNANNNTSALALTAPTGVDGTKTINWDAGTRNGQNKNTVTMKAWGNSFNAGGGNRETVFEVSDSQGYYFYGQR*

*TNPASGETVGPINFKFNGSVETGHFSSLGNISASGTGSFGGNVTMTNGLFVQGGASINGQVKMGGTADALRIW*

*NAEYGMIFRRSETGSSASFHLIPTLQNAGENGGISDLRPSINLASGTVIMGNKSTGGPLFTVDNVSKFVQTDC*

*RLRVNMDSDGIVLNASSQAASNFIQGRKADVTKWYLGIGDGGNVVRMHNYTYSHGIALNSDTVDITKPLKIGS*

*DIRIGTDGNIIGSATLDNFKNLNTTLDHKVNMGGWSGGATTGWYKFATVEIPQATGTASFKIFGGSGFNFKSY*

*GQASIAEIILRTGNNNPKGLNATLWNRTSEAISQIASVNTSEDIYDIYVYLGGYSNSLVVEYTCSSNSKVTVV*

*GMDGGVQPLVETLPEGHVVGKSVRMLNNLDGMFAAGESDIVTRGEYVTNNQKGMRIKSKGNDLDSNAALLRND*

*GGSFYILATDKNTTEKPDAANGDWNGLRPFSINMADGRVGMNHGLNITGGGLNVTGGNTNLGNITSRVVSSAR*

*AGSGWGDNSDAMKSKITFMADHGDLSNSGSYYPIVGAYSNYGSAGYRQTFEFGWVGSGSTANWERGIIRIRGD*

*NANGQQARWRFTMDGILGCPGKVEMPETSAFGINTTNGFGGNSIVIGDSDTGFRQVGDGLLEVWTNASRRMRF*

*QGGDTYSDMNINAPNVYIRSDIRLKSNFKPEINALDKVEQLDGLIYDKADYIGGEVVHTEAGVIAQSLEKVLP*

*EAVREVDDIKGNKVLTVSTQAQVALLIEAVKTLSAKVKELEAKLN*

WW14 gp38

(SEQ ID NO: 146)

```
MAIVGVPGWIGQSAVDETGQRWMDAAMRDVRVAVPGWMGSMAGQSEKIYLSIGANNSYDRNSLINWMRAQGGA

PVVITITGNLVSNSTGNACLEFPSNLPNAYIQLIINSGVTVYGRGGNGSTNGSAGGNGGTAIHNAAGTKLRIR

NNGAIAGGGGGGGAVSLQNSYPTNGTCGGGGGRPFGVGGKIGSDAILSGSNASLTAAGTGGATVQYGGGNGGN

VGAGGGRGWGKNVYTSAGGSAGAAVTGNAPNWQNVGTIYGSRV
```

WW14 gp57A (SEQ ID NO: 147)

```
MSEQTIEQKLQAEIVALKSRILDTQDVAAQAQQESRILQDALSKIAARLGITGDQIQIEDLIAAVPDLTAESA

DEE
```

WW170-G8

(SEQ ID NO: 148)

*MAVKISGVLKDGTGKPVQNCTIQLKARRNSTTVVVNTVGSENPDEAGRYSMDVEYGQYSVILQVDGFPPSHAG*

*TITVYEDSQPGTLNDFLCAMTEDDARPEVLRRLELMVEEVARMASVVAQSTADAKKSAGDASASAAQVAALVT*

-continued

DATDSARAASTSAGQAASSAQEASSGAEAASAKATEAEKSAAAAESSKNAAATSAGAAKTSETNAAASQQSAA

TSASTAATKASEAATSARDAVASKEAAKSSETNASSSAGRAASSATAAENSARAAKTSETNARSSETAAERSA

SAAADAKTAAAGSASTASTKATEAAGSAVSASQSKSAAEAAAIRAKNSAKRAEDIASAVALEDADTTRKGIVQ

LSSATNSTSETLAATPKAVKVVMDETNRGAIINLSCPPVYDRDVTMAGKVKGNNYILSKTANYLEDQTARDLN

YFGAFRTNGQDGLLDLTLNVPHSAGVNHGRGFTFRYATGGSRVETYGYNAQGQKAFSYKMYHEGDKPTPSELN

VYSKQEVDRMFVKTVKLATVPVDIVDGYFKLATAMIPQNGRSVFFRIHGGNGYNVTAYDQVDIVEIVIRSGNN

RPKGVNVIAYRRNTNKAFDVLANVTSGDNYDIYVKYQRYTDNVIVEFGKSVDVDLVVHDVPDFVVFRPVGDNV

IGGRAVTLFNTENKRGVLSFDDNTQNSYDIVHLSNDRGTGRKYIRKFRSNYNEMIWHETVQGSTYRLATGSTD

AQEILSVESSSSIAGTHKGNILSGRMMLGGGSNVITLRRPAGQSNHIAFQDNRTGSITRQGWIGYGNADTNVF

EWYSDVGGTSIRHHIDGQIELATGNTKRVYTNAQFISMNSDAYRMIFGNYGAFWRNDGTKVYLLSTAEDDKFG

GWNGNRPFIYDLTNGKVTLGGDGNEGALVLERDSRAARFAGDVYVEKGFLHFSSGRQGASGFMKINHLGDIAS

GRHNILQIEDPTGIHFSTERNDETGNITARFKGFVRVEAGEIAFDANRGSQSQFTLHTWGENQRKQVFECKDA

TGYHWYTERTQGGTGNVLFSMAGSLNVTSNITTTGADITFKRAGNKHIWFRDPDGLELGLMYCDDAGAIRFRG

QKQAQAWKFADKMIQLESGTVSGGGNGLIRGEVAGGSWSSWRDRAAGLMVGCPQSTNSAHNVWKATHWGKYHI

AAMGIHVPDGTIGNALARLHVHDTNFDFSASGDMTAGRNGSFNDVYIRSDARLKINKEEYKENATDKINRLTV

YTYDKVKSLTDRTVIAHEVGIIAQDLEKELPEAVTTSKVGDPDKPEEILTISNSAVNALLIKAFQEMSEELKA

VKAELAELKKN

WW170 gp38
(SEQ ID NO: 149)
MAISSGWVGSSAVSETGQRWMSAAMQAVRLGRPAYMSAMVGRSKEIHYSIGASNSYNKDTLINWMKAQGSTPV

VITITGNIVSQSTGVPCLDFPSSLTNEYVTLIINPGVHVWGRGGNGGNNSAGGAGGNAINNGIGTRLRITNNG

AICGGGGGGGGGYYSPFSQMRLTFGGGGGRPFGAAGGSANMEQGATAGTISAPGKGSVNGVYNGGNGGDAGGA

GGKCNIRGQGSEYNGGAAGKAVTGNAPGWDKVGTIYGARV

WW170 gp57A
(SEQ ID NO: 150)
MSNQHEQMINVLKVRLFDTQEKAAFLEGQLKDRERVLMELVRILGIQPDENGTVSLDAIVEEVKALLPKDEAA

EDAKEEVELITEA

WW202-G8
(SEQ ID NO: 151)
MAVKISGVLKDGTGKPVQNCTIQLKARRNSTTVVVNTVGSENPDEAGRYSMDVEYGQYSVILQVDGFPPSHAG

TITVYEDSQPGTLNDFLCAMTEDDARPEVLRRLELMVEEVARNASVVAQSTADAKKSAGDASASAAQVAALVT

DATDSARAASTSAGQAASSAQEASSGAEAASAKATEAEKSAAAAESSKNAAATSAGAAKTSETNAAASQQSAA

TSASTAATKASEAATSARDAVASKEAAKSSETNASSSAGRAASSATAAENSARAAKTSETNARSSETAAERSA

SAAADAKTAAAGSASTASTKATEAAGSAVSASQSKSAAEAAAIRAKNSAKRAEDIASAVALEDADTTRKGIVQ

LSSATNSTSETLAATPKAVKVVMDETNRGQIVNLSCPPVYDKGFDVRGRVVVDDLVWSNTANYFDDPTARNLD

KFGAFRTNDMDGHLAFLAIPHPSGINHARGFDFTYGSNVVPTVKTYGYNADGVLAYSYRMYHEGDKPSPSELN

VYSKQEVDRMFQKTINFGVETGWFKIATAFIPQNDGRSLKIRLVGGNGWNVGQTGQCNIIELVIRTSNGSPKG

INFVAYHHVSGYENQFCAINTGDDYDIYAYYYEFTNMVMAEYQASSDVNLTVFDRPEYVGEKPVAEHIFDAYT

IHSFNSFSNRGTLNFAGNHQGQYDIEHMNEQPTNAKKMLRRFRSSASATIWHETVDDQNYRLATGGTDSVQQL

LLSSGTGLHIRRLTIDGGLGSGSNAGIDIRRGPNESSHFNFMDYRTGQGVRNGWFGFGDLTTKDFIWWNDNGQ

NSINLIENGELHITGGRGQKIVMNSEVALSENARLAVKGGNYGLILRNDGTGFHILTTDLKDSFGSWNNRRPF

SYNFADGGLYLGGTETARCLHLGIDGSTRLEDNLFFKAGSRQSMDYMELVHWGASNTRGRNNVLSLRDSKGFL

AEFERVGGTDGVKTRFFGETFTDGTLYLNQMNNSSERFSINNWGNSEVGRAAVMEVGDSKGYHFYAERRTDDT

VLFDVSGALTVHGPNGITVKNSTGARHIWFRDDSDTEKAVIWATDDGMLHIRNNEGSFAHHFQGAMIKLEGRV

PYGAAKGLIRGEVDGGAYVAWRDRPAGLLVDCQKSIDSAHAVWKAVDWGRQYIAAMDVHCPGDGNNTAAAVLH

VQAADYQFHASGEFHASGNGNFNDVYIRSDRRLKDNIEDYTGNALSLIGKLKVKTYDKVKSLKDREIIGHEIG

IIAQDLQEILPEAVKSSKVGNLDNPDDVLTISNSAVNALLIKAIQEMSEEIKELKTPFFTKIARKISKYFKF

WW202 gp38
(SEQ ID NO: 152)
MAVVGVPGWIGSSAANETGQRWMSQAAGQLRLGVPCWMSQFSGRSREIIHTLGADHNFNGQWFRDRCFEAGST

PIVFNITGDLVSYSKDVPLFFMYGDTPNEYVQLNIHGVTMYGRGGNGGSNSPGSAGGHCIQNDIGGRLRINNG

GAIAGGGGGGGGYYSPRSQMRLTFGGGGGRPFGAGPPSIDMQSGATAGTLYAPGSGSVNGIYNGGSGGEVGA

AGGRCNIRGQGYEYNGGDAGYAVIGSSPTWQNRGAIYGPAV

WW202 gp57A
(SEQ ID NO: 153)
MSNQHEQMINVLKVRLFDTQEKAAFLEGQLKDRERVLMELVRVLGIQPDENGTVSLDAIVEEVKALLPKDEAA

EDAKEEVELITEA

20

Chimeras Nucleotide Sequence

WW13 13.0
(SEQ ID NO: 154)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAAGGCACCTCTGGACAGTCCGGCACTGACCGGAACGCCAACAGCACCAACCGC

GCTCAGGGGAACAAACAATACCCAGATTGCGAACACCGCTTTTGTACTGGCCGCGATTGCAGATGTTATCGACGCGTCACCTGACGCA

CTGAATACGCTGAATGAACTGGCCGCAGCGCTCGGGAATGATCCAGATTTTGCTACCACCATGACTAACGCGCTTGCGGGTAAACAAC

CGAAGAATGCGACACTGACGGCGCTGGCAGGGCTTTCCACGGCGAAAAATAAATTACCGTATTTTGCGGAAAATGATGCCGCCAGCCT

GACTGAACTGACTCAGGTTGGCAGGGATATTCTGGCAAAAAATTCCGTTGCAGATGTTCTTGAATACCTTGGGGCCGGTGAGAATTCG

ATCATCCAGTTAGAAGATAGTCAAGGCGCCCATTTTTCCACTGAACGTACTTTAGCGACAGGTGCAATTAAAACTCGTTTCTTTGGCG

AAACATTTACTGATGGTACATTATACCTAAATCAGATGAATAATAGTTCTGAACGATTCTCTATTAATAATTGGGGAAATTCAGAAGT

TGGTCGCCCGGCAGTGTTGGAAGTCGGTGATTCCAAAGGTTATCACTTCTATACGGAACGCGGGACAGATAACAGTTTGAATTTTGAT

GTTGCTGGCAATTTTACTGTGCATGGACCTTCCGGGATTACTATCAAAACCTCTACTGGTGCTCGCCATATCTGGTTTAGAGATGATA

GCGATGCAGAAAAGGCTGTTATCTGGGCTACAGATGAGGGTATTTTACATATACGAAATAATTATGGGGGTTCATTTAGTCATCACTT

CCAGGGTGCAATGATTCTAGCGGGAGAGCGTGTTCCATATAATAGTGAATACGCTCTTATCCGTGGTAATATTTCCGGTGGTGCATGG

GTAGACTGGCGAGGTCGTCCGGCTGGATTGTTGGTAGACTGTCAGGACTCACGAAATCAAGCATATAACATTTGGAAAGCTACTCATT

GGGGCGACCAGCACCTTGCGGCGATGGGTGTTCATGCTGGCGGTGGTAATCCTCAGGTTGTATTGCATGTGGGTGGGAATGATTATGC

-continued

ATTTGCATCTAACGGTGATTTTACTGCTGGTGCTGCTGTATATTGTAACGACGTTTATATTCGTTCTGACCGTCGTCTGAAAATTAAT

GTTAAAGACTACGAAGAGAATGCGGTGGATAAGGTAAATAAACTCAAAGTTAAAACCTATGATAAAGTTAAATCTCTTTCTGACCGCG

AAGTTATCGGCCATGAGATTGGTATTATCGCACAGGATTTGCAAGAAGTATTACCGGAAGCTGTTAGCACTTCTAGTGTCGGATCTCA

GGATAACCCAGAAGAAATTTTAACAATTTCTAACTCTGCTGTGAACGCGCTTTTAATTAAGGCTATTCAGGAAATGAGTGAAGAAATT

AAAGAATTGAAAACGCCTCTCTTTACTAAAATTGCTCGCAAAATTAGTAAATATTTTAAATTCTAA

WW13 10.0

(SEQ ID NO: 155)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTGTTGACCGAGCAGTTCACACCCTTGGCGAAATCACTACAAATGCTGTTAATGG

TCTTCGTATTTGGAATAATGATTATGGAGTCATTTTTAGACGTTCAGAAGGAAGTCTTCATATTATTCCTACCGCATTTGGTGAAGGA

GAAACCGGTGATATTGGACCTTTACGTCCTCTCAGTATAGCTTTAGATACCGGTAAAGTTACTATTCCGGATTTACAATCAAGTTACA

ATACGTTCGCTGCTAACGGTTATATTAAATTTGTTGGTCATGGAGCGGGGCCGGCGGTTATGACATTCAATATGCTCAAGCGGCTCC

TATTTTCCAGGAAATCGATGATGATGCTGTAAGCAAATATTATCCTATTGTTAAACAGAAGTTTTTAAACGGTAAATCCGTTTGGTCT

TTAGGTACCGAAATTGAATCAGGTACATTCGTTATTCATCATCTGAAAGAAGATGGTTCACAAGGCCATGCGTCTCGTTTTAATCAAG

ACGGTACTGTTAACTTCCCGGATAACGTTCTGGTCGGCGGTGATATTAACATGAAAGGCATGATGACTTTTGACGCCGGACGTTTAGG

ATCACGAGATTATTTTAAATTTAACCATTGGGGTGATAGTAATAATGGTCGTGATAACATCATCCAGTTAGAAGATAGTCAAGGCGCC

CATTTTTCCACTGAACGTACTTTAGCGACAGGTGCAATTAAAACTCGTTTCTTTGGCGAAACATTTACTGATGGTACATTATACCTAA

ATCAGATGAATAATAGTTCTGAACGATTCTCTATTAATAATTGGGGAAATTCAGAAGTTGGTCGCCCGGCAGTGTTGGAAGTCGGTGA

TTCCAAAGGTTATCACTTCTATACGGAACGCGGGACAGATAACAGTTTGAATTTTGATGTTGCTGGCAATTTTACTGTGCATGGACCT

TCCGGGATTACTATCAAAACCTCTACTGGTGCTCGCCATATCTGGTTTAGAGATGATAGCGATGCAGAAAAGGCTGTTATCTGGGCTA

CAGATGAGGGTATTTTACATATACGAAATAATTATGGGGGTTCATTTAGTCATCACTTCCAGGGTGCAATGATTCTAGCGGGAGAGCG

TGTTCCATATAATAGTGAATACGCTCTTATCCGTGGTAATATTTCCGGTGGTGCATGGGTAGACTGGCGAGGTCGTCCGGCTGGATTG

TTGGTAGACTGTCAGGACTCACGAAATCAAGCATATAACATTTGGAAAGCTACTCATTGGGGCGACCAGCACCTTGCGGCGATGGGTG

TTCATGCTGGCGGTGGTAATCCTCAGGTTGTATTGCATGTGGGTGGGAATGATTATGCATTTGCATCTAACGGTGATTTTACTGCTGG

TGCTGCTGTATATTGTAACGACGTTTATATTCGTTCTGACCGTCGTCTGAAAATTAATGTTAAAGACTACGAAGAGAATGCGGTGGAT

AAGGTAAATAAACTCAAAGTTAAAACCTATGATAAAGTTAAATCTCTTTCTGACCGCGAAGTTATCGGCCATGAGATTGGTATTATCG

CACAGGATTTGCAAGAAGTATTACCGGAAGCTGTTAGCACTTCTAGTGTCGGATCTCAGGATAACCCAGAAGAAATTTTAACAATTTC

TAACTCTGCTGTGAACGCGCTTTTAATTAAGGCTATTCAGGAAATGAGTGAAGAAATTAAAGAATTGAAAACGCCTCTCTTTACTAAA

ATTGCTCGCAAAATTAGTAAATATTTTAAATTCTAA

-continued

WW13-G8
(SEQ ID NO: 156)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTGGAAATATTATTGATCTGGGTTTTGCTAAAGGCGGTAGTATTGACGGAAATGT

TATTCATATAGGAAATTATAATCAAACTGGTGATTATACTTTAAATGGCACCTTCACTCAGACAGGTAATTTTAATTTAACTGGTATT

GCTCGAGTAACTCGCGATATTATTGCCGCCGGGCAAATTATGACTGAGGGCGGAGAACTTATTACAAAAAGTTCAGGTACAGCACATG

TTCGTTTTTCGATGGCAATAGCCGCGAACGTGGAATCATTTATGCCCCGGCCAATGATGGTTTAACTACGCAAGTTCTTAATATCAG

GGTTCAAGACTACGCCGCTGGTAGCGAAAGCACTTATGCATTTTCAGGCAGTGGCCTATTTACTTCACCTGAAGTATCGGCATGGAAA

TCTATGTCAACTCCTCAGATTTTGACCGATAAAGTTATTACAAATGGGAAGAAGACAGGCGATTATGATATCTATTCATTATCAAATA

ACACTCCATTGGCAGAAAGCGAAACGGCTATTAACCACCTCCGTGTTATGCGAAATGCTGTAGGAGCAGGTATTTTCCACGAAGTTAA

TGTTAATGACGGAATAACCTGGTATTCCGGAGATGGCTTAGACACTTATCTTTGGTCGTTTAACTGGGCCGGTGGATTGAAAGCTGGT

CATTCTATTTCTGTAGGTCTTCCGGGTGGCTCTAAAGGATATTCTGAATTAGGAACGGCCTCAATTGCTCTTGGTGATAATGACACCG

GATTTAAATGGCATCAGGACGGATATTTTCATACAGTAAACAATGGAACAAGAACTTTCATCTACGCCCTGCGGAAACACAAAGCCT

TAGAAAAATGGTTATGGGTTATTCTCCGGACGGGATTCTTATGACAACGCCACCGACAGAAAACTATGCTCTTGCTACTGTAGTGACA

TACCACGATAATAACGCGTTTGGAGATGGTCAAACTCTTTTAGGATATTATCAAGGCGGTAACTATCATCACTATTTCCGCGGTAAGG

GTACTACAAACATTAATACTCATGGCGGTTTGTTAGTTACTCCAGGCAATATTGACGTTATTGGTGGTTCTGTTAATATCGATGGTAG

AAATAATAATTCAACTTTAATGTTTAAAGGCTATACCATGGGTCAAAGCTCCGTTGATAACATGTATATAGCTGTTTGGGGAAATACA

TTTACTAATCCTAGTGAAGGCACCCGTAAAAATGTCATGGAAATTTCTGATGATATTGGATGGATGCATTATATTCAACGAAATAAAG

ATAATACAGTTGAAGCCGTATTAAATGGTCAACAGACAATTAACGAAAATATTATTGCGAAAAAGGATATTTGGGTTGACCGAGCAGT

TCACACCCTTGGCGAAATCACTACAAATGCTGTTAATGGTCTTCGTATTTGGAATAATGATTATGGAGTCATTTTTAGACGTTCAGAA

GGAAGTCTTCATATTATTCCTACCGCATTTGGTGAAGGAGAAACCGGTGATATTGGACCTTTACGTCCTCTCAGTATAGCTTTAGATA

CCGGTAAAGTTACTATTCCGGATTTACAATCAAGTTACAATACGTTCGCTGCTAACGGTTATATTAAATTTGTTGGTCATGGAGCGGG

GGCCGGCGGTTATGACATTCAATATGCTCAAGCGGCTCCTATTTTCCAGGAAATCGATGATGATGCTGTAAGCAAATATTATCCTATT

GTTAAACAGAAGTTTTTAAACGGTAAATCCGTTTGGTCTTTAGGTACCGAAATTGAATCAGGTACATTCGTTATTCATCATCTGAAAG

AAGATGGTTCACAAGGCCATGCGTCTCGTTTTAATCAAGACGGTACTGTTAACTTCCCGGATAACGTTCTGGTCGGCGGTGATATTAA

CATGAAAGGCATGATGACTTTTGACGCCGGACGTTTAGGATCACGAGATTATTTTAAATTTAACCATTGGGGTGATAGTAATAATGGT

CGTGATAACATCATCCAGTTAGAAGATAGTCAAGGCGCCCATTTTTCCACTGAACGTACTTTAGCGACAGGTGCAATTAAAACTCGTT

TCTTTGGCGAAACATTTACTGATGGTACATTATACCTAAATCAGATGAATAATAGTTCTGAACGATTCTCTATTAATAATTGGGGAAA

TTCAGAAGTTGGTCGCCCGGCAGTGTTGGAAGTCGGTGATTCCAAAGGTTATCACTTCTATACGGAACGCGGGACAGATAACAGTTTG

-continued

AATTTTGATGTTGCTGGCAATTTTACTGTGCATGGACCTTCCGGGATTACTATCAAAACCTCTACTGGTGCTCGCCATATCTGGTTTA

GAGATGATAGCGATGCAGAAAAGGCTGTTATCTGGGCTACAGATGAGGGTATTTTACATATACGAAATAATTATGGGGGTTCATTTAG

TCATCACTTCCAGGGTGCAATGATTCTAGCGGGAGAGCGTGTTCCATATAATAGTGAATACGCTCTTATCCGTGGTAATATTTCCGGT

GGTGCATGGGTAGACTGGCGAGGTCGTCCGGCTGGATTGTTGGTAGACTGTCAGGACTCACGAAATCAAGCATATAACATTTGGAAAG

CTACTCATTGGGCGACCAGCACCTTGCGGCGATGGGTGTTCATGCTGGCGGTGGTAATCCTCAGGTTGTATTGCATGTGGGTGGGAA

TGATTATGCATTTGCATCTAACGGTGATTTTACTGCTGGTGCTGCTGTATATTGTAACGACGTTTATATTCGTTCTGACCGTCGTCTG

AAAATTAATGTTAAAGACTACGAAGAGAATGCGGTGGATAAGGTAAATAAACTCAAAGTTAAAACCTATGATAAAGTTAAATCTCTTT

CTGACCGCGAAGTTATCGGCCATGAGATTGGTATTATCGCACAGGATTTGCAAGAAGTATTACCGGAAGCTGTTAGCACTTCTAGTGT

CGGATCTCAGGATAACCCAGAAGAAATTTTAACAATTTCTAACTCTGCTGTGAACGCGCTTTTAATTAAGGCTATTCAGGAAATGAGT

GAAGAAATTAAAGAATTGAAAACGCCTCTCTTTACTAAAATTGCTCGCAAAATTAGTAAATATTTTAAATTCTAA

WW13 GP38
(SEQ ID NO: 157)
ATGGCAGTAGTTGGAGTTCCTGGCTGGATTGGAAGTTCAGCCGTAAATGAAACGGGTCAGCGCTGGATGAGTCAAGCAGCTGGTCAAT

TAAGATTGGGTGTTCCTTGCTGGATGAGTCAATTTGCAGGTCGCTCAAGAGAAATTATTCATACACTTGGAGCAGACCATAACTTCAA

TGGTCAATGGTTCCGAGATAGATGTTTTGAGGCAGGTAGTACACCTATAGTGTTTAATATCACTGGAGATTTAGTATCATATTCTAAA

GATGTTCCTTTATTCTTCATGTACGGAGATACACCGAATGAATATGTTCAACTGAATATACACGGCGTAACGATGTATGGACGTGGCG

GTAATGGCGGTAGCAATAGTCCTGGTTCAGCTGGAGGTCATTGTATTCAAAACGATATTGGTGGGAGACTAAGAATTAATAACGGTGG

AGCTATTGCCGGCGGCGGCGGTGGCGGCGGTGGCGGTAGATATGGCAGACTATCATTTGGTGGTGGCGGTGGTCGCCCATTCGGTGCT

GGCGGGTCTTCCTCTCATATGAGTTCCGTGCAACTGCTGGCACCATTTCCGCTCCGGGTGCAGGATCTGTCGGTGAGGGATCTCTTT

GGGTATATACAGGCGGTTCGGGTGGTAATGTCGGTGCTGCTGGAGGAAGATGTAATATTCAAGGTAACGGTACAGAATATGATGGCGG

TGCTGCTGGTTATGCTGTTATAGGGTCTGCTCCAACTTGGATAAATGTTGGAGCAATATATGGTCCAAGAGTATAA

WW13 GP57A
(SEQ ID NO: 158)
ATGTCTGAACAAACTATTGAACAAAAACTGTCTGCTGAAATCGTAACTCTGAAGTCTCGTATCCTTGATACGCAGGACCAAGCGGCTC

GTCTGATGGAAGAATCCAAAATTCTGCAAGGAACTTTGGCTGAAATTGCTCGTGCAGTAGGTATCACTGGCGATACTATCAAAGTTGA

AGAAATCGTTGAAGCTGTCAAGAATCTTACTGCTGAATCTGCAGATGAAGCAAAAGATGAAGAATGA

PP-1
(SEQ ID NO: 159)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAAGGCACCTCTGGACAGTCCGGCACTGACCGGAACGCCAACAGCACCAACCGC

GCTCAGGGGAACAAACAATACCCAGATTGCGAACACCGCTTTTGTACTGGCCGCGATTGCAGATGTTATCGACGCGTCACCTGACGCA

CTGAATACGCTGAATGAACTGGCCGCAGCGCTCGGGAATGATCCAGATTTTGCTACCACCATGACTAACGCGCTTGCGGGTAAACAAC

-continued

```
CGAAGAATGCGACACTGACGGCGCTGGCAGGGCTTTCCACGGCGAAAAATAAATTACCGTATTTTGCGGAAAATGATGCCGCCAGCCT

GACTGAACTGACTCAGGTTGGCAGGGATATTCTGGCAAAAAATTCCGTTGCAGATGTTCTTGAATACCTTGGGGCCGGTGAGAATTCG

ATCGCTACCCGCGTGTCCAAAGAAGGTGACACTATGACTGGTAAGCTGACTCTGTCTGCGGGTAACGATGCGCTGGTGCTGACTGCGG

GCGAGGGCGCGTCCTCGCACATTCGCTCTGACGTGGGCGGGACGAACAACTGGTATATCGGTAAAGGCAGTGGGGATAACGGTTTAGG

CTTCTACTCATACATCACTCAGGGCGGGGTGTATATTACCAACAACGGGGAAATCGCTTTAAGCCCGCAGGGTCAGGGTACGTTTAAC

TTCAACCGTGATCGTCTGCACATCAACGGCACGCAATGGACGGCACATCAAGGCGGTGGCTGGGAAAACCAGTGGAATCAGGAAGCGC

CGATTTTTATTGATTTCGGCAACGTGGGCAATGATAGCTACTACCCGATTATCAAAGGTAAGTCCGGCATTACCAACGAAGGTTATAT

TTCTGGCGTGGACTTCGGTATGCGTCGGATTACTAACACGTGGGCGCAGGGTATTATCCGCGTAGGCAATCAGGAAAACGGTAGCGAT

CCGCAGGCCATCTACGAGTTCCATCATAATGGCGTACTGTACGTTCCTAATATGGTAAAAACGGGTGCGCGTCTGAGCGCAGGTGGGG

GGGATCCGGTATGGCAGGGTGCATGTGTTGTTATCGGTGACAATGACACGGGCTTAGTGCATGGTGGCGATGGTCGCATCAATATGGT

TGCAAACGGTATGCACATTGCGTCTTGGAGTTCCGCGTATCATTTACATGAGGGTTTATGGGATACTACGGGCGCGTTATGGACGGAG

CAAGGGCGTGCAATTATCAGCTTCGGTCATCTGGTACAACAAAGCGATGCCTATTCCACCTTTGTCCGTGATGTATACGTTCGTTCGG

ATATTCGCGTTAAAAAAGATCTGGTGAAATTCGAAAACGCTAGCGAAAAACTGTCCAAAATCAACGGTTATACTTATATGCAGAAACG

CGGGTTAGACGAAGAAGGTAATCAGAAATGGGAGCCTAACGCCGGATTAATCGCGCAGGAAGTGCAGGCGATTCTGCCGGAACTGGTA

GAAGGCGATCCGGACGGTGAAGCATTATTACGTCTGAACTACAATGGCGTGATCGGCCTGAATACTGCGGCGATTAATGAACATACGG

CAGAGATCGCGGAGCTGAAAAGCGAGATTGAAGAACTGAAAAAAATTGTCAAAAGCCTGTTAAAGTAA
```

PP-1 GP38
                                                                                                                                                    (SEQ ID NO: 160)

```
ATGGCAGTAACAGGACCGTGGGTAGGATCGTCTGCAGTAGTTAATACAGGACAAAATTGGATGGTCGGCGCGGCCCAACGATTAAGAA

TGGGTGCTCCGTTCTGGATGAGCAACATGATTGGGCGCTCTGTTGAAGTGATTCATACGTTAGGCGCAGATCATAATTTTAATGGTCA

ATGGTTTCGTGACCGTTGCTTTGAGGCGGGCAGTGCGCCGATCGTGTTTAACATCACTGGCGATTTAGTTTCTTACTCCCGTGACGTT

CCGCTGTTTTTCATGTATGGTGACACGCCGAACGAGTATGTACAATTAAACATTCACGGTGTCACGATGTACGGGCGCGGGGGCAACG

GTTGGGCGGCGGGTGCAATCGGTGCGAGCGATGGCGGGGTGTGCATCCAGAATGATATTGGAGGCCGACTGCGTATCAACAATGGTGG

GGCAATCGCGGGCGGTGGCGGTGGTGGGGGTGGTTATTCTCAGGCTAACAATTGGGCAGGTAAGTACGTTTGCGGTGGCGGTGGCGGT

CGTCCGTTCGGCTTAGGTGGCAACAACGGTGCGCGTTGGCCTGGGGGCAACGCTAGCCTGACCTCGCCGGGCGCAGGTGGGAACACTG

GCACGCGTTATTACGCTGGCGGGGGAGGTGAGGTTGGTCAGCCGGGTCAGTATGCAAACCCCGGCGCGGGTTACTCCACCCCACCAAC

GTCGCCGGGCGCGGCAGTTGCAGGTAGTGCGCCAACTTGGCAAAACGTGGGCGCTATTTATGGCCCGCGTGTTTAA
```

PP-1 GP57A
                                                                                                                                                    (SEQ ID NO: 161)

```
ATGAGTGAACAGACCATCGAACAAAAATTAAGCGCGGAAATCGTGACTCTGAAAAGTCGCATTCTGGATACTCAGGACCAGGCAGCAC

GTCTGATGGAAGAGTCTAAAATCTTGCAGGGCACTCTGGCAGAAATTGCCCGTGCGGTGGGTATCACAGGCGACACGATCAAAGTAGA

AGAAATTGTGGAGGCCGTAAAGAATCTCACAGCGGAGAGCACCGATGAAGCAAAAGACGAAGAATAA
```

WW55 3.0
                                                                                                                                                    (SEQ ID NO: 162)

```
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA
```

-continued

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTACTCCAGGAGAATTGAACGTCTATAGCAAACAAGAAATTGACCGTATGTTTGT

TAAGAACGTTAAAATGGTTGTTCCTTCTGGTGGTGCAACCCGTGGTTATTTTAAAATTGCATCCGCAATGATCCCGCAGAGTGGTCGG

ATGGCGTTTCTGCGAATCTATGGTGGTAATGGATATAATGTAAACTCATATGATCAAGTTGATTTTCTTGAAATTGTGATTCGTAGTG

GTAATAATAACCCTAAAGGCGTTAGTATTGCTGCATATCGTCGAAATTCTTTGAACGTCCATGAAGTATTTGCAATTAATACTTCCGG

TGATAACTATGACATTTATGTTAACTATGGTCGCTTCACCGATAACGTTATTGTAGAGTTTGGAAAAACTGTTGACGTCGCATTGACT

GTTCATGATGTTCCTGAATTTTCGGCGACTAAACCAGAAACCGGAACTAAATTTGATGCTCGTGTTATTACGATGTTCAACACCGAAA

ACAAAGCCGGAACATTGATGTTTGATAATAACAATCAGTTAACCTATGATATTGTTAGCCTTAGCAATGGTCCTGATGATGTTAGAAA

TTATCTGCGTAAATTCCGAAGTAAAGCGGGTGAAATGATTTGGCATGAAACCGTTCAGGGTGCTGTATATCGTCTTGCTACTGGAACT

ACTGATTCTACGGAAGTTCTTAGAGTTGATTCTAACAGTGCTCTCCCGGGTAGCTATAAAGGATATGTAATTACTGGTAAAATGGAAT

TGCACGGTAGCGGTAGTGCGATGAATTTACACCGCCAGACTGGTCAAGCTGCATATATGGCGTGGTGGGATCGTCGTGATGGTAAAAA

CCAACGTAGCGGTTATATCGGTCATGCGGATGGTACTACTGATGGTTTTGTGTGGCGTAATGATGTTGGTGCGAACTCATTTGATTTG

GAAAGTAGTGGACAAGTAAATTTGACTACAGGAAAAACAAAAATTGTATATACCAACGGACAATATTATTCCGCTAACTCTGATGCAT

TCCGTATGATTTACGGCAATTATGGCGCATTCTGGCGAAATGATGGTGGTAAAGTTTATCTGTTGTCTACTGCCGAAAATGATAGATT

TGGTGGATGGAACGGCAACCGACCATTCATTTACGACCTGTCAACTGGTAAAGTTACTTTAGGTGGCGACGGTAACGAAGGCGCATTA

GTTCTCGAAAGAGATAGCCGTGCGGCTAGATTTAGCAACAGCGTATTCTTAGAAAAAGGATTGCTTACTTTCTCTGCGGGTGGGAATC

AGTCAATGGATTCTTTCACGATTAACCATTGGGGAATAGTAACGCTGGACGATATAATGTTTTACAATTTGAAGACACGAAAGGAAC

ACATTTTACAACCGAACGTAATGCTGATGGTGGATTGCTTGCTCACTTCCGAGGGGATTTAACCACAGAAGGGAAATTAACGTGGGGT

AAGGGTACAGCCACATCTAGCTTTAACATTCGTGCATGGGGTAATAGTGATTCCCGTAAACAGGTTTTCGAGTGTGTAGATGAAAGTG

GTTGGCATTGGTATACCCAGCGACCGGGCGGTCCTGGTACTTCTGCAATTGAGTTTGCCATCAATGGTACTGTTAAGCCTCAAGCAAT

TCACACTGGCGGTAATATTCTTTTGAACGGTGCTGATATTGAGTTTCGTCGCACTGGTAATAAGCATTTGTGGTTTAGAGATCCAAAC

GGATTAGAATTGGGTTTGATTTATTGTGATGACAACGGTGTCATTCGTTTTCGTGGTCAGAAACAAGGTCAAGATTGGGTATTTGCCA

ATAAGATGATCCAATTAGGGACCGCTTCTACTGTTGGTGGATCTGGTAACGGTTTGATTCGCGGACAAGTTCAAGGTGGTGCTTGGGC

ACAATGGAGAGACCGTGCTGCTGGAATCCTTGTAGACTGTCAGCAATCTACTGATTCCGCTCATAACATCTGGAAAGCGACTCATTGG

GGAAAATATCATATTGCGGCAATGGGTGTACACGTTCCTAGCGGCACTATAGGTAATGCTATGGCACGTCTAAACGTAAATGACGCCA

ACTTTGACTTTAGCGCCTCCGGTGACATGTCGGCAGGGCGTAACGGTTCGTTTAACGATGTTTATATTCGTTCTGATGCTCGCCTTAA

AATCAATAAGGAAGAGTATAAAGAGAATGCCACCGATAAAGTTAATCGCTTAACTGTATACACCTATGACAAGGTTAAATCTTTAACC

GACCGTACTGTCATTGCTCATGAAGTTGGCATTATCGCACAGGATCTTGAGAAAGAATTGCCGGAAGCAGTAACAACCTCGAAGATCG

GCGATCCAGATAAACCAGAAGAGATCTTAACAATTTCTAACTCTGCTGTCAACGCTCTTTTAATTAAGGCGTTTCAGGAAATGAGCGA

AGAATTGAAAGCCGTTAAAGCTGAACTAGCGGAACTTAAAAAGTAA

WW55-G8

(SEQ ID NO: 163)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

-continued

```
CGTCAGAAACGAATGCTGCAGCGTCACAACAATCAGCCGCCACGTCTGCCTCCACCGCGGCCACGAAAGCGTCAGAGGCCGCCACTTC
AGCACGAGATGCGGTGGCCTCAAAAGAGGCAGCAAAATCATCAGAAACGAACGCATCATCAAGTGCCGGTCGTGCAGCTTCCTCGGCA
ACGGCGGCAGAAAATTCTGCCAGGGCGGCAAAAACGTCCGAGACGAATGCCAGGTCATCTGAAACAGCAGCGGAACGGAGCGCCTCTG
CCGCGGCAGACGCAAAAACAGCGGCGGCGGGGAGTGCGTCAACGGCATCCACGAAGGCGACAGAGGCTGCGGGAAGTGCGGTATCAGC
ATCGCAGAGCAAAGTGCGGCAGAAGCGGCGGCAATACGTGCAAAAAATTCGGCAAAACGTGCAGAAGATATAGCTTCAGCTGTCGCG
CTTGAGGATGCGGACACAACGAGAAAGGGGATAGTGCAGCTCAGCAGTGCAACCAACAGCACGTCTGAAACGCTTGCTGCAACGCCAA
AGGCGGTTAAGGTGGTAATGGATGAGACTAATCGTGGTGCTATTATCAATTTAAGTTGTCCTCCTGTTTATGACCGCGATGTTACAAT
GGCGGGTAAGGTTAAAGGTAATAATTATATCTTAAGTAAAACCGCTAACTATCTGGAAGATCAGACAGCGAGAGATCTTAACTACTTT
GGCGCTTTCCGTACCAATGGTCTTGATGGTCTTCTCGAACTCACGCTAAACGTTCCTCACTCTTCCGGTGTCCAACATGGTCGAGGAT
TTACTTTCCAGTATGGGCACACTGGATCGCGTGTAGAAACTTATGGCTATAATAAAGAAGGTCAAAAAGCATTTAGTTATAAAATGTA
TCACGAAGGTGATAAACCAACTCCAGGAGAATTGAACGTCTATAGCAAACAAGAAATTGACCGTATGTTTGTTAAGAACGTTAAAATG
GTTGTTCCTTCTGGTGGTGCAACCCGTGGTTATTTTAAAATTGCATCCGCAATGATCCCGCAGAGTGGTCGGATGGCGTTTCTGCGAA
TCTATGGTGGTAATGGATATAATGTAAACTCATATGATCAAGTTGATTTTCTTGAAATTGTGATTCGTAGTGGTAATAATAACCCTAA
AGGCGTTAGTATTGCTGCATATCGTCGAAATTCTTTGAACGTCCATGAAGTATTTGCAATTAATACTTCCGGTGATAACTATGACATT
TATGTTAACTATGGTCGCTTCACCGATAACGTTATTGTAGAGTTTGGAAAAACTGTTGACGTCGCATTGACTGTTCATGATGTTCCTG
AATTTTCGGCGACTAAACCAGAAACCGGAACTAAATTTGATGCTCGTGTTATTACGATGTTCAACACCGAAAACAAAGCCGGAACATT
GATGTTTGATAATAACAATCAGTTAACCTATGATATTGTTAGCCTTAGCAATGGTCCTGATGATGTTAGAAATTATCTGCGTAAATTC
CGAAGTAAAGCGGGTGAAATGATTTGGCATGAAACCGTTCAGGGTGCTGTATATCGTCTTGCTACTGGAACTACTGATTCTACGGAAG
TTCTTAGAGTTGATTCTAACAGTGCTCTCCCGGGTAGCTATAAAGGATATGTAATTACTGGTAAAATGGAATTGCACGGTAGCGGTAG
TGCGATGAATTTACACCGCCAGACTGGTCAAGCTGCATATATGGCGTGGTGGGATCGTCGTGATGGTAAAAACCAACGTAGCGGTTAT
ATCGGTCATGCGGATGGTACTACTGATGGTTTTGTGTGGCGTAATGATGTTGGTGCGAACTCATTTGATTTGGAAAGTAGTGGACAAG
TAAATTTGACTACAGGAAAAACAAAATTGTATATACCAACGGACAATATTATTCCGCTAACTCTGATGCATTCCGTATGATTTACGG
CAATTATGGCGCATTCTGGCGAAATGATGGTGGTAAAGTTTATCTGTTGTCTACTGCCGAAAATGATAGATTTGGTGGATGGAACGGC
AACCGACCATTCATTTACGACCTGTCAACTGGTAAAGTTACTTTAGGTGGCGACGGTAACGAAGGCGCATTAGTTCTCGAAAGAGATA
GCCGTGCGGCTAGATTTAGCAACAGCGTATTCTTAGAAAAAGGATTGCTTACTTTCTCTGCGGGTGGGAATCAGTCAATGGATTCTTT
CACGATTAACCATTGGGGGAATAGTAACGCTGGACGATATAATGTTTTACAATTTGAAGACACGAAAGGAACACATTTTACAACCGAA
CGTAATGCTGATGGTGGATTGCTTGCTCACTTCCGAGGGGATTTAACCACAGAAGGGAAATTAACGTGGGGTAAGGGTACAGCCACAT
CTAGCTTTAACATTCGTGCATGGGGTAATAGTGATTCCCGTAAACAGGTTTTCGAGTGTGTAGATGAAAGTGGTTGGCATTGGTATAC
CCAGCGACCGGGCGGTCCTGGTACTTCTGCAATTGAGTTTGCCATCAATGGTACTGTTAAGCCTCAAGCAATTCACACTGGCGGTAAT
ATTCTTTTGAACGGTGCTGATATTGAGTTTCGTCGCACTGGTAATAAGCATTTGTGGTTTAGAGATCCAAACGGATTAGAATTGGGTT
TGATTTATTGTGATGACAACGGTGTCATTCGTTTTCGTGGTCAGAAACAAGGTCAAGATTGGGTATTTGCCAATAAGATGATCCAATT
AGGGACCGCTTCTACTGTTGGTGGATCTGGTAACGGTTTGATTCGCGGACAAGTTCAAGGTGGTGCTTGGGCACAATGGAGAGACCGT
GCTGCTGGAATCCTTGTAGACTGTCAGCAATCTACTGATTCCGCTCATAACATCTGGAAAGCGACTCATTGGGGAAAATATCATATTG
CGGCAATGGGTGTACACGTTCCTAGCGGCACTATAGGTAATGCTATGGCACGTCTAAACGTAAATGACGCCAACTTTGACTTTAGCGC
CTCCGGTGACATGTCGGCAGGGCGTAACGGTTCGTTTAACGATGTTTATATTCGTTCTGATGCTCGCCTTAAAATCAATAAGGAAGAG
TATAAAGAGAATGCCACCGATAAAGTTAATCGCTTAACTGTATACACCTATGACAAGGTTAAATCTTTAACCGACCGTACTGTCATTG
CTCATGAAGTTGGCATTATCGCACAGGATCTTGAGAAAGAATTGCCGGAAGCAGTAACAACCTCGAAGATCGGCGATCCAGATAAACC
AGAAGAGATCTTAACAATTTCTAACTCTGCTGTCAACGCTCTTTTAATTAAGGCGTTTCAGGAAATGAGCGAAGAATTGAAAGCCGTT
AAAGCTGAACTAGCGGAACTTAAAAAGAATTAA
```

>WW55 GP38

(SEQ ID NO: 164)
ATGGCAATATCTTCTGGATGGGTAGGATCATCTGCTGTGTCCGAGACTGGTCAACGGTGGATGAGCGCCGCAATGCAAGCTGTTCGCT

TAGGTCGTCCGGCGTATATGTCGGCAATGGTCGGACGCTCTAAAGAGATTCATTATAGCATTGGTGCTAGTAACTCTTACAATAAAGA

CACTCTTATTAACTGGATGAAAGCACAAGGATCTACTCCGGTAGTAATTACTATCACGGGTAATATTGTTTCCCAATCTACTGGCGTT

CCTTGTCTTGATTTCCCTAGCTCACTGACAAACGAATATGTAACACTCATTATTAACTCTGGTGTTCATGTATTAGGTCGTGGAGGAA

ATGGCGGAAGTAACTCTGCTGGTGGAGCAGGAGGAAATGCAATAAATAACGGAATTGGAACTCGTTTAAGAATAAACAATAATGGTAT

TATTGGTGGTGGCGGTGGTGGCGGTGCTGGTGCTAGATACAATCCTTTCCCTCAAATGGATATGAAATTTGGCGGCGGTGGAGGCCGT

CCATTTGGTGCTGCGGGTGCGGCAGGAGGCGGCGCAGCGGCAGCATCTGCTGGTACAATTTCTGCCCCAGGTAAAGGCACTGTTTCTG

GGGTTCATTATGGAGGAGATGGTGGAGATTTGGGAGCTGCTGGCAAATCTTCATATATTAAAGGTGGTACTGGTGGAACTGTTCACTC

GGGTGGTGCTGCGGGTAAAGCTGTTACTGGTAATGCCCCTCGCTGGGATAAAGTAGGCACGATCTACGGTGCTCGCGTG

WW55 GP57A (SEQ ID NO: 165)
ATGTCCAATCAGCATGAACAAATGATTAATGTCCTGAAAGTACGTCTGTTTGACACTCAAGAAAAGGCCGCATTCTTAGAAGGCCAAC

TGAAAGATCGTGAGCGTGTATTGATGGAACTGGTACGCATTCTGGGTATTCAGCCAGACGAAAACGGCACTGTTTCCCTTGATGCTAT

TGTCGAAGAAGTGAAAGCACTTCTCCCTAAAGACGAAGCAGCGGAAGACGCAGAAGAGGAAGTAGAACTGATCACGGAGGCTTGA

WW34 3.0

(SEQ ID NO: 166)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTACTCCAGGAGAATTGAACGTCTATAGCAAACAAGAAATTGACCGTATGTTTGT

TAAGAACGTTAAAATGTCTACTCCTTCTGGTGAAGCAACCCGTGGTTATTTTAAAATTGCATCCGCAATGATCCCGCAGAGTGGTCGG

ATGGCGTTTCTGCGAATCTATGGTGGGAACGGATTTAATGTTAACTCCTACGATCAGGTGGATTTCCTTGAAATTGTGATTCGTAGTG

GTAATAATAACCCTAAAGGCGTTAGTATTGCTGCATATCGTCGAAATTCTTTGAACGTCCATGAAGTATTTGCAATTAATACTTCCGG

TGATAACTATGACATTTATGTTAACTATGGTCGCTTCACCGATAACGTTATTGTAGAGTTTGGAAAAACTGTTGATGTTGCATTGACT

GTTCACGATGTTCCTGAATTTTCGGCGACTAAACCAGAAACCGGAACTAAATTTGATGCTCGTGTTATTACGATGTTCAACACCGAAA

ACAAAGCCGGAACGTTGATGTTTGATAATAACAATCAGTTAACCTATGATATTGTTAGCCTTAGCAATGGTCCTGATGATGTTAGAAA

TTATCTGCGTAAATTCCGAAGTAAAGCGGGTGAAATGATTTGGCATGAAACAGTTCAGGGTGCTGTATATCGTCTTGCTACTGGAACT

ACTGATTCTACGGAAGTTCTTAGAGTTGATTCTAATAGTGCTATACCAGGTAGCTATAAAGGATATGTAATTACTGGTAAAATGGAAT

TGCATGGTAGTGGTAATTCGATGATTTTACATCGCCAGACTGCTCAAGCCGCGTACATGTCGTGGTGGGATCGTCGTGATGGCAAAAA

CCAACGTAGCGGTTATATCGGTCATGCAGATGGGACTAGTGATGCTATTGTGTGGAATAATGATATTGGACAAAACAGTGCTGTTCTA

GAAACATCTGGTCAAATATCTTTCAGAACAGGTGCAACCAAAATTGTATATACCAACGGACAATATTATTCCGCTAACTCTGATGCAT

-continued

ACCGTATGATCTTTGGTAATTACGGTGCATTCTGGCGTAATGACGGCACTAAAGTTTATCTTCTTTCTACTGCTGAAAATGATAAGTA

TGGTGGATGGAATGCCTATCGTCCATTCATTTATGATTTAACTTCCGGTAACGTTCAATTAGGCGGTGATGGTAACGAAGATGCATTA

ACGTTAGAATGTGCTTCTCGTGCCGCTCGCTTTAGTAATGACGTTTACATTAAGAAAGGGCTTTTGACTTTCGACGCTGGGCGCGCTG

GATCTCGCGATTATATTCGATTTAATCATTGGGGTGATAGTAATAATGCCCGTGATAACGTTTTGTGCATAGAAGATAGTCAAGGCCG

ACATTTTAGCACAGAACGTGCGATGGGTACTGGTGCTCTTAAAGCATACTTCTTAGGCGATCTTGAAGTCGGTGGTAAGTTTACTTGG

GGTAAAAATACAGCTACATCTAGCTTTAATATTCGTGCATGGGGTAATGATTCCCGTAAACAAGTATTAGAATGCGCGGATGAAAGTG

GGTGGCATTGGTACACACAACGAACGGGCGGTCCTGATACTTCTGCAATTGATTTTGCCATCAATGGTACTGTTAGGCCTCAAGCAAT

TCACACTGGCGGTAATATCACTATCAACGGTGCTGATATTGAGTTTAAACGCACTGGCAATAAGCACATCTGGTTTAGAGATCCGAAC

GGTTTAGAGTTAGGCTTGATGTACTGCGATGATGCTGGTGCTATTCGCTTCCGTGGTCAGAAACAAGCCCAGGCGTGGAAATTTGCAG

ATAAAATGATCCAGTTGGAATCTGGCACTGTATCCGGTGGCGGTAATGGCCTGATTCGTGGTGAAGTTGCTGGCGGTAGTTGGGCTAG

CTGGCGTGACCGTGCTGCTGGTCTTATGGTTGGGTGTCCTCAATCCACCAACTCGGCACATAACGTATGGAAAGCGACGCATTGGGGT

AAATATCACATTGCAGCAATGGCTGTACATGTTCCTGATGGTACTATTACCAATGCTTTAGCTCGCCTAAACGTTCATGACGCCAACT

TTGACTTTAGCGCCTCCGGTGACCTGTCGGCAGGGCGTAATGGTTCGTTTAACGATGTTTATATTCGTTCTGATGCTCGCCTTAAAAT

CAACAAGGAAGAGTATAAGGAGAATGCCACCGATAAAGTTAATCGCTTGACGGTATACACCTATGACAAGGTTAAATCTTTAACCGAC

CGTACTGTCATTGCTCATGAAGTTGGTATTATTGCTCAGGATCTTGAGAAAGAATTGCCGGAAGCAGTAACAACTTCTAAGATCGGCG

ATCCTGATAAGCCAGAAGAGATCTTAACAATTTCTAACTCTGCTGTCAACGCTCTTTTAATTAAGGCGTTTCAGGAAATGAGCGAAGA

ATTGAAAGCCGTTAAAGCTGAACTAGCGGAACTTAAAAAGAATTAA

WW34 GP38

(SEQ ID NO: 167)

ATGGCAATATCTTCTGGATGGGTAGGATCATCTGCGGTGTCCGAGACTGGTCAACGGTGGATGAGCGCCGCAATGCAAGCTGTTCGCT

TAGGTCGTCCGGCGTATATGTCGGCAATGGTCGGACGCTCTAAAGAGATTCATTATAGCATTGGTGCTAGTAACTCTTACAATAAAGA

CACTCTTATTAACTGGATGAAAGCACAGGGATCTACTCCGGTAGTAATTACTATCACGGGTAATATTGTTTCCCAATCTACTGGAGTT

CCTTGTCTTGACTTCCCTAGCTCGTTAACAAACGAATATGTAACATTGATCATTAACCCAGGTGTTCATGTTTGGGGCGTGGTGGTA

ATGGTGGCAATAACTCCGCTGGTGGCGCTGGTGGTAATGCAATTAACAACGGTATAGGCACACGCTTACGCATCACAAATAACGGCGC

TATTTGCGGTGGTGGCGGCGGCGGCGGCGCGGGTATTATTCTCCTTTTTCACAAATGAGATTAACCTTTGGTGGTGGCGGTGGGCGT

CCGTTTGGTGCTGCCGGTGGGTCTGCTAATATGGAACAGGGTGCTACTGCTGGTACTATTTCCGCGCCAGGTAAAGGGTCTGTAAACG

GTGTATATAATGGCGGTAACGGTGGTGATGCTGGTGGTGCTGGTGGTAAATGTAATATCCGTGGACAGGGATCGGAATATAACGGTGG

TGCGGCTGGTAAGGCTGTTACTGGCAATGCCCCTCGCTGGGATAAAGTAGGCACGATCTACGGTGCTCGCGTG

WW34 GP57A (SEQ ID NO: 168)

ATGTCCAATCAGCATGAACAAATGATTAATGTCCTGAAAGTACGTCTGTTTGACACTCAAGAAAGGCCGCATTCTTAGAAGGCCAAC

TGAAAGATCGTGAGCGTGTATTGATGGAACTGGTACGCATTCTGGGTATTCAGCCAGACGAAAACGGCACTGTTTCCCTTGATGCTAT

TGTCGAAGAAGTGAAAGCACTTCTCCCTAAAGACGAAGCAGCGGAAGACGCAGAAGAGGAAGTAGAACTGATCACGGAGGCTTGA

WW14-G8

(SEQ ID NO: 169)

ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

-continued

```
ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTAACCAGATTATTGATTTAGGCTTTGCAAAGGGTGGACAAGTTGACGGTGATGT

AACTATTAACGGAACTCTGAATTTAAACGGCCCTGAAATTGTTGCCTCCGGTGGTTATATAGAATTTAACTATCGTACGACAGGTAGT

GGCTCTTGGGCGGGTCAGCACGCGGCCAAAGCTCCTATTTTTGTTGATTTAAGTGCGGCGTTATCTACTTCAGAATACAACCCACTGT

TTAAGCAGCGTTACAAAGATGGAACATTTTCAGCAGGTACATTAGTTACTGAAGGTAGTTTTAAATTTCACTATATTAATGAAGCTGG

TGATTCGAAATATTGGACCTTTAATCGTAATGGTAATTTTCAAGTTGATACCGGTAGTTTATTTGTATCGGGTGGTAATATTTCCGCT

TCAGGCAATATCAACTCTGCCTCAGGGTTTGTGTCTGCGCCTCAGATTAATACTAAAAATATTATTTTAGATACAAAAGCATTTGGAC

AATACGACAGTCAGTCTTTAGTTAATTACGTATACCCAGGCACCGGCGAAACAAATGGTGTAAACTATCTTCGTAAAGTTCGTGCTAA

ATCCGGCGGCACTATGTGGCATGAGCTTTGCACTGCCCAATTAGGCCAAGCCGATGAAATGTCTTGGTGGACAGGTAATACCCCTCAG

TCTAAACAATACGGTGTTCGTAACGACGGCCGTTTGATTGGTAGAAATAGCCTTGCATTAGGTACTATGACTACCGATTTCCCATCTA

GCGATTATGGTAATACCGGAGCTATGGGTGACAAATACCTAGTTTTAGGTGATACTGCAACCGGTTTAAAATATATCAAACAAGGCAA

TTTTGATTTAGTTGGTGGTGGATATTCTGTTGCGTCAATTACCACAGACGGTTTCCGTGGCACAAGTAAAACCTTATTTGGTCGTAGT

AATGACCAAGGTTTAACATGGCTTCTTCCTGGTCAAAACTCTGCAATGGTTTCTATCAGAACCGAAATAGATGGTAATAACTCTGGCG

ATGGCCAAACCCATTTAGGTTATAATTCTAATGGTAAACTTTATCATTATTTCCGTGGTACCGGTCGTGTAGCCATTTCTATGGCAGA

AGGTATGATTATTGAACCTGGTATTTTAAATATTAAGACCGGGGTTAACGAATTAAATCTTAGAGCAGACGGCACAGTTTCTACTACA

CAGCGTTTAATGGTTAATAACGGCTTAGTTCTTAACGCAAACAATAATACTTCTGCATTGGCATTAACTGCTCCTACCGGTGTTGATG

GTACAAAAACCATTAACTGGGACGCTGGTACCCGAAATGGCCAGAACAAAAATACCGTTACCATGAAAGCATGGGGTAACTCATTTAA

CGCGGGTGGTGGTAATAGAGAAACTGTATTCGAAGTATCAGATTCACAAGGATATTATTTCTATGGCCAACGTACTAATCCGGCTTCC

GGTGAAACTGTAGGCCCTATTAACTTCAAGTTCAACGGTTCTGTTGAAACAGGTCATTTTTCTAGTCTCGGAAATATAAGTGCATCTG

GTACCGGTTCTTTTGGTGGCAATGTTACCATGACTAATGGCCTGTTTGTCCAAGGCGGCGCTTCAATTAATGGCCAAGTTAAAATGGG

TGGTACTGCTGACGCATTAAGAATTTGGAACGCTGAATATGGTATGATTTTCCGTCGTTCAGAAACGGGTTCTTCTGCTTCATTCCAT

CTTATTCCTACCCTTCAAAACGCCGGTGAAAATGGCGGAATAAGTGACCTTCGTCCACTATCTATCAATTTAGCTAGCGGCACGGTTA

TAATGGGTAATAAAAGCACAGGTGGCCCACTTTTCACAGTAGACAACGTAAGTAAATTTGTTCAAACCGACTGTAGATTGCGTGTTAA

TATGGATTCTGATGGTATTGTTTTGAATGCTTCATCTCAAGCAGCATCCAACTTTATTCAAGGACGTAAAGCAGATGTTACAAAATGG

TATCTAGGTATTGGCGATGGTGGCAACGTCGTTCGTATGCACAACTATACTTATTCACATGGTATTGCATTAAACTCTGATACCGTTG

ATATAACCAAGCCTCTTAAAATAGGTTCTGATATTCGTATCGGTACTGATGGGAATATTATAGGCAGTGCTACTTTAGATAACTTTAA

AAACCTGAATACAACATTAGACCATAAAGTTAATATGGGCGGTTGGTCCGGCGGTGCTACTACAGGTTGGTATAAATTTGCTACTGTA

GAAATTCCACAGGCAACAGGCACGGCATCTTTTAAAATATTTGGCGGTTCCGGGTTTAATTTTAAAAGTTACGGTCAGGCTTCAATAG

CTGAAATAATTCTTAGAACCGGTAATAATAACCCTAAAGGCCTTAATGCCACGTTGTGGAATAGGACTTCTGAAGCTATTTCCCAGAT

TGCTTCGGTTAATACAAGCGAAGATATCTATGATATTTACGTTTACTTAGGTGGGTATTCTAATTCTTTGGTGGTAGAATATACCTGC

AGCAGCAATAGTAAAGTAACCGTAGTAGGTATGGATGGTGGTGTCCAGCCTTTGGTAGAAACATTACCTGAAGGTCATGTTGTAGGTA

AATCTGTAAGAATGCTGAACAACCTTGACGGAATGTTTGCCGCTGGCGAATCGGATATTGTTACTCGTGGTGAATATGTTACCAATAA

CCAAAAAGGTATGCGTATTAAATCTAAAGGTAATGATTTAGATTCTAATGCTGCTTTACTTAGAAACGACGGTGGAAGTTTTTATATT

TTAGCTACAGATAAAAATACGACAGAAAAACCCGATGCGGCTAATGGTGATTGGAATGGCTTAAGACCTTTCTCGATTAATATGGCTG

ATGGTCGCGTTGGTATGAACCACGGATTGAATATTACTGGCGGTGGTCTGAACGTTACCGGCGGTAATACTAACCTTGGTAATATTAC

ATCTCGTGTAGTTTCTTCGGCACGCGCCGGGTCCGGTTGGGGTGATAACTCTGATGCTATGAAATCCAAAATTACCTTTATGGCTGAC

CACGGTGATTTATCTAATTCAGGCAGTTATTATCCTATCGTAGGCGCATACAGCAACTATGGTTCAGCGGGTTATCGTCAAACCTTTG
```

-continued

AATTTGGATGGGTCGGCTCTGGTAGCACCGCAAATTGGCGAGAAGGTATTATTCGTATTCGCGGTGATAATGCTAACGGCCAGCAAGC
AAGATGGCGCTTTACAATGGACGGTATTTTAGGTTGCCCTGGTAAAGTAGAGATGCCAGAAACAAGCGCATTTGGTATCAACACAACA
AATGGATTTGGTGGTAACTCGATTGTAATTGGTGATAGCGATACTGGTTTTAGACAAGTCGGTGATGGGCTTTTAGAAGTTTGGACTA
ACGCCTCACGCCGAATGAGATTCCAAGGCGGTGATACCTATTCAGATATGAATATTAACGCCCCGAACGTTTATATTCGTTCTGATAT
TCGTTTGAAATCTAACTTCAAACCGATTGAAAATGCTCTTGATAAGGTTGAACAGCTAGACGGTTTAATCTATGATAAAGCTGATTAT
ATTGGCGGCGAAGTTGTTCATACCGAGGCCGGTGTTATTGCTCAGAGTTTGGAAAAAGTATTGCCTGAAGCTGTCCGTGAAGTTGACG
ACATTAAAGGTAACAAAGTTCTTACCGTTTCAACCCAGGCACAAGTTGCTCTGTTAATTGAAGCAGTTAAAACTCTGTCGGCTAAAGT
TAAAGAACTTGAAGCAAAACTTAATTAA

WW14 GP38
(SEQ ID NO: 170)
ATGGCAATTGTAGGTGTTCCTGGTTGGATTGGACAATCTGCCGTAGATGAAACGGGACAACGTTGGATGGATGCCGCTATGCGCGATG
TGCGAGTTGCAGTACCCGGTTGGATGGGGTCGATGGCAGGACAATCAAAAGAAATTTATCTATCTATAGGGGCTAATAACTCTTATGA
TAGAAACTCCCTTATTAACTGGATGAGGGCTCAAGGTGGCGCGCCTGTAGTTATTACAATCACCGGTAACTTAGTATCCAATAGCACC
GGTAACGCTTGTTTGGAATTTCCTAGCAATCTTCCTAACGCGTATATTCAACTTATCATTAATAGCGGTGTGACTGTTTATGGCCGAG
GAGGTAATGGTTCTACTAATGGTTCGGCAGGTGGAAACGGTGGTACAGCTATCCATAACGCAGCCGGAACTAAACTCCGTATTCGTAA
TAACGGCGCTATTGCCGGTGGTGGTGGTGGCGGTGGCGCAGTATCATTGCAAAATAGCTACCCGACTAATGGTACATGCGGTGGTGGT
GGTGGTAGACCATTTGGCGTAGGTGGTAAAATAGGCTCTGACGCTATATTGTCCGGTTCGAATGCGTCTTTAACAGCTGCCGGTACAG
GTGGTGCTACAGTCCAATATGGTGGAGGTAATGGCGGTAACGTTGGAGCTGGCGGTGGACGAGGATGGGCAAAAATGTTTATACCTC
TGCAGGTGGCTCAGCTGGTGCTGCTGTCACTGGCAATGCTCCTAACTGGCAAAACGTAGGAACTATTTACGGCTCAAGAGTCTAG

WW14 GP57A
(SEQ ID NO: 171)
ATGTCTGAACAAACTATTGAACAAAAACTGCAAGCCGAAATCGTAGCTCTTAAATCCCGCATTCTGGACACCCAGGATGTTGCAGCTC
AAGCTCAACAGGAATCACGTATTCTGCAGGATGCGCTGAGTAAAATCGCTGCTCGCTTAGGCATCACCGGTGACCAGATTCAGATTGA
AGACCTGATTGCCGCTGTTCCTGATTTGACCGCTGAAAGTGCTGACGAAGAATAA

WW170-G8
(SEQ ID NO: 172)
ATGGCAGTAAAGATTTCAGGAGTCCTGAAAGACGGCACAGGAAAACCGGTACAGAACTGCACCATTCAGCTGAAAGCCAGACGTAACA
GCACCACGGTGGTGGTGAACACGGTGGGCTCAGAGAATCCGGATGAAGCCGGGCGTTACAGCATGGATGTGGAGTACGGTCAGTACAG
TGTCATCCTGCAGGTTGACGGTTTTCCACCATCGCACGCCGGGACCATCACCGTGTATGAAGATTCACAACCGGGGACGCTGAATGAT
TTTCTCTGTGCCATGACGGAGGATGATGCCCGGCCGGAGGTGCTGCGTCGTCTTGAACTGATGGTGGAAGAGGTGGCGCGTAACGCGT
CCGTGGTGGCACAGAGTACGGCAGACGCGAAGAAATCAGCCGGCGATGCCAGTGCATCAGCTGCTCAGGTCGCGGCCCTTGTGACTGA
TGCAACTGACTCAGCACGCGCCGCCAGCACGTCCGCCGGACAGGCTGCATCGTCAGCTCAGGAAGCGTCCTCCGGCGCAGAAGCGGCA
TCAGCAAAGGCCACTGAAGCGGAAAAAAGTGCCGCAGCCGCAGAGTCCTCAAAAAACGCGGCGGCCACCAGTGCCGGTGCGGCGAAAA
CGTCAGAAACGAATGCTGCAGCGTCACAACAATCAGCCGCCACGTCTGCCTCCACCGCGGCCACGAAAGCGTCAGAGGCCGCCACTTC
AGCACGAGATGCGGTGGCCTCAAAAGAGGCAGCAAAATCATCAGAAACGAACGCATCATCAAGTGCCGGTCGTGCAGCTTCCTCGGCA
ACGGCGGCAGAAAATTCTGCCAGGGCGGCAAAAACGTCCGAGACGAATGCCAGGTCATCTGAAACAGCAGCGGAACGGAGCGCCTCTG
CCGCGGCAGACGCAAAAACAGCGGCGGCGGGGAGTGCGTCAACGGCATCCACGAAGGCGACAGAGGCTGCGGGAAGTGCGGTATCAGC
ATCGCAGAGCAAAAGTGCGGCAGAAGCGGCGGCAATACGTGCAAAAAATTCGGCAAAACGTGCAGAAGATATAGCTTCAGCTGTCGCG
CTTGAGGATGCGGACACAACGAGAAAGGGGATAGTGCAGCTCAGCAGTGCAACCAACAGCACGTCTGAAACGCTTGCTGCAACGCCAA
AGGCGGTTAAGGTGGTAATGGATGAGACTAATCGTGGTGCTATTATCAATTTAAGTTGCCCTCCGGTGTATGACCGCGATGTTACAAT
GGCGGGTAAGGTTAAAGGAAATAATTATATTTTAAGTAAAACCGCCAACTATCTGGAAGATCAGACAGCGCGAGATCTTAATTACTTT
GGTGCTTTCCGAACTAATGGACAAGATGGTCTTTTAGATCTAACTCTTAATGTTCCTCATTCTGCTGGCGTTAATCATGGTCGAGGAT
TTACTTTCCGTTATGCGACTGGCGGATCTCGTGTTGAAACCTATGGGTATAATGCACAGGGACAAAAAGCATTTAGCTATAAAATGTA
TCATGAAGGTGATAAACCTACCCCATCGGAATTGAACGTTTATAGCAAACAAGAAGTTGACCGTATGTTTGTTAAAACCGTTAAACTT

-continued

```
GCTACAGTTCCTGTTGATATCGTTGACGGTTATTTTAAATTAGCAACTGCGATGATTCCGCAAAACGGTCGTAGCGTATTTTTCCGTA

TTCATGGTGGTAACGGATATAACGTTACTGCATACGATCAAGTTGATATTGTAGAAATTGTTATTCGCAGTGGAAATAATCGTCCTAA

AGGTGTTAACGTTATTGCATACCGCCGAAATACAAACAAAGCATTTGATGTTTTGGCTGTTAATACTTCTGGTGATAACTATGATATC

TACGTGAAATATCAGCGTTACACTGATAACGTTATTGTTGAATTTGGTAAAAGTGTTGATGTTGATCTGGTAGTCCATGACGTTCCAG

ACTTTGTTGTTGATCGTCCTGTTGGCGATAATGTTATTGGCGGTCGCGCGGTAACTCTTTTCAACACCGAAAACAAACGAGGTGTGTT

GAGTTTTGACGATAACACACAAAATAGTTATGATATTGTTCACTTGAGTAATGATAGGGGTACTGGACGAAAATATATTCGTAAATTC

CGTAGCAACTATAACGAAATGATCTGGCATGAGACGGTTCAAGGTTCTACTTATCGACTCGCCACGGGTAGCACAGATGCCCAGGAGA

TTCTATCCGTTGAATCTAGTAGCTCTATTGCTGGAACTCATAAAGGTAATATTCTTTCTGGTCGAATGATGTTGGGTGGCGGTAGTAA

TGTTATTACCTTGCGGCGTCCTGCTGGTCAATCCAACCATATTGCGTTTCAAGATAATCGTACTGGATCTATTACCCGTCAAGGGTGG

ATCGGTTATGGTAATGCTGATACTAACGTTTTTGAATGGTATAGTGATGTAGGTGGTACTTCTATTCGTCACCACATCGACGGACAGA

TCGAACTTGCAACCGGTAACACAAAACGCGTTTATACTAACGCTCAATTCATCTCAATGAATAGCGACGCCTACCGTATGATCTTTGG

TAATTACGGTGCATTCTGGCGTAATGACGGCACTAAAGTTTATCTTCTTTCTACTGCCGAAGATGATAAATTTGGCGGGTGGAATGGA

AACAGACCGTTCATTTACGATTTGACCAACGGTAAAGTTACTTTAGGTGGTGATGGTAACGAAGGTGCATTAGTTCTCGAAAGAGATA

GCCGTGCTGCTCGATTTGCTGGTGATGTTTATGTAGAAAAAGGATTTCTTCATTTTTCTAGTGGGCGTCAGGGTGCTAGCGGTTTCAT

GAAAATAAACCATTTGGGTGATATTGCCAGTGGACGACACAACATTCTTCAAATAGAAGACCCTACAGGTATACATTTCTCTACTGAA

CGCAATGATGAAACCGGAAATATTACTGCACGTTTTAAAGGCTTTGTACGTGTAGAAGCTGGTGAAATTGCATTTGATGCTAATCGGG

GGTCGCAGTCTCAATTTACCTTACACACATGGGGTAACGAGCAACGCAAACAGGTTTTTGAATGTAAGGATGCTACAGGTTATCACTG

GTATACTGAACGTACTCAGGGTGGCACTGGAAATGTTCTGTTCTCTATGGCTGGTAGTCTAAACGTTACTAGCAATATCACAACAACT

GGTGCTGATATTACGTTTAAACGCGCTGGCAATAAGCACATCTGGTTTAGAGATCCAGACGGTTTAGAGTTGGGCTTGATGTATTGCG

ATGATGCTGGTGCTATTCGCTTCCGTGGTCAGAAACAAGCCCAGGCGTGGAAATTTGCAGATAAAATGATCCAGTTGGAATCTGGTAC

TGTATCTGGTGGCGGTAATGGCCTGATTCGTGGTGAAGTTGCTGGCGGTAGTTGGTCTAGCTGGCGTGACCGTGCTGCTGGCCTTATG

GTTGGGTGTCCTCAATCCACCAACTCGGCACATAACGTATGGAAAGCGACGCATTGGGGTAAATATCACATTGCAGCAATGGGTATAC

ATGTTCCTGACGGTACTATCGGTAACGCTCTTGCTCGTCTCCATGTTCATGATACTAACTTTGACTTTAGCGCCTCCGGTGATATGAC

GGCAGGTCGTAACGGTTCGTTTAACGATGTGTATATTCGTTCTGATGCTCGCCTTAAAATCAATAAGGAAGAGTATAAAGAGAATGCC

ACCGATAAAATTAATCGCTTGACGGTATACACCTATGACAAGGTTAAATCTTTAACCGACCGTACTGTCATTGCTCATGAAGTTGGTA

TTATTGCTCAGGATCTTGAAAAAGAATTGCCGGAAGCAGTAACAACTTCTAAGGTCGGCGATCCTGATAAGCCAGAAGAGATCTTAAC

AATTTCTAACTCTGCTGTCAACGCTCTTTTAATTAAGGCGTTTCAGGAAATGAGCGAAGAATTGAAAGCCGTTAAAGCTGAACTAGCG

GAACTTAAAAAGAATTAA
WW170 GP38
                                                                                      (SEQ ID NO: 173)
ATGGCAATATCTTCTGGATGGGTAGGATCATCTGCGGTGTCCGAGACTGGTCAACGGTGGATGAGCGCCGCAATGCAAGCTGTACGCT

TAGGTCGTCCGGCGTATATGTCGGCAATGGTCGGACGCTCTAAAGAGATTCATTATAGCATTGGTGCTAGTAACTCTTACAATAAAGA

CACTCTTATTAACTGGATGAAAGCACAAGGATCTACTCCGGTAGTAATTACTATCACTGGTAATATTGTTTCCCAATCTACTGGCGTT

CCTTGTCTTGACTTCCCTAGCTCGTTAACAAACGAATATGTAACATTGATCATTAACCCCGGTGTTCATGTTTGGGGCGTGGTGGTA

ATGGTGGCAATAACTCCGCTGGTGGTGCTGGTGGTAATGCAATTAACAACGGTATAGGCACACGCTTACGCATCACAAATAACGGCGC

TATTTGCGGTGGCGGTGGCGGTGGCGGCGGTGGGTATTATTCTCCTTTTTCACAAATGAGATTAACCTTTGGCGGTGGTGGTGGGCGT

CCGTTTGGTGCTGCCGGTGGGTCTGCTAATATGGAACAGGGTGCTACTGCTGGTACTATTTCCGCGCCAGGTAAAGGGTCTGTCAACG

GTGTATATAATGGCGGTAACGGTGGTGATGCTGGTGGTGCTGGTGGTAAATGTAATATCCGTGGACAGGGATCGGAATATAACGGTGG

TGCGGCTGGTAAGGCTGTTACTGGCAATGCCCCTCGCTGGGATAAAGTAGGCACGATCTACGGTGCTCGTGTGTAA
```

-continued

WW170 GP57A (SEQ ID NO: 174)
ATGTCCAATCAGCATGAACAAATGATTAATGTCCTGAAAGTACGTCTGTTTGACACTCAAGAAAAGGCCGCATTCTTAGAAGGCCAAC

TGAAAGATCGTGAGCGTGTATTGATGGAACTGGTACGCATTCTGGGTATTCAGCCAGACGAAAACGGCACTGTTTCCCTTGATGCTAT

CGTCGAAGAAGTGAAAGCACTTCTCCCTAAAGACGAAGCAGCGGAAGACGCTAAAGAGGAAGTAGAACTGATCACGGAGGCTTGA

WW202-G8

(SEQ ID NO: 175)
ATGGCAGTAAAGATTTCAGGAGTCCTGAAAGACGGCACAGGAAAACCGGTACAGAACTGCACCATTCAGCTGAAAGCCAGACGTAACA

GCACCACGGTGGTGGTGAACACGGTGGGCTCAGAGAATCCGGATGAAGCCGGGCGTTACAGCATGGATGTGGAGTACGGTCAGTACAG

TGTCATCCTGCAGGTTGACGGTTTTCCACCATCGCACGCCGGGACCATCACCGTGTATGAAGATTCACAACCGGGGACGCTGAATGAT

TTTCTCTGTGCCATGACGGAGGATGATGCCCGGCCGGAGGTGCTGCGTCGTCTTGAACTGATGGTGGAAGAGGTGGCGCGTAACGCGT

CCGTGGTGGCACAGAGTACGGCAGACGCGAAGAAATCAGCCGGCGATGCCAGTGCATCAGCTGCTCAGGTCGCGGCCCTTGTGACTGA

TGCAACTGACTCAGCACGCGCCGCCAGCACGTCCGCCGGACAGGCTGCATCGTCAGCTCAGGAAGCGTCCTCCGGCGCAGAAGCGGCA

TCAGCAAAGGCCACTGAAGCGGAAAAAAGTGCCGCAGCCGCAGAGTCCTCAAAAAACGCGGCGGCCACCAGTGCCGGTGCGGCGAAAA

CGTCAGAAACGAATGCTGCAGCGTCACAACAATCAGCCGCCACGTCTGCCTCCACCGCGGCCACGAAAGCGTCAGAGGCCGCCACTTC

AGCACGAGATGCGGTGGCCTCAAAAGAGGCAGCAAAATCATCAGAAACGAACGCATCATCAAGTGCCGGTCGTGCAGCTTCCTCGGCA

ACGGCGGCAGAAAATTCTGCCAGGGCGGCAAAAACGTCCGAGACGAATGCCAGGTCATCTGAAACAGCAGCGGAACGGAGCGCCTCTG

CCGCGGCAGACGCAAAAACAGCGGCGGCGGGGAGTGCGTCAACGGCATCCACGAAGGCGACAGAGGCTGCGGGAAGTGCGGTATCAGC

ATCGCAGAGCAAAAGTGCGGCAGAAGCGGCGGCAATACGTGCAAAAAATTCGGCAAAACGTGCAGAAGATATAGCTTCAGCTGTCGCG

CTTGAGGATGCGGACACAACGAGAAAGGGGATAGTGCAGCTCAGCAGTGCAACCAACAGCACGTCTGAAACGCTTGCTGCAACGCCAA

AGGCGGTTAAGGTGGTAATGGATGAGACTAATCGTGGGCAAATTGTTAATTTAAGTTGCCCTCCTGTTTATGACAAAGGCTTTGATGT

AAGAGGCCGCGTGGTTGTGGATGACCTTGTGTGGAGTAATACCGCAAACTATTTCGATGACCCGACCGCACGAAATCTTGATAAATTT

GGGGCATTTCGTACTAATGATATGGATGGTCATCTAGCATTTGCTTTGCATATTCCCCATCCTAGCGGTATAAATCATGCTCGTGGGT

TTGATTTTACTTATGGTTCTAACGTTGTTCCTACTGTAAAAACCTATGGTTATAACGCTGATGGTGTATTGGCATATTCATATCGCAT

GTATCACGAAGGTGATAAGCCTAGTCCGTCAGAATTAAATGTATACAGCAAACAAGAAGTAGATCGGATGTTCCAAAAAACCATCAAC

TTTGGTGTAGAAACTGGATGGTTTAAAATTGCTACAGCATTTATTCCGCAAAATGATGGACGTAGCTTGAAAATTAGATTGGTTGGTG

GAAATGGGTGGAACGTAGGCCAAACGGGACAATGTAATATTATTGAACTTGTTATAAGGACTAGCAACGGTTCCCCTAAAGGAATTAA

CTTTGTTGCATATCATCATGTTTCTGGTTACGAAAATCAATTTTGTGCCATTAATACAGGTGATGACACTTATGATATCTATGCATAC

TACTACGAATTTACTAATATGGTAATGGCTGAATATCAAGCGTCCAGCGATGTTAATTTAACTGTATTTGATCGACCTGAATATGTAG

GCGAAAAACCTGTAGCCGAACATATATTCGATGCATATACAATACACTCCTTTAACAGTTTCAGTAACCGTGGAACATTAAATTTTGC

TGGCAACCATCAAGGACAATATGACATTGAGCATATGAACGAACAACCGACAAATGCTAAAAAGATGTTGCGTCGGTTTCGAAGCTCT

GCCAGCGCGACAATCTGGCATGAAACCGTTGATGACCAGAATTATCGTCTTGCCACTGGAGGTACAGACTCAGTTCAACAATTATTGT

TGTCTTCTGGGACTGGTTTGCATATTCGTAGATTGACCATCGATGGTGGCTTAGGTTCCGGTTCTAATGCTGGTATTGATATTCGTCG

AGGACCAAACGAATCAAGCCATTTTAATTTTATGGATTATCGCACTGGTCAAGATGTTCGTAATGGTTGGTTTGGTTTTGGTGATTTG

ACGACCAAAGATTTTATTTGGTGGAACGATAACGGTCAAAACTCGATAAACTTGATCGAAACGGTGAATTACATATTACTGGCGGTA

GAGGCCAGAAAATTGTAATGAATAGCGAAGTTGCATTATCTGAAAATGCTCGTTTGGCTGTCAAAGGTGGTAACTATGGTTTAATCCT

TCGTAATGATGGGACTGGTTTCCATATACTGACTACCGATTTAAAAGATTCTTTTGGTAGTTGGAATAATCGCAGACCATTCAGCTAT

AATTTTGCGGACGGTGGATTATATTTAGGTGGTACTGAAACTGCTCGTTGTTTGCATCTTGGAATTGATGGTAGCACTCGTCTAGAAG

ACAACCTTTTCTTTAAAGCTGGTTCTCGTCAATCTATGGACTATATGGAACTCGTCCATTGGGGGGCAAGCAATACAGGTCGAAATAA

CGTTTTAAGTCTTCGTGACTCAAAAGGATTTTTAGCAGAATTTGAACGCGTGGGGGGGACTGACGGCGTTAAAACCAGATTCTTTGGC

GAAACATTCACTGACGGTACATTATACCTAAATCAGATGAATAATAGCTCTGAACGATTCTCTATCAATAACTGGGGAAATTCAGAAG

TTGGTCGCGCGGCAGTAATGGAAGTTGGCGATTCCAAAGGTTATCACTTCTATGCGGAACGTAGAACAGATGACACCGTTTTATTTGA

-continued

TGTATCTGGTGCTTTGACCGTGCATGGACCTAACGGAATAACCGTCAAAAACTCAACTGGTGCACGCCATATCTGGTTTAGAGATGAT

AGCGATACGGAAAAGGCTGTTATCTGGGCTACAGATGATGGTATGTTACATATACGAAATAATCATGAGGGTTCATTTGCTCATCACT

TCCAGGGCGCAATGATTAAACTGGAAGGGCGTGTTCCTTATGGTGCAGCAAAAGGGCTTATTCGAGGCGAGGTAGACGGTGGTGCATA

TGTTGCATGGAGAGATCGCCCTGCTGGTTTGTTGGTTGACTGCCAGAAAAGTATTGACAGTGCTCATGCTGTTTGGAAAGCGGTTGAT

TGGGGGCGTCAATATATCGCTGCTATGGACGTTCATTGTCCGGGTGATGGTAATAATACTGCGGCAGCGGTTCTTCATGTTCAGGCTG

CTGATTATCAATTCCATGCAAGCGGAGAATTTCATGCCTCTGGTAACGGGAACTTTAACGATGTGTATATTCGTTCAGACCGTCGCCT

TAAAGACAATATAGAAGATTATACAGGAAATGCGTTAAGTTTGATCGGCAAACTGAAAGTGAAAACTTACGATAAAGTTAAATCTCTT

AAAGACCGTGAAATTATCGGTCACGAGATCGGCATTATCGCACAGGATTTACAAGAAATATTACCGGAAGCTGTAAAATCTTCAAAAG

TTGGCAATCTTGATAATCCAGACGATGTTCTGACAATTTCTAACTCTGCTGTGAATGCTCTTTTAATTAAGGCTATTCAGGAAATGAG

TGAAGAAATTAAAGAATTGAAAACTCCTTTCTTTACTAAAATTGCTCGCAAAATTAGTAAATATTTTAAATTCTAA

WW202 GP38

(SEQ ID NO: 176)
ATGGCAGTAGTTGGTGTTCCTGGTTGGATTGGAAGTTCAGCCGCAAATGAAACAGGGCAACGATGGATGAGTCAAGCGGCTGGTCAAT

TAAGATTGGGTGTTCCTTGCTGGATGAGCCAATTCTCCGGTCGTTCAAGAGAAATTATTCATACACTTGGAGCAGACCATAACTTCAA

TGGTCAGTGGTTCCGTGATAGATGCTTTGAAGCAGGTAGTACACCTATAGTGTTTAATATCACCGGAGATTTAGTATCATATTCTAAA

GATGTTCCTTTATTCTTTATGTACGGAGATACACCTAATGAATATGTTCAGTTGAATATACATGGCGTAACGATGTATGGTCGTGGCG

GGAATGGCGGTAGCAATAGTCCTGGATCAGCTGGGGGTCATTGTATTCAAAATGATATTGGTGGGAGACTAAGAATTAATAATGGTGG

AGCTATTGCAGGTGGCGGTGGCGGTGGCGGTGGCGGGTATTATTCTCCTTTTTCACAAATGAGATTAACCTTTGGCGGTGGCGGTGGG

CGTCCGTTTGGTGCACCCGGCGGATCTATTGATATGCAATCAGGCGCAACTGCTGGTACTCTTTATGCTCCTGGATCGGGGTCCGTGA

ACGGTATCTATAATGGCGGAAGCGGTGGTGAGGTAGGCGCCGCAGGAGGTAGATGTAATATTCGTGGTCAAGGATATGAATACAATGG

CGGCGATGCTGGTTATGCTGTTATAGGTTCTTCTCCAACGTGGCAAAATCGCGGAGCTATTTACGGACCTGCTGTTTAA

WW202 GP57A (SEQ ID NO: 177)
ATGTCCAATCAGCATGAACAAATGATTAATGTCCTGAAAGTCCGTCTGTTTGACACTCAAGAAAAAGCCGCATTCTTAGAAGGCCAAC

TGAAAGATCGTGAGCGTGTATTGATGGAACTGGTGCGTGTTCTGGGTATTCAGCCAGATGAAAATGGCACTGTTTCCCTTGATGCTAT

CGTCGAAGAAGTAAAAGCACTTCTCCCTAAAGACGAAGCAGCGGAAGACGCTAAAGAGGAAGTAGAACTGATCACGGAGGCTTGA

Payloads p7.3 (p513)

(SEQ ID NO: 178)
CCTTTAGGGAAATATGCTAAGTTTTCACCGTAACACGCCACATCTTGACT

ATATATGTGTAGAAACTGCCGGAAATCGTCGTGGTATTCTGACCAGAGCG

ATGAAAACGTTTCAGTTTGCTCATGGAAAACGGTGTAACAAGGGTGAACA

CTATCCCATATCACCAGCTCACCGTCTTTCATTGCCATACGAAACTCCGG

ATGTGCATTCATCAGGCGGGCAAGAATGTGAATAAAGGCCGGATAAAACT

TGTGCTTATTTTTCTTTACGGTTTTTAAAAAGGCCGTAATATCCAGCTGA

ACGGTTTGGTTATAGGTGCACTGAGCAACTGACTGGAATGCCTCAAAATG

TTCTTTACGATGCCATTGACTTATATCAACTGTAGTATATCCAGTGATTT

TTTTCTCCATTTTAGCTTCCTTAGCTTGCGAAATCTCGATAACTCAAAAA

ATAGTAGTGATCTTATTTCATTATGGTGAAAGTTGTCTTACGTGCAACAT

TTTCGCAAAAGTTGGCGCTTTATCAACACTGTCCCTCCTGTTCAGCTAC

TGACGGTACTGCGGAACTGACTAAAGTAGTGCGTAACGGCAAAAGCACCG

CCGGACATCTGCGCTAGCGGAGTGTATACTGGCTTACTATGTTGGCACTG

ATGAGGGTGTAAGTGAAGTGCTTCATGTGGCAGGAGAAAAAAGGCTGCAT

CGGTGCGTCAGCAGAATATGTGATACAGGATATATTCCGCTTCCTCGCTC

ACTGACTCGCTACGCTCGGTCGTTCGACTGTGGCGAGCGGAAATGGCTTA

CGAACGGGGCGGAGATTTCCTGGAAGATGCCAGGAAGATACTTAACAGGG

AAGTGAGAGGGTCGCGGCAAAGCCGTTTTTCCATAGGCTCCGCCCCCCTG

ACAAGCATCACGAAATCTGACGCTCAAATCAGTGGTGGCGAAACCTGACA

GGACTATAAAGATACCAGGCGTTTCCCCCTGGCGGCTCCCTCGTGCGCTC

TCCTGTTCCTGCCTTTCGGTTTGCCGGTGTCATTCCTCTGTTACGGCCGA

GTTTGTCTCATTCCACGCCTGACACTCAGTTCCGGGTAGGCAGTTCGCTC

CAAGCTGGACTGTATGCACGAACCCCCCGTTCAGTCCGACCGCTGCGCCT

TATCCGGTAACTATCGTCTTGAGTCCAACCCGGAAAGACATGCAAAAGCA

CCACTGGCAGCAGCCACTGGTAATTGATTTAGAGGAGTTAGTCTTGAAGT

CATGCGCCGGATAAGGCTAAACTGAAAGGACAAGTTTTGGCGACTGCGCT

CCTCCAAGCCAGTTACCTCGGTTCAAAGAGTTGGTAGCTCAGAGAACCTT

CGAAAAACCGCCCTGCAAGGCGGTTTTTTCGTTTTCAGAGCAAGAGATTA

-continued

CGCGCAGACCAAAACGATCTCAAGAAGATCATCTTATTAATCAGATAAAA

TATTTCTAGATTTCAGTGCAATTTATCTCTTCAAATGTAGCACTTTATAG

CTAGCTCAGCCCTTGGTACAATGCTAGCGTTTTCATTAAAGAGGAGAAAG

GAAGCCATGAGTAAAGGTGAGGAATTATTTACTGGTGTTGTTCCGATCTT

AGTTGAACTGGACGGCGATGTTAACGGTCATAAATTCAGTGTTCGTGGTG

AAGGTGAAGGTGATGCAACCAACGGTAAGCTGACCCTGAAATTCATCTGC

ACTACTGGAAAATTACCAGTACCGTGGCCTACTCTGGTGACTACCCTGAC

CTATGGTGTTCAGTGTTTTCTCGTTACCCTGACCACATGAAGCAACATG

ATTTCTTCAAATCTGCAATGCCGGAAGGTTATGTACAGGAGCGCACCATT

TCTTTCAAAGACGATGGCACGTATAAAACCCGTGCAGAGGTTAAATTTGA

AGGTGACACTCTGGTGAATCGTATTGAACTGAAAGGCATTGATTTCAAAG

AGGACGGCAATATTTTAGGCCACAAACTGGAATATAACTTCAACTCCCAT

AACGTTTACATCACCGCAGACAAACAAAAGAACGGTATCAAAGCTAACTT

CAAAATTCGCCATAACGTTGAAGACGGTAGCGTACAGCTGGCGGATCATT

ACCAACAGAACACTCCGATTGGAGATGCTCCTGTTTTACTGCCGGATAAC

CACTACCTGTCCACCCAGTCTAAACTGTCGAAGGATCCGAACGAAAAGCG

CGACCACATGGTGTTATTAGAGTTCGTTACCGCTAGTGGTATCACGCACG

GTATGGATGAACTCTACAAATAAGTCAGTTTCACCTGTTTTACGTTAAAA

CCCGCTTCGGCGGGTTTTTACTTTGGGTTTAGCCGAACGCCCCAAAAAG

CCTCGCTTTCAGCACCTGTCGTTTCCTTTCTTTTCAGAGGGTATTTTAAA

TAAAAACATTAAGTTATGACGAAGAAGAACGGAAACGCCTTAAACCGGAA

AATTTTCATAAATAGCGAAAACCCGCGAGGTCGCCGCCCCGTAACCTGTC

GGATCACCGGAAAGAACCTGTAAAGTGATAATGATTATCATCTACATATC

ACAACGTGCGTAAAGGGACTATAACAAGACGCAAACGGAGGTAGGCTCAC

TCCTACTTCGGAAACTTAACCGAAGAACTAGGACGGTATTGTTTGCGCTT

GGAATTGGCCTTGAAGTAAGTCAGGTTTTGACGGAACGATTAGTTACAGG

GGGGGAACAGTCGTTGGTCGCCACCAAGTCGATTTTTGGCTTACCTCTTA

TCTCGTAGTTGGTGAGGGTTGGGATTCACGGGACGAGATCCAGCCTAAGT

ATATTGTCACTTCTGATTCGTTCGATCACTTACTCCCCTTACTTATCCTG

CGGCTACTGTTTCCGCTGGCTCGTAAGCTCTACGTTCGGCAATCTACCCG

CGAGGTCAGACGTGACACTCTTAAACTAAAAATTGGTAGCTTCTTTGGCT

GAATTGCTGGATCTTATTCGTTCACCCAATAAAACGGTACAGCTTCAAGC

AATATCCTCAGTAAGTTAATACCCGTTGTACTATTACTTTCACGACCGTT

CGACGTTCCCGCTCTATTTATTAAGAGCTGTCACTTCGAGTCTTTAGCTC

ACTTAGGAATTAGCTGAGTTTAGGCTCAGCCCTCTTGGGTTGCTTGTACT

TTCAGAGTTATTCGCACGGCTGGTTTTGTCGAGTGGGGAATTGTGGTTGA

CCGAAAGTCCGCTATCCTTCAACGCCGAATCAGCTCTTGCCCTTTACTAT

CTTCAATCTCTTGGAGGCTATTACGGGCGGGGCAAGAGATTAGAACTGC

AAGACACCCGTTGATAATCGAGTCGCTCGATAGATTGTCGAGAGCCGGAG

AGATTAGTACGTTATTCAAGGCAATACGTGCAGGGTTAATCTGGGCGCGT

TGTAGTCTACGCTGGCGTAAGTCCCCAATAACACGCTCGTCCGGCGAGTC

-continued

ACGATCCTCTAGGCGGTGTTCAACGCGTACGCCAGCTATTTGGGATACTT

AGCTACGTTACACGTAAGAATATCTTAGCGGAGGATCGCCCTGCTTCCGC

TTGGACGGATAAACGGGAGAGTGGGCGCGTATAGCGCAGGCGGTGTGAAG

GCTTTTAAGTAATTCTAGCCCTCTTTGAACGGTATTTCCCAATTTGGAGA

TTACCGGATAGCGCGTTTAAATGAGTGTCAGAGAAACGGAAGCCGAAGTC

TTTCCATTCCGGATGTTTGGAAATGCTCTGTTTATAGAAGTCGATGAACT

TACGGCAGTCCTCTATATTAAATTCGAATTTTTCATACCCTTTCTGCGGG

CTACCGTTTTTAGTGTGCGTGCTATGATTGCGGATGCGCAGAATATCCTC

AGACGGGTTGTAGAATTTGATGCTTTTCGCGGAAAAGAACACTTTCGGTA

ACATTTTATTCGCACCCGGCAGGAGCTTGTACACGATTTTCTTATAGCCT

TCACCCTTGTTTTCTTTGATCGCTTTATCGTCGAAGATCTTGTTGTTCTT

CTTGTTCATTACGCCCAGATAGTATTTGTCGTCTTTGATGAACAGGATTG

CGGTGTTGTCCGGCTCTTTGTTCTTATCCCAGCCGTTCGCCAGCGTGCTG

TTTTCGAAGTTCAGTTTGAATTTCTCGTCAGAGTAAGGCTTCTGCGTGAT

GTAGTTGCGGATTTTATTGTAGAGAGGGACGATGTTTGCCAGTTCGAAGT

AACATTCTTCGAACACCAGATAGAAGTGTTCATCTTTATCCAGAATGTTC

GCCTTGTCCTCGCTCTGGCTGATGTGGAAGATTTTGAGCTTGTGTAATAA

GTTATTCGTCGATCTAATAAGTCTTTAATTGCTTTCACATCGTCCTCCG

CAGATGCTTGAAGCAGATCTTTCTTACCCTGATTCTGGTACTTGATAGAG

ATCTGCGCCAGATTGTCTTTGTTTTGAGCAATTTCGTCGAAGATCATCGG

GATTGCCGCAAAGTTCGCCAGAATTTCCTCAAAACGACACTGTTTATCAA

TATCACGATGTTTATTAAATTCCTCAAGTGCCAGTTTGATAGTTTCTAAG

CTCAGGTATTTAGCTTTTTCTGTTTTCTTTGCAATCAGTTCCTGTTCCTT

CTTGGACGGGTGTCCAGATTTTTCGGCGCGATTTGTTGGGTGATGTATT

CCAAAACTGCCGTGCCGATCACGCTATAGTCATCGAAAACTTGTTGACTG

AGATCGGTCAGAGATTTGTCGTTTTTAAAGTAAATCTTAGACAGATCTAG

TTTCTGCGCTTTGAGGTCGTCAAAGAGCAGGGACAGAGTTTCTTTAATAG

ATTTCTCTTCCACGGTTTTGAACGCCGCAATCTGCTCATAAAAGCTCTGC

ATCGTGGTGACAACGTCGCTATCATCTTCCAGTTTATCAATTACGAAGGA

TTTAGATTCGGTGTCCGATAAAATCTGTTTAAACAGAACGGACATTTTAT

ACTTTTTCAGGGTTTTGTCGTTGATTTGTTGGCTATACAGGTTAATGTAT

TCGTTGATGCCCTTACGCTTGGTGTTTTCGCCGTTAACAAATTTGCCACC

AATAATGGTGTTGAATTTGGTGATGCCAGATTGATTCAGGTAATTGTTGA

AATTAGCGATTTCGAAAACCTCGTCCAGTGAGAAAACACGCTGGTTAACT

TCGGAGGTTTTATAGTCGATGTCGAAGGTCAGTTCTTCCGCCAGATCTTT

CTTGATCTGTTCATAGTTAATAGCTTCCGGTGCTTTGTCTTTCAGAGATT

CATATTTCGCTTTGTTTTCCAGAAACTTCGGCAGGTTGTCGTCCACGATA

CGATAAATAATAGAGGTCGGAATATCGTTGCTCGAATATACATTCTTACG

GTTTTCATGAAAACCTTTGAAATACGTCGTCCAGCCTTTGAAAGACTTGA

TGATTTCGGTATTCGAATATGACCTGATCAAAGATAAACGTTTCACCGAA

-continued

```
GATAAGTTCTTTTTCCACTGTCCGATTACCATCAACTTCAAATCTAGCGG
TGCGAACAAGTTCAACGATGAAATTAACTTATTACTGAAAGAGAAAGCTA
ATGACGTACACATCTTATCTATTGATCGCGGTGAACGTCATTTAGCATAC
TATACACTGGTAGATGGTAAAGGTAATATTATTAAACAGGATACTTTCAA
TATTATCGGTAATGACCGTATGAAAACCAACTATCACGATAAGCTGGCGG
CGATCGAAAAGATCGTGATTCTGCGCGTAAAGATTGGAAGAAAATTAAC
AATATCAAAGAAATGAAAGAAGGCTATCTGAGCCAAGTGGTGCACGAGAT
CGCAAAACTGGTGATTGAATATAACGCTATCGTGGTTTTCGAAGATCTGA
ACTTTGGTTTTAAACGTGGTCGCTTCAAAGTAGAAAAACAGGTGTACCAA
AAACTGGAAAAAATGCTGATTGAAAAACTGAACTATCTGGTTTTTAAAGA
CAACGAATTTGACAAAACGGGTGGCGTACTCCGTGCCTATCAGCTGACCG
CTCCGTTCGAAACGTTCAAGAAAATGGGTAAACAAACGGGGATTATCTAT
TATGTGCCAGCTGGTTTCACCTCCAAGATTTGTCCAGTTACGGGCTTCGT
TAACCAGCTGTACCCGAAATACGAGAGCGTTAGCAAATCTCAAGAATTTT
TCAGCAAATTCGACAAGATCTGCTATAATCTGGATAAAGGCTATTTCGAG
TTCAGCTTCGATTACAAAAACTTCGGCGATAAAGCGGCTAAAGGTAAGTG
GACTATTGCTAGCTTTGGTAGCCGTCTGATTAACTTTCGCAACTCCGACA
AAACCATAATTGGGACACGCGTGAAGTGTATCCGACCAAAGAACTGGAA
AAATTACTGAAAGACTATTCCGGACACTCAGAAGGGTTATAGGAATAGTC
ACTACTGGGGTAAGCACTTCGGAAATTATATTATTCTCGCTTCTTATTGC
GGTAACGTGATCCTGAACGATACTTATTACTTTGTAATTTACTTAACGTC
GGAGTCCCTGCAATCTTCTAGTACCCGCTTCCCGAATACAGGAGATAACT
TTTTAACACTCAAGAGTTGCTTCGTGCTTAGCCAGTCTTGGATTTGATTG
CTCTAATCCTTCAACGTGTCAAAGACAGTGTATCTGGTCAAGTAAAGTCT
AGAGAAAGGCGTAGTCAGTTACGGAGTTATCCCACCTTAGTGTTACTCCG
ATTTAATTTCTGCTTTCTTTGATTTCTACCCGACTTTCGCCGTGACTTCA
ATAGAGAGGCAGGCTCTTGCTATTTCTTTCAAGGGCTTGTCCAACTACCT
AATTAAGATAAAGATACGGCAGTTGACGCACTGCCGATAATTTCTTTACG
TCAGCGAAATTAAATCGAGCACCAGTCGTAGAGTCGCGGTTGCCTAGCAG
TTTATCTCGCGTACGGGCCTTCGCTACTTACACGATACCTAGTACGTGGA
TTCGGGTAGCACCAGAAGTCTATAGCATGTGCATACCTTTGGTCGAAAA
AAAAGCCCGCACTGTCAGGTGCGGCTTTTTTCAGTGTTTCCTTGCCGGA
TTACGCCCCGCCCTGCCACTCATCGCAGTATTGTTGTAATTCATTAAGCA
TTCTGCCGACATGGAAGCCATCACAAACGGCATGATGAACTTGGATCGCC
AGTGGCATTAACACCTTGTCGCCTTGCGTATAATATTTTCCCATAGTGAA
AACGGGGGCGAAGAAGTTGTCCATATTTGCTACGTTTAAATCAAAACTGG
TGAAACTCACCCAGGGATTGGCACTGACGAAAAACATATTTTCGATAAAC
``` gpJ Variant

1A2

(SEQ ID NO: 179)
```
ATGGGTAAAGGAAGCAGTAAGGGGCATACCCCGCGCGAAGCGAAGGACAA
CCTGAAGTCCACGCAGTTGCTGAGTGTGATCGATGCCATCAGCGAAGGGC
CGATTGAAGGTCCGGTGGATGGCTTAAAAAGCGTGCTGCTGAACAGTACG
CCGGTGCTGGACACTGAGGGGAATACCAACATATCCGGTGTCACGGTGGT
GTTCCGGGCTGGTGAGCAGGAGCAGACTCCGCCGGAGGGGATTTGAATCCT
CCGGCTCCGAGACGGTGCTGGGTACGGAAGTGAAATATGACACGCCGATC
ACCCGCACCATTACGTCTGCAAACATCGACCGTCTGCGCTTTACCTTCGG
TGTACAGGCACTGGTGGAAACCACCTCAAAGGGTGACAGGAATCCGTCGG
AAGTCCGCCTGCTGGTTCAGATACAACGTAACGGTGGCTGGGTGACGGAA
AAAGACATCACCATTAAGGGCAAAACCACCTCGCAGTATCTGGCCTCGGT
GGTGATGGGTAACCTGCCGCCGCGCCCGTTTAATATCCGGATGCGCAGGA
TGACGCCGGACAGCACCACAGACCAGCTGCAGAACAAAACGCTCTGGTCG
TCATACACTGAAATCATCGATGTGAAACAGTGCTACCCGAACACGGCACT
GGTCGGCGTGCAGGTGGACTCGGAGCAGTTCGGCAGCCAGCAGGTGAGCC
GTAATTATCATCTGCGCGGGCGTATTCTGCAGGTGCCGTCGAACTATAAC
CCGCAGACGCGGCAATACAGCGGTATCTGGGACGGAACGTTTAAACCGGC
ATACAGCAACAACATGGCCTGGTGTCTGTGGGATATGCTGACCCATCCGC
GCTACGGCATGGGGAAACGTCTTGGTGCGGCGGATGTGGATAAATGGGCG
CTGTATGTCATCGGCCAGTACTGCGACCAGTCAGTGCCGGACGGCTTTGG
CGGCACGGAGCCGCGCATCACCTGTAATGCGTACCTGACCACACAGCGTA
AGGCGTGGGATGTGCTCAGCGATTTCTGCTCGGCGATGCGCTGTATGCCG
GTATGGAACGGGCAGACGCTGACGTTCGTGCAGGACCGACCGTCGGATAA
GACGTGGACCTATAACCGCAGTAATGTGGTGATGCCGGATGATGGCGCGC
CGTTCCGCTACAGCTTCAGCGCCCTGAAGGACCGCCATAATGCCGTTGAG
GTGAACTGGATTGACCCGAACAACGGCTGGGAGACGGCGACAGAGCTTGT
TGAAGATACGCAGGCCATTGCCCGTTACGGTCGTAATGTTACGAAGATGG
ATGCCTTTGGCTGTACCAGCCGGGGGCAGGCACACCGCGCCGGGCTGTGG
CTGATTAAAACAGAACTGCTGGAAACGCAGACCGTGGATTTCAGCGTCGG
CGCAGAAGGGCTTCGCCATGTACCGGGCGATGTTATTGAAATCTGCGATG
ATGACTATGCCGGTATCAGCACCGGTGGTCGTGTGCTGGCGGTGAACAGC
CAGACCCGGACGCTGACGCTCGACCGTGAAATCACGCTGCCATCCTCCGG
TACCGCGCTGATAAGCCTGGTTGACGGAAGTGGCAATCCGGTCAGCGTGG
AGGTTCAGTCCGTCACCGACGGCGTGAAGGTAAAAGTGAGCCGTGTTCCT
GACGGTGTTGCTGAATACAGCGTATGGGAGCTGAAGCTGCCGACGCTGCG
CCAGCGACTGTTCCGCTGCGTGAGTATCCGTGAGAACGACGACGGCACGT
ATGCCATCACCGCCGTGCAGCATGTGCCGGAAAAAGAGGCCATCGTGGAT
AACGGGGCGCACTTTGACGGCGAACAGAGTGGCACGGTGAATGGTGTCAC
GCCGCCAGCGGTGCAGCACCTGACCGCAGAAGTCACTGCAGACAGCGGGG
```

-continued

```
AATATCAGGTGCTGGCGCGATGGGACACACCGAAGGTGGTGAAGGGCGTG

AGTTTCCTGCTCCGTCTGACCGTAACAGCGGACGACGGCAGTGAGCGGCT

GGTCAGCACGGCCCGGACGACGGAAACCACATACCGCTTCACGCAACTGG

CGCTGGGGAACTACAGGCTGACAGTCCGGCGGTAAATGCGTGGGGGCAG

CAGGGCGATCCGGCGTCGGTATCGTTCCGGATTGCCGCACCGGCAGCACC

GTCGAGGATTGAGCTGACGCCGGGCTATTTTCAGATAACCGCCACGCCGC

ATCTTGCCGTTTATGACCCGACGGTACAGTTTGAGTTCTGGTTCTCGGAA

AAGCAGATTGCGGATATCAGACAGGTTGAAACCAGCACGCGTTATCTTGG

TACGGCGCTGTACTGGATAGCCGCCAGTATCAATATCAAACCGGGCCATG

ATTATTACTTTTATATCCGCAGTGTGAACACCGTTGGCAAATCGGCATTC

GTGGAGGCCGTCGGTCGGGCGAGCGATGATGCGGAAGGTTACCTGGATTT

TTTCAAAGGCAAGATAACCGAATCCCATCTCGGCAAGGAGCTGCTGGAAA

AAGTCGAGCTGACGGAGGATAACGCCAGCAGACTGGAGGAGTTTTCGAAA

GAGTGGAAGGATGCCAGTGATAAGTGGAATGCCATGTGGGCTGTCAAAAT

TGAGCAGACCAAAGACGGCAAACATTATGTCGCGGGTATTGGCCTCAGCA
```

-continued

```
TGGAGGACACGGAGGAAGGCAAACTGAGCCAGTTTCTGGTTGCCGCCAAT

CGTATCGCATTTATTGACCCGGCAAACGGGAATGAAACGCCGATGTTTGT

GGCGCAGGGCAACCAGATATTCATGAACGACGTGTTCCTGAAGCGCCTGA

CGGCCCCCACCATTACCAGCGGCGGCAATCCTCCGGCCTTTTCCCTGACA

CCGGACGGAAAGCTGACCGCTAAAAATGCGGATATCAGCGGTAACGTGAA

TGCGAACTCCGGGACGCTCAACAACGTCACGATTAACGAGAACTGTCGGG

TTCTGGGAAAATTGTCCGCGAACCAGATTGAAGGCGATCTCGTTAAAACA

GTGGGCAAAGCTTTCCCCCGGGACTCCCGTGCACCGGAGCGGTGGCCATC

AGGAACCATTACCGTCAGGGTTTATGACGATCAGCCGTTTGACCGGCAGA

TTGTTATTCCGGCGGTGGCATTCAGCGGCGCTAAACATGAGAAAGAGCAT

ACTGATATTTACTCCTCATGCCGTCTGATAGTGCGGAAAAACGGTGCTGA

AATTTATAACCGTACCGCGCTGGATAATACGCTGATTTACAGTGGCGTTA

TTGATATGCCTGCCGGTCACGGTCACATGACACTGGAGTTTTCGGTGTCA

GCATGGCTGGTAAATAACTGGTATCCCACAGCAAGTATCAGCGATTTGCT

GGTTGTGGTGATGAAGAAAGCCACTGCAGGCATCACGATTAGCTGA
```

STFs

>WT STF
(SEQ ID NO: 180)
```
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGTGGT

AATGGATGAGACTAATCGTAAGGCACCTCTGGACAGTCCGGCACTGACCGGAACGCCAACA

GCACCAACCGCGCTCAGGGGAACAAACAATACCCAGATTGCGAACACCGCTTTTGTACTGG

CCGCGATTGCAGATGTTATCGACGCGTCACCTGACGCACTGAATACGCTGAATGAACTGGCC

GCAGCGCTCGGGAATGATCCAGATTTTGCTACCACCATGACTAACGCGCTTGCGGGTAAACA
```

-continued

```
ACCGAAGAATGCGACACTGACGGCGCTGGCAGGGCTTTCCACGGCGAAAAATAAATTACCG

TATTTTGCGGAAAATGATGCCGCCAGCCTGACTGAACTGACTCAGGTTGGCAGGGATATTCT

GGCAAAAAATTCCGTTGCAGATGTTCTTGAATACCTTGGGGCCGGTGAGAATTCGGCCTTTC

CGGCAGGTGCGCCGATCCCGTGGCCATCAGATATCGTTCCGTCTGGCTACGTCCTGATGCAG

GGGCAGGCGTTTGACAAATCAGCCTACCCAAAACTTGCTGTCGCGTATCCATCGGGTGTGCT

TCCTGATATGCGAGGCTGGACAATCAAGGGGAAACCCGCCAGCGGTCGTGCTGTATTGTCTC

AGGAACAGGATGGAATTAAGTCGCACACCCACAGTGCCAGTGCATCCGGTACGGATTTGGG

GACGAAAACCACATCGTCGTTTGATTACGGGACGAAAACAACAGGCAGTTTCGATTACGGC

ACCAAATCGACGAATAACACGGGGGCTCATGCTCACAGTCTGAGCGGTTCAACAGGGGCCG

CGGGTGCTCATGCCCACACAAGTGGTTTAAGGATGAACAGTTCTGGCTGGAGTCAGTATGGA

ACAGCAACCATTACAGGAAGTTTATCCACAGTTAAAGGAACCAGCACACAGGGTATTGCTT

ATTTATCGAAAACGGACAGTCAGGGCAGCCACAGTCACTCATTGTCCGGTACAGCCGTGAGT

GCCGGTGCACATGCGCATACAGTTGGTATTGGTGCGCACCAGCATCCGGTTGTTATCGGTGC

TCATGCCCATTCTTTCAGTATTGGTTCACACGGACACACCATCACCGTTAACGCTGCGGGTA

ACGCGGAAAACACCGTCAAAAACATTGCATTTAACTATATTGTGAGGCTTGCATAA
```

>WT STF accessory protein 1 (SEQ ID NO: 181)
```
ATGGCATTCAGAATGAGTGAACAACCACGGACCATAAAAATTTATAATCTGCTGGCCGGAA

CTAATGAATTTATTGGTGAAGGTGACGCATATATTCCGCCTCATACCGGTCTGCCTGCAAAC

AGTACCGATATTGCACCGCCAGATATTCCGGCTGGCTTTGTGGCTGTTTTCAACAGTGATGA

GGCATCGTGGCATCTCGTTGAAGACCATCGGGGTAAAACCGTCTATGACGTGGCTTCCGGCG

ACGCGTTATTTATTTCTGAACTCGGTCCGTTACCGGAAAATTTTACCTGGTTATCGCCGGGAG

GGGAATATCAGAAGTGGAACGGCACAGCCTGGGTGAAGGATACGGAAGCAGAAAAACTGT

TCCGGATCCGGGAGGCGGAAGAAACAAAAAAAAGCCTGATGCAGGTAGCCAGTGAGCATAT

TGCGCCGCTTCAGGATGCTGCAGATCTGGAAATTGCAACGAAGGAAGAAACCTCGTTGCTG

GAAGCCTGGAAGAAGTATCGGGTGTTGCTGAACCGTGTTGATACATCAACTGCACCTGATAT

TGAGTGGCCTGCTGTCCCTGTTATGGAGTAA
```

>SIED6 (SEQ ID NO: 182)
```
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG
```

-continued
```
CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTGATCCTGCTTCTGTCCCTCCGCTTCCTGATATCTGGCTACCCTTGAATGATTCTCTG

GAAGCGATAACAGGGTATGCGCCGGGGTATAAAACAATAACCATCGGCAGCGATGAAATCA

CTGTGCCAGTTAATGGCATATGCCAATTTAGCCGGGCTTCATCTGCAACGTATATTGATAAG

TCCGGGCATATTACCGTGGCAGGGAATAACGTTCCTCGTTTTGAAAAATATGGTTTGCTGAT

AGAGAATCAGCGAACAAACATGTTCGTAAATAGTTTTAATCCTGATGCGTGGAATAAAAGC

GGTGGTATATCTGTAACATCATCAACAGATGAATTTGAGTTTAAATATGGACGTTTCACAGT

AGGAAGCGACATAGCAGGAACGACAACAGGGAGAAATATATGCACAGTTGCTGGTAATAG

AGGCATAGATGTGACTGGCGATGATCAGTACAGTAAAGGTCCGTATGTTACCGCGTCGTTCA

GGGTAAGAAGTGATCTCAATGTTCGCGCACGTATCCGTTTTGAACGGTATAACTCGGAAGGA

TACACTTTCCTTTGTGACGCCTATTTGTCATTACAGACCCATGAACTACAAATTACGGGTGAT

AATGCCCAGCTATTAACAGCAAACTTTGAAATCGATCCAGGTAGTGGATGGATATATTTTCA

GGCAACCCTGAAATGTCTGCCAGAATGGGGAATGGTTGGTACGCAGTTGCAAATTGCAGCC

GACAGAGCTGTGGGTCTTTTGCAACAGGTGACTGGATAGAAGTAACCACCCCGCAATTTGA

GTATGGTGCTTGTGCAACTTCCTTTATCATAACGACAACAGAGCCAGCGACTCGTGCATCAG

ATTTATGTAAATTTCCGCTGATGAAAAATATGTATACCATGCCTTTTACGTTCATGGTGGAAG

TCCATAAAAACTGGTTTATTGCTCATAATGCTGCACCGCGAGTAATTGATACAGAAAACCAT

CAGTCAGGTGCTCCATTTATCATGGGATTTGGCTCTTCTGGAACTATCAGTCAGGACGGTTAT

CCCTATTGTGATATAGGCGGGGCTAACCGACGTGTATATGAGTCATGCGGAGTAAGAGATCT

TGTTATGGGATTCAGGGTTAAGGCTGACGGCATGACATGCTCATTTGCAAATAAGCATATAA

GCACAGAAACAAAAACAGTATGGAAATATATTCGTGAAGCTGCTGTGATTCGTATCGGGGG

ACAAACGACGACAGGATTACGACACCTTAATGGTCATATAAAAAACCTCCGTTTCTGGAACA

GAGCATTGTCAGATACGCAGCTTAAGGAATACGTATAA
```
>SIED6 accessory protein 1
(SEQ ID NO: 183)
```
ATGCGGGATATAACATTACGATTCGATAACAGAGAACAGTTTAACGCAATTGTATATGACAG

TGGCCTGTTCAGTCTTGAAGAAGAAACGGGATTCTTGTTGATGTTATTGGCCGCGTTATCG

ATTACGAGGAGCCAGAAAACGAAAGATGTACAGGCATTGATCGCGGCGGTTTTTTCGTAAA

CATGAGGATTGTTGATAGCAGTAAAAACATATCTTCTTTAATGCCTTTCATTACGACAGATC

AGCATGTAAGGACATGGGCTTAA
```
>SIED6 accessory protein 2
(SEQ ID NO: 184)
```
ATGGTTACAAAAACAGTAATTCCTGATGACATCAAAACGCTAAAATCCGATGTTAGTAAACT

AAAAAACGATCAAGGAAGCTACGCAACAAAATCATATGTAGACAGCAAAGATGAAACCGTT

GGTGACTGGTCTGCTTCATGGTATCAGCAGGTATTGCCAACTAGCGGAGCTATATTTGGGAG

AAAACTCCGCTCAACTCACCGGACGGCAGGTGTTGAGGATGCGTATTGCGAACTATACCTTA

AAAAATGGATAGACAGCCCAGGGAACGCAATGGCGCGCCTTAACCTGAACGATAACGGTGA

AAATATTTGCTGGGATTTTACCAACCTTTACGGCGGAACAATGATCTTCCCTGGAACTTCAG

GCTATCTGAAAATGGGGAACTGTCTCATGTCGTATGGTGTGCGGGGAAGTAACGCGCTTATT

AAGTTTGATAATACAGACTCATTGCAGATCAAATATGCTAATCACGGGTCGACCATGACACT
```

-continued

AAACACGCAAGGCACGGCGTATTCTGGTGTGTCGACGTTATTATGGGGAAATTCCAGTCGTC

CAGTTGTTTATGAGATTAGGGATGATGGCGGGCTTTTTTGTTTTATGCACAAAGGAACCCA

GATAAAACCTATCAGCTTGAGATAAACGGGCCATGTAAGGCTACATCATTCGACCAGGTGTC

GGACAGAGATCTTAAAGAAAACATTCGGGTTATTGATAATGCCACTGAACGCATCAGATTA

ATGAATGGGTATACTTACCGTCTCAAGTCTAATGGTATGCCTTATGCTGGCGTTATTGCGCAA

GAGGCACTTAATGCAATCCCTGAATCAGTTGGTAGCACAATAAAGTACAAGAGCGGGGACA

ATGGGTCTGATGGAGAATAG

SIEA11

(SEQ ID NO: 185)
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGCAGC

AAATGACAACGCAAATTCACGTCTGGCGAAAAATCAGAATGGTGCAGATATCCAGGATAAA

TCAGCTTTTCTGGACAATGTTGGCGTTACCAGCCTGACGTTTATGAAAAACAATGGCGAAAT

GCCGGTTGATGCTGATCTGAATACGTTTGGTTCTGTTAAGGCTTATTCAGGTATCTGGTCTAA

AGCAACGTCCACCAACGCAACACTGGAGAAAAACTTCCCTGAAGATAATGCTGTCGGTGTG

CTTGAGGTTTTTACTGGCGGCAATTTTGCAGGCACGCAACGCTATACCACACGTGACGGAAA

TTTGTATATCCGCAAACTCATTGGAACATGGAATGGTAATGATGGACCATGGGGAGCATGGC

GCCATGTTCAGGCTGTAACGCGAGCTCTAAGTACGACCATTGACCTTAACTCTCTCGGTGGC

GCAGAACATTTAGGTCTATGGAGAAACAGCAGTTCAGCAATAGCTTCTTTTGAACGACATTA

CCCCGAGCAGGGAGGAGACGCGCAGGGCATTCTGGAAATTTTCGAAGGTGGGCTATATGGA

CGCACACAGCGTTATACAACCCGTAACGGGACTATGTATATTCGCGGCCTGACAGCCAAATG

GGATGCAGAAAATCCACAGTGGGAAGACTGGAACCAAATTGGTTATCAGACCAGTAGTACC

TTCTATGAGGATGACCTGGATGATTTGATGTCTCCAGGTATTTACAGTGTGACAGGCAAAGC

GACCCACACCCCAATCCAGGGGCAGTCTGGTTTTCTGGAAGTCATCAGGCGCAAGGATGGTG

-continued

```
TCTATGTTTTGCAACGTTACACGACCACAGGAACCAGCGCAGCTACAAAAGACCGTTTATAT

GAGCGAGTGTTTCTTGGTGGCTCATTTAACGCGTGGGGGGAGTGGCGACAGATTTATAACTC

AAACTCTTTGCCGTTAGAGTTGGGTATCGGTGGCGCAGTGGCAAAACTCACCAGCCTGGACT

GGCAGACATACGATTTTGTGCCGGGCAGTCTGATAACCGTTCGGCTGGATAACATGACCAAT

ATTCCCGACGGTATGGACTGGGGCGTCATTGATGGCAACCTGATAAACATCTCAGTCGGTCC

GAGTGATGATTCTGGTTCGGGACGCTCAATGCATGTATGGCGCAGCACTGTAAGTAAAGCCA

ACTACCGCTTTTTTATGGTGCGTATTTCAGGAAATCCGGGAAGCCGCACGATCACGACAAGA

CGTGTGCCAATTATCGACGAAGCCCAGACATGGGGCGCGAAACAGACATTCAGTGCTGGCC

TTTCTGGTGAACTGTCCGGCAATGCGGCGACAGCAACAAAGCTGAAAACAGCCCGTAAAAT

TAATAACGTTTCGTTTGATGGAACATCAGATATTAACCTGACGCCGAAAAATATTGGTGCAT

TTGCTTCAGGAAAAACAGGAGACACCGTTGCGAATGATAAAGCCGTTGGATGGAACTGGAG

TAGCGGAGCCTATAACGCAACTATTGGTGGGCATCAACGTTAATTCTTCATTTTAATATCG

GGGAAGGAAGTTGTCCCGCCGCCCAGTTTCGCGTTAATTATAAGAACGGTGGTATTTTTTAT

CGTTCTGCTCGTGACGGTTACGGATTCGAGGCTGACTGGTCTGAGTTTTATACCACAACGCG

AAAACCTACAGCGGGAGATGTCGGTGCACTGCCGTTATCTGGTGGTCAATTGAATGGTGCTC

TGGGTATAGGAACATCCAGTGCTCTTGGCGGTAATTCGATTGTTTTGGGTGATAATGACACG

GGCTTTAAACAAATGGTGATGGTAATCTGGATGTTTATGCTAATAGCGTCCATGTTATGCG

CTTTGTCTCCGGAAGCGTTCAAAGTAATAAAACCATAAATATTACGGGGCGTGTTAATCCCT

CGGATTACGGTAACTTTGATTCCCGCTATGTGAGAGATGTCAGACTTGGCACACGTGTTGTC

CAGACCATGCAGAAAGGGGTGATGTATGAGAAAGCAGGGCACGTAATTACCGGGCTTGGTA

TTGTCGGTGAAGTCGATGGTGATGACCCCGCAGTATTCAGACCAATACAAAAATACATCAAT

GGCACATGGTATAACGTCGCACAGGTGTAA
```

SIEA11 accessory protein 1

(SEQ ID NO: 186)
```
ATGCAGCATTTAAAAAATATTACTGCGGGTAATCCAAAAACTGTTGCCCAATATCAACTGAC

AAAAAATTTTGATGTTATCTGGTTATGGTCCGAAGAGGGAAAAAAACTGGTATGAGGAAGTA

AGTAATTTTCAGGAAGACACGATAAAGATTGTTTACGATGAGAATAATATAATTGTCGGCAT

CACCAGAGATGCTTCAACGCTCAACCCTGAAGGTTTTAGCGTTGTCGAGGTTCCTGATATTA

CCGCCAACCGACGTGCTGATGACTCAGGTAAATGGATGTTTAAGGATGGTGCCGTGATTAAG

CGGATTTATACGGCAGACGAACAGCTGCAACTGGCGGAATTACAGAAGTCAGCTTTGCTTTC

CGAAGCTGAAACTATCATTCAGCCACTGGAACGCTCTGTCAGACTGAATATGGCAACAGATG

AGGAGCGTAGCCGACTGGAAGCATGGGAACGCTACAGTGTTCTGGTCAGCCGTGTGGATCC

TGCAAATCCTGAATGGCCGGAAATGCCGCAATAA
```

EB6

(SEQ ID NO: 187)
```
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC
```

-continued

```
GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGATTGC

GATGGATAATGCCAATGCCCGTCTGGCAAAAGACCGGAACGGAGCAGATATTCCCAATAAG

CCGCTGTTTATCCAAAACCTCGGTTTACAGGAAACGGTAAACAAGGCTGGTAACGCCGTTCA

AAAGACAGGCGATACCTTGTCCGGCGGACTTACTTTTGAAAACGACTCAATCCTTGCCTGGA

TTCGGAATACTGACTGGGCAAAGATTGGATTTAAAAATGATGCCGACAGCGACACTGATTCA

TACATGTGGTTTGAAACAGGCGACAACGGCAATGAATATTTCAAATGGAGAAGCCGCCAGA

GCACCACAACAAAGACCTGATGAATCTTAAATGGGATGCTTTGTATGTTCTTGTCAATGCC

ATTGTAAATGGCGAAGTCATATCAAAATCAGCAAACGGCCTACGTATTGCTTATGGTAATTA

CGGATTCTTTATTCGTAATGATGGTTCAAATACATACTTCATGTTGACAAACTCCGGTGACAA

CATGGGACTTATAACGGATTAAGGCCATTATGGATTAATAACGCTACTGGCGCTGTTTCGA

TGGGGCGTGGTCTTAATGTTTCAGGGGAGACACTTTCAGACCGTTTTGCTATTAACAGCAGT

AATGGTATGTGGATTCAGATGCGCGATAACAACGCTATCTTTGGGAAAAATATAGTTAACAC

TGATAGCGCTCAGGCGTTACTTCGCCAGAATCACGCCGACCGAAAGTTCATGATAGGTGGAC

TGGGGAACAAGCAATTTGGCATCTACATGATTAATAACTCAAGGACAGCCAATGGCACCGA

TGGTCAGGCGTACATGGATAATAACGGTAACTGGCTTTGTGGTGCGCAAGTTATTCCCGGCA

ATTATGGCAATTTTGACTCACGCTATGTGAGAGATGTCCGACTTGGCACACGTGTTGTTCAAT

TGATGGCGCGTGGTGGTCGTTATGAAAAAGCCGGACACGCAATTACCGGATTAAGAATCATT

GGTGAAGTAGATGGCGATGATGAAGCCATCTTCAGGCCAATACAAAAATACATCAATGGCA

CATGGTATAACGTCGCACAGGTGTAA
```

EB6 accessory protein 1  
(SEQ ID NO: 188)
```
ATGCAGCATTTAAAAAATATTAAGTCTGGAAATCCTAAAACGAAAGAACAATATCAGCTAA

CAAAGAATTTTGATGTTATCTGGTTATGGTCCGAAGACGGTAAAAACTGGTATGAAGAAGTA

AATAACTTTCAGGACGACACCATAAAGATTGTATACGACGAAAATAATATTATTGTTGCCAT

AACCAAAGATGCCTCAACGCTTAATCCCGAAGGCTTTAGCGTCGTTGAGATTCCAGATATAA

CAGCCAATCGTCGTGCCGATGATTCAGGGAAGTGGATGTTTAAGGACGGAGCTGTGGTTAA

ACGGATTTATACGGCAGACGAGCAACAACAACAGGCCGAATCACAAAAGGCCGCGTTACTT

TCCGAAGCAGAAAACGTTATTCAGCCACTGGAACGCGCTGTCAGACTGAATATGGCGACGG

ATGAGGAACGCGCACGACTGGAGTCATGGGAACGCTACAGTGTTCTGGTCAGCCGTGTGGA

TACGGCAAAGCCAGAATGGCCACAAAAGCCTGAATAA
```

AH11L
(SEQ ID NO: 189)
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGCAGC

AAATGACAACGCAAATTCACGTCTGGCGAAAAATCAGAACGGTGCAGATATCCAGGATAAA

TCAGTTTTTCTGGACAATGTTGGCGTTACCAGCCTGACGTTTATGAAAAACAATGGCGAAAT

GCCGCTTGATGCTGATCTGAATACATTTGGTCCCGTTAAGGCTTATCTGGGGATCTGGTCTAA

AGCTACCTCAACTAACGCAACACTGGAGAAAAATTTCCCGGAAGATAATGCTGTCGGTGTGC

TTGAGGTTTTTGCTGCCGGCAATTTTGCAGGTACGCAACGCTTTACCACAAGAGACGGCAAT

GTATACATGCGTAAACTCGCCAATAAGTGGAATGGCACTGATGGTCCGTGGGGCGTATGGC

GTCACACTCAATCAGCTACCCGCCCTTTGAGTACGACTATAGACCTGAATACGCTTGGAGCC

GCCGAACATCTTGGTTTATGGCGTAACAGTAGCTCGGCTATAGCTTCATATGAACGCAATTA

TCCAGAGGAAGGCGGCTTTGCTCAGGGGACGCTTGAGATCCTCGAAGGCGGGAATTATGGA

AGAACGCAACGTTATACCACTCGCCGTGGAAATATGTATGTCCGCTGCCTTGCGGCAAGCTG

GGATGCATCAAATCCGCAGTGGGAACCGTGGTTAAGAGTCGGTCATCAGTCAGAGAGTCGT

TATTACGAAGGTGATTTGAATGATGTAACCTCACCAGGTATTTACAGCGTTACAGGTAAAGC

GACCAACGGTCCAGTACTGGACGGAAACGGCGTGACTGTACTCGGCATTCTGGAAGTGTTG

AGGCGGTTTGATGGTGTTAATGTATGGCAGCGTTATACAACTGCCGGAACAGGTACAACCCT

TAAAGGCCGCACCTTTGAGCGCGTCTTTACCGGCAGCTCATGGAGCGAATGGCGGGAAGTCT

ACACCTCGTATTCACTTCCCCTGAATCTGGGTATCGGCGGTGCTGTGGCAAAGCTCACCAGC

CTGGACTGGCAGACCTACGATTTTGTGCCGGGCAGTCTGATAACCGTTAGGCTGGATAATAT

GACCAATATTCCCGACGGTATGGACTGGGGCGTCATTGATGGCAACCTGATAAACATCGCAG

TTGGTCCGAGTGATGATTCCGGTACGGGGCGCTCAATGCATGTATGGCGCAGCACTGTAAGT

AAAGCGAACTACCGATTTTTTATGGTGCGTATTTCAGGAAATCCGGGAAGCCGCACGATCAC

-continued

AGCAAGACGAGTACCAATCATTGACGAAGCCCAGACATGGGCGCGAAACAGACATTCAGT

GCTGGCCTTTCTGGTGAACTGTCCGGCAATGCGGCGACAGCAACAAAGCTGAAAACAGCCC

GTAAAATTAATAACGTTTCGTTTGATGGAACATCAGATATTAACCTGACGCCGAAAAATATT

GGTGCATTTGCTTCAGGAAAAACAGGAGACACCGTTGCGAATGATAAAGCCGTTGGGTGGA

ACTGGAGTAGCGGAGCCTATAACGCAACTACTGGTGGGGCATCAACGTTAATTCTTCATTTT

AATATCGGTGAAGGAAGTTGTCCCGCCGCCCAGTTCCGCGTTAATTATAAGAACGGCGGTAT

TTTTTATCGTTCTGCTCGTGACGGTTACGGATTCGAGGCTGACTGGTCTGAGTTTTATACCAC

AACGCGAAAACCTACAGCGGGAGATGTCGGTGCACTGCCGTTATCTGGTGGTCAATTGAATG

GTGCTCTGGGTATAGGAACATCCAGTGCTCTTGGCGGTAATTCGATTGTTTTGGGTGATAAT

GACACGGGCTTTAAACAAAATGGTGATGGTAATCTGGATGTTTATGCTAATAGCGTCCATAT

TATGCGCTTTGTCTCGGGAAGTATTCAAAGTAATAAAACCATAAATATTACGGGGCGTGTTA

ATCCCTCGGATTACGGTAACTTTGATTCCCGCTATGTCCGGGATATCCGGCTTGGTGGTGCTG

CCACATACAAACCTGCGAACAATGGCATGACATGGACACATCAGGCACCGTCCGGGTGTGT

ATATTCCGGCATTATTGTTCAGGATACCGGCTCAAACTCTGCCGATAACATTGGTGGTGTAT

ATTACAGGCCGGTTCAGAAATACATTAACGGGACATGGTATAACGTGGCGCAGGTATAA

AH11L accessory protein 1
(SEQ ID NO: 190)
ATGCAGCATTTGAAAAATATTACGGCGGGTAATCCAAAAACGGTTGAACAATATCAATTGA

CAAAGGGTTTTGATGTTGTCTGGTTTTTTTCAGAAGATGGTAAGAACTGGTACGAAGAACAA

AAGTATTTTGCTGATGACACGATAAAAATAGCGTACGACAAAGATAATATTATCCGCTATGT

GGAAAAGGATGTGACAGCTATCAGACCGGATGGATTAAGTGTTGTTGAAGTGGCGGATATT

ACTGCTAACCGACGGGCGGACATTTCAGGGGGCTGGATGTTTAAGGACGGCAAAGTGATTA

AACGCATTTATACGGCAGAGGAATTGCTGCAGCAGGCAGAAAACCGGAAAGCCAGACTTCT

TGCAGATGCTGAATCCGTGATTTTGCCGCTGGAGCGCGCGGTCAGACTGAACATGGCAACAG

ATGAGGAGCGTAGCCGACTGGATGCATGGGAGCGTTACAGCGTTCTGGTCAGTCGTGTGGAT

CCTGCAAATCCTGAATGGCCGGAAATGCCGCAATAA

WW55 3.0 accessory protein 1
(SEQ ID NO: 191)
ATGGCAATATCTTCTGGATGGGTAGGATCATCTGCTGTGTCCGAGACTGGTCAACGGTGGAT

GAGCGCCGCAATGCAAGCTGTTCGCTTAGGTCGTCCGGCGTATATGTCGGCAATGGTCGGAC

GCTCTAAAGAGATTCATTATAGCATTGGTGCTAGTAACTCTTACAATAAAGACACTCTTATT

AACTGGATGAAAGCACAAGGATCTACTCCGGTAGTAATTACTATCACGGGTAATATTGTTTC

CCAATCTACTGGCGTTCCTTGTCTTGATTTCCCTAGCTCACTGACAAACGAATATGTAACACT

CATTATTAACTCTGGTGTTCATGTATTAGGTCGTGGAGGAAATGGCGGAAGTAACTCTGCTG

GTGGAGCAGGAGGAAATGCAATAAATAACGGAATTGGAACTCGTTTAAGAATAAACAATAA

TGGTATTATTGGTGGTGGCGGTGGTGGCGGTGCTGGTGCTAGATACAATCCTTTCCCTCAAA

TGGATATGAAATTTGGCGGCGGTGGAGGCCGTCCATTTGGTGCTGCGGGTGCGGCAGGAGG

CGGCGCAGCGGCAGCATCTGCTGGTACAATTTCTGCCCCAGGTAAAGGCACTGTTTCTGGGG

TTCATTATGGAGGAGATGGTGGAGATTTGGGAGCTGCTGGCAAATCTTCATATATTAAAGGT

GGTACTGGTGGAACTGTTCACTCGGGTGGTGCTGCGGGTAAAGCTGTTACTGGTAATGCCCC

TCGCTGGGATAAAGTAGGCACGATCTACGGTGCTCGCGTGTAA

WW55 3.0 accessory protein 2

(SEQ ID NO: 192)

ATGTCCAATCAGCATGAACAAATGATTAATGTCCTGAAAGTACGTCTGTTTGACACTCAAGA

AAAGGCCGCATTCTTAGAAGGCCAACTGAAAGATCGTGAGCGTGTATTGATGGAACTGGTA

CGCATTCTGGGTATTCAGCCAGACGAAAACGGCACTGTTTCCCTTGATGCTATTGTCGAAGA

AGTGAAAGCACTTCTCCCTAAAGACGAAGCAGCGGAAGACGCAGAAGAGGAAGTAGAACT

GATCACGGAGGCTTGA

STF68B (SEQ ID NO: 193)

ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGCTTCTGCCACTGCATCTGCCAACAGTCAA

AAAGCTGCAAAGACGAGCGAAACCAACGCAAAGACAAGCGAGACTGCGGCGGCTAACTCG

GCGAAAGCATCAGCTGCAAGCCAGACGGCTGCAAAAGCGAGTGAAGACGCAGCCAGAGAG

TATGCAAGCCAGGCTGCGGAGCCGTATAAACAAGTTTTGCAGCCGCTTCCCGATGTGTGGAT

ACCGTTTAACGATTCACTGGAAATGATTACTGGTTTCGCTCCTGGTTATAAAAAAGTAACTA

TCGGTGATGATGTTATTACTTTTCCATCAGAGAAGGTTGTATCTTTCACTCGCTCCACTTCTG

CAACGTATATAAACAAATCAGGTTCATTTGCTTTTGCAGAAATTAACGAGCCGCGCTTTGAA

AAGGAAGGTTTATTAATTGAAGGTCAGAGGACAAATACATTTACTAATAGTAACAATCCTTC

ATTATGGAATTATGACGACAAGAATATAGAAATAACCACATCGGTTGATGAATATGGTTTTA

AATATGGTTTGTTCGATGTAAAGGAAACATCAACTACTGAAAGGGCGACGATAATATCTACT

GGATACAGTAGGGTTATTGATGTTGCTGCAAATGAATCTGTTACTTTGTCCTGTAGGGTTAA

GAAGATAAATGGAGAAGGTATTATAACGTTAAGACCCAGAATATCTTTCGTTAACGATGAC

GGTACAAGCAACACGCTGGTAGCTGGTTCCTACATAGATTGCGAAACTGGTGATGTTTTAGG

TTTTTCTGGTGGGGATGCTGTAAATCATGTCATATACAGAGAAGCTAACGGATGGTTACGCG

TCGAATTTACATATAAATCACCAGAAGCAAAAAGCATGTATGGGCGCTTTGAAATGGGAGC

AGATAAAAGGGCGATCAAAAAAGGCGATCAGATAATGTTTACTACGCCGCAATTTGAAAAA

GGATCGTGTGCATCATCATTTATCGTTACATCAGATGTGGCAGTTACACGGGCTAGTGACGT

GGTAATAATGCCAATAAGACTGAACTGGTCAACACCTCCGTTAAGCGTTCTTATGGAAGTTA

ATATCAACTGGGACAAAATGCCAAACAGTGAAGGTTCAGCAAGGCTTCTTAACGTGTCAAT

-continued

```
AACTGGCGCAACAACGGATGTTGCTGATGAAAGTTATATGTATTTTGGTTTTACCTCTGGAG

GCGCGCGCTCAATTATAACTAACGGAAAAGGAACAAAGACCGAGTATAAAGCCTACTGTAA

CAGGACAACCCGCAGGTTTATTGCTGGGTTTAAGTTTACAGAGCAGAAAGAATTGCGTGCTG

TTATAAACGGTAACTTTGGCGCTGTTGATGTATCACAACACACAAGACAACGTTATACAGAA

GGGCCAATAAATATAGGCGGTCAATCAATATCAGGTAACAGGCATTTATTTGGACACGTGCG

CAATTTACGTATCTGGCATAAGGAACTGACAGATGCACAAATGGGAGAAAGAATATAA
```

STF68B accessory protein 1
(SEQ ID NO: 194)
```
ATGCGAGACTTAACCCTCAAATTCATAAACAAGGCCGACTTTTCGGCCTTTATGGATAGCAT

TGGTTATGAAGATGACGAGGTAATGCAGAACAATGTTCTCATTGATGTGATAGGTAACGTGT

ACAAAGAAACCGGAGAACTTACTGAAGATGGCGAGCCGGTATGTGTTAAGGAAGACGGATA

TTTTGTAAACGTGCGCATCATTAATGATGCAAAAAAATCGTCAATATTCGATAAATACGCGG

TTGTTGTTGAGCATCAACTTCGTGGCTGGATGTGA
```

STF68B accessory protein 2
(SEQ ID NO: 195)
```
ATGGCTACATCGACAGTAATTCCTGATGACATCAAAACGCTAAAATCCGACGTTAGCAAATT

AAAAAACGATCAAGGAAGCTACGCAACAAAATCATATGTAGACAGCAAAGATGAAACCGTT

GGTGACTGGTCTGCTTCATGGTATCAGCAAGTATTGCCAACTAGCGGAGCTATATTTGGGAG

AAAACTCCGCTCAACTCACAGGACGGCAGGTGTTGAGGATGCGTATTGCGAACTATACCTCA

AAAAATGGATAGACAGTCCAGGTAACGCAATGGCGCGCCTTAACCTGAACGATAACGGGAC

AAACATTTGCTGGGACTTTACCAACCTTTATGGCGGTACGATGATTTTTCCCGGTGACAGCG

GATACCTCAAAATGGGTAACTGCCTTATGTCATACAGCAAGCGTGGAAGTAACGCGCTTATT

AAATTTGATTACACCGACACATTACAGATCAAATATGCTAATCATGGGTCAACCATGACATT

AAACACACAGGGAACCGCTCACGCTGGCGTAACAACTAGACTATGGGGTAATTCTAGCCGT

CCGGTTGTTTATGAAGTTGGCGTAGATGAGGCTCTGTATATGTTCTACGCACAGAAAACTAC

CAGCAATACCTACGAATTAACGGTTAACGGCGCGTGCAATGCAAGTGCATTTAATCAAGGCT

CTGACCGGGATCTGAAAGACAATATTCAGGTGATCGATAATGCAACCGACCGCATTCGTAA

AATGAACGGCTATACATACACGCTTAAAGAAAACGGTATGCCTTACGCTGGTGTTATTGCAC

AAGAAACCCTGGAAGCCATCCCCGAAGCCGTAGGGGCTATGATGAAATATCCAGACGGCGG

GAGTGGATTAGATGGAGAAGAAGGTGAACGGTATTACACTGTAGATTATTCTGGTGTTACTG

GCTTGCTTGTTCAGGTAGCCAGAGAGTCAGACGACAGGATAACAGCACTGGAAGAAGAAAA

CGCAGAATTAAGACAAAGATTATCTGCAATTGAGGCGGCGCTTGCGTCTAAATAA
```

>STF90B
(SEQ ID NO: 196)
```
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA
```

-continued

```
AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGTGGT

AATGGATGAGACTAATCGTAAATATACCGCACAGGACGCCACCACCGCGCGAAAAGGCCTT

GTCCAGCTAAGTAGCGTCACCAACAGCGATTCTGAAACGCTTGCGGCAACGCCAAAGGCGG

TTAAGACAGCGTATGACCTTGCTAACGGGAAATACACTGCACAGGATGCCACCACAGCGCG

AAAAGGTCTTGTCCAGCTCAGTAGCGCCACCAACAGCGATTCTGAAACGCTTGCGGCAACAC

CAAAAGCGGTGAAGTCTGCCTATGACAATGCTGAAAAACGTCTTCAGAAAGATCAGAACGG

TGCGGATATTCCGGGAAAGGATACTTTCACGAAAAATATCGGTGCCTGTCGTGCTTATAGCG

GTGCTTTGAGCACTGACGCCGGAAACTGGACAACCGCTCAGTTTATTGACTGGCTAGAGTCT

CAGGGAGCCTTTAATCATCCCTACTGGATGTGCAAGTGTTCCTGGTCATACGGTAATAACAA

AATTATTACCGATACTGACTGTGGGACTATTCATCTTGCAGGTTGCGTGATTGAGGTTATGG

GCGTTAAAGCTGCAATGACCATTCGTGTGACCACTCCGAGTACATCAAGCGGTGGTGGTACC

ACCAGTGCGCAATTCACGTATATCAATCACGGAGCTGATTATGCGCCGGGCTGGCGACGCGA

CTACAATACGAAAAATAAGCAACCGGCTTTTGCATTAGGGAAAACAGGAAATACGGTTGCA

AATAATAAAGCGGTAGGATGGAACTGGGACAGTGGTGCTTATTGTGCACAGGATGGCGGAG

CATCAAAAATGGTGCTGCATTTTTACACGGGTGAGGGAAGTTGTCCGGCAATGCAGTTTCTT

GTGGATTATAAAAACAGGGGGATTTTTTACAGGTCGGCACGTGATGGGTATGGATTTGAGGC

TGACTGGTCAGAGTTTTATACCACATCACGAAAGCCAACACCTGCGGATATTCTTGCTCTGG

CATTATCAGGCGGAAGCATGTCAGGCAGCATAAAATTTATCAATGATGCCTTCCTGATTTGG

GAAAGAAACACTGACTGGGCGAAAATTGGATTTAAAAATGATTCAGATGCTGATTCTGACTC

ATACATGTGGTTTGAAACTGGTGATAATGGCAATGAATATTTTAAATGGCGCATCAGGTCTG

GCAGCACAACAAAAGACCTGATGACGCTTAAGTCTGATGCACTACGGGTTACCGGGCAGGT

GATACCATCAAATTTCAGCAATTTTGACTCCCGCTATGTCCGGGATATCCGGCTTGGTGGTGC

CGCCACATACAAACCTGCGAACAATGGCATGACATGGACACATCAGGCACCGTCCGGGTGT

GTATATACCGGCATTATTGTTCAGGATACCGGCTCAAACTCTGCCGATAACATTGGTGGCGT

ATATTACAGACCGGTGCAGAAATACATTAACGGGACATGGTATAACGTGGCGCAGGTATAA
```

STF90B accessory protein
(SEQ ID NO: 197)

```
ATGCAGCATTTAAAAAATATTACGGCGGGTAATCCAAAAACGGTTGAACAATATCAATTGA

CAAAGGACTTTGATGTTGTCTGGTTTTTTTCAGAAGATGGTAAGAACTGGTACGAAGAACAA

AAGTATTTTGCTGATGACACGATAAAAATAGCGTACGACAAAGATAATATCATCCGCTATGT

GGAAAAGGATGTGACAGCTATCAGACCGGATGGATTAAGTGTTGTTGAAGTGGCGGATATT

ACTGCTAACCGACGGGCGGATATTTCAGGGAACTGGATGTTTAAGGATGGCACAGTGATCA

AACGAATTTATACGGCAGAGGAATTGCAACAGCAGGCAGAAAACAGGAAAGCCAGACTTCT
```

-continued
TGCAGATGCTGAATCCGTGATTTTGCCGCTGGAGCGCGCTGTCAGGCTGAATATGGCAACAG

AGGAGGAGCGTAGCAGACTGGAAAGATGGGAACGCTACAGCGTTCTGGTCAGTCGTGTGGA

TCCTGCAAATCCCGAATGGCCGGAAATGCCGCAATAA

STF117

(SEQ ID NO: 198)
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGTGGT

AATGGATGAGACTAATCGTAAATATACTGCGCAGGATGCCACCACAGCGCGAAAAGGGCTT

GTCCAGCTCAGTAGCGCCACCAACAGTGATTCTGAAACCCTCGCGGCAACGCCAAAAGCAG

TGAAGTCTGCCTATGACAATGCTGAAAAACGTCTTCAGAAAGATCAGAACGGTGCGGATATT

CCGGGAAAGGATACCTTCACGAAAAATATCGGTGCCTGTCGTGCTTATAGCGGCGCTTTGAG

CACTGAAGCCGGAAACTGGACAACCGCTCAGTTTATTGAATGGCTGGATTCCCGTGGTGCAT

TTAATCATCCGTACTGGATGTGCAAAGGCTCCTGGTCATATGCAAATAACAAAATCATTACG

GATACCGGATGTGGTGATATCCACCTGGCTGGTTGTGTCGTCGAGGTCATGGGAACTAAATC

TGCAATCACTATCCGAGTGACCACGCCGACAACATCAAGCGGTGGCGGTACAACCAGCGCG

CAATTCACTTACATTAATCATGGGGACGGCTACTCCCCCGGCTGGCGTCGTGACTGGAATCG

TCAGGGCGACGCAATGACCGGAACGATTAATCAGGATGGCGGAAGCCAGAATGCCTATATG

TCTACGGCCTTATGTTCAGGCACCAGAGGCGGCAAAAAATATCTCAGAAAGTTTCGTGGTGG

AGAAGGAGACACTATCTGGCATGAAACAGTACAGGGCGGGGTAGTTCGCTGGGCGACTGGT

AATACTGATGCTCAGGAAGAATTATCACTCAGCTCCGCTTATGGTCTCCGTTCAAGAGGTGA

GATTACATCAAGCAGTGCTAATGGTCTGCGCATTGCTTATGGCAATTATGGATTCTTTATCAG

GAATGATGGCAGCAGCACTTATTTTATGTTGACTAAATCAGGTGACAGATTAGGCACTTATA

ATAATTTAAGACCACTGATTATAAATGATGCCACGGGTGCTGTATCAATGGGGCATGGCCTG

AGTGTTACTGGTGATATTGCCTCAAGTACCAAAGTACGTGCCGGTAGCGGGAAAAAATTCAC

GGTCAGCAGCAGTAATACATCCACGAAGGAAGCCGCATTCAATTTGTGGGGAAACTCAAGT

-continued

CGTCCGGTGGTGGCTGAATTAGGTGATGATGCAGGCTGGCATTTTTACAGTCAGAGAAATAC

AGATAACAGCATCACTTTTGCTGTTAACGGGCAGGTATCACCATCTAACTATAGTAATTTTG

ATTCACGCTATGTCCGGGATATCCGGCTTGGTGGTGCTGCCACATACAAACCTGCGAACAAT

GGCATGACATGGACACATCAGGCACCGTCCGGGTGTGTATATTCCGGCATTATTGTTCAGGA

TACCGGCTCAAACTCTGCCGATAACATTGGTGGCGTATATTACAGACCGGTGCAGAAATACA

TTAACGGGACATGGTATAACGTGGCACAGGTATAA

STF117 accessory protein 1
(SEQ ID NO: 199)
ATGCAGCATTTGATAAATATAACCGCGGGTAATCCAAAAACGGTTGAACAATATCAATTGAC

AAAGGACTTTGATGTTGTCTGGTTTTTTACAGAAGATGGTAAGAACTGGTACGAAGAACAAA

AGTATTTTGCTGATGACACGATAAAAATAGCGTACGACAAGGATAATATTATCCGCTATGTG

GAAAAAGATGTGACAGCTATCAGACCAGATGGATTAAGTGTGGTTGAAGTGGCGGATATTA

CTGCTAACCGACGGGCGGACATTTCAGGGAACTGGATGTTTAAGGACGGCAAAGTGATTAA

ACGCATTTATACGGCAGAGGAATTGCAGCAGCAGGCAGAAAACCGGAAAGCCAGACTTCTT

GCAGATGCTGAATCCGTGATTTTGCCACTGGAGCGCGCTGTCAGGCTGAACATGGCAACAGA

TGAGGAGCGTAGCCGACTGGAAGCATGGGAACGCTACAGTGTTCTGGTCAGCCGTGTGGAT

CCTGCAAATCCTGAATGGCCGGAAATGCCGCAATAA

O111
(SEQ ID NO: 200)
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGTGGT

AATGGATGAGACTAATCGTAAGGCACCTCTGGACAGTCCGGCACTGACCGGAACGCCAACA

GCACCAACCGCGCTCAGGGGAACAAACAATACCCAGATTGCGAACACCGCTTTTGTACTGG

CCGCGATTGCAGATGTTATCGACGCGTCACCTGACGCACTGAATACGCTGAATGAACTGGCC

GCAGCGCTCGGGAATGATCCAGATTTTGCTACCACCATGACTAACGCGCTTGCGGGTAAACA

-continued
```
ACCGAAGAATGCGACACTGACGGCGCTGGCAGGGCTTTCCACGGCGAAAAATAAATTACCG

TATTTTGCGGAAAATGATGCCGCCAGCCTGACTGAACTGACTCAGGTTGGCAGGGATATTCT

GGCAAAAAATTCCGTTGCAGATGTTCTTGAATACCTTGGGGCCGGTGAGAATTCGGCATCAG

GTGCATTACAGAAGAATCAAAACGGTGCAGACATTCCGGGCAAAGATACCTTTACCAAGAA

TATCGGTGCTTGTCGTGCTTATTCGGCATGGCTTAATATCGGAGGTGATTCTCAGGTATGGAC

TACGGCTCAGTTTATCTCTTGGCTCGAGAGTCAGGGTGCGTTTAATCATCCGTACTGGATGTG

CAAAGGCTCTTGGGCGTACGCGAACAACAAAGTCATCACCGACACTGGTTGTGGTAACATCT

GTCTGGCGGGTGCAGTAGTGGAAGTTATCGGTACGCGCGGTGCGATGACGATCCGTGTAACT

ACTCCATCTACCTCCTCCGGTGGCGGTATCACCAACGCCCAGTTCACTTACATTAACCACGG

CGATGCCTATGCTCCGGGCTGGCGCCGTGATTACAACACTAAAAACCAACAACCTGCGTTTG

CACTGGGTCAGACGGGTAGTCGTGTGGCGAACGATAAAGCGGTCGGTTGGAATTGGAACTC

TGGTGTGTACAACGCTGATATTAGTGGAGCTTCTACTCTGATCCTTCATTTTAACATGAATGC

TGGAAGTTGTCCGGCAGTGCAGTTTCGTGTTAACTATCGTAATGGAGGAATCTTTTACCGCTC

TGCACGTGACGGCTACGGCTTCGAAGCGAACTGGAGTGAATTTTACACGACCACTCGTAAGC

CGAGTGCTGGAGATGTGGGAGCTTATACTCAGGCAGAATGCAATTCGCGTTTCATTACTGGT

ATTCGTCTGGGAGGTTTAAGTTCCGTGCAGACTTGGAACGGTCCAGGTTGGAGTGATCGTAG

TGGCTATGTTGTGACAGGCAGTGTTAACGGCAACCGTGACGAACTGATCGACACTACTCAAG

CGCGTCCGATCCAGTACTGCATTAACGGAACTTGGTATAACGCGGGAAGTATCTAA 0111 accessory protein
                                              (SEQ ID NO: 201)
ATGATGCACTTAAAAAACATTACTGCTGGCAACCCTAAAACAAAAGAGCAATACCAGCTAA

CGAAACAATTTAACATCAAATGGCTTTATTCAGAGGATGGAAAAAACTGGTATGAGGAACA

AAAGAATTTCCAGCCAGACACTTTGAAAATGGTTTATGACCATAACGGCGTTATTATTTGTA

TTGAAAAGGATGTTTCAGCAATTAATCCGGAAGGCGCAAGCGTCGTTGAATTACCTGATATT

ACAGCAAATCGCCGTGCTGACATTTCGGGTAAATGGATGTTCAAAGATGGCGTAGTGGTAA

AGCGTACTTACACAGAAGAAGAGCAACGTCAACAGGCGGAAAATGAAAAGCAAAGCCTGC

TACAGCTCGTCAGGGATAAAACCCAGCTATGGGACAGTCAGCTACGGCTGGGCATCATTTCC

GACGAGAATAAACAAAAATTAACAGAGTGGATGCTCTTTGCGCAGAAAGTCGAATCTACAG

ACACTTCCAGCCTGCCAGTAACGTTTCCCGAACAACCAGAATGA

DC1
                                              (SEQ ID NO: 202)
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA
```

-continued

```
GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGCAGC

ATATGACCTTGCTAACGGGAAATACACTGCACAGGACGCCACCACAGCGCGAAAAGGTCTT

GTCCAGCTCAGTAGCGTCACCAACAGTGATTCTGAAACCCTCGCGGCAACGCCAAAAGCAG

TGAAGTCTGCCTATGACAATGCTGAAAAACGTCTTCAGAAAGATCAGAACGGTGCGGATATT

CCGGGAAAGGATACCTTCACGAAAAATATCGGTGCCTGTCGTGCTTATAGCGGCGCTTTGAG

CACTGAAGCCGGAAACTGGACAACCGCGCAGTTTATTGACTGGCTAGAGTCTCAGGGAGCC

TTTAATCATCCCTACTGGATGTGCAAGTGTTCCTGGTCATACGGTAATAACAAAATTATTACC

GATACTGACTGTGGGACGATTCATCTTGCAGGTTGCGTGATTGAGGTTATGGGTGTTAAAGC

AGCAATGACCATTCGTGTGACCACTCCGAGTACATCAAGCAGTGGTGGTACCACCAGTGCGC

AATTCACGTATATCAATCACGGAGCTGATTATGCGCCGGGCTGGCGACGCGACTACAATACG

AAAAATAAGCAACCGGCTTTTGCATTAGGGAAAACAGGAAATACGGTTGCAAATAATAAG

CAGTAGGATGGAACTGGGACAGTGGTGCTTATTGTGCACAGGATGGCGGAGCATCAAAAAT

GGTGCTGCATTTTTACACGGGTGAGGGAAGTTGTCCGGCAATGCAGTTTCTTGTGGATTATA

AAAACAGGGGGATTTTTTACAGGTCGGCACGTGATGGGTATGGATTTGAGGCTGACTGGTCA

GAGTTTTATACCACATCACGAAAGCCAACACCTGCGGATATTCTTGCTCTGGCATTATCAGG

CGGAAGCATGTCAGGCAGCATAAAATTTATCAATGATGCCTTCCTGATTTGGGAAAGAAACA

CTGACTGGGCGAAAATTGGATTTAAAAATGATTCAGATGCTGATTCTGACTCATACATGTGG

TTTGAAACTGGTGATAATGGCAATGAATATTTTAAATGGCGCATCAGGTCTGGCAGCACAAC

AAAAGACCTGATGACGCTTAAGTCTGATGCACTACGGGTTACCGGGCAGGTGATACCATCA

AATTTCAGCAATTTTGACTCCCGCTATGTCCGGGATATCCGGCTTGGTGGTGCCGCCACATAC

AAACCTGCGAACAATGGCATGACATGGACACATCAGGCACCGTCCGGGTGTGTATATACCG

GCATTATTGTTCAGGATACCGGCTCAAACTCTGCCGATAACATTGGTGGCGTATATTACAGA

CCGGTTCAGAAATACATTAACGGGACGTGGTACAACGTGGCGCAGGTA
```

DC1 accessory protein 1
(SEQ ID NO: 203)
```
ATGCAGCATTTGATAAATATAACGGCAGGTAATCCAAAAACGGTTGAACAATATCAATTGA

CAAAGGACTTTGATGTTGTCTGGTTTTTTTCAGAAGATGGTAAGAACTGGTACGAAGAACAA

AAGTATTTTGCTGATGACACGATAAAAATAGCGTACGACAAAGATAATATTATCCGCTATGT

GGAAAAGGATGTGACAGCTATCAGACCAGATGGATTAAGTGTTGTTGAAGTGCCGGATATT

ACTGCTAATCGACGGGCGGACATTTCAGGGGCTGGATGTTTAAGGACGGCAAAGTGATTA

AACGCATTTATACGGCAGAGGAATTGCAGCAGCAGGCAGAAAACCGGAAAGCCAGACTTCT

TGCAGATGCTGAATCCGTGATTTTGCCGCTGGAGCGCGCGGTCAGACTGAACATGGCAACAG

ATGAGGAGCGTAGCCGACTGGATGCATGGGAGCGTTACAGCGTTCTGGTCAGTCGTGTGGAT

CCTGCAAATCCTGAATGGCCGGAAATGCCGCAATAA
```

STF94A (SEQ ID NO: 204)

ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGTGGT

AATGGATGAGACTAATCGTAAATATACCGCACAGGACGCCACCACAGCGCGAAAAGGCCTT

GTTCAGCTGAGTAGCGCCATCAACAGCGATTCTGAAACGCTTGCGGCAACGCCAAAGGCGG

TTAAGACAGCGTATGACCTTGCTAACAGGAAATACACTGCACAGGATGCCACCACAGCGCG

AAAAGGTCTTGTCCAGCTAAGTAGCGCCACCAACAGTGATTCTGAAACGCTGGCCGCAACAT

CAAAAGCGGTGAAGTCTGCCTATGACAATGCTGAAAAACGTCTTCAGAAAGATCAGAATGG

TGCGGATATTCCGGGAAAGGATACCTTCACGAAAAATATCGGTGCCTGTCGTGCTTATAGCG

GCGCTTTGAGCACTGAAGCCGGAAACTGGACAACCGCTCAGTTTATTGAATGGCTGGATTCC

CGTGGTGCATTTAATCATCCGTACTGGATGTGCAAAGGCTCCTGGTCATATGCAAATAACAA

AATCATTACGGATACCGGATGTGGTGATATCCACCTGGCTGGTTGTGTCGTCGAGGTCATGG

GAACTAAATCTGCAATCACTATCCGAGTGACCACACCGACAACATCAAGCGGTGGCGGTAC

AACCAGCGCACAATTCACTTACATTAATCATGGGACGGCTACTCCCCCGGCTGGCGTCGTG

ACTGGAATCGTCAGGGCGACGCAATGACCGGAACGATTAATCAGGACGGTGGAAGCCAGAA

TGCCTATATGTCTACGGCCTTATGTTCAGGCACAAGAGGCGGCAAAAAATATCTCAGAAAGT

TTCGTGGTGGAGAAGGAGACACTATCTGGCATGAAACAGTACAGGGCGGGGTAGTTCGTTG

GGCGACTGGTAATACTGATGCTCAGGAAGAATTATCACTCAGCTCCGCTTATGGTCTCCGTT

CAAGAGGTGAGATTACATCACTCAGTGCTAATGGTCTGCGCATTGCTTATGGCAATTATGGT

TTCTTTATCAGGAATGATGGCAGCAGCACTTATTTTATGTTGACTAAATCAGGTGACAGATT

AGGAACTTATAATAATTTAAGACCGCTGATTATAAATGATGCCACTGGTGCTGTATCAATGG

GGCATGGCCTGAATGTTACTGGTGATATTGTCTCAAGTACCAAAGTACGTGCCGGTAGCGGG

AAAAAAATTCACGGTCAGCAGCAGTAATACATCCACGAAGGAAGCCGCATTCAATTTGTGGG

-continued

```
GAAACTCAAGTCGTCCGGTGGTGGCTGAATTAGGTGATGATGCAGGCTGGCATTTTTACAGT

CAGAGAAATACAGATAACAGCATCACTTTTGCTGTTAACGGGCAGGTATCACCATCTAACTA

TGGCAACTTTGATTCACGCTATGTCCGGGATATCCGGCTTGGTGGTGCTGCCACATACAAAC

CTGCGAACAATGGCATGACATGGACACATCAGGCACCGTCCGGGTGTGTATATTCCGGCATT

ATTGTTCAGGATACCGGCTCAAACTCTGCCGATAACATTGGTGGCATATATTACAGACCGGT

GCAGAAATACATTAACGGGACATGGTATAACGTAGCGCAGGTATAA
```

>STF94A accessory protein (SEQ ID NO: 205)
```
ATGCAGCATTTGATAAATATAATGGCGGGTAATCCAAAAACAGTTGAACAATATCAATTGAC

AAAGGGCTTTGATGTTGTCTGGTTTTTTACAGAAGATGGTAAGAACTGGTACGAAGAACAAA

AGTATTTTGCTGATGACACGATAAAAATAGCGTACGACAAAGATAATATCATCCGCTATGTG

GAAAAGGATGTGACAGCTATCAGACCGGATGGATTAAGTGTGGTTGAAGTGGCGGATATTA

CTGCTAACCGACGGGCGGATATTTCAGGGGGCTGGATGTTTAAGGACGGCAAAGTGATTAA

ACGCATTTATACGGCGGAGGAATTACAGCAGCAGGCAGAAATTCGGAAAGCCAGACTTCTT

GCAGATGCTGAATCCGTGATTTTGCCGCTGGAGCGCGCGGTCAGACTGAACATGGCAACAG

AGGAGGAGCGCACACGGCTGGAGGCTTGGGAACGCTACAGCGTTCTGGTCAGTCGTGTGGA

TCCTGCAAATCCTGAATGGCCGGAAATGCCGCAATAA
```

STF69A (SEQ ID NO: 206)
```
GCTTCTGCCACTGCATCAGCTAACAGTCAAAAAGCAGCAAAAACCAGTGAAACCAACGCAA

AGGCGAGCGAAACAGCGGCTGCGAACTCAGCGAAAGCATCGGCAGCAAGCCAGACGGCAG

CTAAAGCAAGCGAAGATGCAGCCAGAGAGTACGCAAGCCAGGCTGCGGAGCCGTATAAATA

TGTCTTACAGCCGTTACCTGAGGTGTGGATACCGTTTAACGATTCACTGGATATGATTACCG

GGTTTGCTCCTGGATATAAGAGCATCACAGTTGGTGACGATGTTATTGCATTGCCGTCTGAA

AAGGTTGTTTCATTTACCAGGGCGTCAACTGCAACGTATATAGATAAGTCTGGGTGTTTTGCT

GAATCAGCGATAAATGAACCACGTTTTGAAAAAGATGGTCTGCTCATTGAAGGTCAGAGAA

CGAATACTTTTTCTTATACGAATACACCAGTATCGTGGAACTATGACACTGCTAACTTAACTA

TTACCACGGGAGTTGATGAGTATGGTTTCAGTTATGGTTTGTTTGGCGTTAAAGAAACATCC

ACAACTGAAAGGGCGACATTAATTTCTACTGGATATACCAGGGTTATTTCAGTTTCGGCAAA

TGAATCAGTTACTTTATCCTGCAGAGTTAAAAAAGTAAGTGGGGATGGTATTATCACGTTGC

GTCCAAGAATATCATATGTTAACGACGATGGCTCAAGTAACACACTGACCGCTGGCGCATAT

ATTGATTGCGAGACTGGCGATATGTTGAGTTATTCTGGAGGTGAGGCGGCAACTTATAACAT

ATTCAGAGAGTCTAATGGATGGATTCGTGTTGAGTTTACCTACAAATCACCAGAAGCAAAAA

ATATGTATGGGCGTTTTGAGTTTGGAGCACATCAACGATCAATCAAGTCTGGCGATAAATTA

ATGTTAACAACCCCTCAATTCGAAAAGGGACTAAACGCGTCATCTTTTATCATCACAACAGA

GGTCGGTGCCACGAGAGCAAGTGACCAGGTAATCATACCTATACCTTTCAATTGGGCAACTC

CACCAGTTAGTGTTCTCATGGAAGTTAATGTTAATTGGGATTCTGAAATGCCTAATTTAGAA

GGCTCTGCGCGTTTGCTTAATATCTCAATTACAGGGGCGACGACTGAAGTTTCTGATGAAAG

TTATATGTATTTTGGTTTTACCACTCGTGGTAAAAGGCTAATTATCACCAATGGCAAAGGAA

CAAAAACAGAATATAAAGCATATGGGAATAGAGAGAAAGGAAATTTGTTACTGGCTTTAA

GTTTACAGAAGATAAACAGTTGCAGGTTGTTGTTGATGGAATTTTAGGTGGCAGCTCCCCGT

CTCTGCATACATTGCAACGTTATACTGCCGGTAATATTAATATCGGTGGACAATCATCCAGT
```

```
GGCAACAGACACCTGTTCGGTCATGTGAAAAATTTACGCATTTGGCATAAAGAATTAACTGA

GGCACAAATGGGGGAGTCAATCTAA
```

>STF69A accessory protein 1

(SEQ ID NO: 207)
```
ATGAAAGATTTAACACTCAAATTTGAAGACAGGGCCGACTTTTCGGCCTTTATGGAGAGTAT

TGGCTATTATGATGACGAGTCGATGCAGGATGATATTCTTATCGACGTGATAGGTAACGTGT

ACAAAGAAACCGGAGAACTGACTGAAGATGGCGAACCGGTATGTGTTAAGGAAGACGGAT

ATTTTGTAAACGTGCGCATCATTAATGATTCGCAAATATCGTCATTATTCGATGAATACGTGG

TTGCTGTTGAGCATCAACTTCGTGGCTGGATGTGA
```

>STF69A accessory protein 2

(SEQ ID NO: 208)
```
ATGGCTACATCGACAGTAATTCCTGATGACATCAAAACGCTAAAATCCGACGTTAGCAAATT

AAAAAACGATCAAGGAAGCTACGCAACAAAATTATATGTAGACAGCAAAGATGAAATCGTT

GGTGACTGGTCTGCTTCATGGTATCAGCAGGTATTGCCAACTAGCGGAGCTATATTTGGGAG

AAAACTCCGCTCAACTCACAGGACGGCAGGTGTTGAGGATGCGTATTGCGAACTATACCTCA

AAAAATGGATAGACAGTCCAGGTAACGCAATGGCGCGCCTTAACCTGAACGATAACGGGAC

AAACATTTGCTGGGACTTTACCAACCTTTATGGCGGTACGATGATTTTTCCCGGTGACAGCG

GATACCTCAAAATGGGTAACTGCCTTATGTCATACAGCAAGCGTGGAAGTAACGCGCTTATT

AAATTTGATTACACCGACACATTACAGATCAAATATGCCAATCATGGGTCAACCATGACATT

AAACACACAGGGAACCGCTTATGCTGGTGTTACTGCTCAATTGTGGGGCAACTCCAGCCGTC

CTGTTGTTTATGAAGTCGGTGTTGATGGTGGCGCTTATATGTTCTATGCGCAGAAAAATACC

GATAACACCTATATGTTAAGCGTTAATGGTGCATGTCATGCCACCGCATTTAACCAGCATTC

CGACCGGGATCTGAAAGACAACATTCAGGTGATCGATAATGCAACCGACCGCATCCGTAAA

ATGAACGGCTATACATACACGCTTAAAGAAAACGGTATGCCCTATGCTGGTGTCATTGCACA

GGAAGCTCTGGAAGCAATCCCAGAAGTTGTAGGTTCCGCAATGAAATATCAGGACGGTGCG

AGCGGATCGGAAGGTGAAGAAGGTGAACGTTATTACACAGTAGATTATTCTGGTGTTACTGG

CTTGCTTGTTCAGGTAGCCAGAGAGTCAGACGACAGAATAACAGCACTGGAAGAAGAAAC

GCAGAATTAAGACAAAGATTATCTGCAATTGAGGCGGCGCTTGCGTCTAAATAA
```

>STF118

(SEQ ID NO: 209)
```
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA

GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG
```

-continued
```
CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGTGGT

AATGGATGAGACTAATCGTAAAGCGCCATTAAACAGCCCTGCACTGACCGGAACGCCAACG

ACGCCAACTGCGCGACAGGGAACGAATAATACTCAGATCGCAAACACGGCTTTCGTTATGG

CCGCGATTGCCGCCCTTGTAGACTCGTCGCCTGACGCACTGAATACGCTGAACGAGCTGGCA

GCGGCGCTGGGCAACGACCCGAATTTTGCTACCACTATGACTAATGCGCTTGCGGGTAAGCA

ACCGAAAGATGCTACCCTGGCGGCGCTGGCGGGGCTTGCTACTGCGGCAGACAGGTTTCCGT

ATTTTACGGGGAATGATGTTGCCAGTCTGGCAACTCTGACAAAAGTCGGGCGGGATATTCTT

GCGAAATCGACCGTTTCCGCCGTTATCGAATATCTCGGTTTACAGGAAACGGTAAACCGAGC

CGGGAACGCCGTGCAAAAAAATGGCGATACCTTGTCCGGTGGACTTACTTTTGAAAACGACT

CAATCCTTGCCTGGATTCGAAATACTGACTGGGCGAAGATTGGATTTAAAAATGATGCCGAT

GGTGACACTGATTCATATATGTGGTTTGAAACAGGTGACAACGGCAATGAATACTTCAAATG

GAGAAGTCGCCAGAGCACCACAACAAAAGACCTGATGAATCTTAAATGGGATGCTCTGTAT

GTTCTTGTTAAAGCCCTTTTCAGCAGTGAAGTAAAAATATCTACAGTCAATGCACTGAGGAT

ATTTAATTCATCTTTTGGTGCTATTTTTCGCCGTTCTGAAGAAAACCTGTATATCATCCCTAC

ACGAGAAAATGAGGGTGAAAATGGAGATATTGGGCCATTAAGGCCATTCGGCATCAACTTA

AGAACAGGAGTTGTGTCTGTTGGTAATGGTGCCAGGATTGATGGCGGGCTGGCACTTGGCAC

GAATAACGCGTTGGGTGGGAACTCTATTGTTCTTGGTGATAACGACACCGGATTTAAACAAA

ATGGCGATGGTAATCTGGATGTTTATGCTAATAACGTCCATGTTATGCGCTTTGTTTCCGGAA

GCATTCAAAGTAATAAGACCATAAATATTACGGGGCGTGTTAATCCCTCGGATTACGGTAAC

TTTGATTCCCGCTATGTGAGAGATATCAGACTTGGCACACGTGTTGTCCAGACCATGCAGAA

AGGGGTGATGTATGAGAAAGCAGGGCACGTAATTACCGGGCTTGGTATTGTCGGTGAAGTC

GATGGTGATGACCCCGCAGTATTCAGGCCAATACAAAAATACATCAATGGCACATGGTATA

ACGTCGCACAGGTGTAA
```

>STF118 accessory protein (SEQ ID NO: 210)
```
ATGCAGCATTTAAAAAATATTACTGCGGGTAATCCAAAAACTGTTGCCCAATATCAACTGAC

AAAAAATTTTGATGTTATCTGGTTATGGTCCGAAGAGGGAAAAAACTGGTATGAGGAAGTA

AGTAATTTTCAGGAAGACACGATAAAGATTGTTTACGACGAGAATAATATAATTGTCGGCAT

CACCAGAGATGCTTCAACGCTTAACCCTGAAGGTTTCAGCGTTGTCGAGGTTCCTGATATTA

CCTCCAACCGACGTGCTGATGACTCAGGTAAATGGATGTTTAAGGATGGTGCCGTGATTAAG

CGGATTTATACGGCAGATGAACAGGAGCAACAGGCAGAATCACAAAAGGCAGCTTTACTTT

CCGAAGCTGAATCCGTGATTTTGCCGCTGGAACGCGCTGTCAGGCTGAATATGGCGACGGAT

GAGGAACGCAGCCGACTGGAAGCATGGGAACGCTACAGCGTTCTGGTCAGTCGTGTGGATC

CTGCAAATCCCGAATGGCCGGAAATGCCGCAATAA
```

K1F (SEQ ID NO: 211)
```
ATGGCAGTAAAGATTTCAGGAGTCCTGAAAGACGGCACAGGAAAACCGGTACAGAACTGCA

CCATTCAGCTGAAAGCCAGACGTAACAGCACCACGGTGGTGGTGAACACGGTGGGCTCAGA
```

-continued

```
GAATCCGGATGAAGCCGGGCGTTACAGCATGGATGTGGAGTACGGTCAGTACAGTGTCATC

CTGCAGGTTGACGGTTTTCCACCATCGCACGCCGGGACCATCACCGTGTATGAAGATTCACA

ACCGGGGACGCTGAATGATTTTCTCTGTGCCATGACGGAGGATGATGCCCGGCCGGAGGTGC

TGCGTCGTCTTGAACTGATGGTGGAAGAGGTGGCGCGTAACGCGTCCGTGGTGGCACAGAG

TACGGCAGACGCGAAGAAATCAGCCGGCGATGCCAGTGCATCAGCTGCTCAGGTCGCGGCC

CTTGTGACTGATGCAACTGACTCAGCACGCGCCGCCAGCACGTCCGCCGGACAGGCTGCATC

GTCAGCTCAGGAAGCGTCCTCCGGCGCAGAAGCGGCATCAGCAAAGGCCACTGAAGCGGAA

AAAAGTGCCGCAGCCGCAGAGTCCTCAAAAAACGCGGCGGCCACCAGTGCCGGTGCGGCGA

AAACGTCAGAAACGAATGCTGCAGCGTCACAACAATCAGCCGCCACGTCTGCCTCCACCGC

GGCCACGAAAGCGTCAGAGGCCGCCACTTCAGCACGAGATGCGGTGGCCTCAAAAGAGGCA

GCAAAATCATCAGAAACGAACGCATCATCAAGTGCCGGTCGTGCAGCTTCCTCGGCAACGG

CGGCAGAAAATTCTGCCAGGGCGGCAAAAACGTCCGAGACGAATGCCAGGTCATCTGAAAC

AGCAGCGGAACGGAGCGCCTCTGCCGCGGCAGACGCAAAAACAGCGGCGGCGGGGAGTGC

GTCAACGGCATCCACGAAGGCGACAGAGGCTGCGGGAAGTGCGGTATCAGCATCGCAGAGC

AAAAGTGCGGCAGAAGCGGCGGCAATACGTGCAAAAAATTCGGCAAAACGTGCAGAAGAT

ATAGCTTCAGCTGTCGCGCTTGAGGATGCGGACACAACGAGAAAGGGGATAGTGCAGCTCA

GCAGTGCAACCAACAGCACGTCTGAAACGCTTGCTGCAACGCCAAAGGCGGTTAAGGTGGT

AATGGATGAGACTAATCGTAAGGCACCTCTGGACAGTCCGGCACTGACCGGAACGCCAACA

GCACCAACCGCGCTCAGGGGAACAAACAATACCCAGATTGCGAACACCGCTTTTGTACTGG

CCGCGATTGCAGATGTTATCGACGCGTCACCTGACGCACTGAATACGCTGAATGAACTGGCC

GCAGCGCTCGGGAATGATCCAGATTTTGCTACCACCATGACTAACGCGCTTGCGGGTAAACA

ACCGAAGAATGCGACACTGACGGCGCTGGCAGGGCTTTCCACGGCGAAAAATAAATTACCG

TATTTTGCGGAAAATGATGCCGCCAGCCTGACTGAACTGACTCAGGTTGGCAGGGATATTCT

GGCAAAAAATTCCGTTGCAGATGTTCTTGAATACCTTGGGGCCGGTGAGAATTCGGGTGCGA

AGGGCGATGGCGTTACCGACGACACTGCAGCGCTGACTTCCGCCCTGAACGATACTCCGGTG

GGTCAGAAAATCAACGGTAACGGTAAAACTTATAAAGTTACGTCCCTGCCGGACATCTCCCG

CTTTATCAACACCCGTTTCGTGTATGAACGTATCCCAGGCCAGCCGCTGTACTACGCATCGG

AAGAGTTCGTTCAGGGTGAGCTTTTTAAAATCACCGACACTCCGTATTATAACGCCTGGCCA

CAGGATAAGGCTTTCGTGTACGAAAACGTTATCTATGCTCCGTACATGGGTTCCGACCGTCA

CGGTGTCAGCCGACTGCACGTAAGCTGGGTGAAATCGGGCGACGATGGTCAGACCTGGAGC

ACGCCTGAGTGGCTGACCGACCTTCATCCGGACTATCCGACCGTTAACTATCACTGCATGAG

CATGGGCGTCTGTCGCAACCGTCTGTTCGCAATGATCGAAACCCGTACGCTGGCAAAAAACG

CTCTGACTAACTGCGCCCTGTGGGATCGTCCAATGAGCCGCTCTCTGCACCTGACGGGTGGT

ATTACCAAAGCAGCGAACCAGCGTTACGCCACCATTCACGTACCGGATCATGGTCTGTTCGT

TGGTGACTTTGTAAATTTCTCTAATTCTGCAGTTACCGGTGTGTCTGGCGACATGACCGTTGC

GACCGTAATCGATAAGGACAATTTCACCGTCCTGACCCCGAACCAGCAAACCTCTGATCTTA

ACAACGCTGGCAAGAACTGGCACATGGGCACTAGCTTTCACAAATCTCCGTGGCGTAAAAC

CGATCTGGGCCTGATCCCGTCTGTAACTGAAGTGCACTCCTTCGCGACCATTGATAACAACG

GTTTCGCTATGGGTTATCACCAAGGTGATGTTGCACCGCGTGAAGTCGGCCTCTTTTATTTTC

CGGACGCATTCAACAGCCCGTCCAACTACGTGCGCCGTCAGATTCCGTCTGAATATGAACCG
```

-continued

```
GACGCCTCCGAGCCGTGCATTAAGTACTATGACGGTGTGCTGTACCTGATTACCCGTGGCAC
CCGTGGTGATCGTCTGGGTTCATCTCTGCATCGCTCCCGCGACATTGGTCAGACGTGGGAAA
GTCTGCGCTTCCCGCACAATGTTCATCACACCACCCTGCCGTTCGCGAAAGTCGGCGATGAC
CTGATCATGTTTGGCTCCGAACGTGCTGAAAACGAATGGGAAGCGGGCGCCCCAGACGATC
GCTACAAGGCATCTTACCCGCGCACCTTCTACGCGCGTCTGAACGTGAACAACTGGAACGCA
GACGATATCGAATGGGTAAACATCACCGACCAGATCTACCAGGGTGGTATCGTGAACTCTG
GTGTGGGCGTTGGTTCCGTTGTAGTTAAAGATAACTACATCTATTATATGTTCGGCGGCGAA
GACCACTTCAACCCGTGGACTTACGGCGATAACTCCGCGAAAGACCCGTTCAAATCCGATGG
TCACCCTTCTGACCTCTATTGTTACAAAATGAAAATCGGTCCGGACAACCGTGTTTCCCGCG
ATTTTCGCTACGGCGCTGTTCCAAACCGTGCAGTTCCGGTATTCTTCGACACGAACGGCGTG
CGTACCGTTCCGGCTCCGATGGAATTCACCGGCGACCTGGGTCTGGGCCACGTAACCATTCG
TGCCTCCACCAGCTCTAACATCCGTTCCGAAGTACTCATGGAAGGTAATACGGCTTTATCG
GTAAGTCTATCCCGACGGACAACCCGGCAGGTCAGCGTATCATCTTCTGCGGCGGTGAGGGT
ACCTCTAGCACCACCGGCGCGCAAATCACCCTGTACGGCGCTAACAACACCGACTCTCGTCG
TATCGTATACAACGGTGATGAACATCTGTTCCAGTCCGCAGACGTGAAACCGTACAACGACA
ACGTCACCGCACTGGGTGGTCCATCCAACCGTTTCACCACTGCGTACCTGGGTTCCAACCCG
ATCGTTACTAGCAATGGTGAACGCAAAACTGAACCGGTAGTGTTTGACGACGCTTTTCTGGA
CGCATGGGCGATGTTCATTACATCATGTATCAGTGGCTGGATGCCGTGCAGCTGAAAGGTA
ACGACGCGTATCCACTTTGGTGTGATCGCACAGCAGATTCGCGATGTCTTCATCGCACAC
GGTCTGATGGATGAAAATAGTACTAACTGTCGCTATGCGGTGCTGTGCTATGACAAATACCC
GCGTATGACCGACACCGTGTTCTCGCACAATGAGATTGTTGAACATACCGATGAAGAAGGTA
ACGTGACTACTACCGAAGAACCGGTTTATACCGAAGTGGTTATTCACGAAGAAGGTGAAGA
ATGGGGCGTGCGTCCTGATGGTATCTTTTTCGCGGAGGCAGCGTACCAGCGTCGCAAACTGG
AACGCATCGAAGCTCGTCTGTCGGCACTGGAACAGAAA
```

STF66

(SEQ ID NO: 212)
```
ATGGCAGTAAAGATTTCAGGAGTCCTGAAAGACGGCACAGGAAAACCGGTACAGAACTGCA
CCATTCAGCTGAAAGCCAGACGTAACAGCACCACGGTGGTGGTGAACACGGTGGGCTCAGA
GAATCCGGATGAAGCCGGGCGTTACAGCATGGATGTGGAGTACGGTCAGTACAGTGTCATC
CTGCAGGTTGACGGTTTTCCACCATCGCACGCCGGGACCATCACCGTGTATGAAGATTCACA
ACCGGGGACGCTGAATGATTTTCTCTGTGCCATGACGGAGGATGATGCCCGGCCGGAGGTGC
TGCGTCGTCTTGAACTGATGGTGGAAGAGGTGGCGCGTAACGCGTCCGTGGTGGCACAGAG
TACGGCAGACGCGAAGAAATCAGCCGGCGATGCCAGTGCATCAGCTGCTCAGGTCGCGGCC
CTTGTGACTGATGCAACTGACTCAGCACGCGCCGCCAGCACGTCCGCCGGACAGGCTGCATC
GTCAGCTCAGGAAGCGTCCTCCGGCGCAGAAGCGGCATCAGCAAAGGCCACTGAAGCGGAA
AAAAGTGCCGCAGCCGCAGAGTCCTCAAAAAACGCGGCGGCCACCAGTGCCGGTGCGGCGA
AAACGTCAGAAACGAATGCTGCAGCGTCACAACAATCAGCCGCCACGTCTGCCTCCACCGC
GGCCACGAAAGCGTCAGAGGCCGCCACTTCAGCACGAGATGCGGTGGCCTCAAAAGAGGCA
GCAAAATCATCAGAAACGAACGCATCATCAAGTGCCGGTCGTGCAGCTTCCTCGGCAACGG
CGGCAGAAAATTCTGCCAGGGCGGCAAAAACGTCCGAGACGAATGCCAGGTCATCTGAAAC
AGCAGCGGAACGGAGCGCCTCTGCCGCGGCAGCTTCTGCCACTGCAGCAGCCAACAGTCAA
AAAGCTGCAAAAACCAGTGAAACCAACTCAAAGGCGAGCGAAACAGCGGCTGCGAACTCA
```

-continued

```
GCGAAAGCATCGGCAGCAAGCCAGACGGCTGCAAAAGCAAGTGAGGATGCAGCCAGAGAG
TATGCAAGCCAGGCTGCGGAGCCGTATAAACAAGTTTTGCAGCCGCTTCCCGATGTGTGGAT
ACCGTTTAACGATTCACTGGATATGATTACGGGCTTTTCGCCGTCATATAAAAAGATTGTTAT
TGGTGATGATGAAATAACGATGCCTGGCGATAAGGTTGTAAAGTTTAAACGCGCATCGAAA
GCAACCTATATTAATAAATCTGGTGTGCTGACAGAGGCTGCCATTGACGAGCCACGATTTGA
ACGTGATGGCCTGCTTATTGAGGGCAAAGAACAAACTACATGCTCAATTCGGAAAACCCT
GCCAGTTGGGGGCGATCGTCAAATATGGATGTTCCCGAAACCGGGACGGATAGTTTTGGTTT
TACCTATGGAAAGTTTGTCTGCAACGATTCTCTGATTGGGCAAACCTCAGCCATTAATATGG
CATCAATTGCTGCAACAAAGTCAGTTGATGTCTCAGGCGATAATAAATACGTGACAACCTCA
TGTCGTTTTAAAACAGAACTGCAGGTAAGGTTGCGTATCCGATTTGATAAATATGACGGTAG
CGCAACAACTTTTCTTGGTGATGCGTATATTGATACACAAACGCTTGAAATTAATATGACAG
GTGGTGCTTCCGGTAGAATTACGGCACGAGTCAGGAAGGATGAAACTACAGGATGGATTTTT
GCTGAGGCAACAATTCAGGCAATTGATGGTGAGTTAAAAATAGGCTCTCAGATACAGTATTC
ACCTAAGCAGGGAGGGGCAACCGTATCAGGTGACTATATTTATCTGGCTACCCCACAAGTAG
AGAATGGGGCTTGTGTATCATCTTTTATTATATCAGGAACGACGGCGGCGACTCGTGCGAGT
GATATGGTTACGATCCCGACCGAAAACAACATTTATAACAGACCGCTTACTTGTTTGGTCGA
GGTTAACAGGAATTGGGGCGATATTCCTCCTAATGTAGCACCGCGTATTTTGATTTTCTGG
TGTGCCGCCTATTGAGTCAATCACATACGCTTTTAACACAACCGAGAAATATTACGGTCAGC
TTTATATGCAAACTTATAAAGCGTCGACAAGTAGTTACGTTTCTAGTTTGTTTACTGGTCGAA
CGGATGTTCGAAAACTCATTGGTGGTTTTAATATTTATTCTGATGGTACTAAACGAGTAGTTT
CTAACGGTGAGGCTACTAAAACCATGAAAACGGAATGGACGGGCGTAAAAACGCGGACCTT
TATTCGAATAGGAGGTCAAGCCACATCAGGGACACGTCATCTATTCGGCCATTTGAGAAATC
TTCGTCTCTGGCATAAAGAATTAACTGATGCGCAAATGGGGGAGAGTATTAAATGA
```

STF66 accessory protein (SEQ ID NO: 213)

```
ATGAAAGATTTAACACTCAAATTTGCCGACAGGGCCGACTTTTCGGCCTTTATGGAGAGTAT
TGGCTATTATGATGACGAGTCGATGCAGGATGATATTCTTATTGACGTGATAGGTAACGTGT
ACAAAGAAACCGGAGAACTGACTGAAGATGGCGAACCGGTATGTGTTAAGGAAGACGGAT
ATTTTGTAAACGTGCGCATCATTAATGATTCGCAAATATCGTCATTATTCGATGAATACGTGG
TTGCTGTTGAGCATCAACTTCGTGGCTGGATGTGA
``` gpJ Variant 1A2 (SEQ ID NO: 214)

MGKGSSKGHTPREAKDNLKSTQLLSVIDAISEGPIEGPVDGLKSVLLNST
PVLDTEGNTNISGVTVVFRAGEQEQTPPEGFESSGSETVLGTEVKYDTPI
TRTITSANIDRLRFTFGVQALVETTSKGDRNPSEVRLLVQIQRNGGWVTE
KDITIKGKTTSQYLASVVMGNLPPRPFNIRMRRMTPDSTTDQLQNKTLWS
SYTEIIDVKQCYPNTALVGVQVDSEQFGSQQVSRNYHLRGRILQVPSNYN
PQTRQYSGIWDGTFKPAYSNNMAWCLWDMLTHPRYGMGKRLGAADVDKWA
LYVIGQYCDQSVPDGFGGTEPRITCNAYLTTQRKAWDVLSDFCSAMRCMP
VWNGQTLTFVQDRPSDKTWTYNRSNVVMPDDGAPFRYSFSALKDRHNAVE
VNWIDPNNGWETATELVEDTQAIARYGRNVTKMDAFGCTSRGQAHRAGLW
LIKTELLETQTVDFSVGAEGLRHVPGDVIEICDDDYAGISTGGRVLAVNS
QTRTLTLDREITLPSSGTALISLVDGSGNPVSVEVQSVTDGVKVKVSRVP
DGVAEYSVWELKLPTLRQRLFRCVSIRENDDGTYAITAVQHVPEKEAIVD
NGAHFDGEQSGTVNGVTPPAVQHLTAEVTADSGEYQVLARWDTPKVVKGV
SFLLRLTVTADDGSERLVSTARTTETTYRFTQLALGNYRLTVRAVNAWGQ
QGDPASVSFRIAAPAAPSRIELTPGYFQITATPHLAVYDPTVQFEFWFSE
KQIADIRQVETSTRYLGTALYWIAASINIKPGHDYYFYIRSVNTVGKSAF
VEAVGRASDDAEGYLDFFKGKITESHLGKELLEKVELTEDNASRLEEFSK

-continued
```
EWKDASDKWNAMWAVKIEQTKDGKHYVAGIGLSMEDTEEGKLSQFLVAAN

RIAFIDPANGNETPMFVAQGNQIFMNDVFLKRLTAPTITSGGNPPAFSLT

PDGKLTAKNADISGNVNANSGTLNNVTINENCRVLGKLSANQIEGDLVKT
```

-continued
```
VGKAFPRDSRAPERWPSGTITVRVYDDQPFDRQIVIPAVAFSGAKHEKEH

TDIYSSCRLIVRKNGAEIYNRTALDNTLIYSGVIDMPAGHGHMTLEFSVS

AWLVNNWYPTASISDLLVVVMKKATAGITIS
```

STFs

```
WT STF accessory protein 1
                                               (SEQ ID NO: 215)
MAFRMSEQPRTIKIYNLLAGTNEFIGEGDAYIPPHTGLPANSTDIAPPDIPAGFVAVFNS

DEASWHLVEDHRGKTVYDVASGDALFISELGPLPENFTWLSPGGEYQKWNGTAWVKDTEA

EKLFRIREAEETKKSLMQVASEHIAPLQDAADLEIATKEETSLLEAWKKYRVLLNRVDTS

TAPDIEWPAVPVME

SIED6
                                               (SEQ ID NO: 216)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIADPASVPPLPDIW

LPLNDSLEAITGYAPGYKTITIGSDEITVPVNGICQFSRASSATYIDKSGHITVAGNNVP

RFEKYGLLIENQRTNMFVNSFNPDAWNKSGGISVTSSTDEFEFKYGRFTVGSDIAGTTTG

RNICTVAGNRGIDVTGDDQYSKGPYVTASFRVRSDLNVRARIRFERYNSEGYTFLCDAYL

SLQTHELQITGDNAQLLTANFEIDPGSGWIYFQATLKCLPEWGMVGTQLQIAADRAVGSF

ATGDWIEVTTPQFEYGACATSFIITTTEPATRASDLCKFPLMKNMYTMPFTFMVEVHKNW

FIAHNAAPRVIDTENHQSGAPFIMGFGSSGTISQDGYPYCDIGGANRRVYESCGVRDLVM

GFRVKADGMTCSFANKHISTETKTVWKYIREAAVIRIGGQTTTGLRHLNGHIKNLRFWNR

ALSDTQLKEYV

SIED6 accessory protein 1
                                               (SEQ ID NO: 217)
MRDITLRFDNREQFNAIVYDSGLFSLEEENGILVDVIGRVIDYEEPENERCTGIDRGGFF

VNMRIVDSSKNISSLMPFITTDQHVRTWA

SIED6 accessory protein 2
                                               (SEQ ID NO: 218)
MVTKTVIPDDIKTLKSDVSKLKNDQGSYATKSYVDSKDETVGDWSASWYQQVLPTSGAIF

GRKLRSTHRTAGVEDAYCELYLKKWIDSPGNAMARLNLNDNGENICWDFTNLYGGTMIFP

GTSGYLKMGNCLMSYGVRGSNALIKFDNTDSLQIKYANHGSTMTLNTQGTAYSGVSTLLW

GNSSRPVVYEIRDDGGLFLFYAQRNPDKTYQLEINGPCKATSFDQVSDRDLKENIRVIDN

ATERIRLMNGYTYRLKSNGMPYAGVIAQEALNAIPESVGSTIKYKSGDNGSDGE

SIEA11
                                               (SEQ ID NO: 219)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR
```

```
KGIVQLSSATNSTSETLAATPKAVKAANDNANSRLAKNQNGADIQDKSAFLDNVGVTSLT

FMKNNGEMPVDADLNTFGSVKAYSGIWSKATSTNATLEKNFPEDNAVGVLEVFTGGNFAG

TQRYTTRDGNLYIRKLIGTWNGNDGPWGAWRHVQAVTRALSTTIDLNSLGGAEHLGLWRN

SSSAIASFERHYPEQGGDAQGILEIFEGGLYGRTQRYTTRNGTMYIRGLTAKWDAENPQW

EDWNQIGYQTSSTFYEDDLDDLMSPGIYSVTGKATHTPIQGQSGFLEVIRRKDGVYVLQR

YTTTGTSAATKDRLYERVFLGGSFNAWGEWRQIYNSNSLPLELGIGGAVAKLTSLDWQTY

DFVPGSLITVRLDNMTNIPDGMDWGVIDGNLINISVGPSDDSGSGRSMHVWRSTVSKANY

RFFMVRISGNPGSRTITTRRVPIIDEAQTWGAKQTFSAGLSGELSGNAATATKLKTARKI

NNVSFDGTSDINLTPKNIGAFASGKTGDTVANDKAVGWNWSSGAYNATIGGASTLILHFN

IGEGSCPAAQFRVNYKNGGIFYRSARDGYGFEADWSEFYTTTRKPTAGDVGALPLSGGQL

NGALGIGTSSALGGNSIVLGDNDTGFKQNGDGNLDVYANSVHVMRFVSGSVQSNKTINIT

GRVNPSDYGNFDSRYVRDVRLGTRVVQTMQKGVMYEKAGHVITGLGIVGEVDGDDPAVFR

PIQKYINGTWYNVAQV

SIEA11 accessory protein 1
                                                (SEQ ID NO: 220)
MQHLKNITAGNPKTVAQYQLTKNFDVIWLWSEEGKNWYEEVSNFQEDTIKIVYDENNIIV

GITRDASTLNPEGFSVVEVPDITANRRADDSGKWMFKDGAVIKRIYTADEQLQLAELQKS

ALLSEAETIIQPLERSVRLNMATDEERSRLEAWERYSVLVSRVDPANPEWPEMPQ

EB6
                                                (SEQ ID NO: 221)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKIAMDNANARLAKDRNGADIPNKPLFIQNLGLQETV

NKAGNAVQKTGDTLSGGLTFENDSILAWIRNTDWAKIGFKNDADSDTDSYMWFETGDNGN

EYFKWRSRQSTTTKDLMNLKWDALYVLVNAIVNGEVISKSANGLRIAYGNYGFFIRNDGS

NTYFMLTNSGDNMGTYNGLRPLWINNATGAVSMGRGLNVSGETLSDRFAINSSNGMWIQM

RDNNAIFGKNIVNTDSAQALLRQNHADRKFMIGGLGNKQFGIYMINNSRTANGTDGQAYM

DNNGNWLCGAQVIPGNYGNFDSRYVRDVRLGTRVVQLMARGGRYEKAGHAITGLRIIGEV

DGDDEAIFRPIQKYINGTWYNVAQV*

EB6 accessory protein 1
                                                (SEQ ID NO: 222)
MQHLKNIKSGNPKTKEQYQLTKNFDVIWLWSEDGKNWYEEVNNFQDDTIKIVYDENNIIV

AITKDASTLNPEGFSVVEIPDITANRRADDSGKWMFKDGAVVKRIYTADEQQQQAESQKA

ALLSEAENVIQPLERAVRLNMATDEERARLESWERYSVLVSRVDTAKPEWPQKPE*

AH11L
                                                (SEQ ID NO: 223)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV
```

```
ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKAANDNANSRLAKNQNGADIQDKSVFLDNVGVTSLT

FMKNNGEMPLDADLNTFGPVKAYLGIWSKATSTNATLEKNFPEDNAVGVLEVFAAGNFAG

TQRFTTRDGNVYMRKLANKWNGTDGPWGVWRHTQSATRPLSTTIDLNTLGAAEHLGLWRN

SSSAIASYERNYPEEGGFAQGTLEILEGGNYGRTQRYTTRRGNMYVRCLAASWDASNPQW

EPWLRVGHQSESRYYEGDLNDVTSPGIYSVTGKATNGPVLDGNGVTVLGILEVLRRFDGV

NVWQRYTTAGTGTTLKGRTFERVFTGSSWSEWREVYTSYSLPLNLGIGGAVAKLTSLDWQ

TYDFVPGSLITVRLDNMTNIPDGMDWGVIDGNLINIAVGPSDDSGTGRSMHVWRSTVSKA

NYRFFMVRISGNPGSRTITARRVPIIDEAQTWGAKQTFSAGLSGELSGNAATATKLKTAR

KINNVSFDGTSDINLTPKNIGAFASGKTGDTVANDKAVGWNWSSGAYNATTGGASTLILH

FNIGEGSCPAAQFRVNYKNGGIFYRSARDGYGFEADWSEFYTTTRKPTAGDVGALPLSGG

QLNGALGIGTSSALGGNSIVLGDNDTGFKQNGDGNLDVYANSVHIMRFVSGSIQSNKTIN

ITGRVNPSDYGNFDSRYVRDIRLGGAATYKPANNGMTWTHQAPSGCVYSGIIVQDTGSNS

ADNIGGVYYRPVQKYINGTWYNVAQV

AH11L accessory protein 1
                                                   (SEQ ID NO: 224)
MQHLKNITAGNPKTVEQYQLTKGFDVVWFFSEDGKNWYEEQKYFADDTIKIAYDKDNIIR

YVEKDVTAIRPDGLSVVEVADITANRRADISGGWMFKDGKVIKRIYTAEELLQQAENRKA

RLLADAESVILPLERAVRLNMATDEERSRLDAWERYSVLVSRVDPANPEWPEMPQ

WW55 3.0 accessory protein 1
                                                   (SEQ ID NO: 225)
MAISSGWVGSSAVSETGQRWMSAAMQAVRLGRPAYMSAMVGRSKEIHYSIGASNSYNKDT

LINWMKAQGSTPVVITITGNIVSQSTGVPCLDFPSSLTNEYVTLIINSGVHVLGRGGNGG

SNSAGGAGGNAINNGIGTRLRINNNGIIGGGGGGGAGARYNPFPQMDMKFGGGGGRPFGA

AGAAGGGAAAASAGTISAPGKGTVSGVHYGGDGGDLGAAGKSSYIKGGTGGTVHSGGAAG

KAVTGNAPRWDKVGTIYGARV

WW55 3.0 accessory protein 2
                                                   (SEQ ID NO: 226)
MSNQHEQMINVLKVRLFDTQEKAAFLEGQLKDRERVLMELVRILGIQPDENGTVSLDAIV

EEVKALLPKDEAAEDAEEEVELITEA

STF68B
                                                   (SEQ ID NO: 227)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAAASAT

ASANSQKAAKTSETNAKTSETAAANSAKASAASQTAAKASEDAAREYASQAAEPYKQVLQ

PLPDVWIPFNDSLEMITGFAPGYKKVTIGDDVITFPSEKVVSFTRSTSATYINKSGSFAF

AEINEPRFEKEGLLIEGQRTNTFTNSNNPSLWNYDDKNIEITTSVDEYGFKYGLFDVKET

STTERATIISTGYSRVIDVAANESVTLSCRVKKINGEGIITLRPRISFVNDDGTSNTLVA

GSYIDCETGDVLGFSGGDAVNHVIYREANGWLRVEFTYKSPEAKSMYGRFEMGADKRAIK

KGDQIMFTTPQFEKGSCASSFIVTSDVAVTRASDVVIMPIRLNWSTPPLSVLMEVNINWD

KMPNSEGSARLLNVSITGATTDVADESYMYFGFTSGGARSIITNGKGTKTEYKAYCNRTT
```

-continued

RRFIAGFKFTEQKELRAVINGNFGAVDVSQHTRQRYTEGPINIGGQSISGNRHLFGHVRN

LRIWHKELTDAQMGERI

STF68B accessory protein 1
(SEQ ID NO: 228)
MRDLTLKFINKADFSAFMDSIGYEDDEVMQNNVLIDVIGNVYKETGELTEDGEPVCVKED

GYFVNVRIINDAKKSSIFDKYAVVVEHQLRGWM

STF68B accessory protein 2
(SEQ ID NO: 229)
MATSTVIPDDIKTLKSDVSKLKNDQGSYATKSYVDSKDETVGDWSASWYQQVLPTSGAIF

GRKLRSTHRTAGVEDAYCELYLKKWIDSPGNAMARLNLNDNGTNICWDFTNLYGGTMIFP

GDSGYLKMGNCLMSYSKRGSNALIKFDYTDTLQIKYANHGSTMTLNTQGTAHAGVTTRLW

GNSSRPVVYEVGVDEALYMFYAQKTTSNTYELTVNGACNASAFNQGSDRDLKDNIQVIDN

ATDRIRKMNGYTYTLKENGMPYAGVIAQETLEAIPEAVGAMMKYPDGGSGLDGEEGERYY

TVDYSGVTGLLVQVARESDDRITALEEENAELRQRLSAIEAALASK

STF90B
(SEQ ID NO: 230)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKVVMDETNRKYTAQDATTARKGLVQLSSVTNSDSET

LAATPKAVKTAYDLANGKYTAQDATTARKGLVQLSSATNSDSETLAATPKAVKSAYDNAE

KRLQKDQNGADIPGKDTFTKNIGACRAYSGALSTDAGNWTTAQFIDWLESQGAFNHPYWM

CKCSWSYGNNKIITDTDCGTIHLAGCVIEVMGVKAAMTIRVTTPSTSSGGGTTSAQFTYI

NHGADYAPGWRRDYNTKNKQPAFALGKTGNTVANNKAVGWNWDSGAYCAQDGGASKMVLH

FYTGEGSCPAMQFLVDYKNRGIFYRSARDGYGFEADWSEFYTTSRKPTPADILALALSGG

SMSGSIKFINDAFLIWERNTDWAKIGFKNDSDADSDSYMWFETGDNGNEYFKWRIRSGST

TKDLMTLKSDALRVTGQVIPSNFSNFDSRYVRDIRLGGAATYKPANNGMTWTHQAPSGCV

YTGIIVQDTGSNSADNIGGVYYRPVQKYINGTWYNVAQV

STF90B accessory protein
(SEQ ID NO: 231)
MQHLKNITAGNPKTVEQYQLTKDFDVVWFFSEDGKNWYEEQKYFADDTIKIAYDKDNIIR

YVEKDVTAIRPDGLSVVEVADITANRRADISGNWMFKDGTVIKRIYTAEELQQQAENRKA

RLLADAESVILPLERAVRLNMATEEERSRLERWERYSVLVSRVDPANPEWPEMPQ

STF117
(SEQ ID NO: 232)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKVVMDETNRKYTAQDATTARKGLVQLSSATNSDSET

-continued

LAATPKAVKSAYDNAEKRLQKDQNGADIPGKDTFTKNIGACRAYSGALSTEAGNWTTAQF

IEWLDSRGAFNHPYWMCKGSWSYANNKIITDTGCGDIHLAGCVVEVMGTKSAITIRVTTP

TTSSGGGTTSAQFTYINHGDGYSPGWRRDWNRQGDAMTGTINQDGGSQNAYMSTALCSGT

RGGKKYLRKFRGGEGDTIWHETVQGGVVRWATGNTDAQEELSLSSAYGLRSRGEITSSSA

NGLRIAYGNYGFFIRNDGSSTYFMLTKSGDRLGTYNNLRPLIINDATGAVSMGHGLSVTG

DIASSTKVRAGSGKKFTVSSSNTSTKEAAFNLWGNSSRPVVAELGDDAGWHFYSQRNTDN

SITFAVNGQVSPSNYSNFDSRYVRDIRLGGAATYKPANNGMTWTHQAPSGCVYSGIIVQD

TGSNSADNIGGVYYRPVQKYINGTWYNVAQV

STF117 accessory protein 1
(SEQ ID NO: 233)
MQHLINITAGNPKTVEQYQLTKDFDVVWFFTEDGKNWYEEQKYFADDTIKIAYDKDNIIR

YVEKDVTAIRPDGLSVVEVADITANRRADISGNWMFKDGKVIKRIYTAEELQQQAENRKA

RLLADAESVILPLERAVRLNMATDEERSRLEAWERYSVLVSRVDPANPEWPEMPQ

O111
(SEQ ID NO: 234)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKVVMDETNRKAPLDSPALTGTPTAPTALRGTNNTQI

ANTAFVLAAIADVIDASPDALNTLNELAAALGNDPDFATTMTNALAGKQPKNATLTALAG

LSTAKNKLPYFAENDAASLTELTQVGRDILAKNSVADVLEYLGAGENSASGALQKNQNGA

DIPGKDTFTKNIGACRAYSAWLNIGGDSQVWTTAQFISWLESQGAFNHPYWMCKGSWAYA

NNKVITDTGCGNICLAGAVVEVIGTRGAMTIRVTTPSTSSGGGITNAQFTYINHGDAYAP

GWRRDYNTKNQQPAFALGQTGSRVANDKAVGWNWNSGVYNADISGASTLILHFNMNAGSC

PAVQFRVNYRNGGIFYRSARDGYGFEANWSEFYTTTRKPSAGDVGAYTQAECNSRFITGI

RLGGLSSVQTWNGPGWSDRSGYVVTGSVNGNRDELIDTTQARPIQYCINGTWYNAGSI

O111 accessory protein
(SEQ ID NO: 235)
MMHLKNITAGNPKTKEQYQLTKQFNIKWLYSEDGKNWYEEQKNFQPDTLKMVYDHNGVII

CIEKDVSAINPEGASVVELPDITANRRADISGKWMFKDGVVVKRTYTEEEQRQQAENEKQ

SLLQLVRDKTQLWDSQLRLGIISDENKQKLTEWMLFAQKVESTDTSSLPVTFPEQPE

DC1
(SEQ ID NO: 236)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKAAYDLANGKYTAQDATTARKGLVQLSSVTNSDSET

LAATPKAVKSAYDNAEKRLQKDQNGADIPGKDTFTKNIGACRAYSGALSTEAGNWTTAQF

IDWLESQGAFNHPYWMCKCSWSYGNNKIITDTDCGTIHLAGCVIEVMGVKAAMTIRVTTP

STSSSGGTTSAQFTYINHGADYAPGWRRDYNTKNKQPAFALGKTGNTVANNKAVGWNWDS

GAYCAQDGGASKMVLHFYTGEGSCPAMQFLVDYKNRGIFYRSARDGYGFEADWSEFYTTS

RKPTPADILALALSGGSMSGSIKFINDAFLIWERNTDWAKIGFKNDSDADSDSYMWFETG

DNGNEYFKWRIRSGSTTKDLMTLKSDALRVTGQVIPSNFSNFDSRYVRDIRLGGAATYKP

ANNGMTWTHQAPSGCVYTGIIVQDTGSNSADNIGGVYYRPVQKYINGTWYNVAQV

DC1 accessory protein 1
(SEQ ID NO: 237)
MQHLINITAGNPKTVEQYQLTKDFDVVWFFSEDGKNWYEEQKYFADDTIKIAYDKDNIIR

YVEKDVTAIRPDGLSVVEVPDITANRRADISGGWMFKDGKVIKRIYTAEELQQQAENRKA

RLLADAESVILPLERAVRLNMATDEERSRLDAWERYSVLVSRVDPANPEWPEMPQ

STF94A
(SEQ ID NO: 238)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKVVMDETNRKYTAQDATTARKGLVQLSSAINSDSET

LAATPKAVKTAYDLANRKYTAQDATTARKGLVQLSSATNSDSETLAATSKAVKSAYDNAE

KRLQKDQNGADIPGKDTFTKNIGACRAYSGALSTEAGNWTTAQFIEWLDSRGAFNHPYWM

CKGSWSYANNKIITDTGCGDIHLAGCVVEVMGTKSAITIRVTTPTTSSGGGTTSAQFTYI

NHGDGYSPGWRRDWNRQGDAMTGTINQDGGSQNAYMSTALCSGTRGGKKYLRKFRGGEGD

TIWHETVQGGVVRWATGNTDAQEELSLSSAYGLRSRGEITSLSANGLRIAYGNYGFFIRN

DGSSTYFMLTKSGDRLGTYNNLRPLIINDATGAVSMGHGLNVTGDIVSSTKVRAGSGKKF

TVSSSNTSTKEAAFNLWGNSSRPVVAELGDDAGWHFYSQRNTDNSITFAVNGQVSPSNYG

NFDSRYVRDIRLGGAATYKPANNGMTWTHQAPSGCVYSGIIVQDTGSNSADNIGGIYYRP

VQKYINGTWYNVAQV

STF94A accessory protein
(SEQ ID NO: 239)
MQHLINIMAGNPKTVEQYQLTKGFDVVWFFTEDGKNWYEEQKYFADDTIKIAYDKDNIIR

YVEKDVTAIRPDGLSVVEVADITANRRADISGGWMFKDGKVIKRIYTAEELQQQAEIRKA

RLLADAESVILPLERAVRLNMATEEERTRLEAWERYSVLVSRVDPANPEWPEMPQ

STF69A
(SEQ ID NO: 240)
ASATASANSQKAAKTSETNAKASETAAANSAKASAASQTAAKASEDAAREYASQAAEPYK

YVLQPLPEVWIPFNDSLDMITGFAPGYKSITVGDDVIALPSEKVVSFTRASTATYIDKSG

CFAESAINEPRFEKDGLLIEGQRTNTFSYTNTPVSWNYDTANLTITTGVDEYGFSYGLFG

VKETSTTERATLISTGYTRVISVSANESVTLSCRVKKVSGDGIITLRPRISYVNDDGSSN

TLTAGAYIDCETGDMLSYSGGEAATYNIFRESNGWIRVEFTYKSPEAKNMYGRFEFGAHQ

RSIKSGDKLMLTTPQFEKGLNASSFIITTEVGATRASDQVIIPIPFNWATPPVSVLMEVN

VNWDSEMPNLEGSARLLNISITGATTEVSDESYMYFGFTTRGKRLIITNGKGTKTEYKAY

GNREKRKFVTGFKFTEDKQLQVVVDGILGGSSPSLHTLQRYTAGNINIGGQSSSGNRHLF

GHVKNLRIWHKELTEAQMGESI

-continued

STF69A accessory protein 1
(SEQ ID NO: 241)
MKDLTLKFEDRADFSAFMESIGYYDDESMQDDILIDVIGNVYKETGELTEDGEPVCVKED

GYFVNVRIINDSQISSLFDEYVVAVEHQLRGWM

STF69A accessory protein 2
(SEQ ID NO: 242)
MATSTVIPDDIKTLKSDVSKLKNDQGSYATKLYVDSKDEIVGDWSASWYQQVLPTSGAIF

GRKLRSTHRTAGVEDAYCELYLKKWIDSPGNAMARLNLNDNGTNICWDFTNLYGGTMIFP

GDSGYLKMGNCLMSYSKRGSNALIKFDYTDTLQIKYANHGSTMTLNTQGTAYAGVTAQLW

GNSSRPVVYEVGVDGGAYMFYAQKNTDNTYMLSVNGACHATAFNQHSDRDLKDNIQVIDN

ATDRIRKMNGYTYTLKENGMPYAGVIAQEALEAIPEVVGSAMKYQDGASGSEGEEGERYY

TVDYSGVTGLLVQVARESDDRITALEEENAELRQRLSAIEAALASK

STF118
(SEQ ID NO: 243)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKVVMDETNRKAPLNSPALTGTPTTPTARQGTNNTQI

ANTAFVMAAIAALVDSSPDALNTLNELAAALGNDPNFATTMTNALAGKQPKDATLAALAG

LATAADRFPYFTGNDVASLATLTKVGRDILAKSTVSAVIEYLGLQETVNRAGNAVQKNGD

TLSGGLTFENDSILAWIRNTDWAKIGFKNDADGDTDSYMWFETGDNGNEYFKWRSRQSTT

TKDLMNLKWDALYVLVKALFSSEVKISTVNALRIFNSSFGAIFRRSEENLYIIPTRENEG

ENGDIGPLRPFGINLRTGVVSVGNGARIDGGLALGTNNALGGNSIVLGDNDTGFKQNGDG

NLDVYANNVHVMRFVSGSIQSNKTINITGRVNPSDYGNFDSRYVRDIRLGTRVVQTMQKG

VMYEKAGHVITGLGIVGEVDGDDPAVFRPIQKYINGTWYNVAQV

STF118 accessory protein
(SEQ ID NO: 244)
MQHLKNITAGNPKTVAQYQLTKNFDVIWLWSEEGKNWYEEVSNFQEDTIKIVYDENNIIV

GITRDASTLNPEGFSVVEVPDITSNRRADDSGKWMFKDGAVIKRIYTADEQEQQAESQKA

ALLSEAESVILPLERAVRLNMATDEERSRLEAWERYSVLVSRVDPANPEWPEMPQ

K1
(SEQ ID NO: 245)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAADAKT

AAAGSASTASTKATEAAGSAVSASQSKSAAEAAAIRAKNSAKRAEDIASAVALEDADTTR

KGIVQLSSATNSTSETLAATPKAVKVVMDETNRKAPLDSPALTGTPTAPTALRGTNNTQI

ANTAFVLAAIADVIDASPDALNTLNELAAALGNDPDFATTMTNALAGKQPKNATLTALAG

LSTAKNKLPYFAENDAASLTELTQVGRDILAKNSVADVLEYLGAGENSGAKGDGVTDDTA

ALTSALNDTPVGQKINGNGKTYKVTSLPDISRFINTRFVYERIPGQPLYYASEEFVQGEL

FKITDTPYYNAWPQDKAFVYENVIYAPYMGSDRHGVSRLHVSWVKSGDDGQTWSTPEWLT

-continued

```
DLHPDYPTVNYHCMSMGVCRNRLFAMIETRTLAKNALTNCALWDRPMSRSLHLTGGITKA

ANQRYATIHVPDHGLFVGDFVNFSNSAVTGVSGDMTVATVIDKDNFTVLTPNQQTSDLNN

AGKNWHMGTSFHKSPWRKTDLGLIPSVTEVHSFATIDNNGFAMGYHQGDVAPREVGLFYF

PDAFNSPSNYVRRQIPSEYEPDASEPCIKYYDGVLYLITRGTRGDRLGSSLHRSRDIGQT

WESLRFPHNVHHTTLPFAKVGDDLIMFGSERAENEWEAGAPDDRYKASYPRTFYARLNVN

NWNADDIEWVNITDQIYQGGIVNSGVGVGSVVVKDNYIYYMFGGEDHFNPWTYGDNSAKD

PFKSDGHPSDLYCYKMKIGPDNRVSRDFRYGAVPNRAVPVFFDTNGVRTVPAPMEFTGDL

GLGHVTIRASTSSNIRSEVLMEGEYGFIGKSIPTDNPAGQR1IFCGGEGTSSTTGAQITL

YGANNTDSRRIVYNGDEHLFQSADVKPYNDNVTALGGPSNRFTTAYLGSNPIVTSNGERK

TEPVVFDDAFLDAWGDVHYIMYQWLDAVQLKGNDARIHFGVIAQQIRDVFIAHGLMDENS

TNCRYAVLCYDKYPRMTDTVFSHNEIVEHTDEEGNVTTTEEPVYTEVVIHEEGEEWGVRP

DGIFFAEAAYQRRKLERIEARLSALEQK

STF66
                                                   (SEQ ID NO: 246)
MAVKISGVLKDGTGKPVQNCTIQLKARRNSTTVVVNTVGSENPDEAGRYSMDVEYGQYSV

ILQVDGFPPSHAGTITVYEDSQPGTLNDFLCAMTEDDARPEVLRRLELMVEEVARNASVV

AQSTADAKKSAGDASASAAQVAALVTDATDSARAASTSAGQAASSAQEASSGAEAASAKA

TEAEKSAAAAESSKNAAATSAGAAKTSETNAAASQQSAATSASTAATKASEAATSARDAV

ASKEAAKSSETNASSSAGRAASSATAAENSARAAKTSETNARSSETAAERSASAAAASAT

AAANSQKAAKTSETNSKASETAAANSAKASAASQTAAKASEDAAREYASQAAEPYKQVLQ

PLPDVWIPFNDSLDMITGFSPSYKKIVIGDDEITMPGDKVVKFKRASKATYINKSGVLTE

AAIDEPRFERDGLLIEGQRTNYMLNSENPASWGRSSNMDVPETGTDSFGFTYGKFVCNDS

LIGQTSAINMASIAATKSVDVSGDNKYVTTSCRFKTELQVRLRIRFDKYDGSATTFLGDA

YIDTQTLEINMTGGASGRITARVRKDETTGWIFAEATIQAIDGELKIGSQIQYSPKQGGA

TVSGDYIYLATPQVENGACVSSFIISGTTAATRASDMVTIPTENNIYNRPLTCLVEVNRN

WGDIPPNVAPRIFDFSGVPPIESITYAFNTTEKYYGQLYMQTYKASTSSYVSSLFTGRTD

VRKLIGGFNIYSDGTKRVVSNGEATKTMKTEWTGVKTRTFIRIGGQATSGTRHLFGHLRN

LRLWHKELTDAQMGESIK

STF66 accessory protein
                                                   (SEQ ID NO: 247)
MKDLTLKFADRADFSAFMESIGYYDDESMQDDILIDVIGNVYKETGELTEDGEPVCVKED

GYFVNVRIINDSQISSLFDEYVVAVEHQLRGWM
```

SEQUENCE LISTING

The patent contains a lengthy sequence listing. A copy of the sequence listing is available in electronic form from the USPTO web site (https://seqdata.uspto.gov/?pageRequest=docDetail&DocID=US11661443B2). An electronic copy of the sequence listing will also be available from the USPTO upon request and payment of the fee set forth in 37 CFR 1.19(b)(3).

What is claimed is:

1. A nucleic acid molecule encoding a chimeric receptor binding protein (RBP), wherein the chimeric RBP comprises a fusion between the N-terminal domain of a RBP from a lambda-like or Lambda bacteriophage, wherein said lambda-like bacteriophage comprises amino acid sequence homology of around 35% identity for 45 amino acids or more, around 50% identity for 30 amino acids or more, or around 90% identity for 18 amino acids or more in one or more of three amino acid regions ranging from positions 1-150, 320-460, and 495-560 with reference to the lambda bacteriophage stf sequence of SEQ ID NO: 1, and the C-terminal domain of a different RBP and wherein said N-terminal domain is fused to said C-terminal domain within one of the amino acids regions selected from positions 1-150, 320-460 or 495-560 of the N-terminal RBP with reference to the lambda stf sequence (SEQ ID NO:1), wherein said region of fusion within the N-terminal RBP from positions 1-150, 320-460 or 495-560 comprises amino acid sequence homology of around 35% identity for 45 amino acids or more, around 50% identity for 30 amino acids or more, or around 90% identity for 18 amino acids or more with reference to the lambda bacteriophage stf sequence of SEQ ID NO: 1.

2. The nucleic acid molecule of claim 1, wherein the different RBP comprises amino acids sequence homology of around 35% identity for 45 amino acids or more, around 50% identity for 30 amino acids or more, or around 90% identity for 18 amino acids or more in one or more of three amino acids regions ranging from positions 1-150, 320-460, and 495-560 with reference to the lambda bacteriophage stf sequence of SEQ ID NO: 1.

3. The nucleic acid molecule of claim 1, wherein said encoded different RBP is derived from any bacteriophage or bacteriocin.

4. The nucleic acid molecule of claim 1, wherein said encoded N-terminal domain of the chimeric RBP is fused to said C-terminal domain within one of the amino acids regions selected from positions 80-150, 320-460, and 495-560 of the N-terminal RBP.

5. The nucleic acid molecule of claim 1, wherein the encoded N-terminal domain and the C-terminal domain are fused within said region at an insertion site having at least 80% identity with insertion site selected from the group consisting of amino acids SAGDAS (SEQ ID NO: 248), ADAKKS (SEQ ID NO: 249), MDETNR (SEQ ID NO: 250), SASAAA (SEQ ID NO: 251), and GAGENS (SEQ ID NO: 252).

6. The nucleic acid molecule of claim 1, wherein the encoded chimeric RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 123-129, 130, 131, 132, 135, 138, 139, 142, 145, 148, 151, 216, 219, 221, 223, 227, 230, 232, 234, 236, 238, 240, 243, 245 or 246.

7. The nucleic acid molecule of claim 1, wherein the encoded C-terminal domain of the different RBP has a depolymerase activity against an encapsulated bacterial strain.

8. The nucleic acid molecule of claim 1 comprising the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172,175 182, 185, 187, 189, 193, 196, 198, 200, 202, 204, 206, 209 or 212.

9. A vector comprising the nucleic acid molecule of claim 1.

10. A cell comprising the nucleic acid molecule of claim 1.

11. A cell comprising the vector of claim 9.

* * * * *